(12) United States Patent
Xia et al.

(10) Patent No.: US 10,662,186 B2
(45) Date of Patent: May 26, 2020

(54) SUBSTITUTED PYRIMIDINES AS CYCLIN-DEPENDENT KINASE INHIBITORS

(71) Applicant: SHANGHAI PHARMACEUTICALS HOLDING CO., LTD., Shanghai (CN)

(72) Inventors: Guangxin Xia, Shanghai (CN); Qian Wang, Shanghai (CN); Chen Shi, Shanghai (CN); Xiong Zhai, Shanghai (CN); Hui Ge, Shanghai (CN); Xuemei Liao, Shanghai (CN); Yu Mao, Shanghai (CN); Zhixiong Xiang, Shanghai (CN); Yanan Han, Shanghai (CN); Guoyong Huo, Shanghai (CN); Yanjun Liu, Shanghai (CN)

(73) Assignee: SHANGHAI PHARMACEUTICALS HOLDING CO., LTD., Shanghai (CN)

( * ) Notice: Subject to any disclaimer, the term of this patent is extended or adjusted under 35 U.S.C. 154(b) by 0 days.

(21) Appl. No.: 16/067,158

(22) PCT Filed: Dec. 30, 2016

(86) PCT No.: PCT/CN2016/113887
§ 371 (c)(1),
(2) Date: Jun. 29, 2018

(87) PCT Pub. No.: WO2017/114512
PCT Pub. Date: Jul. 6, 2017

(65) Prior Publication Data
US 2019/0010153 A1 Jan. 10, 2019

(30) Foreign Application Priority Data

Dec. 31, 2015 (CN) .......................... 2015 1 1028799
Jul. 1, 2016 (CN) .......................... 2016 1 0516637
Sep. 30, 2016 (CN) .......................... 2016 1 0877404

(51) Int. Cl.
| | | |
|---|---|---|
| A61K 31/506 | (2006.01) |
| C07D 239/30 | (2006.01) |
| C07D 471/04 | (2006.01) |
| A61P 35/00 | (2006.01) |
| C07F 5/02 | (2006.01) |
| C07F 7/08 | (2006.01) |
| C07F 9/6561 | (2006.01) |
| C07F 9/6584 | (2006.01) |

(52) U.S. Cl.
CPC .......... *C07D 471/04* (2013.01); *A61P 35/00* (2018.01); *C07F 5/025* (2013.01); *C07F 7/083* (2013.01); *C07F 7/0812* (2013.01); *C07F 7/0816* (2013.01); *C07F 9/6561* (2013.01); *C07F 9/65842* (2013.01); *Y02P 20/55* (2015.11)

(58) Field of Classification Search
CPC ............................ A61K 31/506; C07D 239/30

USPC ......................................... 514/275; 544/297
See application file for complete search history.

(56) References Cited

U.S. PATENT DOCUMENTS

| 7,855,211 B2 | 12/2010 | Coates et al. |
| 2010/0160340 A1 | 6/2010 | Coates et al. |

FOREIGN PATENT DOCUMENTS

| CN | 102264725 A | 11/2011 |
| CN | 105294683 A | 2/2016 |
| CN | 106188038 A | 12/2016 |
| CN | 106928219 A | 7/2017 |
| JP | 2005519909 A | 7/2005 |
| JP | 2009538341 A | 11/2009 |
| JP | 2009542604 A | 12/2009 |
| JP | 2012513396 A | 6/2016 |
| WO | 03062236 A | 7/2003 |
| WO | 2007140222 A | 12/2007 |
| WO | 2008003766 A | 1/2008 |
| WO | 2010075074 A1 | 7/2010 |
| WO | 2016015604 A1 | 2/2016 |
| WO | 2016015605 A1 | 2/2016 |
| WO | 2016192630 A1 | 12/2016 |

OTHER PUBLICATIONS

Jordan, V. C. Nature Reviews: Drug Discovery, 2, 2003, 205.*
Dörwald, F. Zaragoza. Side Reactions in Organic Synthesis: A Guide to Successful Synthesis Design, Weinheim: Wiley-VCH Verlag GmbH & Co. KGaA, 2005, Preface.*
Vippagunta, et al. Advanced Drug Delivery Reviews, 48, 2001, 18.*

(Continued)

*Primary Examiner* — Douglas M Willis
(74) *Attorney, Agent, or Firm* — Piloff Passino & Cosenza LLP; Sean A. Passino; Rachel K. Piloff

(57) ABSTRACT

The present invention discloses a nitrogen-containing fused heterocyclic compound, as well as a preparation method, intermediate, composition and application thereof. The nitrogen-containing fused heterocyclic compound of the present invention as represented by formula (I), as well as the pharmaceutically acceptable salt, enantiomer, diastereomer, tautomer, solvate, metabolite or drug precursor thereof, exhibit a high selectivity and a high inhibitory activity with respect to CDK4 and CDK6 at a molecular level, an excellent inhibitory activity with respect to breast cancer cells at a cellular level, and significant inhibition of tumor cell proliferation associated with cyclin-dependent kinase activity at an animal level. The invention also exhibits a good stability with respect to human or mouse liver microsomes without significant inhibition of metabolic enzymes, good in vivo absorption in mice and rats, a high bioavailability and good druggability.

4 Claims, No Drawings

(56) References Cited

OTHER PUBLICATIONS

Wolff, Manfred E., Ed. Burger's Medicinal Chemistry and Drug Discovery—Fifth Edition, vol. 1: Principles and Practice, New York: John Wiley & Sons, 1994, 975-977.*
International Search Report and Written Opinion for PCT/CN2016/113887, dated Mar. 17, 2017.
International Search Report issued in International Patent Application No. PCT/CN2016/113887, dated Mar. 17, 2017.
Written Opinion of the International Searching Authority issued in International Patent Application No. PCT/CN2016/113887, dated Mar. 17, 2017.
Greene et al., "Protective Groups in Organic Synthesis, Second Edition," 1991, John Wiley & Sons, Inc.
Priority Application—English Translation of Chinese application CN 201511028799.6, filed Dec. 31, 2015 (Not Published).
Priority Application—English Translation of Chinese application CN 201610516637.5, filed Jul. 1, 2016 (Not Published).
Priority Application—English Translation of Chinese application CN 201610877404.8, filed Sep. 30, 2016 (Not Published).
Notice of Reasons for Refusal issued in Japanese patent application No. 2018-534536 dated Jun. 11, 2019.
Extended European Search Report issued in European patent application No. 16881301.2 dated Jul. 4, 2019.
Concepcion Sanchez-Martinez et al., "Cyclin dependent kinase (CDK) inhibitors as anticancer drugs," Bioorganic & Medicinal Chemistry Letters, Jun. 6, 2015, pp. 3,420-3,435, vol. 25.

* cited by examiner

SUBSTITUTED PYRIMIDINES AS CYCLIN-DEPENDENT KINASE INHIBITORS

The present application claims the benefit of the Chinese Patent Application No. CN201511028799.6 filed on Dec. 31, 2015. The present application claims the benefit of the Chinese Patent Application No. CN201610516637.5 filed on Jul. 1, 2016. The present application claims the benefit of the Chinese Patent Application No. CN201610877404.8 filed on Sep. 30, 2016. The content of the above Chinese Patent Applications is incorporated herein by reference in its entirety.

FIELD OF INVENTION

The present invention relates to a nitrogen-containing fused heterocyclic compound, as well as a preparation method, an intermediate, a composition and a use thereof.

PRIOR ARTS

Tumor is a type of cell cycle disease (CCD). Regulating or blocking the cell cycle is one of the ways to treat tumor. At present, many molecules involved in the cell cycle regulation have been discovered, wherein Cyclin-Dependent-Kinases (CDKs) are the core molecules in the cell cycle regulatory network. CDKs are catalytic subunits and are a family of serine (Ser)/threonine (Thr) kinases, they function as important signal transduction molecules in cells, form CDK-cyclin complexes with cyclins and are involved in cell growth, proliferation, dormancy, or entry into apoptosis. Cell cycle regulatory proteins play an important role in the regulation of cell proliferation. In the tumor cells, G1 cyclins and CDK disorders are the most frequent variations in which many mechanisms are involved. These variations often cause tumorigenesis by activating tumor genes and silencing tumor suppressor genes. Malignant cells affect the expression of cell cycle regulatory proteins through genetic and growing mechanisms, causing overexpression of cyclins and expression loss of CDK inhibitors followed by incontrollable CDK activity.

Cell cycle checkpoints are the rate-limiting sites that control cell proliferation cycle, responsible for determining the integrity of DNA synthesis, monitoring DNA replication, repairing DNA damage, and blocking entrance into mitosis period before DNA replication and mitosis, they precisely regulate the progression of cell cycle and prevent errors in the proliferation cycle. Cells respond to DNA damage, which activates the cell cycle checkpoints and cause cell cycle arrest to repair damaged DNA, or induce cell death by apoptosis or termination of growth. Cell cycle arrest often occurs at the G1/S or G2/M junction, and the cell cycle checkpoint regulatory molecules are also new targets for antitumor drugs.

In the development of drugs, the first generation of CDK inhibitors represented by flavopiridol, UCN-01 etc. are "pan-CDK" inhibitors, which blocks all the subtypes of the CDK family in an equivalent manner, exhibits relatively high toxicity in clinical trials and some of them cannot reach the effective therapeutic dose. Therefore, people are inspired to develop selective CDK inhibitors, which are expected to improve the selectivity of treatment and prevent normal cells from damages of side effects. In recent years, selective CDK inhibitors have been reported and entered clinical trials. Therefore, discovering highly specific and low-toxic cell cycle regulators is a frontier in the research of antitumor drugs.

CONTENT OF THE PRESENT INVENTION

The technical problem to be solved in the present invention is to overcome the existing cell cycle regulators accompanied with severe clinical side effects due to low specificity, poor selectivity etc., or poor activity in spite of high selectivity. Thus, the present invention provides a nitrogen-containing fused heterocyclic compound, as well as a preparation method, an intermediate, a composition and a use thereof, the compounds exhibit a high selectivity and a high inhibitory activity with respect to CDK4 and CDK6 at a molecular level, an excellent inhibitory activity with respect to breast cancer cells at a cellular level, and significant inhibition of tumor cell proliferation associated with cyclin-dependent kinase activity at an animal level. The compounds also exhibits a good stability with respect to human or mouse liver microsomes without significant inhibition of metabolic enzymes, good in vivo absorption in mice and rats, a high bioavailability and good druggability.

The present invention provides a nitrogen-containing fused heterocyclic compound represented by formula (I), a pharmaceutically acceptable salt thereof, an enantiomer thereof, a diastereomer thereof, a tautomer thereof, a solvate thereof, an metabolite thereof or a drug precursor thereof;

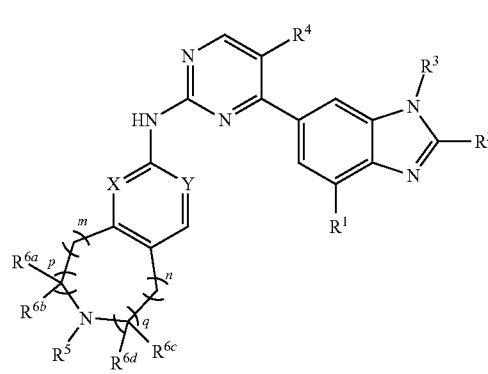

wherein, p and q are independently 0 or 1;
m and n are independently 0, 1 or 2;
X and Y are independently CH or N;
the N atom in the cycle

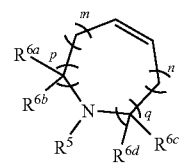

is oxidized or non-oxidized;
preferably, at least one of p and q is 1 (for example, when p and q are both 1, m is 0, 1 or 2, n is 0; or, when p and q are both 1, n is 0, 1 or 2, m is 0; or, when p is 0, q is 1, m and n are independently 0, 1 or 2; or, when p is 1, q is 0, m and n are independently 0, 1 or 2);

$R^1$ is hydrogen, hydroxy, cyano, thio, substituted or unsubstituted $C_2$-$C_{20}$ alkenyl, substituted or unsubstituted $C_2$-$C_{20}$ alkynyl, halogen (e.g. fluorine), substituted or unsubstituted $C_1$-$C_{20}$ alkyl (e.g. methyl, trifluoromethyl), $C_1$-$C_{20}$ alkylthio, substituted or unsubstituted $C_1$-$C_{20}$ alkoxy (e.g.

methoxy), substituted or unsubstituted $C_3$-$C_{12}$ cycloalkyl (e.g. cyclopropyl), substituted or unsubstituted $C_1$-$C_9$ heterocycloalkyl, or "$C_1$-$C_{20}$ alkyl mono-substituted, di-substituted or unsubstituted amino"; wherein, the two substituents in the "$C_1$-$C_{20}$ alkyl di-substituted amino" are the same or different;

$R^2$ is hydrogen, hydroxy, substituted or unsubstituted $C_2$-$C_{20}$ alkenyl, substituted or unsubstituted $C_2$-$C_{20}$ alkynyl, halogen, substituted or unsubstituted $C_1$-$C_{20}$ alkyl (e.g. methyl), substituted or unsubstituted $C_1$-$C_{20}$ alkoxy (e.g. methoxy), substituted or unsubstituted $C_1$-$C_{20}$ alkylthio (e.g. methylthio), substituted or unsubstituted $C_3$-$C_{12}$ cycloalkyl (e.g. cyclopropyl), cyano, "$C_1$-$C_{20}$ alkyl mono-substituted, di-substituted or unsubstituted amino" or

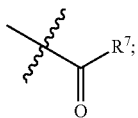

wherein, the two substituents in the "$C_1$-$C_{20}$ alkyl di-substituted amino" are the same or different;

$R^3$ is hydrogen, substituted or unsubstituted $C_1$-$C_{20}$ alkyl (e.g. methyl, ethyl, isopropyl, tert-butyl, 1-ethylpropyl, 1-cyclopropylethyl, 2-fluoroethyl, 2,2-difluoroethyl, 2,2,2-trifluoroethyl, 1-methyl-2,2,2-trifluoroethyl or cyclopropylmethyl), substituted or unsubstituted $C_2$-$C_{20}$ alkenyl, substituted or unsubstituted $C_2$-$C_{20}$ alkynyl, substituted or unsubstituted $C_3$-$C_{12}$ cycloalkyl (e.g. 1-methylcyclopropyl, cyclopropyl, 3-oxocyclobutyl 3-hydroxycyclobutyl, 3-fluorocyclobutyl, 3,3-difluorocyclobutyl, cyclobutyl, cyclopentyl, cyclohexyl, or

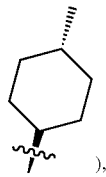

or substituted or unsubstituted $C_1$-$C_9$ heterocycloalkyl (e.g. $C_3$-$C_5$ heterocycloalkyl, preferably $C_3$ heterocycloalkyl; e.g. 3-oxetanyl, 3-methyl-3-azacyclobutyl); wherein, the "heterocycloalkyl" connects to another group via the carbon atom thereof, the heteroatom in the heterocycloalkyl is selected from the group consisting of O, N and S, the number of the heteroatom is 1 to 3, when the heteroatom is N, N can be further substituted with $C_1$-$C_3$ alkyl, the heteroatom can be located at the para-position of the carbon atom that connects to another group (e.g. $R^3$ is

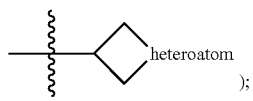

the "substituted" in the "substituted or unsubstituted $C_1$-$C_{20}$ alkyl", "substituted or unsubstituted $C_2$-$C_{20}$ alkenyl", "substituted or unsubstituted $C_2$-$C_{20}$ alkynyl", "substituted or unsubstituted $C_1$-$C_{20}$ alkoxy", "substituted or unsubstituted $C_1$-$C_9$ heterocycloalkyl", "substituted or unsubstituted $C_3$-$C_{12}$ cycloalkyl" and "substituted or unsubstituted $C_1$-$C_{20}$ alkylthio" in the definitions of $R^1$, $R^2$ and $R^3$ refers to be independently substituted with the substituent selected from the group consisting of halogen (e.g. fluorine, the number can be 1, 2 or 3), hydroxyl, oxo (e.g. an oxo group attached to $C_3$, $C_4$ or $C_5$ cycloalkyl, e.g.

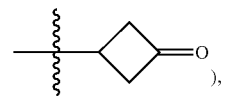 [SMILES: *C1CC(=O)C1]

thio, cyano, amino, nitro, $C_1$-$C_{20}$ alkyl (e.g. methyl), $C_2$-$C_{20}$ alkenyl, $C_2$-$C_{20}$ alkynyl, $C_1$-$C_{20}$ alkoxy, $C_1$-$C_{20}$ alkylthio, $C_3$-$C_{12}$ cycloalkyl (e.g. cyclopropyl) and "$C_1$-$C_{20}$ alkyl mono-substituted, di-substituted or unsubstituted amino"; wherein, the two substituents in the "$C_1$-$C_{20}$ alkyl di-substituted amino" are the same or different; when there are more than one substituents, the substituents are the same or different;

$R^4$ is hydrogen, halogen (e.g. fluorine), $C_1$-$C_6$ alkyl, $C_1$-$C_3$ alkoxy (e.g. methoxy), cyano or

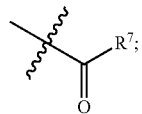

$R^7$ contained in $R^2$ and $R^4$ is independently hydrogen, hydroxyl, $C_1$-$C_6$ alkyl (e.g. methyl or ethyl), substituted or unsubstituted $C_3$-$C_8$ cycloalkyl (e.g. cyclobutyl, cyclopropyl or 4-methylcyclohexyl), $C_1$-$C_6$ alkoxy or "$C_1$-$C_6$ alkyl mono-substituted, di-substituted or unsubstituted amino"; wherein, the "substituted" in the "substituted or unsubstituted $C_3$-$C_8$ cycloalkyl" refers to be substituted by $C_1$-$C_6$ alkyl; the two substituents in the "$C_1$-$C_6$ alkyl di-substituted amino" are the same or different;

at least one of $R^1$ and $R^4$ is halogen;

$R^5$ is hydrogen, substituted or unsubstituted $C_1$-$C_{20}$ alkyl (e.g. substituted or unsubstituted $C_1$-$C_6$ alkyl, preferably substituted or unsubstituted methyl, ethyl or propyl; e.g. substituted or unsubstituted n-propyl or isopropyl; e.g. substituted or unsubstituted 2-methylpropyl; e.g. substituted or unsubstituted 1,2-dimethylpropyl; e.g. 2-methoxyethyl, 2-hydroxyethyl, 2-fluoroethyl, 2,2,2-trifluoroethyl, dimethylaminomethyl or 2-dimethylamino-ethyl), substituted or unsubstituted $C_2$-$C_{20}$ alkenyl (e.g. vinyl), substituted or unsubstituted $C_2$-$C_{20}$ alkynyl (e.g. ethynyl, 2-butynyl or 2-propynyl), substituted or unsubstituted $C_3$-$C_{12}$ cycloalkyl (e.g.

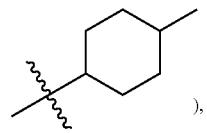 [SMILES: *C1CCC(C)CC1]

substituted or unsubstituted $C_1$-$C_9$ heterocycloalkyl (e.g. tetrahydrogenpyrrolyl,

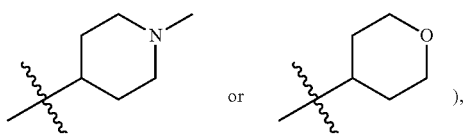

substituted or unsubstituted $C_1$-$C_9$ heteroaryl, substituted or unsubstituted $C_3$-$C_{12}$ aryl,

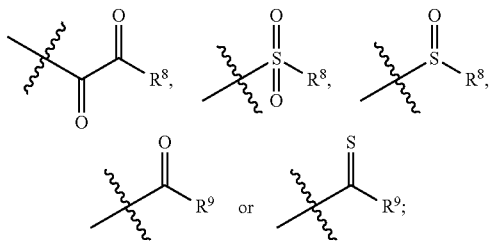

or wherein the "$C_1$-$C_9$ heterocycloalkyl" connects to another group via the carbon atom thereof;

in $R^5$, each $R^8$ is independently hydroxyl, substituted or unsubstituted $C_1$-$C_{20}$ alkyl (the "substituted or unsubstituted $C_1$-$C_{20}$ alkyl" is preferably "substituted or unsubstituted $C_1$-$C_6$ alkyl", preferably "substituted or unsubstituted methyl or ethyl"; e.g. dimethylaminomethyl), substituted or unsubstituted $C_2$-$C_{20}$ alkenyl (e.g. vinyl), substituted or unsubstituted $C_2$-$C_{20}$ alkynyl (e.g. ethynyl), substituted or unsubstituted $C_3$-$C_{12}$ cycloalkyl, substituted or unsubstituted $C_1$-$C_9$ heteroaryl, substituted or unsubstituted $C_3$-$C_{12}$ aryl, substituted or unsubstituted $C_1$-$C_9$ heterocycloalkyl

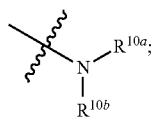

substituted or unsubstituted $C_1$-$C_{20}$alkoxy (e.g. methoxy or ethoxy) or (e.g. 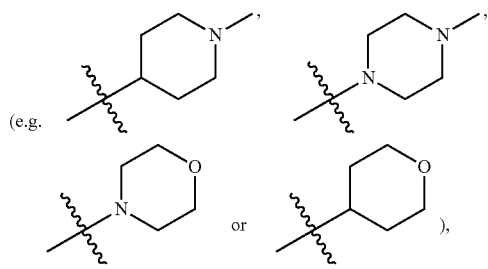), the "$C_1$-$C_9$ heterocycloalkyl" connects to another group via a carbon atom or a heteroatom thereof;

in $R^5$, each $R^9$ is independently hydrogen, hydroxyl, substituted or unsubstituted $C_1$-$C_{20}$ alkyl (e.g. methyl, ethyl, isopropyl, aminomethyl, hydroxymethyl, hydroxyethyl, methylaminomethyl, dimethylaminomethyl, 2-dimethyl-amino-ethyl,

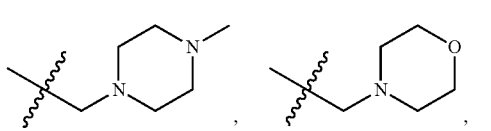

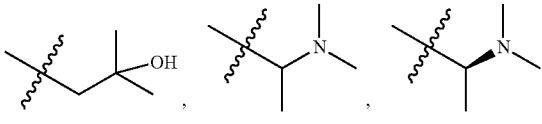

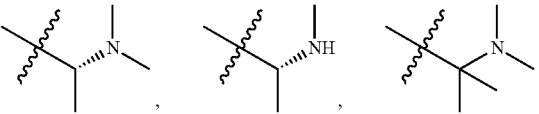

or methoxymethyl; the "$C_1$-$C_{20}$ alkyl" can be methyl, ethyl,

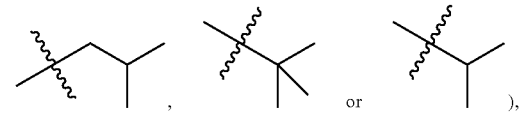

substituted or unsubstituted $C_2$-$C_{20}$ alkenyl (e.g. vinyl), substituted or unsubstituted $C_2$-$C_{20}$ alkynyl (e.g. ethynyl), substituted or unsubstituted $C_3$-$C_{12}$ cycloalkyl (e.g. cyclobutyl,

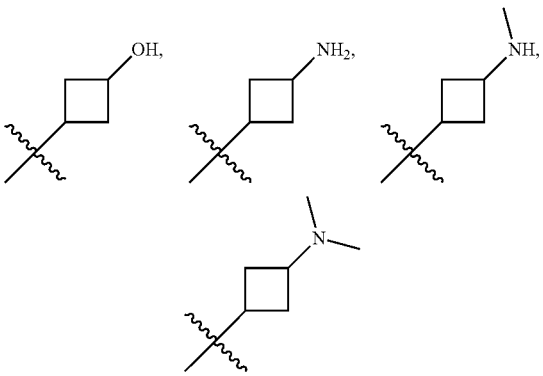

or 4-methylcyclohexyl), substituted or unsubstituted $C_1$-$C_{20}$ alkoxy (e.g. 2-dimethylamino-ethoxy; the "$C_1$-$C_{20}$ alkoxy" can be methoxy or ethoxy), substituted or unsubstituted $C_3$-$C_{12}$ aryl, substituted or unsubstituted $C_1$-$C_9$ heteroaryl, or substituted or unsubstituted $C_1$-$C_9$ heterocycloalkyl (e.g. 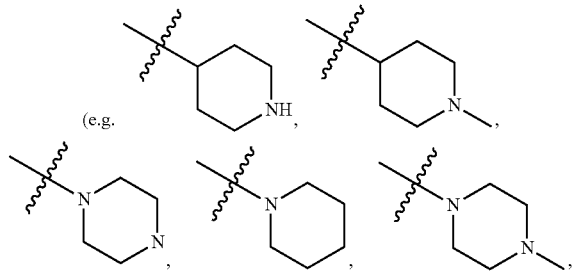 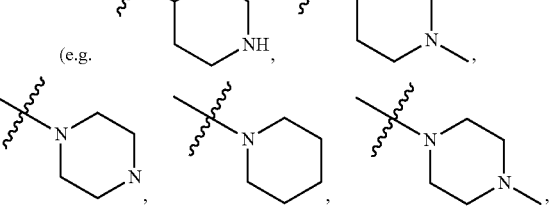

-continued

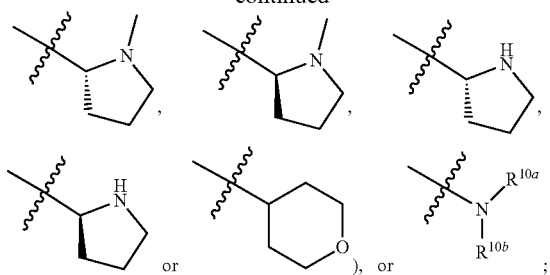

the "$C_1$-$C_9$ heterocycloalkyl" connects to another group via a carbon atom or a heteroatom thereof;

in $R^8$ and $R^9$, each $R^{10a}$ and $R^{10b}$ is independently hydrogen, halogen, substituted or unsubstituted $C_1$-$C_{20}$ alkyl (e.g. 2-dimethylamino-ethyl or 2-hydroxyethyl; wherein the "$C_1$-$C_{20}$ alkyl" can be ethyl), substituted or unsubstituted $C_2$-$C_{20}$ alkenyl, substituted or unsubstituted $C_2$-$C_{20}$ alkynyl, substituted or unsubstituted $C_3$-$C_{12}$ cycloalkyl, substituted or unsubstituted $C_1$-$C_9$ heteroaryl, substituted or unsubstituted $C_3$-$C_{12}$ aryl, substituted or unsubstituted $C_1$-$C_9$ heterocycloalkyl

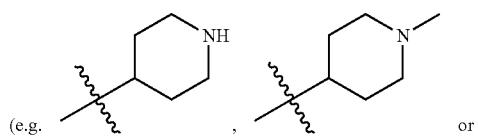

(e.g.

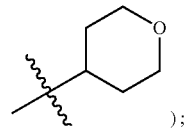

);

wherein the "$C_1$-$C_9$ heterocycloalkyl" connects to another group via a carbon atom or a heteroatom thereof;

the "substituted" in the "substituted or unsubstituted $C_1$-$C_{20}$ alkyl", "substituted or unsubstituted $C_2$-$C_{20}$ alkenyl", "substituted or unsubstituted $C_2$-$C_{20}$ alkynyl", "substituted or unsubstituted $C_3$-$C_{12}$ cycloalkyl", "substituted or unsubstituted $C_1$-$C_9$ heterocycloalkyl", "substituted or unsubstituted $C_3$-$C_{12}$ aryl", "substituted or unsubstituted $C_1$-$C_9$ heteroaryl", "substituted or unsubstituted $C_1$-$C_{20}$ alkylthio" and "substituted or unsubstituted $C_1$-$C_{20}$ alkoxy" in the definitions of $R^5$, $R^8$, $R^9$, $R^{10a}$ and $R^{10b}$ refers to be independently substituted with the substituent selected from the group consisting of

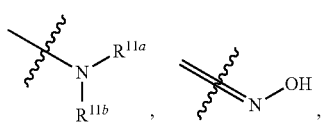

$C_1$-$C_{20}$ alkyl (e.g. methyl, isopropyl), $C_2$-$C_{20}$ alkenyl (e.g. vinyl), $C_2$-$C_{20}$ alkynyl (e.g. 2-propynyl), hydroxy, nitro, carboxyl, formyl, thio, trifluoromethyl, $C_1$-$C_{20}$ silyl (e.g.

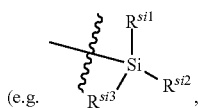

, wherein $R^{si1}$, $R^{si2}$, $R^{si3}$ are each independently $C_1$-$C_3$ alkyl such as methyl), halogen (e.g. fluorine, the number can be 1, 2 or 3), cyano, $C_1$-$C_{20}$ alkoxy (e.g. methoxy), $C_3$-$C_{12}$ cycloalkyl, substituted or unsubstituted $C_1$-$C_9$ saturated or unsaturated heterocycloalkyl (the "substituted" refers to be independently substituted with the substituent selected from the group consisting of methylene, oxo, thio, halogen, trifluoromethyl, hydroxy, —PO(OH)$_2$, —PO(OR$^{ps}$)$_2$, $C_1$-$C_{20}$ alkyl which is optionally substituted with propynyl, $C_1$-$C_{20}$ alkyl which is optionally substituted with ethynyl, $C_1$-$C_6$ alkenyl, $C_1$-$C_{20}$ alkynyl, —B(OH)$_2$ and —B(OR$^b$s)$_2$, wherein $R^{ps}$ and $R^{bs}$ are independently $C_1$-$C_6$ alkyl such as methyl, ethyl or propyl, the $C_1$-$C_{20}$ alkyl can be $C_1$-$C_6$ alkyl such as methyl, ethyl or propyl; unsaturated heterocycloalkyl such as saturated heterocycloalkyl such as

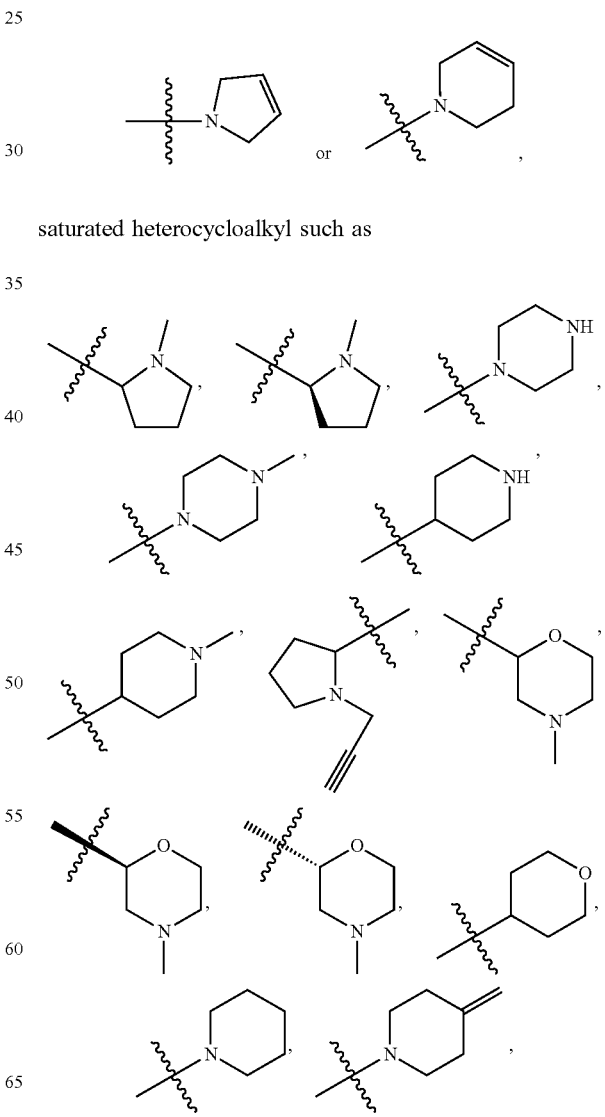

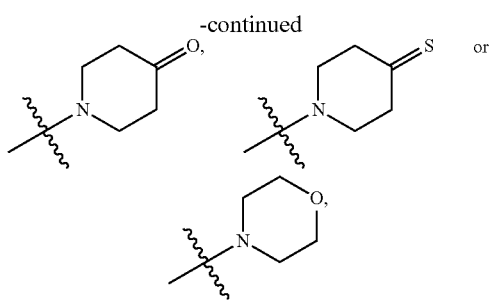

when there are more than one substituents, the substituents are the same or different),

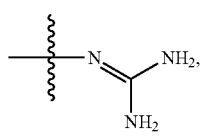 [SMILES: *N=C(N)N]

thioureido, $C_3$-$C_{12}$ aryl, $C_1$-$C_9$ heteroaryl,

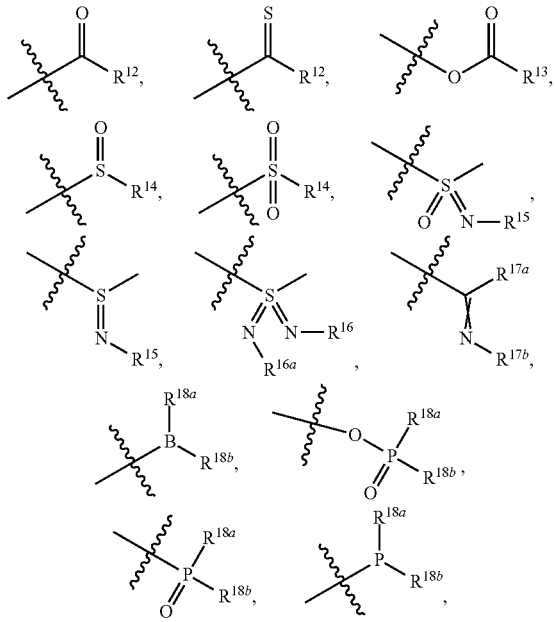

—SeR$^{19}$ and —SF$_5$; wherein heteroatom can be oxidized, N atom can be quaternized; wherein the "heterocycloalkyl" connects to another group via a carbon atom or a heteroatom thereof; the N atom in

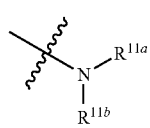

is oxidized or non-oxidized, when there are more than one substituents, the substituents are the same or different;

wherein, R$^{11a}$ and R$^{11b}$ are independently hydrogen, halogen, substituted or unsubstituted $C_1$-$C_{20}$ alkyl (e.g. substituted or unsubstituted $C_1$-$C_6$ alkyl, preferably substituted or unsubstituted $C_1$, $C_2$ or $C_3$ alkyl; e.g. —CF$_3$; e.g. hydroxyethyl, 2-dimethylaminoethyl), substituted or unsubstituted $C_2$-$C_{20}$ alkenyl (e.g. 2-propenyl), substituted or unsubstituted $C_2$-$C_{20}$ alkynyl (e.g. 2-propynyl), substituted or unsubstituted $C_3$-$C_{12}$ cycloalkyl, substituted or unsubstituted $C_1$-$C_9$ heterocycloalkyl

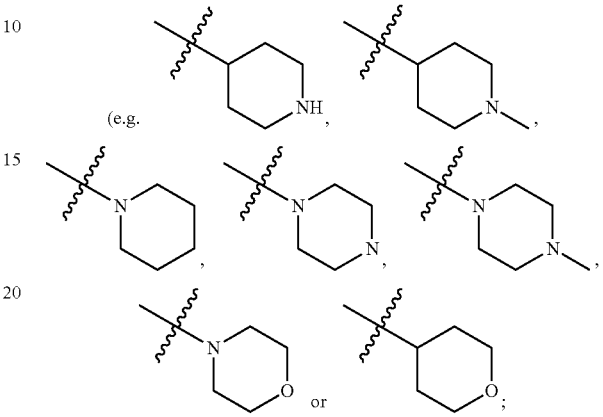

the substituent such as "$C_1$-$C_{20}$ alkyl"), guanidino, thioureido, substituted or unsubstituted $C_3$-$C_{12}$ aryl, substituted or unsubstituted $C_1$-$C_9$ heteroaryl,

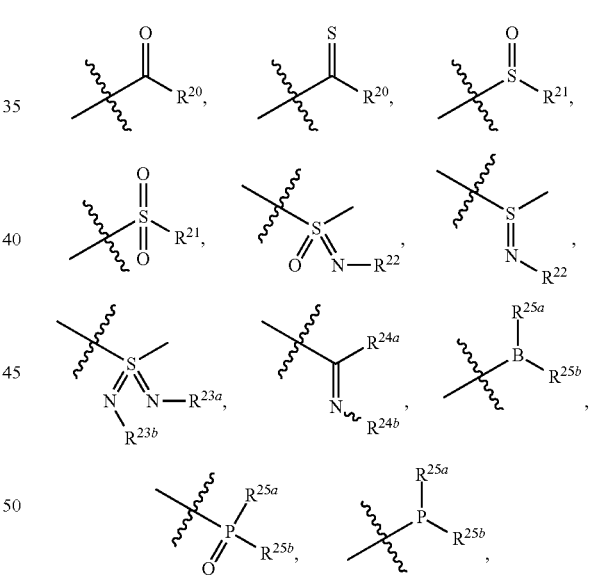

—SeR$^{26}$ or —SF$_5$; wherein the heteroatom can be oxidized, N atom can be quaternized; the "heterocycloalkyl" connects to another group via a carbon atom or a heteroatom thereof; or, in

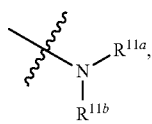

$R^{11a}$ and $R^{11b}$ together with the N atom attached form

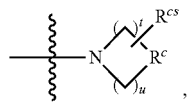

wherein t and u are independently 1, 2 or 3, $R^c$ is $C(R^{cs})_2$, $NR^{cs}$, O, S, $Si(R^{cs})_2$ or Se, each $R^{cs}$ is independently H, $C_1$-$C_6$ alkyl (e.g. methyl, ethyl, propyl or isopropyl), or $B(OH)_2$; or, in

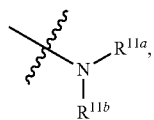

$R^{11a}$ and $R^{11b}$ together with the N atom attached form

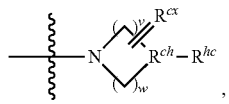

wherein v and w are independently 1, 2 or 3, $R^{ch}$ is CH or $PH_2$, $R^{cx}$ is $CH_2$, O, S or =N—OH, $R^{cx}$ is preferably attached to $R^{ch}$

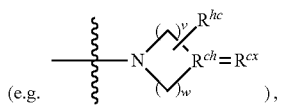

(e.g.)

$R^{hc}$ is H or $C_1$-$C_6$ alkyl (e.g. methyl, ethyl or propyl), preferably when $R^{cb}$ is P, $R^{hc}$ is $C_1$-$C_6$ alkyl; or in

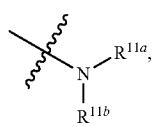

$R^{11a}$ and $R^{11b}$ together with the N atom attached form

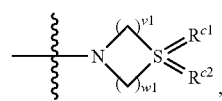

wherein v1 and w1 are independently 1, 2 or 3, $R^{c1}$ and $R^{c2}$ are independently O, NH or N—CN;

wherein the "substituted" in the "substituted or unsubstituted $C_1$-$C_{20}$ alkyl", "substituted or unsubstituted $C_2$-$C_{20}$ alkenyl", "substituted or unsubstituted $C_2$-$C_{20}$ alkynyl", "substituted or unsubstituted $C_3$-$C_{12}$ cycloalkyl", "substituted or unsubstituted $C_1$-$C_9$ heterocycloalkyl", "substituted or unsubstituted $C_3$-$C_{12}$ aryl" and "substituted or unsubstituted $C_1$-$C_9$ heteroaryl" in the definitions of $R^{11a}$ and $R^{11b}$ refers to be independently substituted with the substituent selected from the group consisting of $C_1$-$C_{20}$ alkyl, $C_2$-$C_{20}$ alkenyl (e.g. vinyl), $C_2$-$C_{20}$ alkynyl (e.g. ethynyl), hydroxy, nitro, carboxyl, formyl, thio, $C_1$-$C_{20}$ silyl

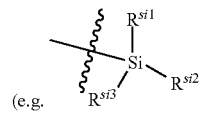

(e.g.)

wherein $R^{si1}$, $R^{si2}$, $R^{si3}$ are each independently $C_1$-$C_3$ alkyl such as methyl), halogen,

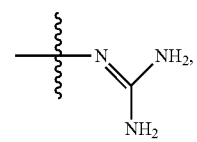

trifluoromethyl, cyano, $C_1$-$C_{20}$ alkoxy, $C_3$-$C_{12}$ cycloalkyl, $C_1$-$C_9$ heterocycloalkyl, $C_3$-$C_{12}$ aryl, $C_1$-$C_9$ heteroaryl,

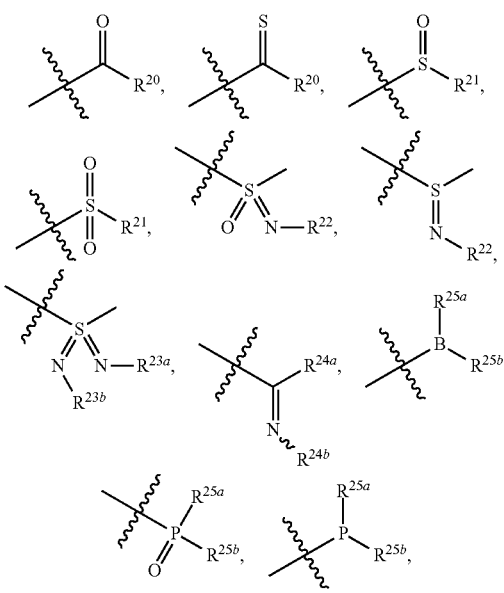

—$SeR^{26}$,

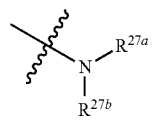

and —$SF_5$, when there are more than one substituents, the substituents are the same or different; wherein the heteroatom can be oxidized, N atom can be quaternized; wherein the "heterocycloalkyl" connects to another group via a carbon atom or a heteroatom thereof;

wherein each $R^{12}$ is independently hydrogen, halogen, $C_1$-$C_{20}$ alkyl (e.g. methyl), $C_2$-$C_{20}$ alkenyl, $C_2$-$C_{20}$ alkynyl, hydroxy, —$CF_3$, —$SF_5$, $C_1$-$C_{20}$ alkoxy (e.g. methoxy or ethoxy) or

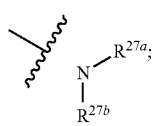

wherein $R^{13}$ is hydrogen, $C_1$-$C_{20}$ alkyl (e.g. methyl), $C_2$-$C_{20}$ alkenyl, $C_2$-$C_{20}$ alkynyl, hydroxy, —$CF_3$, —$SF_5$ or

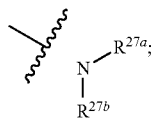

wherein each $R^{14}$ is independently halogen, $C_1$-$C_{20}$ alkyl, $C_2$-$C_{20}$ alkenyl, $C_2$-$C_{20}$ alkynyl, hydroxy, —$CF_3$, —$SF_5$, $C_1$-$C_{20}$ alkoxy or

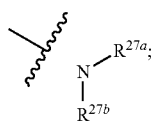

wherein each $R^{15}$, $R^{16a}$ and $R^{16b}$ is independently hydrogen, halogen, hydroxy, cyano, nitro, amino, formyl, $C_1$-$C_{20}$ alkoxy, $C_1$-$C_{20}$ alkylthio, $C_1$-$C_{20}$ alkyl (e.g. methyl), $C_2$-$C_{20}$ alkenyl, $C_2$-$C_{20}$ alkynyl,

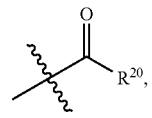

—$CF_3$, —$SF_5$, $C_3$-$C_{12}$ cycloalkyl, or "$C_1$-$C_9$ heterocycloalkyl which is optionally substituted with $C_1$-$C_{20}$ alkyl"

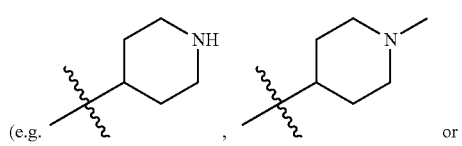

wherein the "$C_1$-$C_9$ heterocycloalkyl" connects to another group via a carbon atom or a heteroatom thereof;

wherein $R^{17a}$ is independently hydrogen, halogen, hydroxy, cyano, nitro, amino, formyl, $C_1$-$C_{20}$ alkoxy, $C_1$-$C_{20}$ alkylthio, $C_1$-$C_{20}$ alkyl (e.g. methyl), $C_2$-$C_{20}$ alkenyl, $C_2$-$C_{20}$ alkynyl, —$CF_3$, —$SF_5$, —$SeR^{26}$,

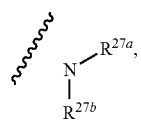

$C_3$-$C_{12}$ cycloalkyl or "$C_1$-$C_9$ heterocycloalkyl which is optionally substituted with $C_1$-$C_{20}$ alkyl"

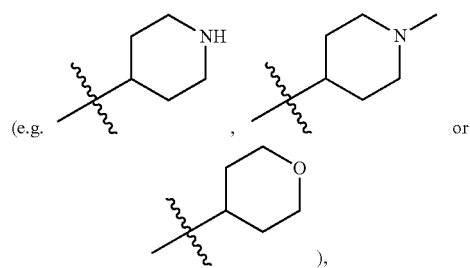

wherein the "$C_1$-$C_9$ heterocycloalkyl" connects to another group via a carbon atom or a heteroatom thereof;

wherein $R^{17b}$ is independently hydrogen, halogen, hydroxy, cyano, nitro, amino, formyl, $C_1$-$C_{20}$ alkoxy, $C_1$-$C_{20}$ alkyl, $C_2$-$C_{20}$ alkenyl, $C_2$-$C_{20}$ alkynyl, —$CF_3$, —$SF_5$,

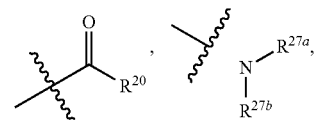

—$OR^{28}$, $C_3$-$C_{12}$ cycloalkyl or "$C_1$-$C_9$ heterocycloalkyl which is optionally substituted with $C_1$-$C_{20}$ alkyl", wherein the "$C_1$-$C_9$ heterocycloalkyl" connects to another group via a carbon atom or a heteroatom thereof;

or, $R^{17a}$ and $R^{17b}$ together with the carbon atom, N atom ( 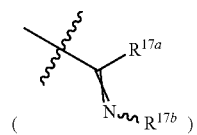 )

attached form substituted or unsubstituted $C_1$-$C_9$ heterocycloalkyl; wherein the "substituted" in the "substituted or unsubstituted $C_1$-$C_9$ heterocycloalkyl" refers to be independently substituted with the substituent selected from the group consisting of $C_1$-$C_{20}$ alkyl, $C_2$-$C_{20}$ alkenyl (e.g. vinyl), $C_2$-$C_{20}$ alkynyl (e.g. ethynyl), hydroxy, nitro, carboxyl, formyl, thio, $C_1$-$C_{20}$ silyl (e.g. 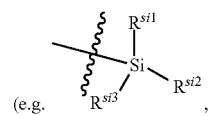 , wherein $R^{si1}$, $R^{si2}$, $R^{si3}$ are each independently $C_1$-$C_3$ alkyl such as methyl), halogen,

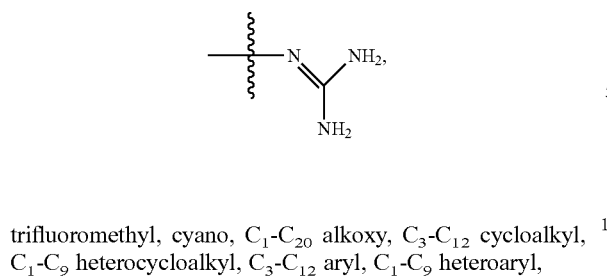

trifluoromethyl, cyano, $C_1$-$C_{20}$ alkoxy, $C_3$-$C_{12}$ cycloalkyl, $C_1$-$C_9$ heterocycloalkyl, $C_3$-$C_{12}$ aryl, $C_1$-$C_9$ heteroaryl,

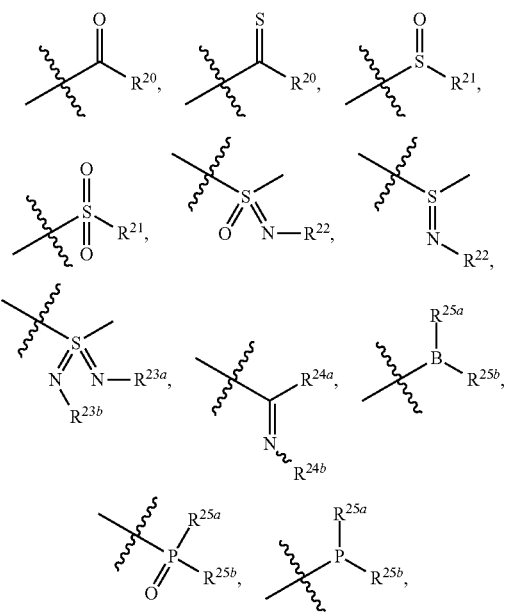

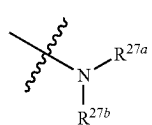

and —$SF_5$, when there are more than one substituents, the substituents are the same or different; wherein the "substituted or unsubstituted $C_1$-$C_9$ heterocycloalkyl" connects to another group via a carbon atom or a heteroatom thereof;

wherein $R^{18a}$ and $R^{18b}$ are independently hydrogen, halogen, cyano, $C_1$-$C_{20}$ alkoxy, $C_1$-$C_{20}$ alkyl, $C_2$-$C_{20}$ alkenyl, $C_2$-$C_{20}$ alkynyl, —$CF_3$, —$SF_5$, $C_3$-$C_{12}$ cycloalkyl or "$C_1$-$C_9$ heterocycloalkyl which is optionally substituted with $C_1$-$C_{20}$ alkyl"; wherein the "$C_1$-$C_9$ heterocycloalkyl" connects to another group via a carbon atom or a heteroatom thereof;

or, $R^{18a}$ and $R^{18b}$ together with the heteroatom attached form substituted or unsubstituted $C_1$-$C_9$ heterocycloalkyl; wherein the "substituted" in the "substituted or unsubstituted $C_1$-$C_9$ heterocycloalkyl" refers to be independently substituted with the substituent selected from the group consisting of $C_1$-$C_{20}$ alkyl, $C_2$-$C_{20}$ alkenyl (e.g. vinyl), $C_2$-$C_{20}$ alkynyl (e.g. ethynyl), hydroxy, nitro, carboxyl, formyl, thio, $C_1$-$C_{20}$ silyl

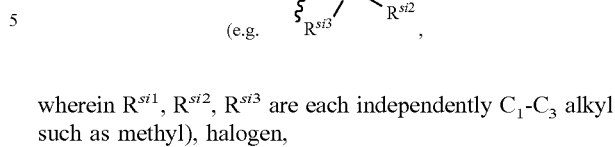

(e.g.

wherein $R^{si1}$, $R^{si2}$, $R^{si3}$ are each independently $C_1$-$C_3$ alkyl such as methyl), halogen,

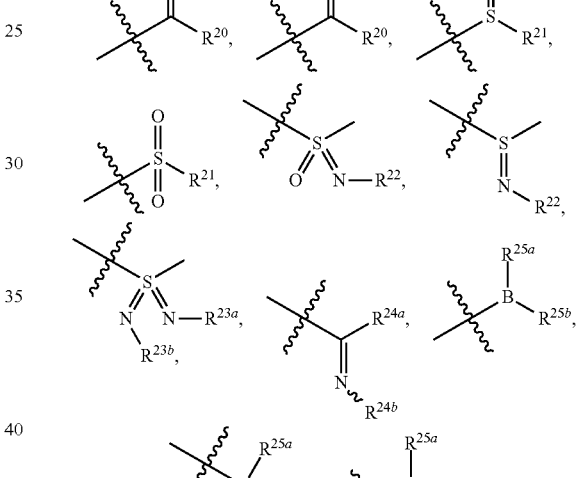

trifluoromethyl, cyano, $C_1$-$C_{20}$ alkoxy, $C_3$-$C_{12}$ cycloalkyl, $C_1$-$C_9$ heterocycloalkyl, $C_3$-$C_{12}$ aryl, $C_1$-$C_9$ heteroaryl,

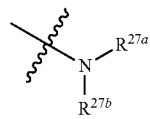

and —$SF_5$, when there are more than one substituents, the substituents are the same or different; wherein the "$C_1$-$C_9$ heterocycloalkyl" connects to another group via a carbon atom or a heteroatom thereof;

wherein $R^{19}$ is $C_1$-$C_{20}$ alkyl, $C_2$-$C_{20}$ alkenyl, $C_2$-$C_{20}$ alkynyl, $C_3$-$C_{12}$ cycloalkyl, $C_1$-$C_9$ heterocycloalkyl, $C_3$-$C_{12}$ aryl, $C_1$-$C_9$ heteroaryl;

wherein the $R^{20}$ is independently hydrogen, halogen, $C_1$-$C_{20}$ alkyl, $C_2$-$C_{20}$ alkenyl, $C_2$-$C_{20}$ alkynyl, hydroxy, —$CF_3$, —$SF_5$, $C_3$-$C_5$ heteroaryl (wherein the number of heteroatom is 1 to 3, the heteroatom is O, N or S,

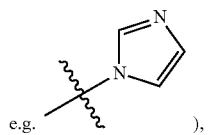

e.g. ), $C_1$-$C_{20}$ alkoxy or

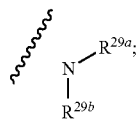

wherein $R^{21}$ in the definitions of $R^{11a}$ and $R^{11b}$ is independently halogen, $C_1$-$C_{20}$ alkyl, $C_2$-$C_{20}$ alkenyl, $C_2$-$C_{20}$ alkynyl, hydroxy, —$CF_3$, —$SF_5$, $C_1$-$C_{20}$ alkoxy or

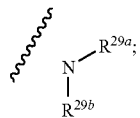

wherein the $R^{22}$, $R^{23a}$ and $R^{23b}$ are independently hydrogen, halogen, hydroxy, cyano, nitro, amino, formyl, $C_1$-$C_{20}$ alkoxy, $C_1$-$C_{20}$ alkylthio, $C_1$-$C_{20}$ alkyl, $C_2$-$C_{20}$ alkenyl, $C_2$-$C_{20}$ alkynyl,

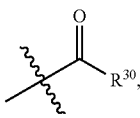

—$CF_3$, —$SF_5$, $C_3$-$C_{12}$ cycloalkyl, or "$C_1$-$C_9$ heterocycloalkyl which is optionally substituted with $C_1$-$C_{20}$ alkyl"; wherein the "$C_1$-$C_9$ heterocycloalkyl" connects to another group via a carbon atom or a heteroatom thereof;

wherein $R^{24a}$ is independently hydrogen, halogen, hydroxy, cyano, nitro, amino, formyl, $C_1$-$C_{20}$ alkoxy, $C_1$-$C_{20}$ alkylthio, $C_1$-$C_{20}$ alkyl(e.g. methyl), $C_2$-$C_{20}$ alkenyl, $C_2$-$C_{20}$ alkynyl, —$CF_3$, —$SF_5$,

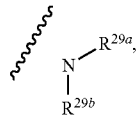

—$SeR^{31}$, $C_3$-$C_{12}$ cycloalkyl or "$C_1$-$C_9$ heterocycloalkyl which is optionally substituted with $C_1$-$C_{20}$ alkyl"; wherein the "$C_1$-$C_9$ heterocycloalkyl" connects to another group via a carbon atom or a heteroatom thereof;

wherein $R^{24b}$ is independently hydrogen, halogen, hydroxy, cyano, nitro, amino, formyl, $C_1$-$C_{20}$ alkoxy, $C_1$-$C_{20}$ alkyl(e.g. methyl), $C_2$-$C_{20}$ alkenyl, $C_2$-$C_{20}$ alkynyl, —$CF_3$, —$SF_5$,

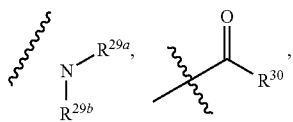

—$OR^{32}$, $C_3$-$C_{12}$ cycloalkyl or "$C_1$-$C_9$ heterocycloalkyl which is optionally substituted with $C_1$-$C_{20}$ alkyl"

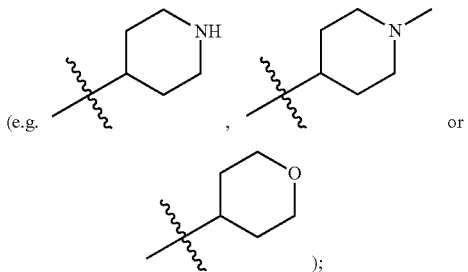

(e.g. , or );

wherein the "$C_1$-$C_9$ heterocycloalkyl" connects to another group via a carbon atom or a heteroatom thereof;

or, $R^{24a}$ and $R^{24b}$ together with the carbon atom, N atom attached form substituted or unsubstituted $C_1$-$C_9$ heterocycloalkyl; wherein the "substituted" in the "substituted or unsubstituted $C_1$-$C_9$ heterocycloalkyl" refers to be independently substituted with the substituent selected from the group consisting of halogen, hydroxy, cyano, nitro, amino, formyl, carboxyl, thio, $C_1$-$C_{20}$ silyl, $C_1$-$C_{20}$ alkoxy, $C_1$-$C_{20}$ alkyl(e.g. methyl), $C_2$-$C_{20}$ alkenyl(e.g. vinyl), $C_2$-$C_{20}$ alkynyl(e.g. ethynyl), —$CF_3$, —$SF_5$,

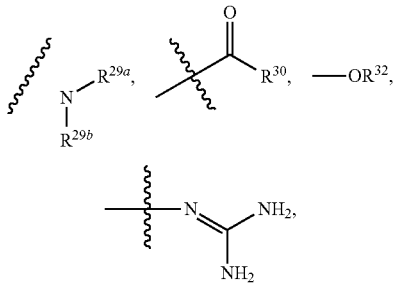

$C_3$-$C_{12}$ cycloalkyl, $C_1$-$C_9$ heterocycloalkyl, $C_3$-$C_{12}$ aryl, $C_1$-$C_9$ heteroaryl,

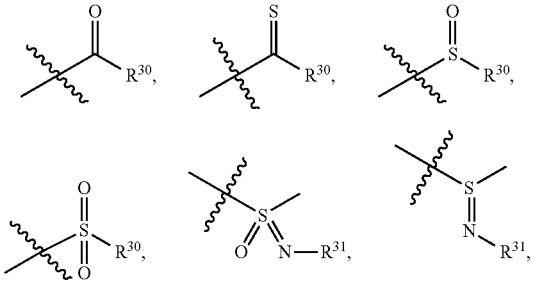

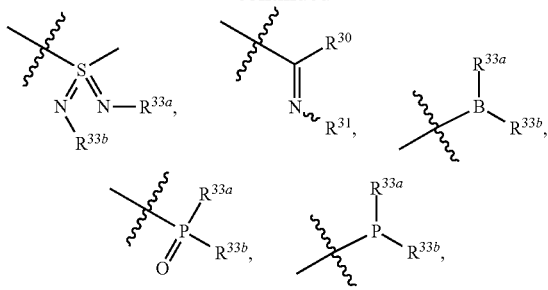

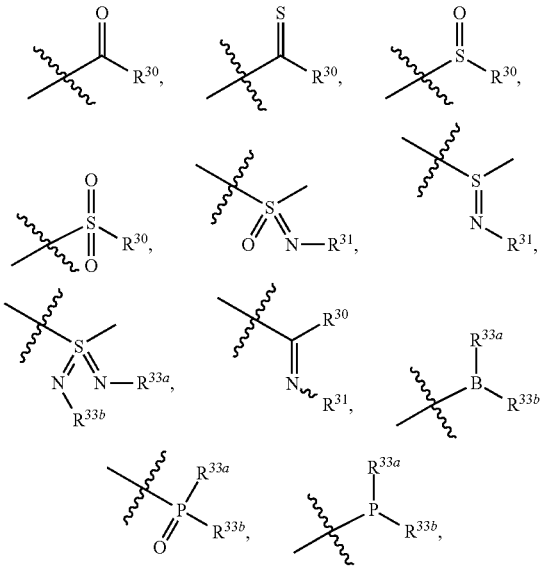

—SeR$^{31}$, "C$_1$-C$_{20}$ alkyl mono-substituted, di-substituted or unsubstituted amino" and —SF$_5$, when there are more than one substituents, the substituents are the same or different; wherein the "substituted or unsubstituted C$_1$-C$_9$ heterocycloalkyl" connects to another group via a carbon atom or a heteroatom thereof;

wherein the R$^{25a}$ and R$^{25b}$ are independently hydrogen, halogen, hydroxy, cyano, C$_1$-C$_{20}$ alkoxy(e.g. ethoxy), C$_1$-C$_{20}$ alkyl(e.g. methyl), C$_2$-C$_{20}$ alkenyl, C$_2$-C$_{20}$ alkynyl, —CF$_3$, —SF$_5$, C$_3$-C$_{12}$ cycloalkyl or "C$_1$-C$_9$ heterocycloalkyl which is optionally substituted with C$_1$-C$_{20}$ alkyl"

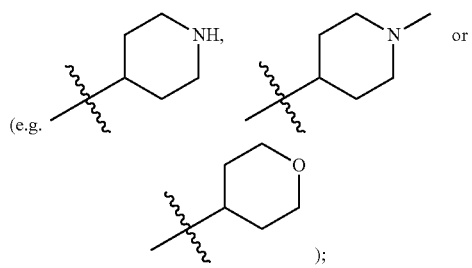

wherein the "C$_1$-C$_9$ heterocycloalkyl" connects to another group via a carbon atom or a heteroatom thereof;

or, R$^{25a}$ and R$^{25b}$ together with the heteroatom attached form substituted or unsubstituted C$_1$-C$_9$ heterocycloalkyl; wherein the "substituted" in the "substituted or unsubstituted C$_1$-C$_9$ heterocycloalkyl" refers to be independently substituted with the substituent selected from the group consisting of halogen, hydroxy, cyano, nitro, amino, formyl, carboxyl, thio, C$_1$-C$_{20}$ silyl, C$_1$-C$_{20}$ alkoxy, C$_1$-C$_{20}$ alkyl(e.g. methyl), C$_2$-C$_{20}$ alkenyl (e.g. vinyl), C$_2$-C$_{20}$ alkynyl(e.g. ethynyl), —CF$_3$, —SF$_5$,

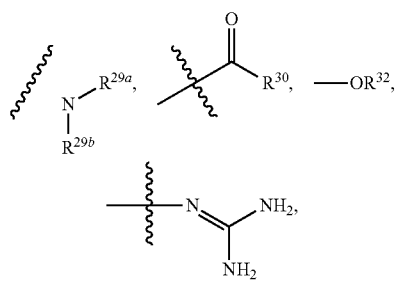

C$_3$-C$_{12}$ cycloalkyl, C$_1$-C$_9$ heterocycloalkyl, C$_3$-C$_{12}$ aryl, C$_1$-C$_9$ heteroaryl, —SeR$^{31}$, "C$_1$-C$_{20}$ alkyl mono-substituted, di-substituted or unsubstituted amino" and —SF$_5$, when there are more than one substituents, the substituents are the same or different; wherein the "C$_1$-C$_9$ heterocycloalkyl" connects to another group via a carbon atom or a heteroatom thereof;

wherein R$^{26}$ is independently C$_1$-C$_{20}$ alkyl, C$_2$-C$_{20}$ alkenyl, C$_2$-C$_{20}$ alkynyl, C$_3$-C$_{12}$ cycloalkyl, C$_1$-C$_9$ heterocycloalkyl, C$_3$-C$_{12}$ aryl or C$_1$-C$_9$ heteroaryl;

wherein R$^{27a}$ and R$^{27b}$ are independently hydrogen, halogen, hydroxy, cyano, formyl, C$_1$-C$_{20}$ alkoxy, C$_2$-C$_{20}$ alkenyl, C$_2$-C$_{20}$ alkynyl, —CF$_3$, —SF$_5$, C$_3$-C$_{12}$ cycloalkyl, substituted or unsubstituted C$_1$-C$_9$ heterocycloalkyl

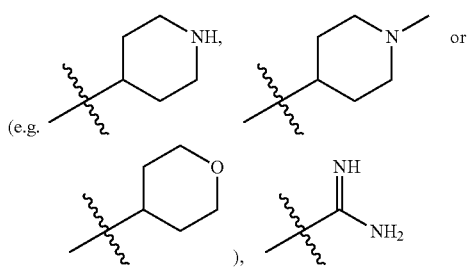

or substituted or unsubstituted C$_1$-C$_{20}$ alkyl(e.g. C$_1$-C$_6$ alkyl, preferably methyl, ethyl or propyl); wherein the "substituted" in the "substituted or unsubstituted C$_1$-C$_{20}$ alkyl" and "substituted or unsubstituted C$_1$-C$_9$ heterocycloalkyl" refers to be independently substituted with the substituent selected from the group consisting of halogen, C$_1$-C$_{20}$ alkoxy, C$_1$-C$_{20}$ alkylthio and C$_1$-C$_{20}$ silyl, when there are more than one substituents, the substituents are the same or different; wherein the "C$_1$-C$_9$ heterocycloalkyl" connects to another group via a carbon atom or a heteroatom thereof;

wherein R$^{28}$ is independently C$_1$-C$_{20}$ alkyl, C$_2$-C$_{20}$ alkenyl, C$_2$-C$_{20}$ alkynyl, or substituted or unsubstituted C$_1$-C$_{20}$ silyl; wherein the substituent in the "substituted or unsubstituted C$_1$-C$_{20}$ silyl" is C$_2$-C$_{20}$ alkenyl or C$_2$-C$_{20}$ alkynyl;

wherein R$^{29a}$ and R$^{29b}$ are independently hydrogen, halogen, hydroxy, cyano, formyl, C$_1$-C$_{20}$ alkoxy, C$_2$-C$_{20}$ alkenyl, C$_2$-C$_{20}$ alkynyl, —CF$_3$, —SF$_5$, C$_3$-C$_{12}$ cycloalkyl, substituted or unsubstituted C$_1$-C$_9$ heterocycloalkyl

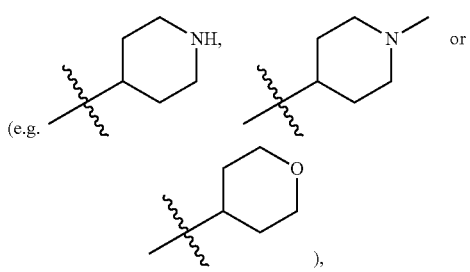

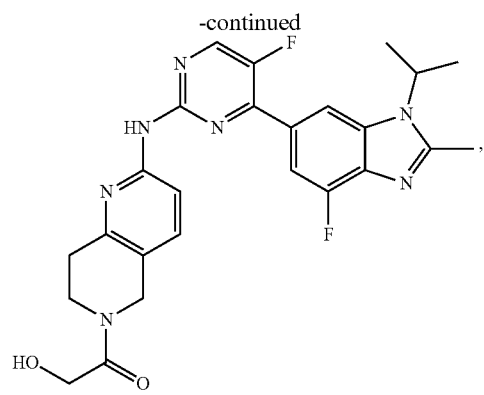

or substituted or unsubstituted $C_1$-$C_{20}$ alkyl; wherein the "substituted" in the "substituted or unsubstituted $C_1$-$C_{20}$ alkyl" and "substituted or unsubstituted $C_1$-$C_9$ heterocycloalkyl" refers to be independently substituted with the substituent selected from the group consisting of halogen, $C_1$-$C_{20}$ alkoxy, $C_1$-$C_{20}$ alkylthio and $C_1$-$C_{20}$ silyl, when there are more than one substituents, the substituents are the same or different; wherein the "$C_1$-$C_9$ heterocycloalkyl" connects to another group via a carbon atom thereof;

wherein $R^{30}$ is independently hydrogen, hydroxy, $C_1$-$C_{20}$ alkyl which is optionally substituted with halogen, or $C_1$-$C_{20}$ alkyl mono-substituted, di-substituted or unsubstituted amino;

wherein $R^{31}$ is independently hydrogen, cyano, nitro, hydroxy, $C_1$-$C_{20}$ alkyl, $C_2$-$C_{20}$ alkenyl, $C_2$-$C_{20}$ alkynyl, $C_3$-$C_{12}$ cycloalkyl, $C_1$-$C_9$ heterocycloalkyl, $C_6$-$C_{12}$ aryl, or $C_1$-$C_9$ heteroaryl;

wherein $R^{32}$ is independently $C_1$-$C_{20}$ alkyl, $C_2$-$C_{20}$ alkenyl, $C_2$-$C_{20}$ alkynyl, or substituted or unsubstituted $C_1$-$C_{20}$ silyl; wherein the substituent in the "substituted or unsubstituted $C_1$-$C_{20}$ silyl" is $C_2$-$C_{20}$ alkenyl or $C_2$-$C_{20}$ alkynyl;

wherein each of $R^{33a}$ and $R^{33b}$ is independently hydrogen, hydroxy, cyano, nitro, halogen, $C_1$-$C_{20}$ alkyl, $C_2$-$C_{20}$ alkenyl, $C_2$-$C_{20}$ alkynyl, $C_1$-$C_{20}$ alkoxy, $C_3$-$C_{12}$ cycloalkyl, $C_1$-$C_9$ heterocycloalkyl, $C_6$-$C_{12}$ aryl, or $C_1$-$C_9$ heteroaryl;

$R^{6a}$, $R^{6b}$, $R^{6c}$ and $R^{6d}$ are independently hydrogen, hydroxy, $C_1$-$C_{20}$ alkyl, $C_3$-$C_{12}$ cycloalkyl or $C_3$-$C_{12}$ heterocycloalkyl, but $R^{6a}$ and $R^{6b}$ are not hydroxy at the same time, $R^{6c}$ and $R^{6d}$ are not hydroxyl at the same time; or $R^{6a}$ and $R^{6b}$ together with the carbon atom attached form carbonyl; or $R^{6c}$ and $R^{6d}$ together with the carbon atom attached form carbonyl;

the number of the heteroatom in the "heterocycloalkyl", "heteroaryl" is 1 to 7 selected from the group consisting of oxygen, nitrogen, phosphorus, sulfur, selenium, boron and silicon;

and, the compound I is not selected from the group consisting of

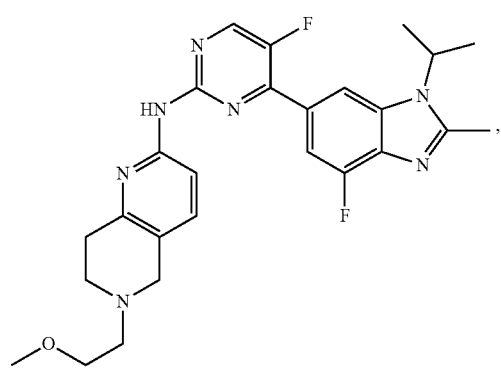

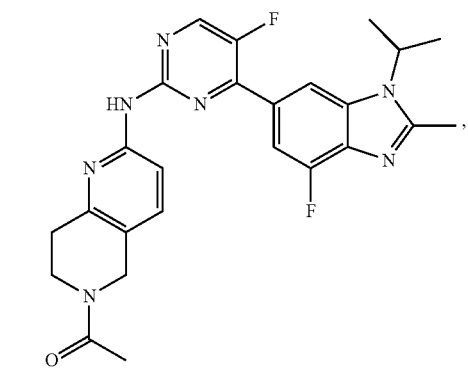

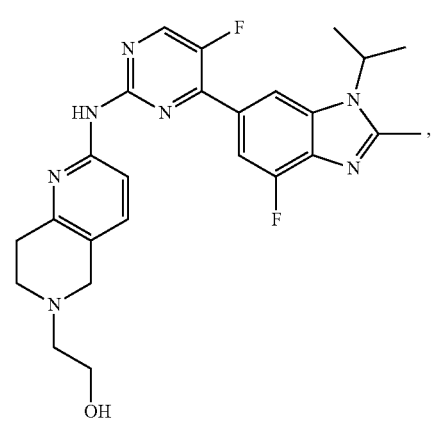

-continued

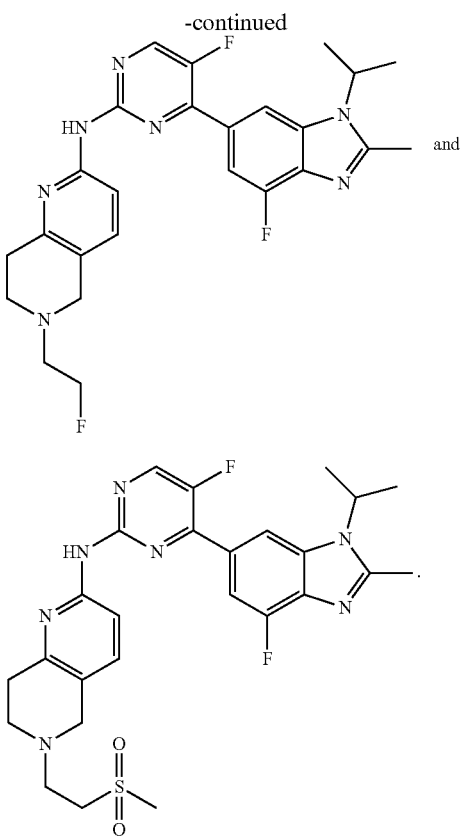

I-201

Preferably, the $C_2$-$C_{20}$ alkenyl contained in the term "substituted or unsubstituted $C_2$-$C_{20}$ alkenyl" and the term "$C_2$-$C_{20}$ alkenyl" is independently $C_2$-$C_{12}$ alkenyl; more preferably, the $C_2$-$C_{20}$ alkenyl contained in the term "substituted or unsubstituted $C_2$-$C_{20}$ alkenyl" is independently $C_2$-$C_6$ alkenyl.

Preferably, the $C_2$-$C_{20}$ alkynyl contained in the term "substituted or unsubstituted $C_2$-$C_{20}$ alkynyl" and the term "$C_2$-$C_{20}$ alkynyl" is independently $C_2$-$C_{12}$ alkynyl; more preferably, $C_2$-$C_{20}$ alkynyl contained in the term "substituted or unsubstituted $C_2$-$C_{20}$ alkynyl" is independently $C_2$-$C_6$ alkynyl.

Preferably, the $C_1$-$C_{20}$ alkyl contained in the term "substituted or unsubstituted $C_1$-$C_{20}$ alkyl", "$C_1$-$C_{20}$ alkyl" and "$C_1$-$C_{20}$ alkyl mono-substituted, di-substituted or unsubstituted amino" is independently $C_1$-$C_{12}$ alkyl; more preferably, the $C_2$-$C_{20}$ alkyl contained in the term "substituted or unsubstituted $C_1$-$C_{20}$ alkyl" is independently $C_1$-$C_6$ alkyl; most preferably, the $C_2$-$C_{20}$ alkyl contained in the term "substituted or unsubstituted $C_1$-$C_{20}$ alkyl" is independently $C_1$-$C_3$ alkyl.

Preferably, the $C_1$-$C_{20}$ alkylthio contained in the term "substituted or unsubstituted $C_1$-$C_{20}$ alkylthio" and "$C_1$-$C_{20}$ alkylthio" is independently $C_1$-$C_{12}$ alkylthio; more preferably, the $C_2$-$C_{20}$ alkylthio contained in the term "substituted or unsubstituted $C_1$-$C_{20}$ alkylthio" is independently $C_1$-$C_6$ alkylthio; most preferably, the $C_2$-$C_{20}$ alkylthio contained in the term "substituted or unsubstituted $C_1$-$C_{20}$ alkylthio" is independently $C_1$-$C_3$ alkylthio.

Preferably, the $C_1$-$C_{20}$ alkoxy contained in the term "substituted or unsubstituted $C_1$-$C_{20}$ alkoxy" and the term "$C_1$-$C_{20}$ alkoxy" is independently $C_1$-$C_{12}$ alkoxy; more preferably, the $C_1$-$C_{20}$ alkoxy contained in the term "substituted or unsubstituted $C_1$-$C_{20}$ alkoxy" is independently $C_1$-$C_6$ alkoxy; most preferably, the $C_1$-$C_{20}$ alkoxy contained in the term "substituted or unsubstituted $C_1$-$C_{20}$ alkoxy" is independently $C_1$-$C_3$ alkoxy.

Preferably, the "$C_1$-$C_{20}$ silyl" is independently "$C_1$-$C_{12}$ silyl"; more preferably, the "$C_1$-$C_{20}$ silyl" is independently "$C_1$-$C_6$ silyl"; most preferably, the "$C_1$-$C_{20}$ silyl" is independently "$C_1$-$C_3$ silyl".

Preferably, the $C_3$-$C_{12}$ cycloalkyl contained in the term "substituted or unsubstituted $C_3$-$C_{12}$ cycloalkyl" is independently $C_3$-$C_8$ cycloalkyl; more preferably, the $C_3$-$C_{12}$ cycloalkyl contained in the term "substituted or unsubstituted $C_3$-$C_{12}$ cycloalkyl" is independently $C_3$-$C_6$ cycloalkyl.

Preferably, the $C_1$-$C_9$ heterocycloalkyl contained in the term "substituted or unsubstituted $C_1$-$C_9$ heterocycloalkyl" is independently $C_3$-$C_8$ heterocycloalkyl having 1 to 4 (e.g. 1 to 3) heteroatom selected from the group consisting of boron, silicon, oxygen, sulfur, selenium, nitrogen and phosphorus; more preferably, the $C_1$-$C_9$ heterocycloalkyl contained in the term "substituted or unsubstituted $C_1$-$C_9$ heterocycloalkyl" is independently $C_3$-$C_8$ heterocycloalkyl having 1 to 4 (e.g. 1 to 3) heteroatom selected from the group consisting of boron, silicon, oxygen, sulfur, selenium, nitrogen and phosphorus.

Preferably, the $C_1$-$C_9$ heteroaryl contained in the term "substituted or unsubstituted $C_1$-$C_9$ heteroaryl" is independently $C_1$-$C_6$ heteroaryl; more preferably, the $C_1$-$C_9$ heteroaryl contained in the term "substituted or unsubstituted $C_1$-$C_9$ heteroaryl" is independently $C_1$-$C_6$ heteroaryl having 1 to 4 heteroatom selected from the group consisting of boron, silicon, oxygen, sulfur, selenium, nitrogen and phosphorus.

Preferably, the $C_3$-$C_{12}$ aryl contained in the term "substituted or unsubstituted $C_3$-$C_{12}$ aryl" is independently $C_6$-$C_{10}$ aryl.

In some embodiments, the definitions are preferably as follows:

In the compound I, preferably, p is 1, q is 1, m is 0 or 1, n is 0.

In the compound I, preferably, X is N.

In the compound I, preferably, $R^1$ is halogen or trifluoromethyl.

In the compound I, preferably, $R^2$ is $C_1$-$C_6$ alkyl.

In the compound I, preferably, $R^3$ is substituted or unsubstituted $C_1$-$C_6$ alkyl, or substituted or unsubstituted $C_3$-$C_8$ cycloalkyl.

In the compound I, preferably, $R^4$ is halogen.

In the compound I, preferably, $R^5$ is hydrogen, substituted or unsubstituted $C_1$-$C_6$ alkyl,

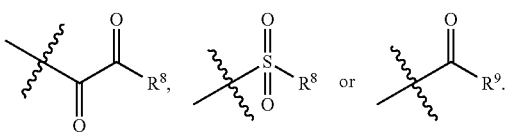

In the compound I, preferably, $R^8$ is independently substituted $C_1$-$C_6$ alkyl, or $C_1$-$C_6$ alkoxy.

In the compound I, preferably, $R^9$ is vinyl, substituted or unsubstituted $C_1$-$C_6$ alkyl, substituted or unsubstituted $C_3$-$C_8$ cycloalkyl, substituted or unsubstituted heterocycloalkyl having 3 to 8 carbon atoms and 1 to 4 heteroatom selected from the group consisting of oxygen, sulfur and nitrogen, substituted or unsubstituted $C_1$-$C_6$ alkoxy or

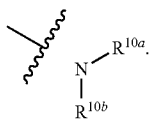

In the compound I, preferably, $R^{10a}$ and $R^{10b}$ are independently hydrogen, or substituted or unsubstituted $C_1$-$C_6$ alkyl.

In the compound I, preferably, the "substituted" in the "substituted or unsubstituted $C_1$-$C_{20}$ alkyl", "substituted or unsubstituted $C_3$-$C_{12}$ cycloalkyl", "substituted or unsubstituted $C_1$-$C_9$ heterocycloalkyl" and "substituted or unsubstituted $C_1$-$C_{20}$ alkoxy" in the definitions of $R^5$, $R^8$, $R^9$, $R^{10a}$ and $R^{10b}$ refers to be independently substituted with the substituent selected from the group consisting of

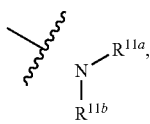

hydroxy, halogen, $C_1$-$C_3$ alkoxy, "substituted or unsubstituted $C_1$-$C_9$ saturated or unsaturated heterocycloalkyl" and

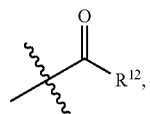

when there are more than one substituents, the substituents are the same or different.

In the compound I, preferably, $R^{11}a$ and $R^{11b}$ are independently hydrogen, or $C_1$-$C_6$ alkyl.

In the compound I, preferably, $R^{12}$ is hydroxy, $C_1$-$C_6$ alkoxy or

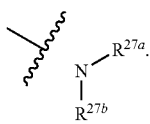

In the compound I, preferably, $R^{27a}$ and $R^{27b}$ are independently $C_1$-$C_6$ alkyl.

In the compound I, preferably, $R^{6a}$, $R^{6b}$, $R^{6c}$ and $R^{6d}$ are independently hydrogen; or $R^{6c}$ and $R^{6d}$ together with the carbon atom attached form carbonyl.

In some embodiments, the definitions are preferably as follows:

p is preferably 1.
q is preferably 1.
n is preferably 0.
m is preferably 1.
X is preferably N.
Y is preferably CH.
N atom in the cycle

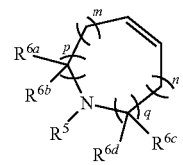

is preferably oxidized or non-oxidized;
$R^{6a}$, $R^{6b}$, $R^{6c}$ and $R^{6d}$ are preferably hydrogen.
$R^1$ is preferably halogen (e.g. fluorine).
$R^2$ is preferably $C_1$-$C_6$ alkyl.
$R^3$ is preferably substituted or unsubstituted $C_1$-$C_{20}$ alkyl (e.g. isopropyl or tert-butyl), or substituted or unsubstituted $C_3$-$C_{12}$ cycloalkyl(e.g. 1-methylcyclopropyl or cyclopropyl).
$R^4$ is preferably halogen (e.g. fluorine).
$R^5$ is preferably substituted $C_1$-$C_{20}$ alkyl (e.g. substituted ethyl; e.g. substitute disopropyl).

The "substituted" in the "substituted $C_1$-$C_{20}$ alkyl" in the definition of $R^5$ refers to preferably be substituted with the substituent selected from the group consisting of substituted or unsubstituted $C_1$-$C_9$ saturated or unsaturated heterocycloalkyl,

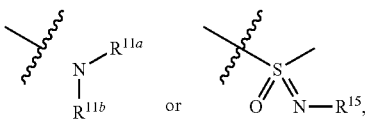

when there are more than one substituents, the substituents are the same or different; N atom in

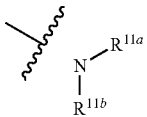

is oxidized or non-oxidized.

Preferably, $R^{11a}$ and $R^{11b}$ are independently hydrogen, substituted or unsubstituted $C_1$-$C_{20}$ alkyl(e.g. substituted or unsubstituted $C_1$-$C_6$ alkyl, preferably substituted or unsubstituted $C_1$, $C_2$ or $C_3$ alkyl; e.g. —$CF_3$; e.g. hydroxyethyl, 2-dimethylaminoethyl), or

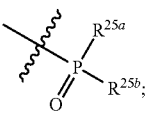

or in

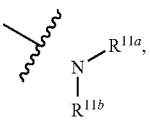

$R^{11a}$ and $R^{11b}$ together with the N atom attached form

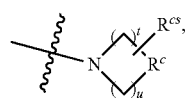

wherein t and u are independently 1, 2 or 3, $R^c$ is $C(R^{cs})_2$, $NR^{cs}$, O, S, $Si(R^{cs})_2$ or Se, each $R^{cs}$ is independently H, $C_1$-$C_6$ alkyl (e.g. methyl, ethyl, propyl or isopropyl), or $B(OH)_2$; or in

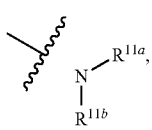

$R^{11b}$ and $R^{11b}$ together with the N atom attached form

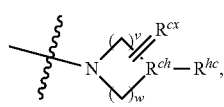

wherein v and w are independently 1, 2 or 3, $R^{cb}$ is CH or $PH_2$, $R^{cx}$ is $CH_2$, O, S or =N—OH, $R^{cx}$ is preferably attached to $R^{ch}$ (e.g. 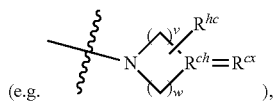 ), $R^{hc}$ is H or $C_1$-$C_6$ alkyl (e.g. methyl, ethyl or propyl), preferably when $R^{ch}$ is P, $R^{hc}$ is $C_1$-$C_6$ alkyl.

Preferably, $R^{15}$ is $C_1$-$C_6$ alkyl.

Preferably, the "substituted" in the term "substituted or unsubstituted $C_1$-$C_{20}$ alkyl" in the definitions of $R^{11a}$ and $R^{11b}$ refers to be independently substituted with the substituent selected from the group consisting of hydroxy, $C_1$-$C_6$ silyl,

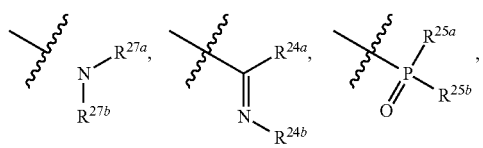

when there are more than one substituents, the substituents are the same or different.

$R^{24a}$ is preferably hydrogen.

$R^{24b}$ is preferably $C_1$-$C_6$ alkyl.

Preferably, $R^{25a}$ and $R^{25b}$ are independently hydroxyl or $C_1$-$C_6$ alkoxy (e.g. ethoxy).

Preferably, $R^{27a}$ and $R^{27b}$ are independently $C_1$-$C_6$ alkyl.

Preferably, the compound I in the present invention is selected from the group consisting of

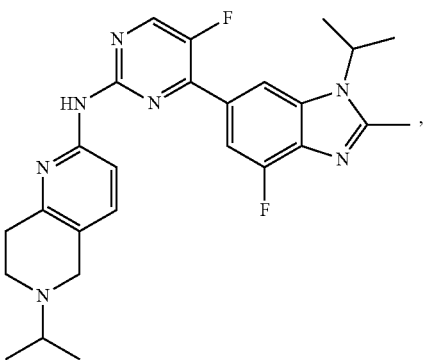
I-3

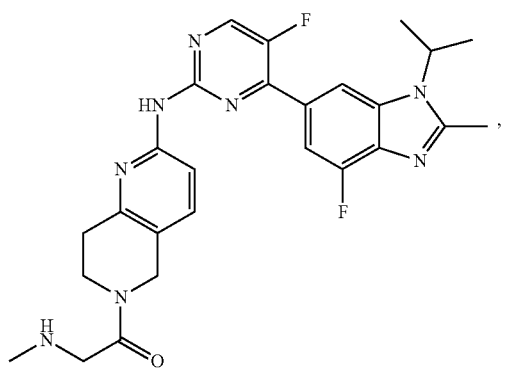
I-4

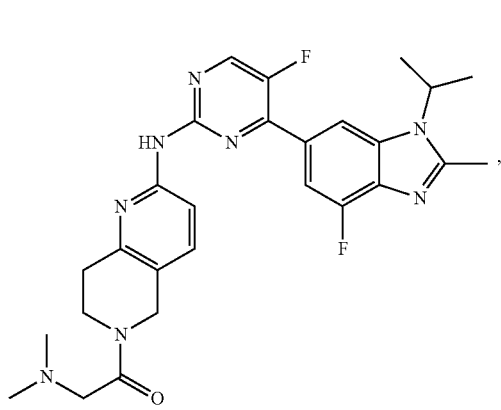
I-5

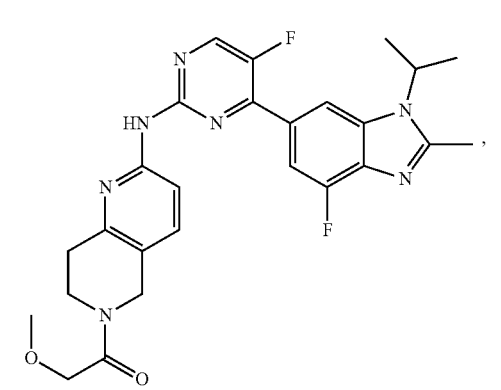
I-6

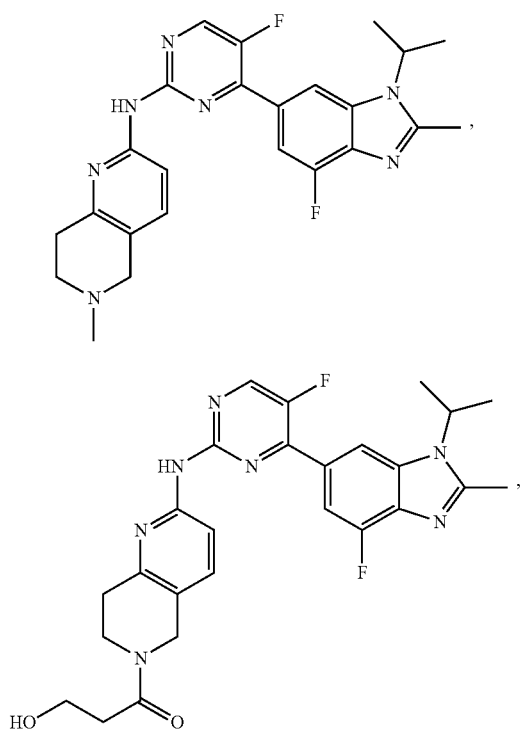
I-8
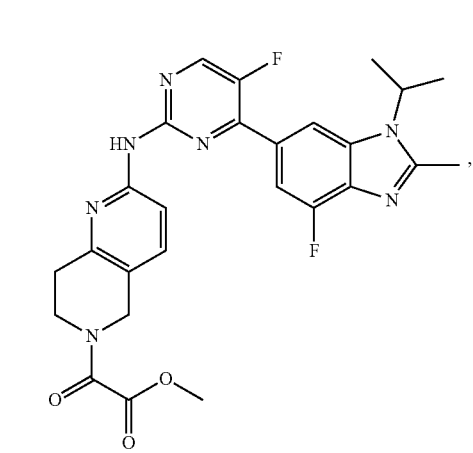
I-9
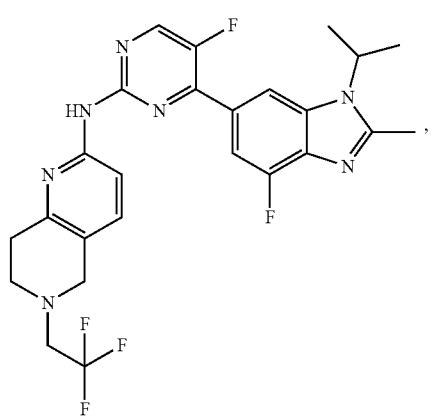
I-10
I-12
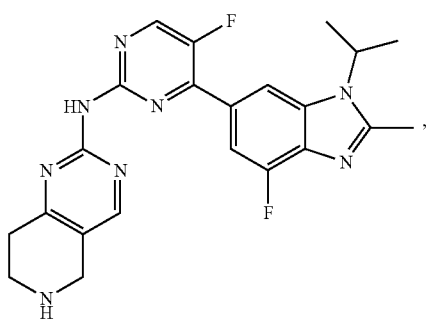
I-13
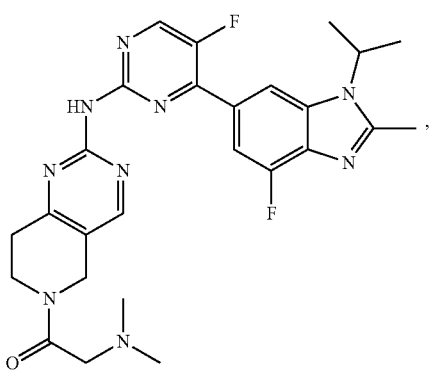
I-14
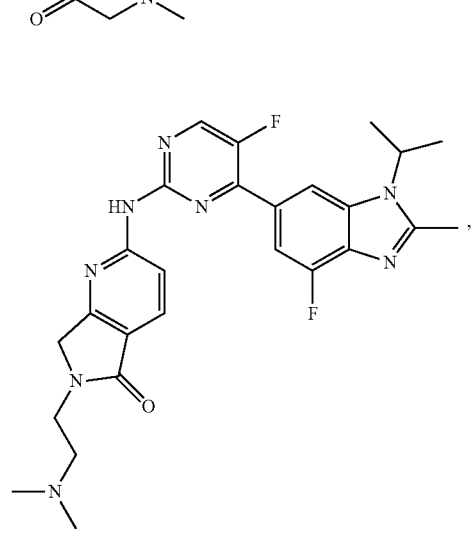
I-15
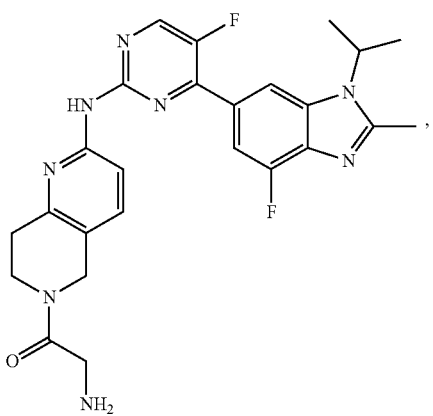
I-17

I-19
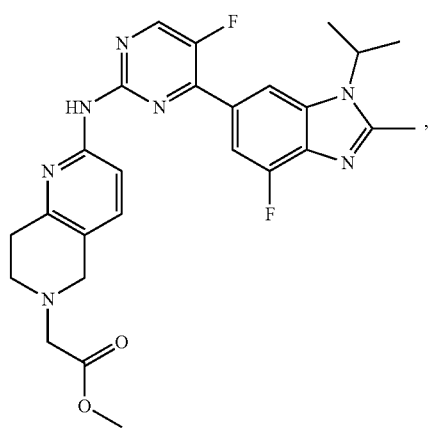
I-20
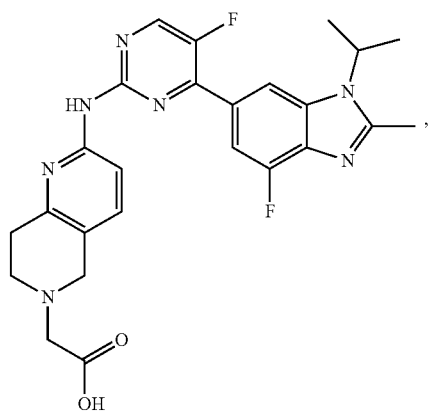
I-21
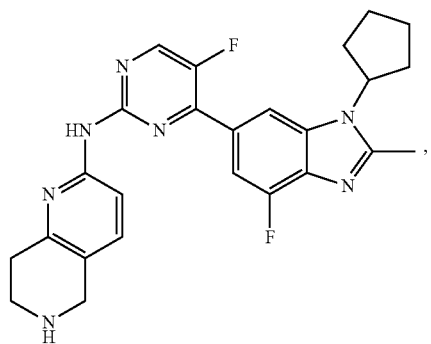
I-22
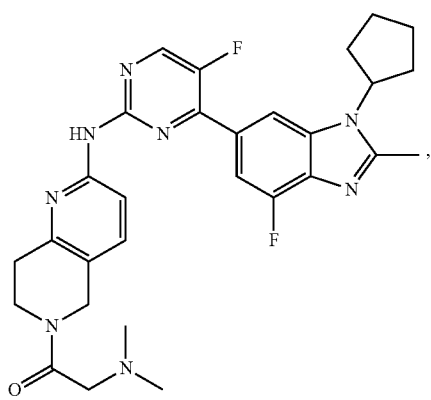
I-23
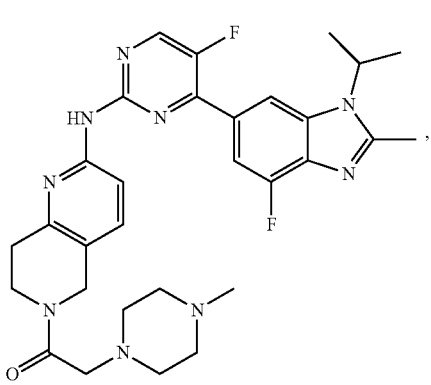
I-24
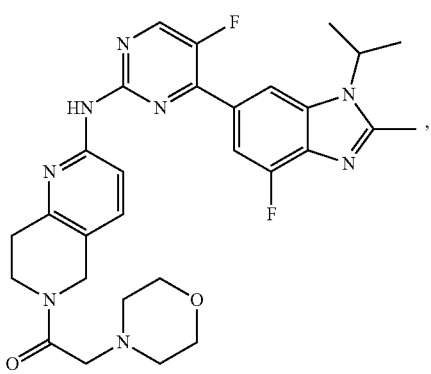
I-25
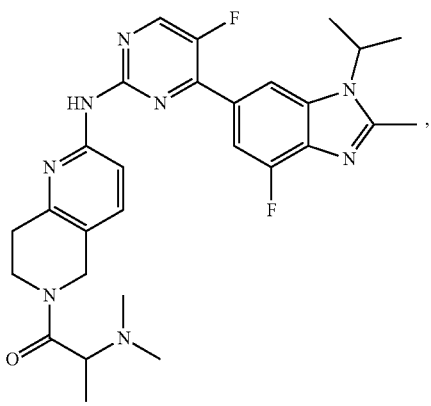
I-26
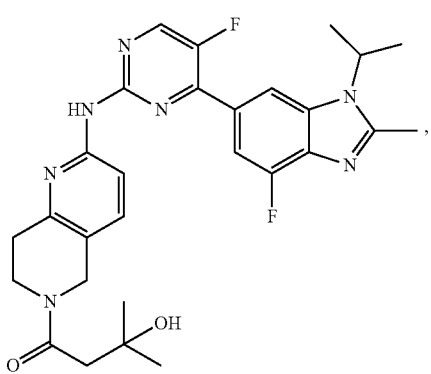

-continued
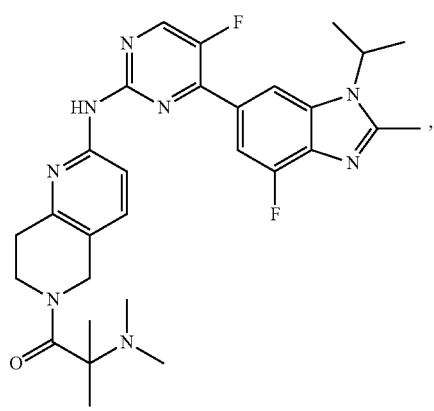
I-27
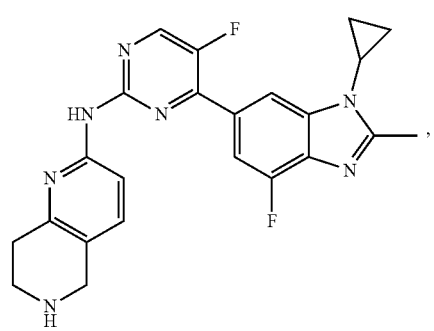
I-28
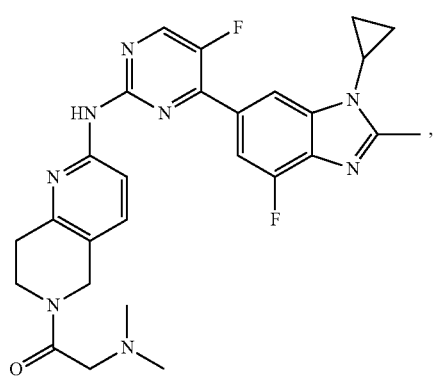
I-29
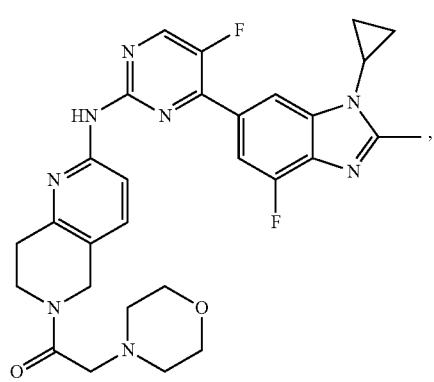
I-30
-continued
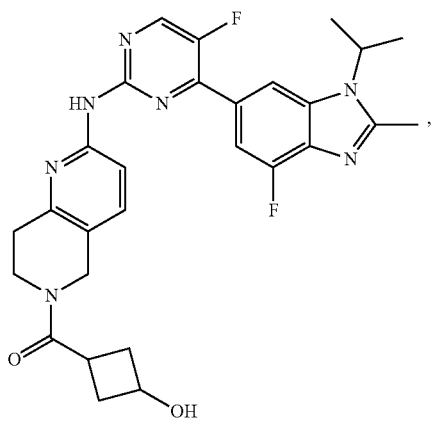
I-31
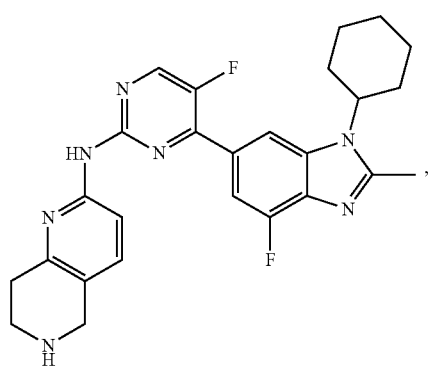
I-32
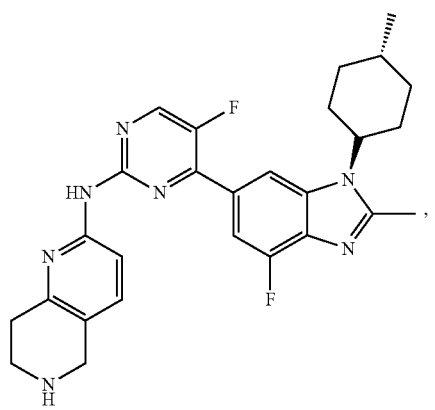
I-33
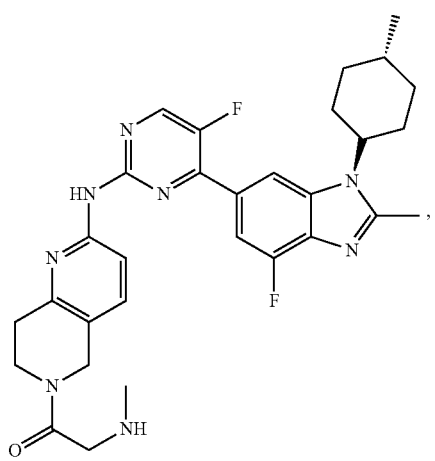
I-34

I-35 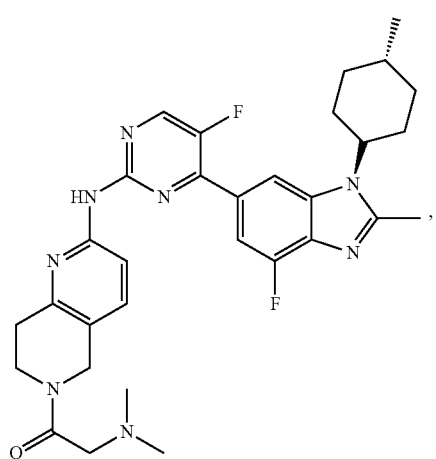
I-36 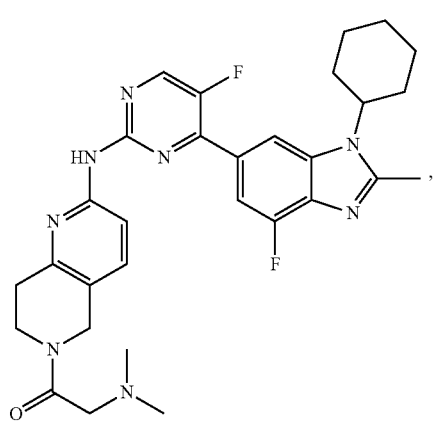
I-37 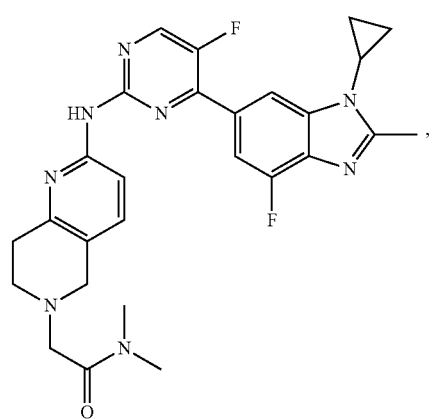
I-38 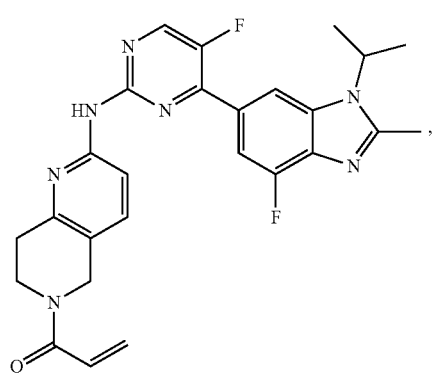
I-39 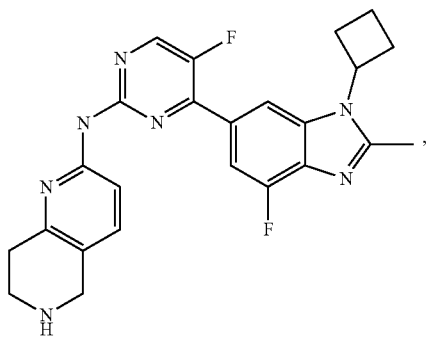
I-40 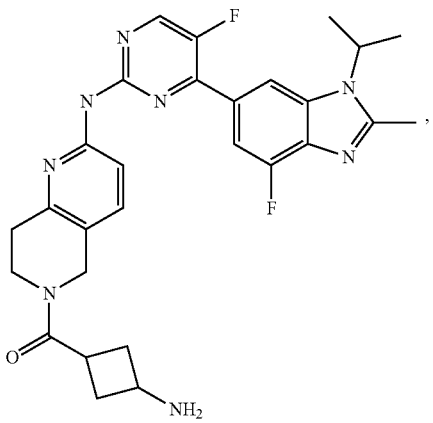
I-41 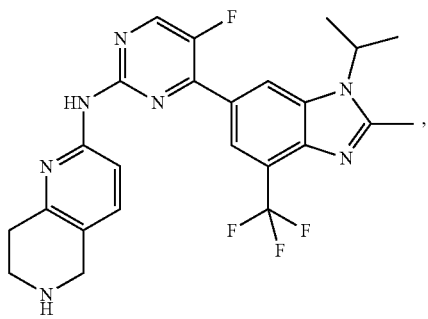
I-42 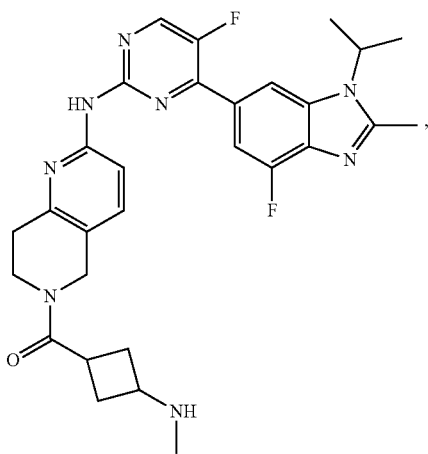

I-43
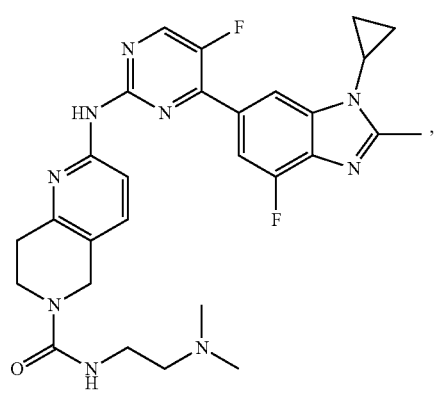
I-44
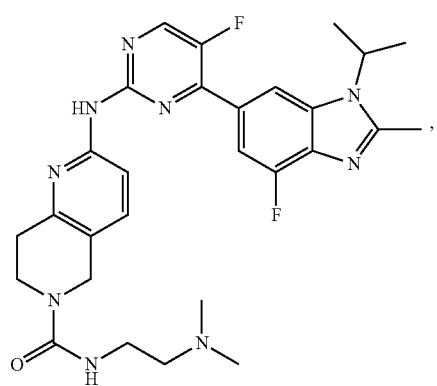
I-45
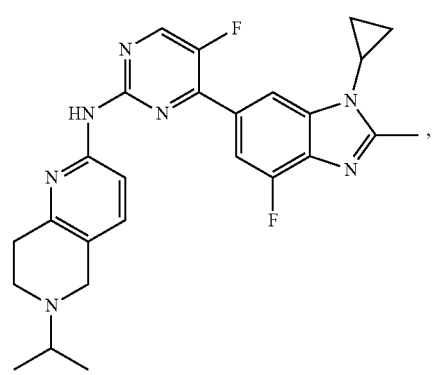
I-46
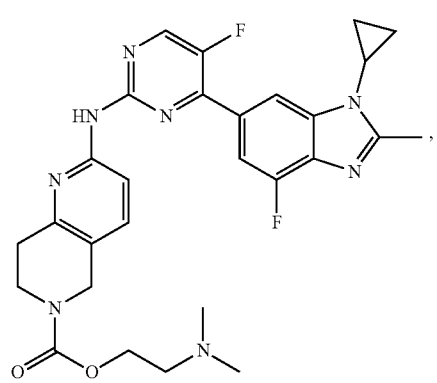
I-47
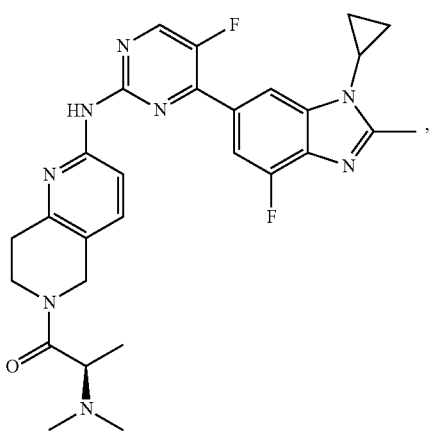
I-48
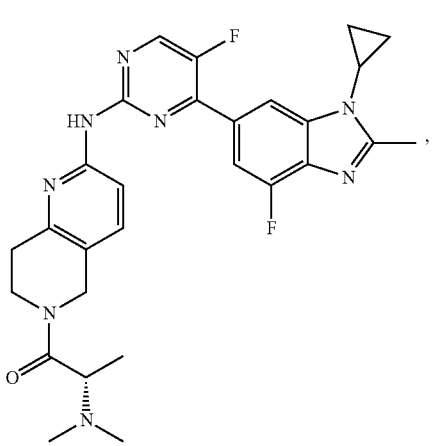
I-49
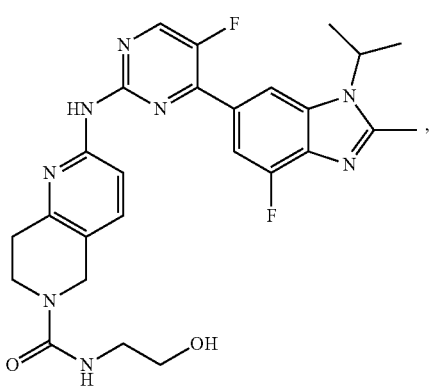
I-50
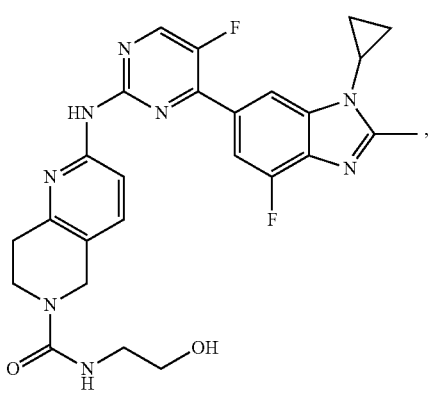

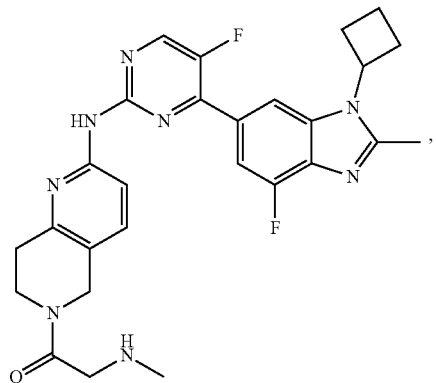
I-51
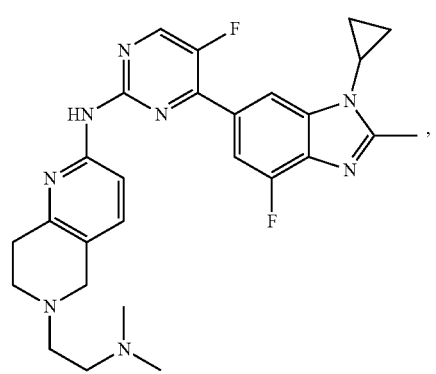
I-52
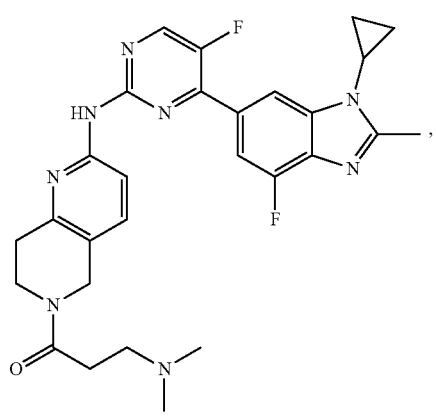
I-53
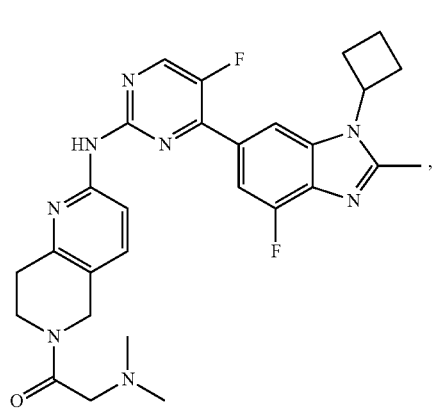
I-54
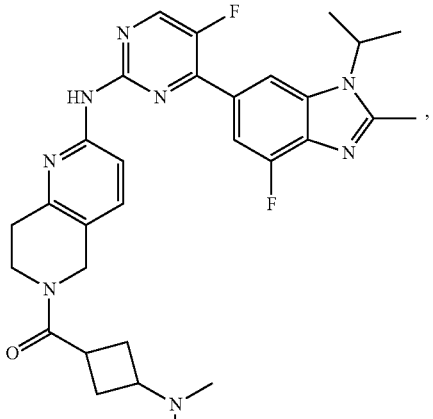
I-55
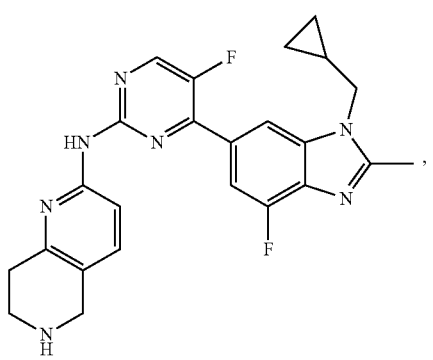
I-57
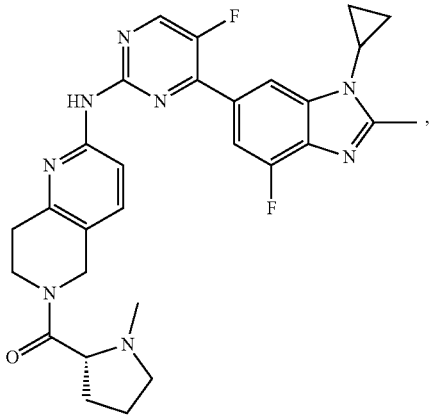
I-58
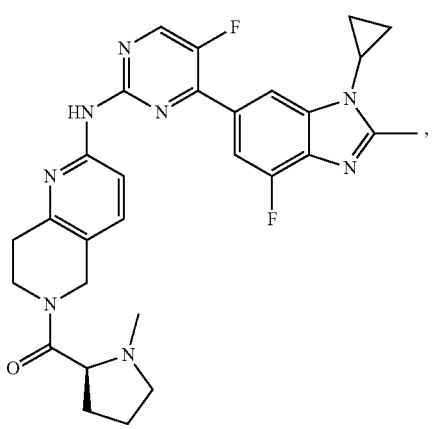
I-59

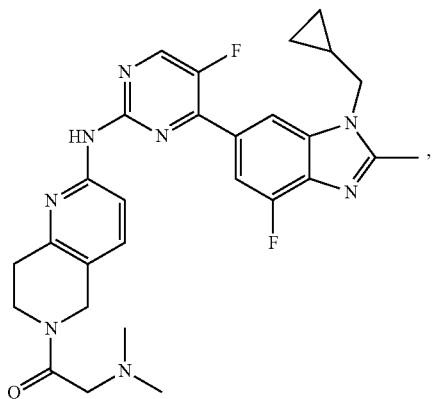
I-60
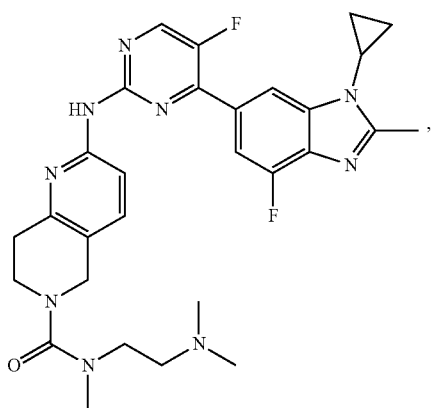
I-61
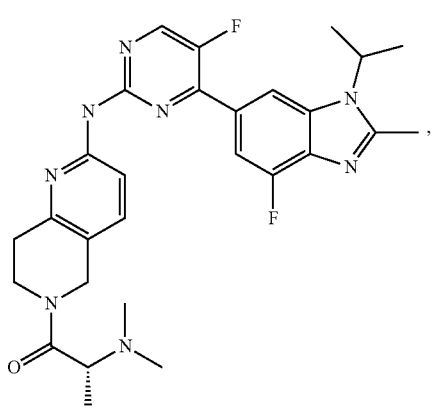
I-62
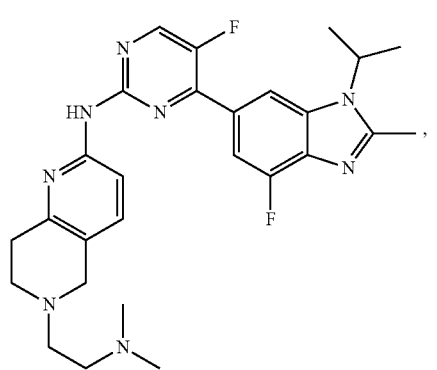
I-63
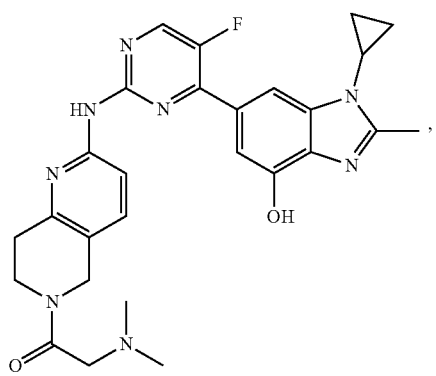
I-64
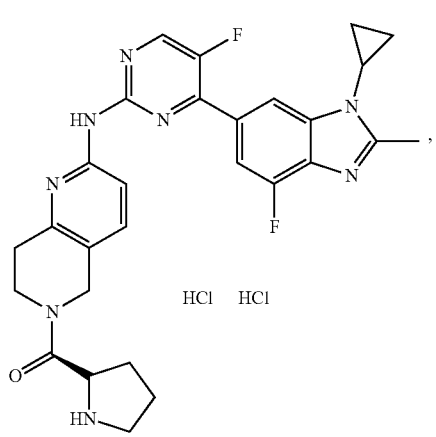
I-65
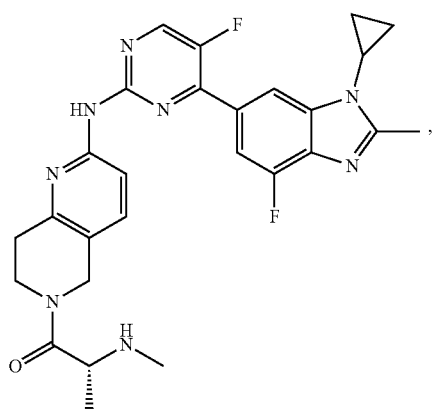
I-66
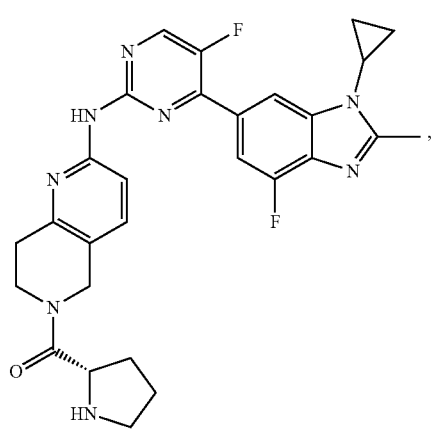
I-67

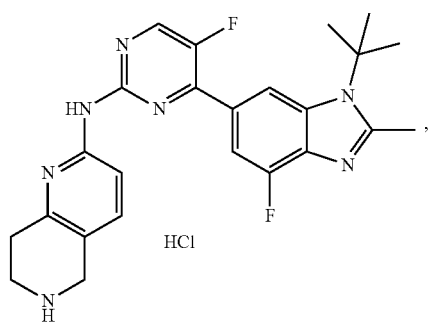
I-68
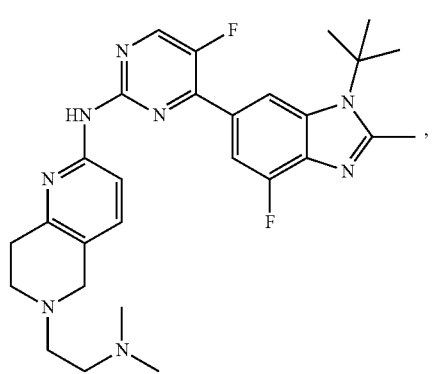
I-69
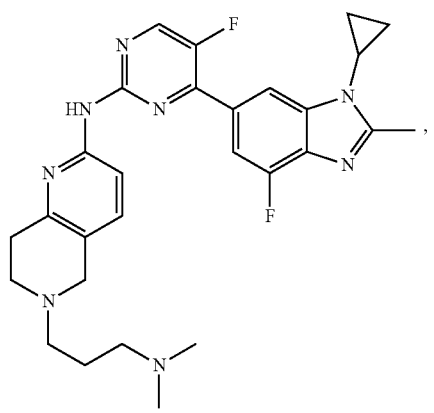
I-70
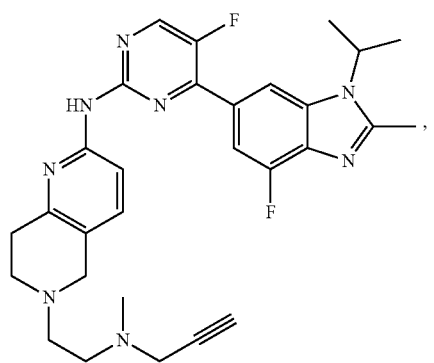
I-71
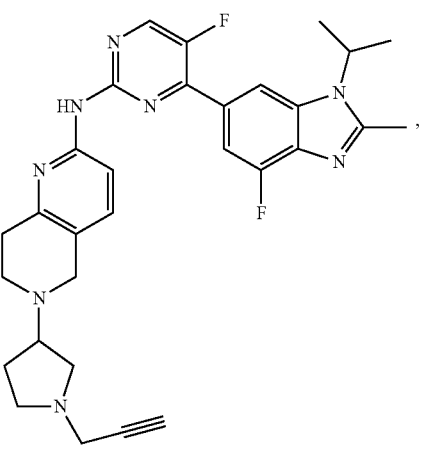
I-72
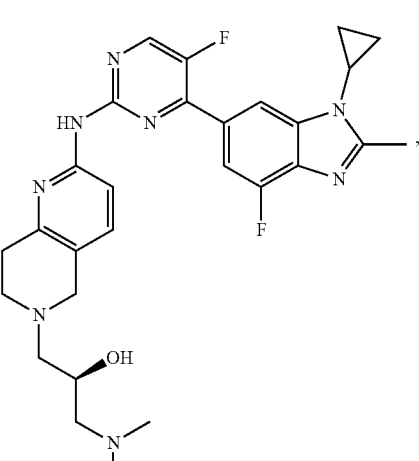
I-73
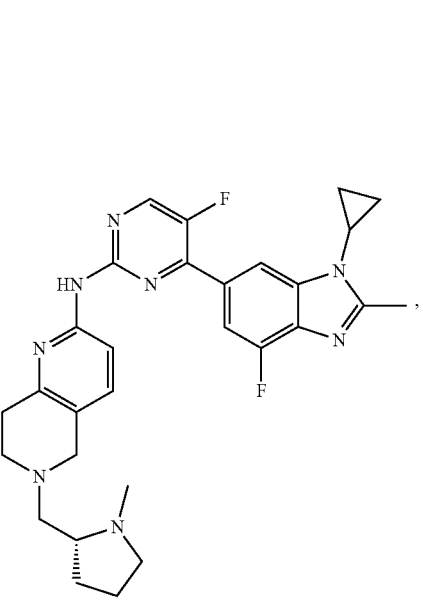
I-74

I-75
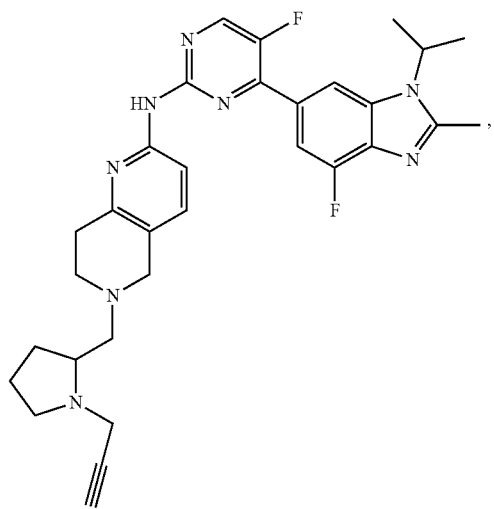
I-76
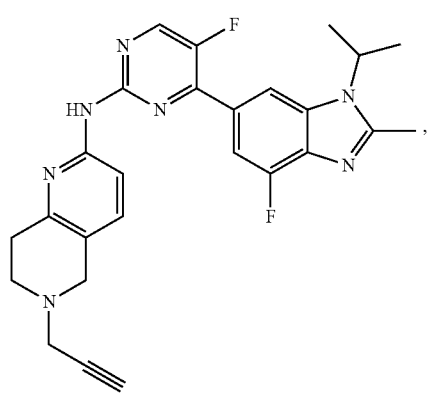
I-77
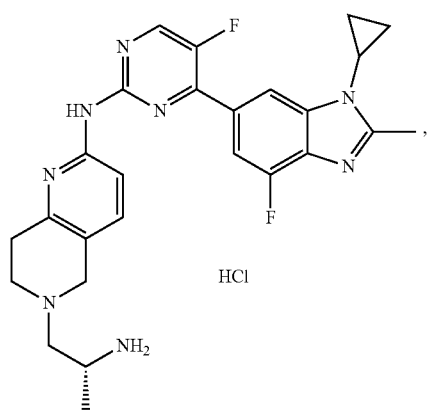
HCl
I-78
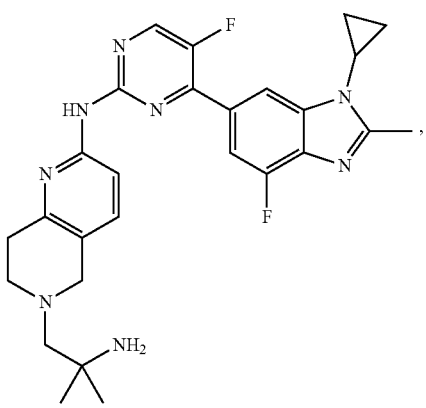
I-79
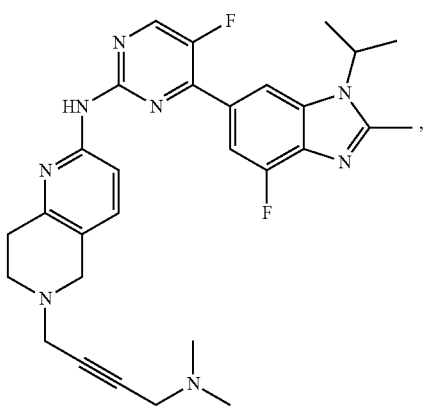
I-80
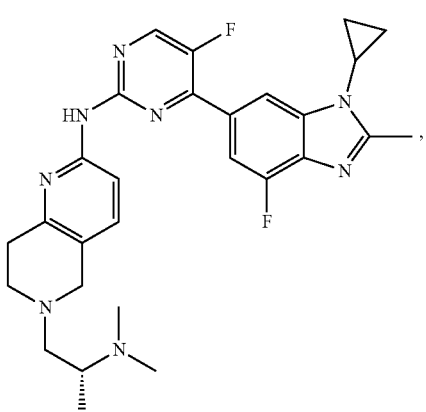
I-81
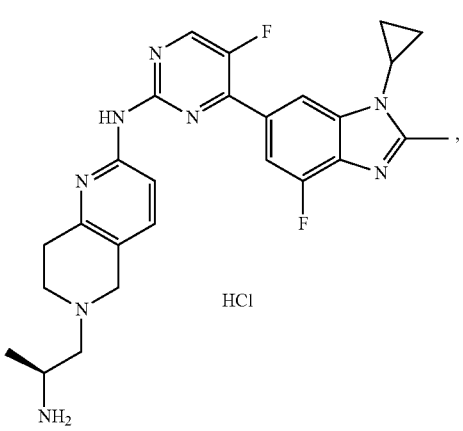
HCl I-82
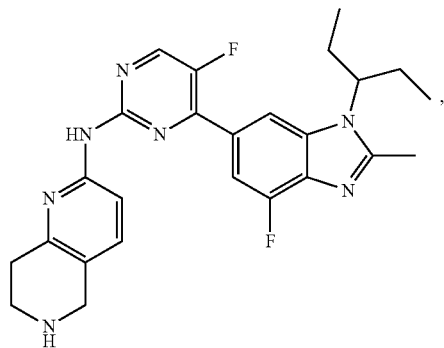
I-83
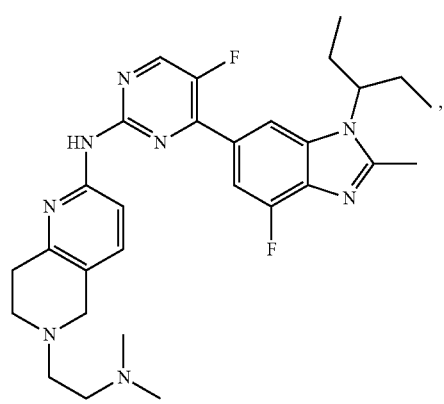
I-84
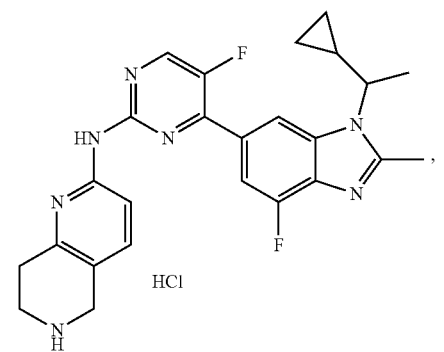
I-85
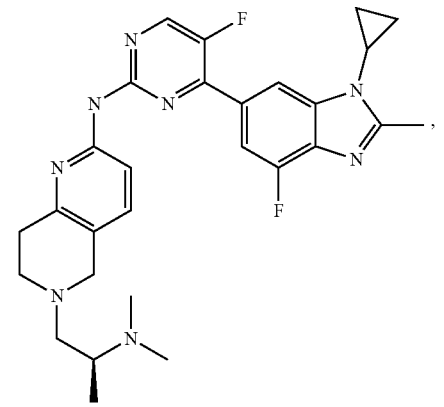
I-86
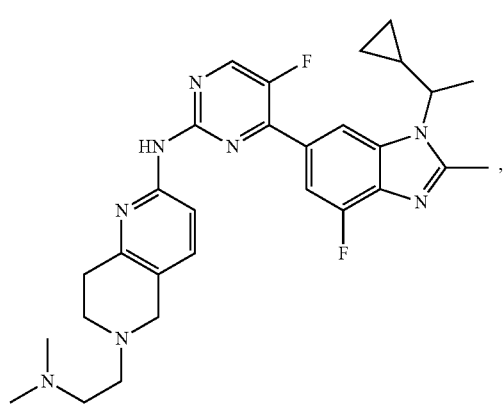
I-87
I-88
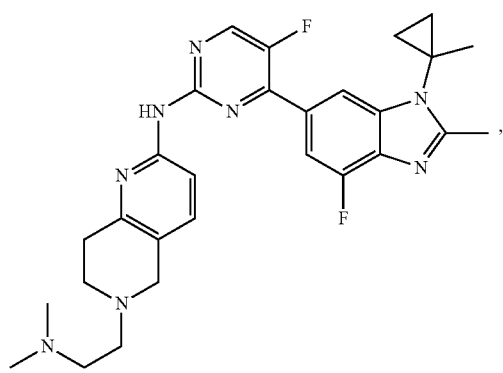
I-89
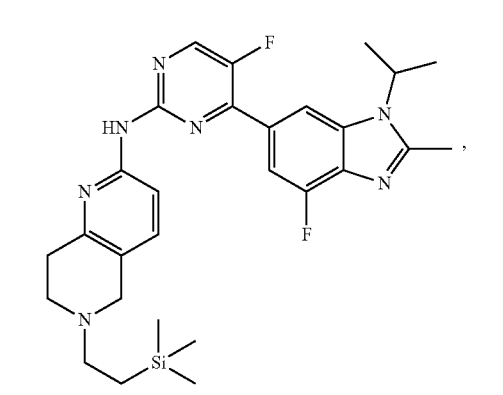

-continued
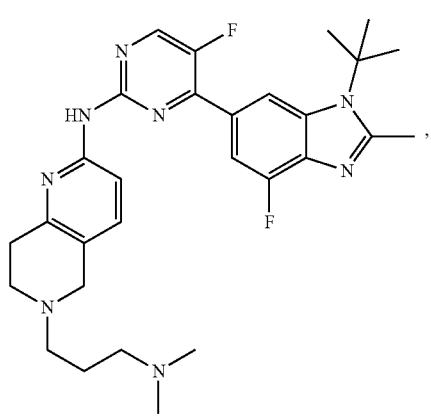
I-90
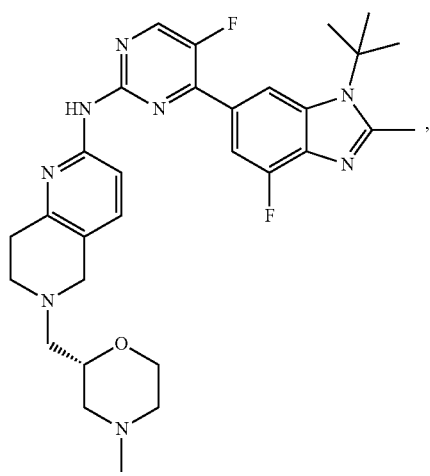
I-93
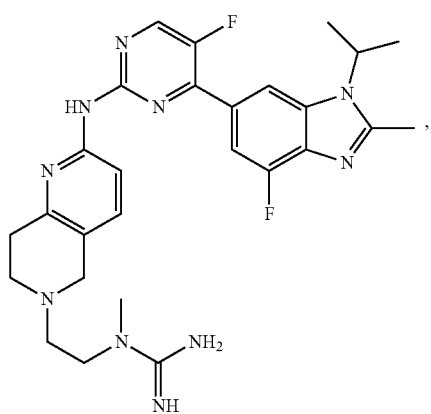
I-91
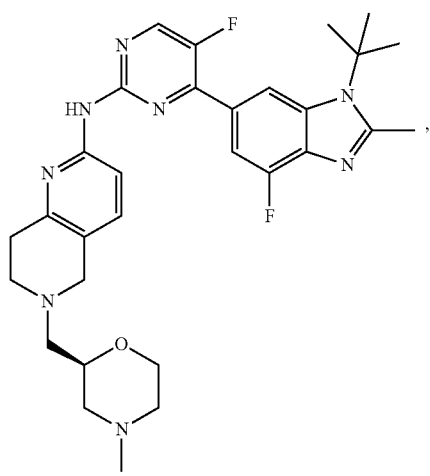
I-94
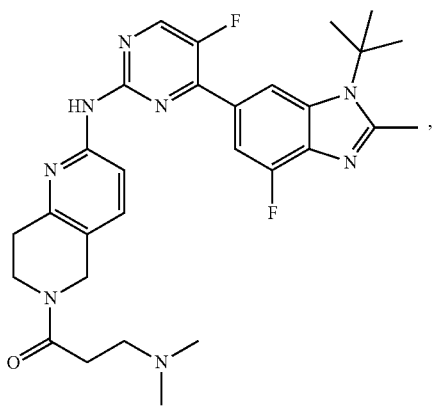
I-92
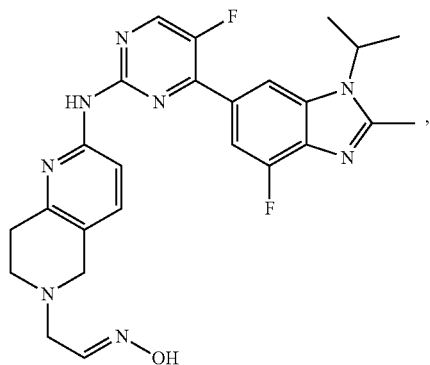
I-95

I-96
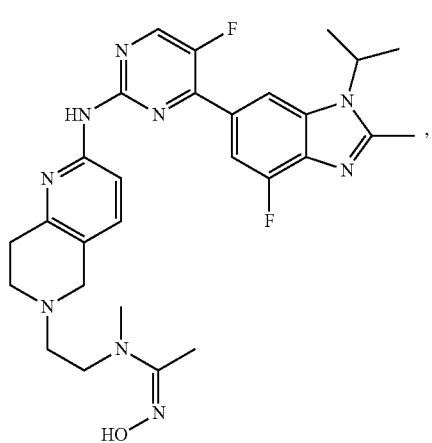
I-97
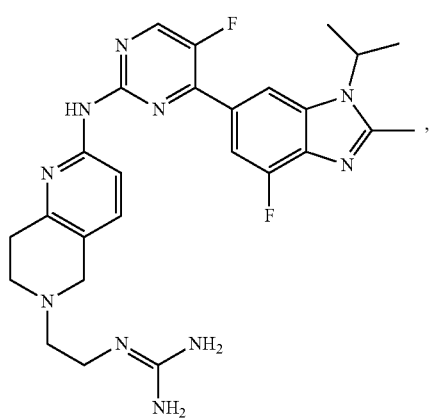
I-98
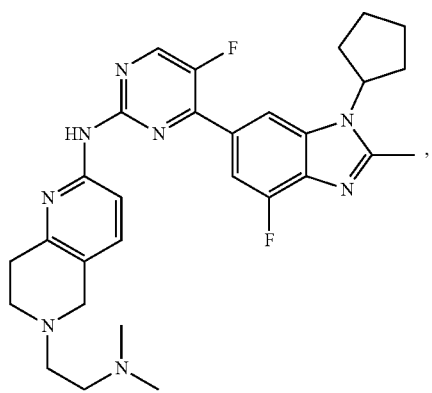
I-99
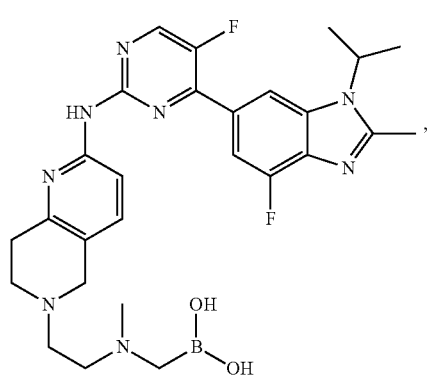
I-100
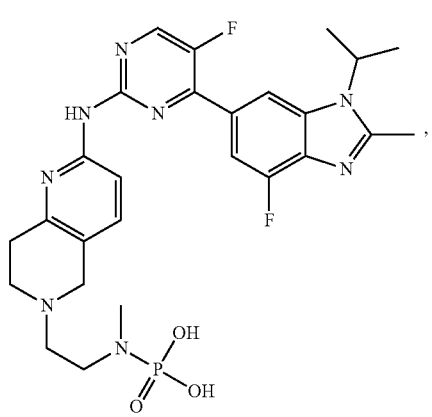
I-101
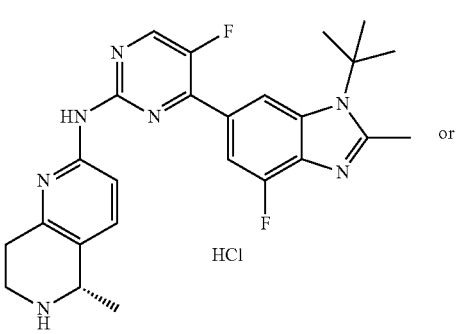
or
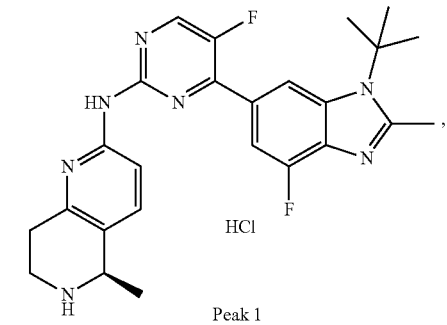
HCl
Peak 1
I-102
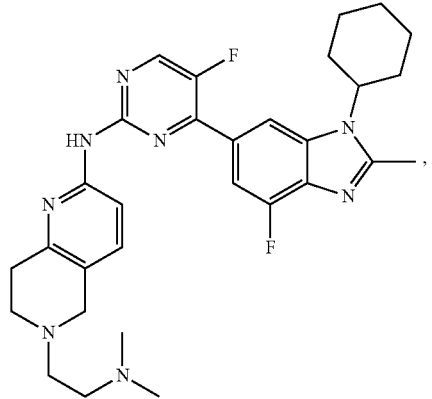

I-103
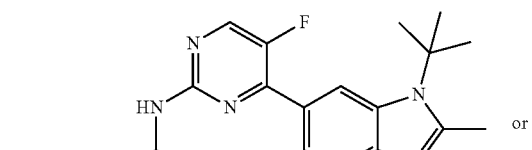
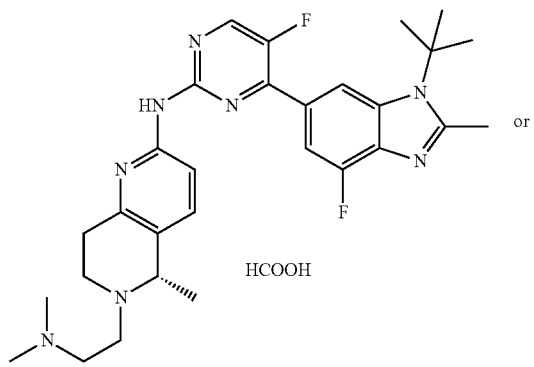
HCOOH
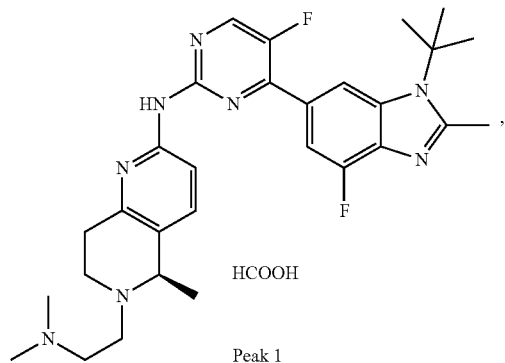
HCOOH
Peak 1
I-104
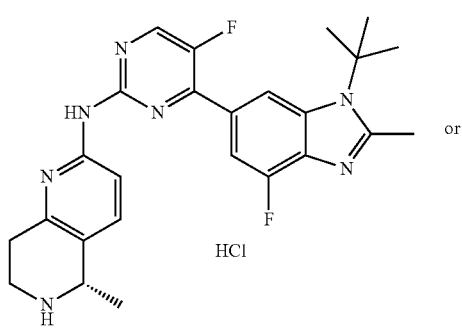
HCl
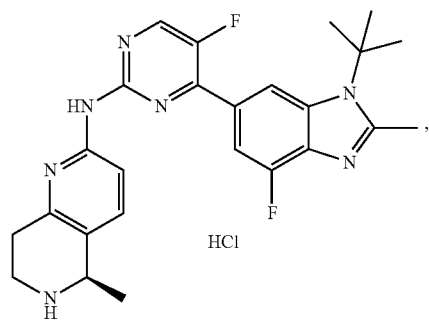
HCl
Peak 3
I-106
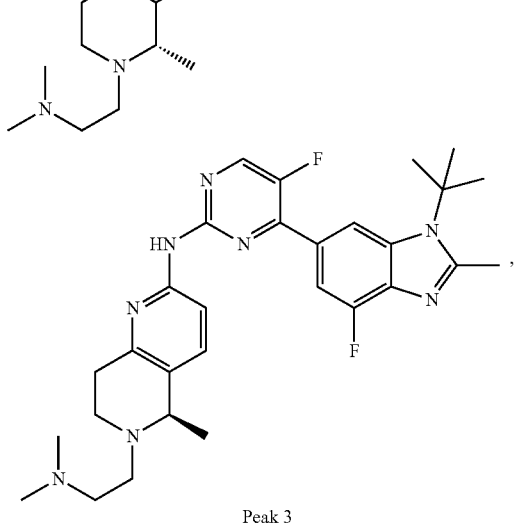
Peak 3
I-107
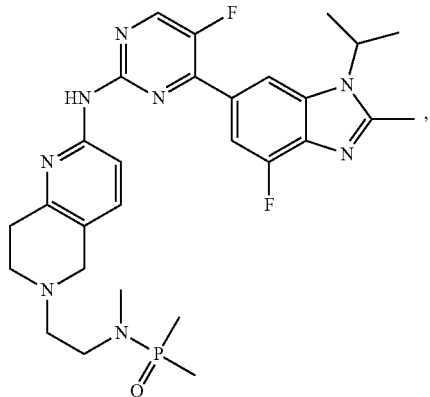
I-108
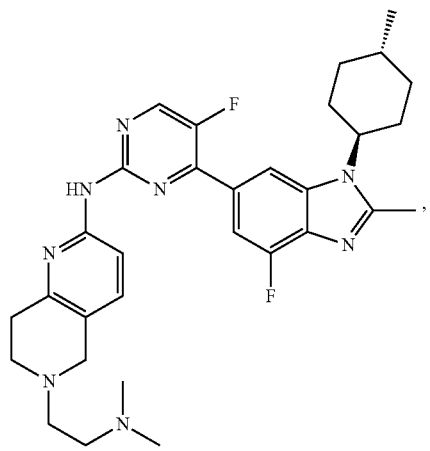

I-109
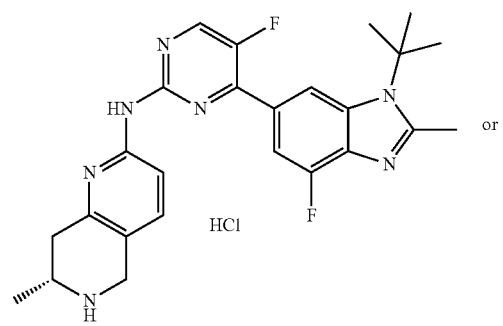
HCl
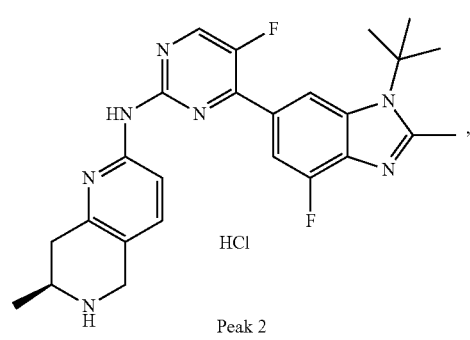
HCl
Peak 2
I-110
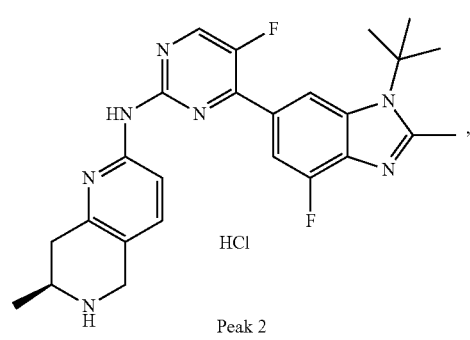
I-113
I-111
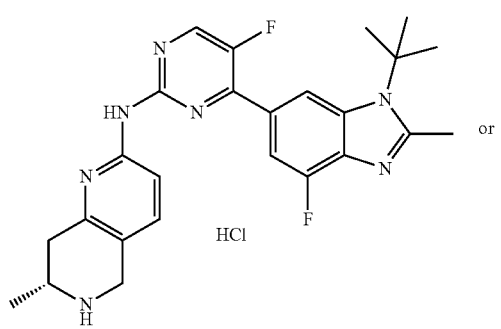
HCl or
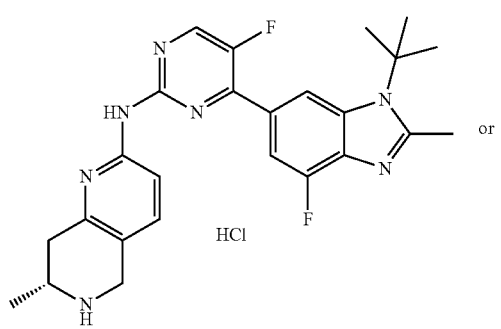
HCl
Peak 4
I-112
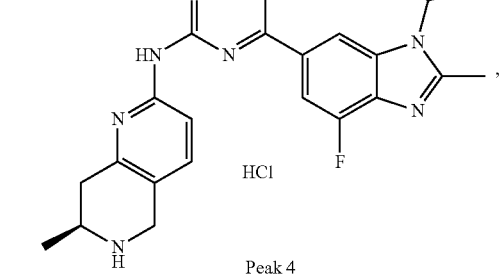
HCOOH or
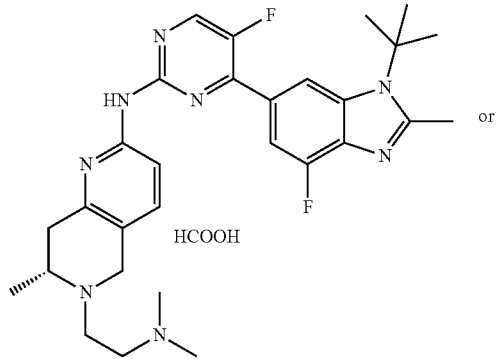
HCOOH
Peak 2

I-114
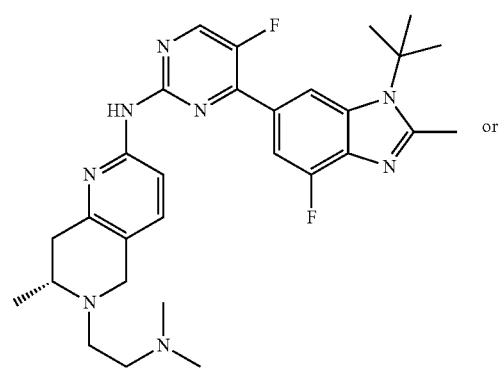
or
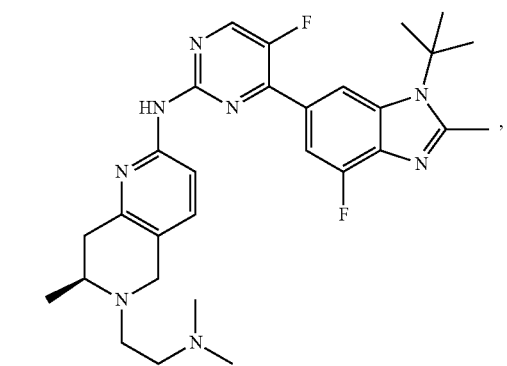
Peak 4
I-115
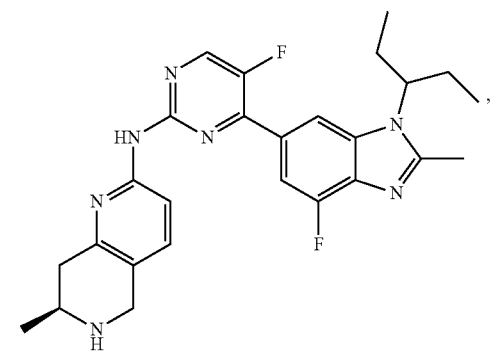
I-116
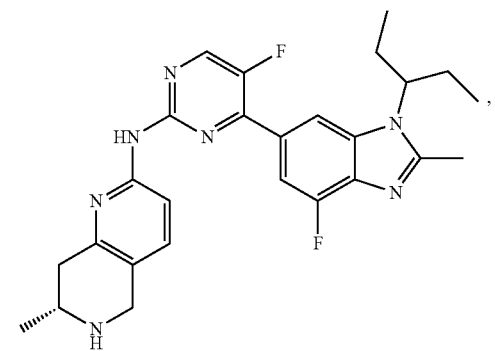
I-117
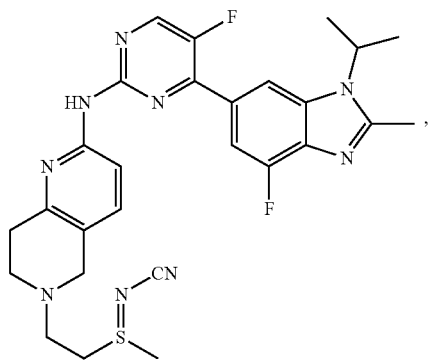
I-118
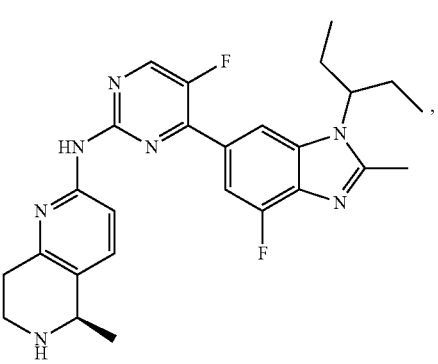
I-119
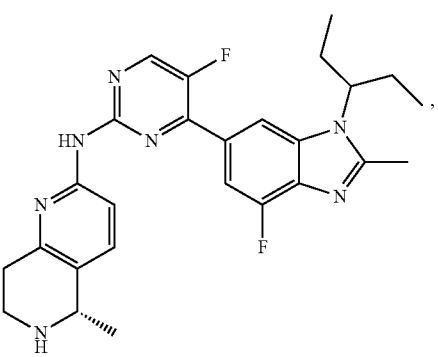
I-120
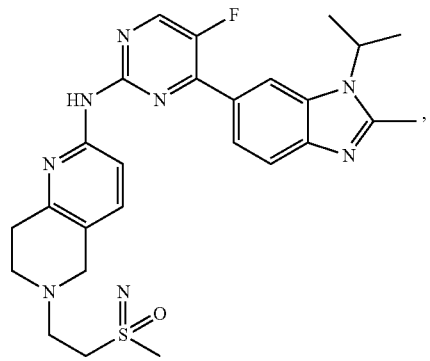

I-121
I-122
I-123
I-124
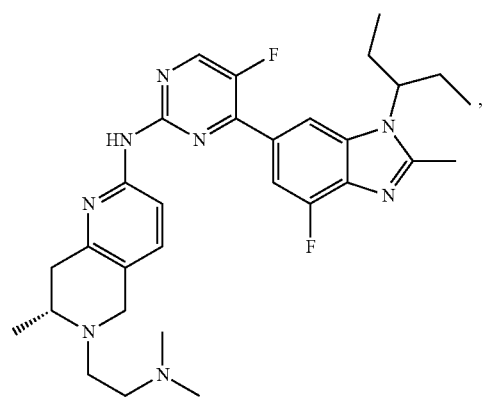
I-125
I-126
I-127
I-128
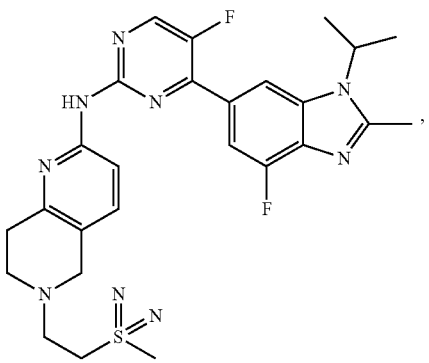
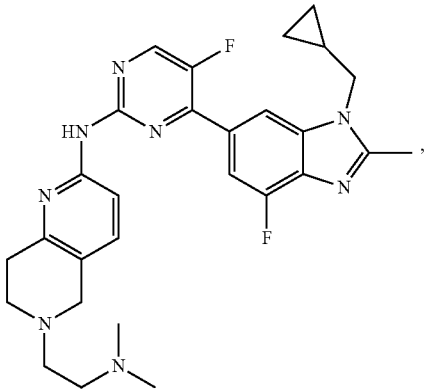
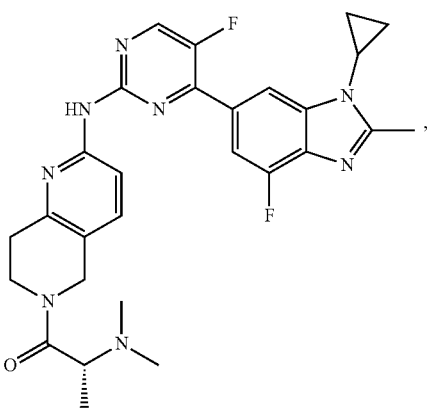
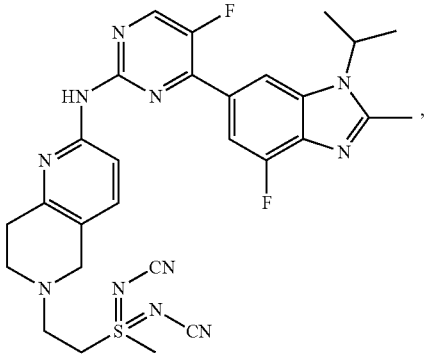

-continued
I-129
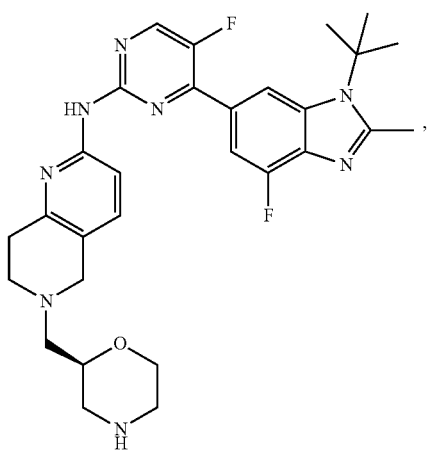
I-130
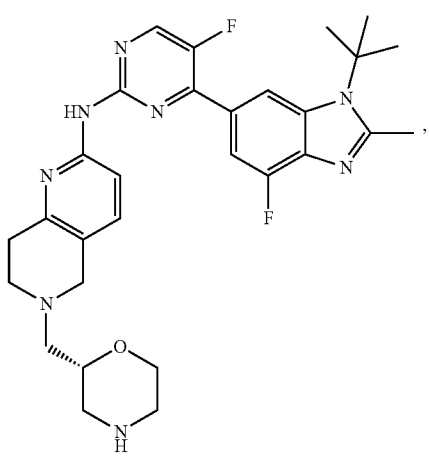
I-131
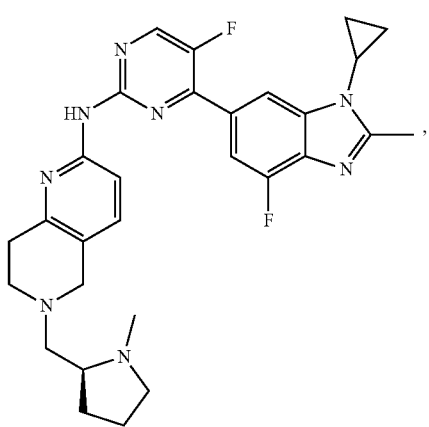
-continued
I-132
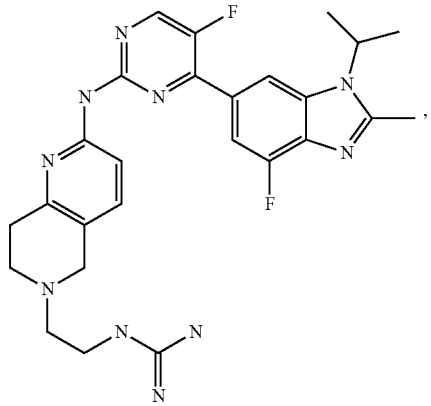
I-133
I-134
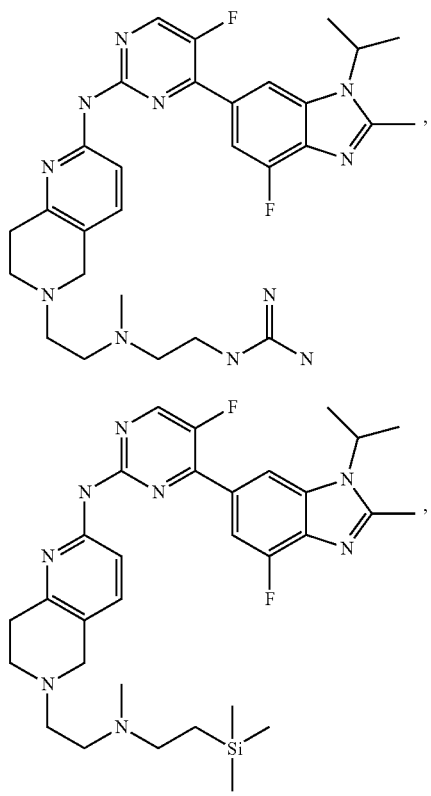
I-135
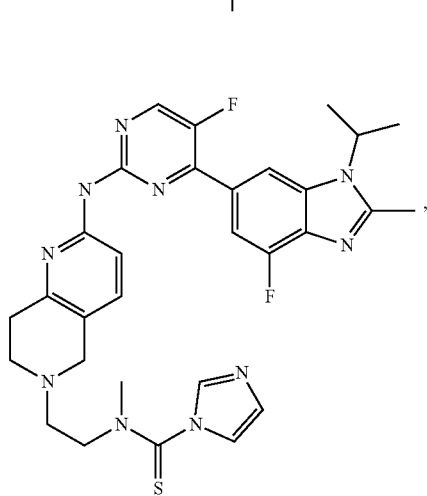

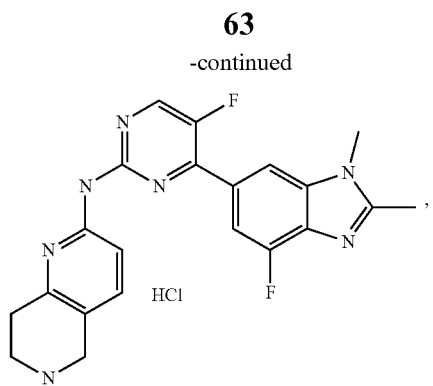
I-136
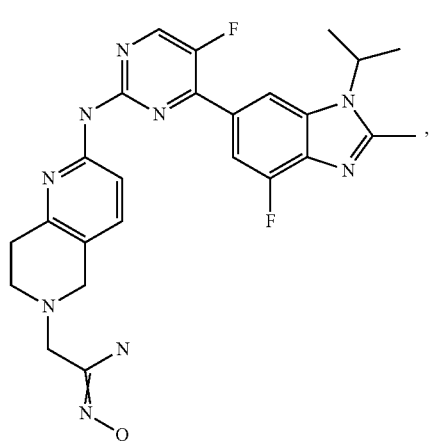
I-137
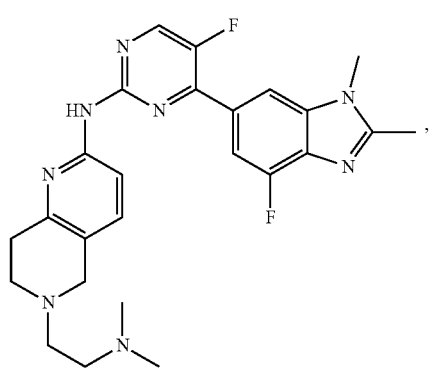
I-138
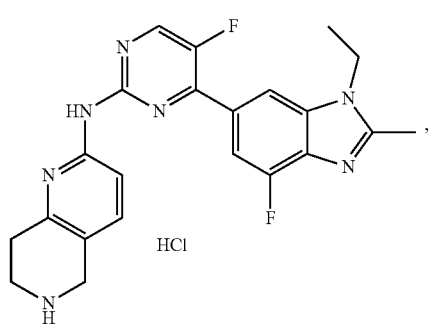
I-139
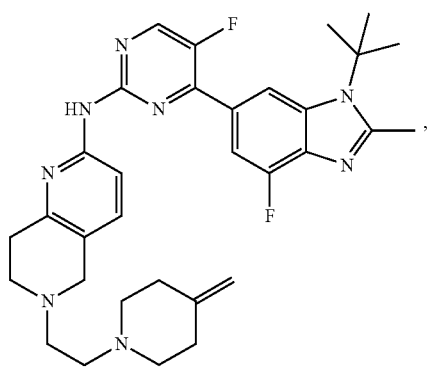
I-140
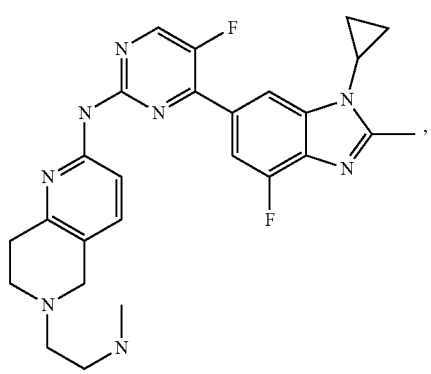
I-141
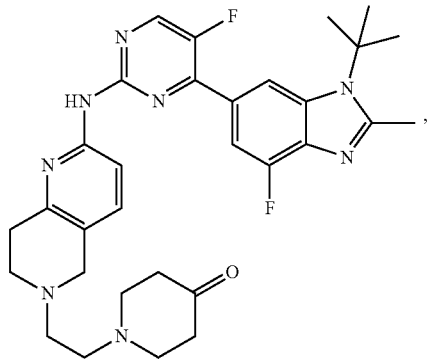
I-142
I-143

I-145
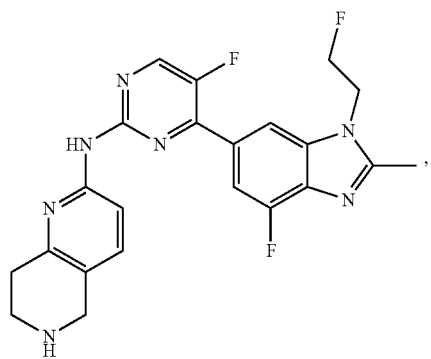
I-146
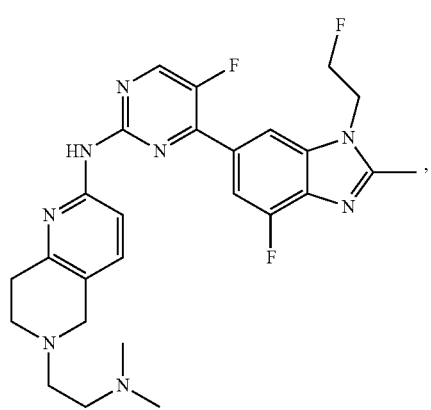
I-147
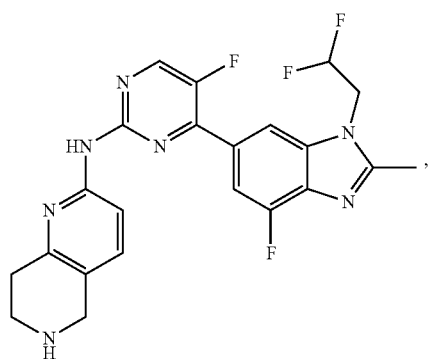
I-148
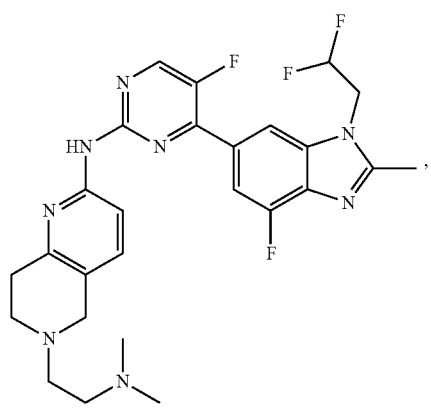
I-149
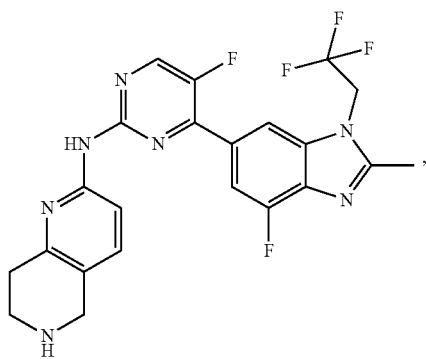
I-150
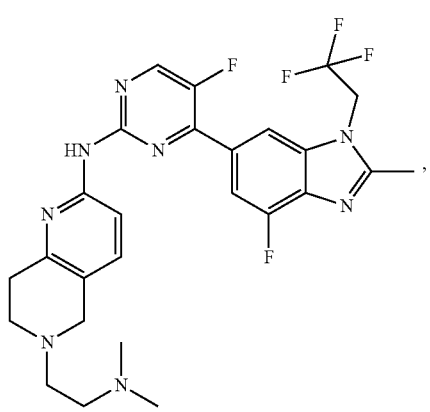
I-151
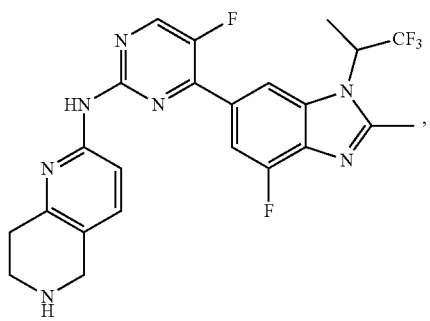
I-152
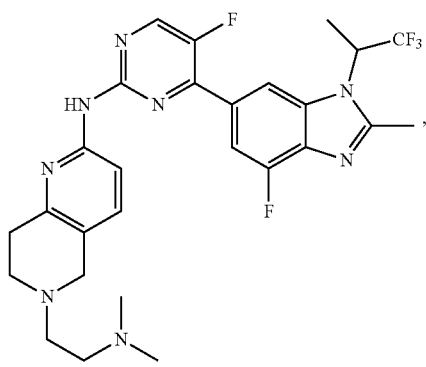

I-153
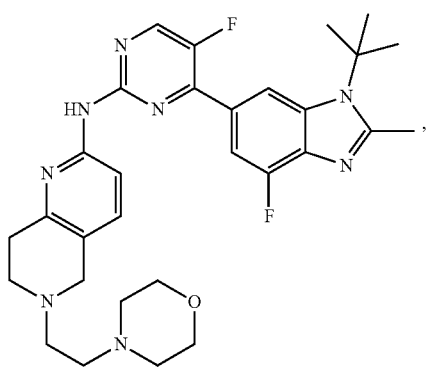
I-154
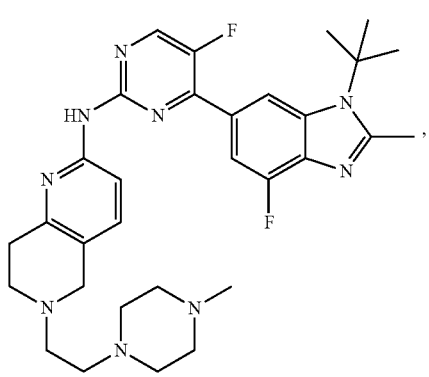
I-155
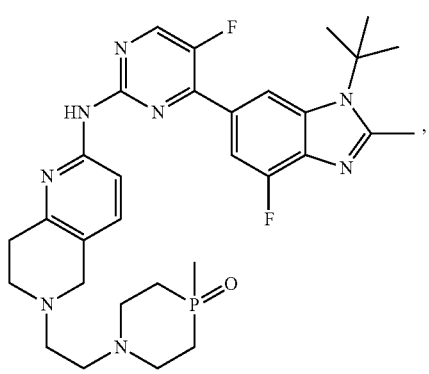
I-156
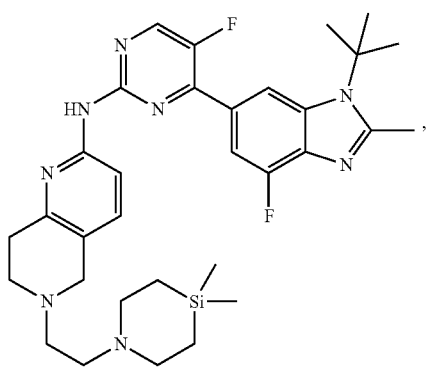
I-157
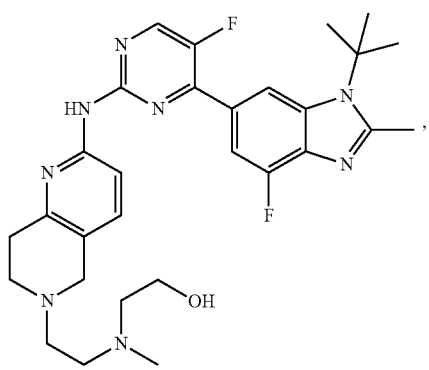
I-158
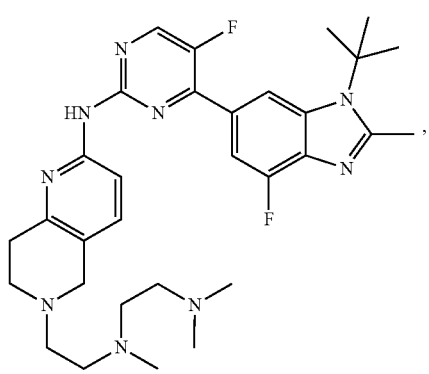
I-159
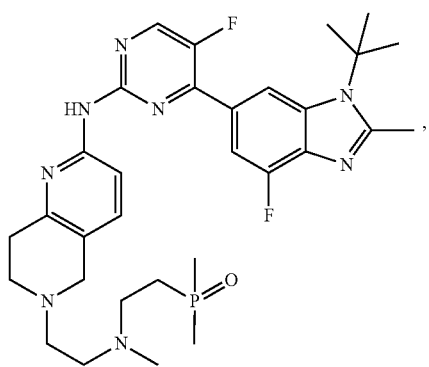
I-160
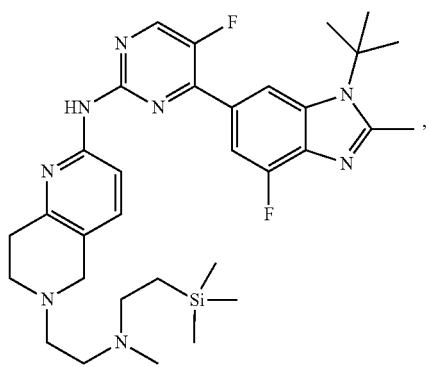

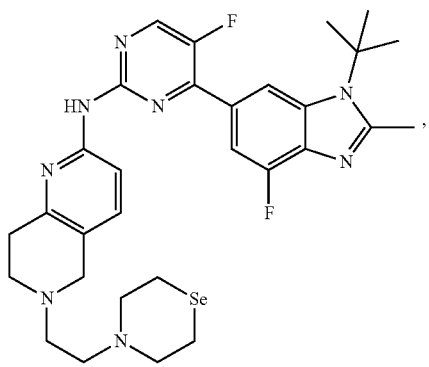
I-161
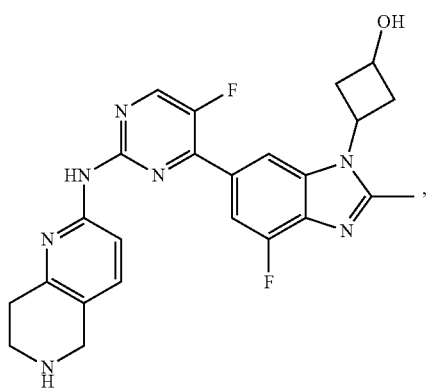
I-165
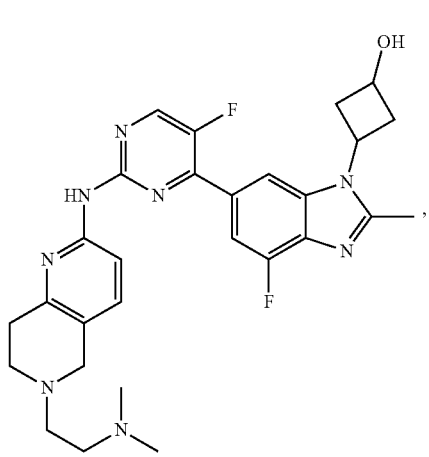
I-162
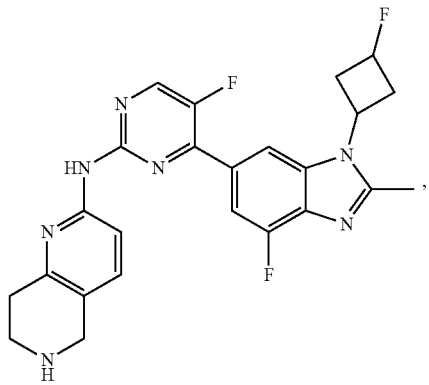
I-166
I-163
I-167
I-164
I-168

71
-continued
I-169
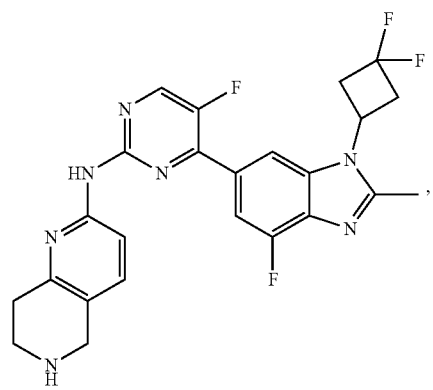
I-170
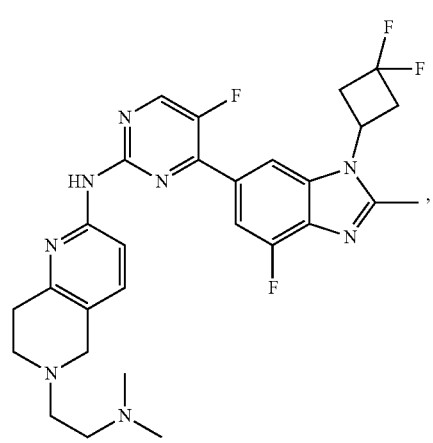
I-171
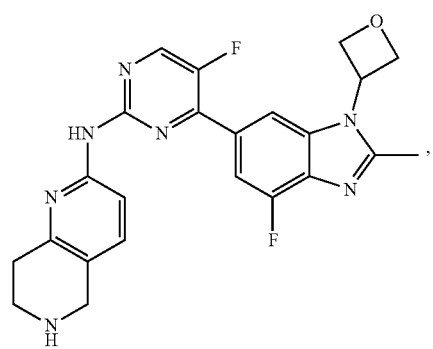
I-172
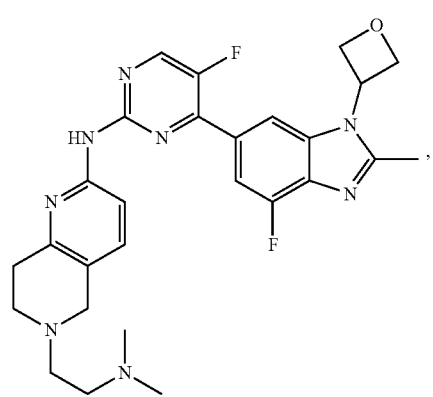
72
-continued
I-173
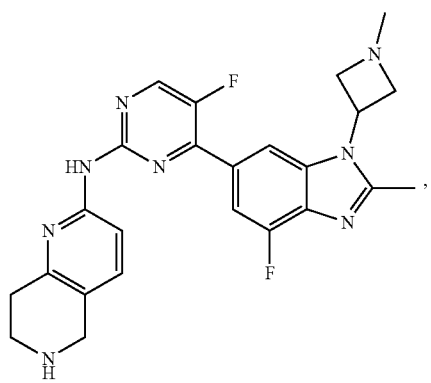
I-174
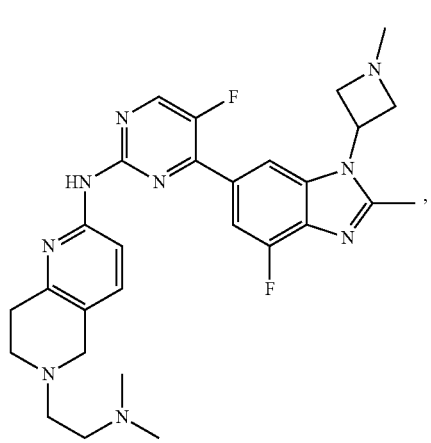
I-175
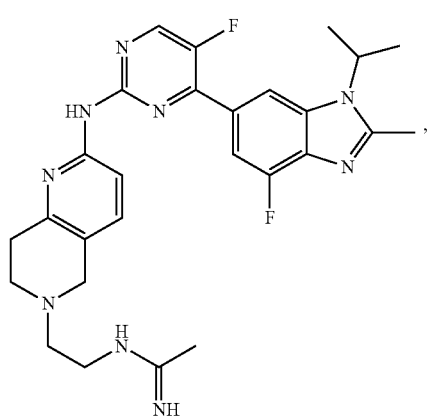
I-176
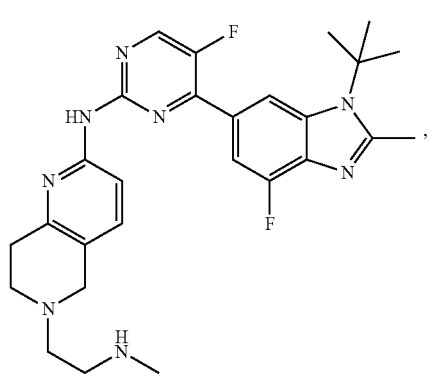

I-177 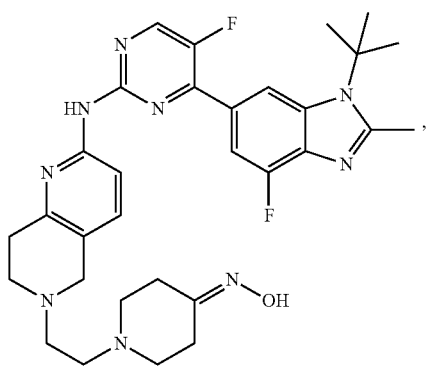
I-181 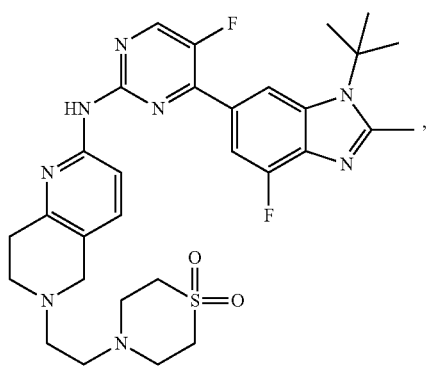
I-178 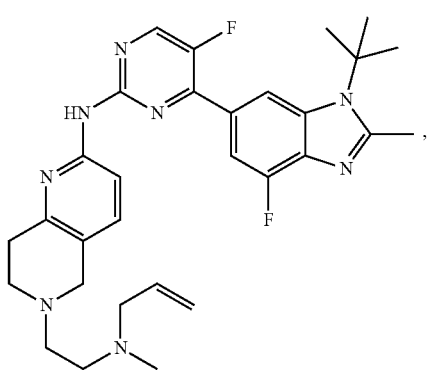
I-182 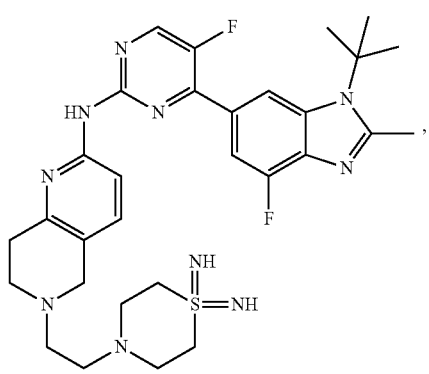
I-179 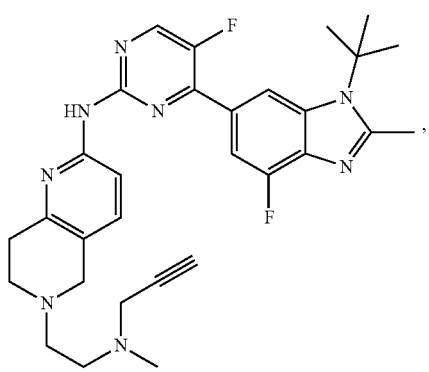
I-183 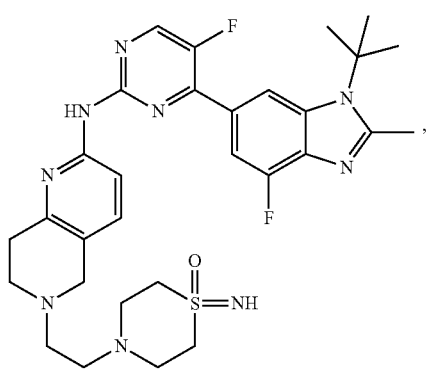
I-180 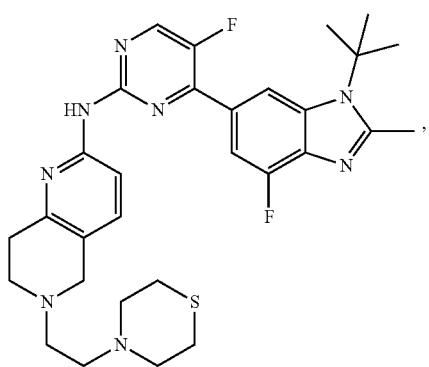
I-185 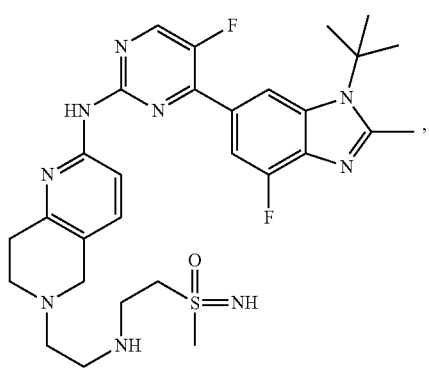

I-186
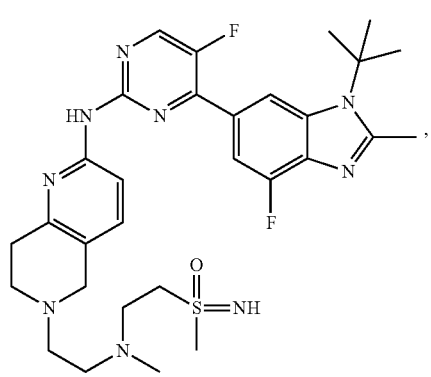
I-187
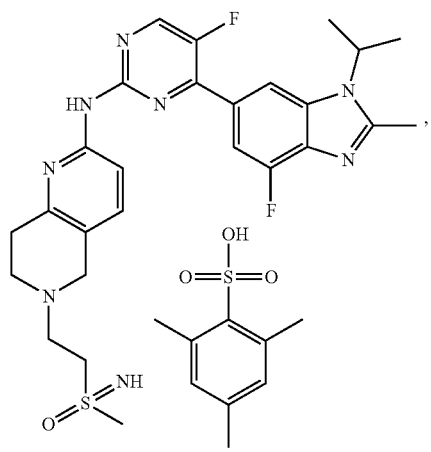
I-188
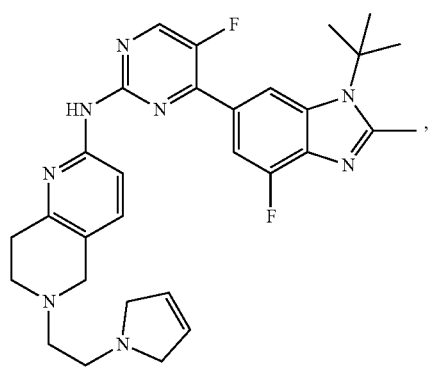
I-189
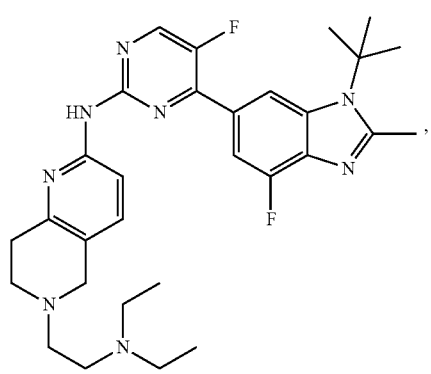
I-190
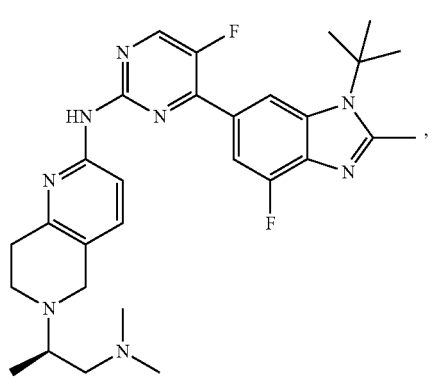
I-191
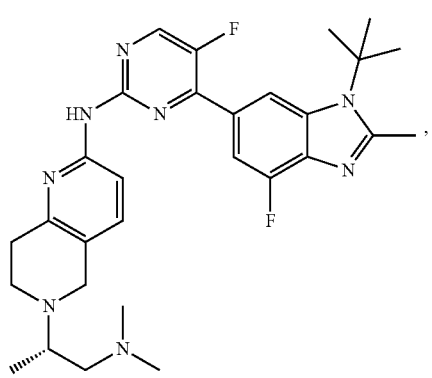
I-192
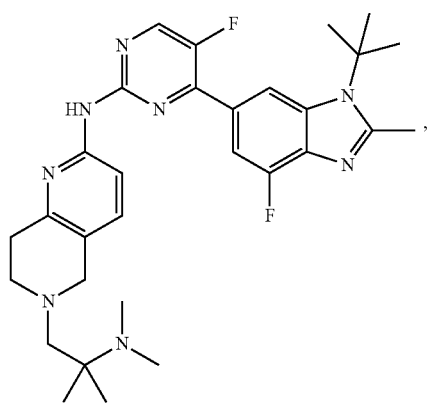
I-193
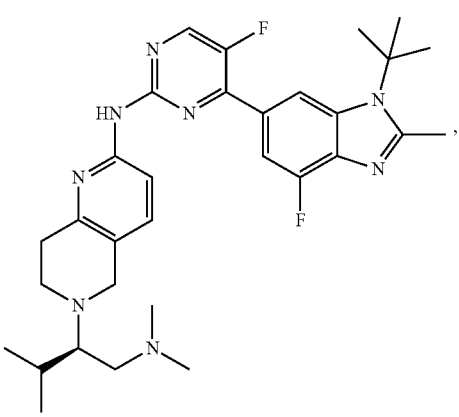

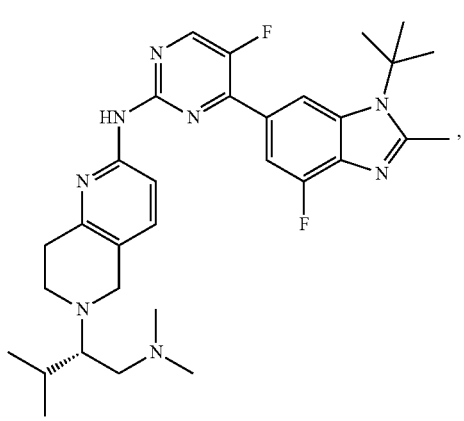
I-194
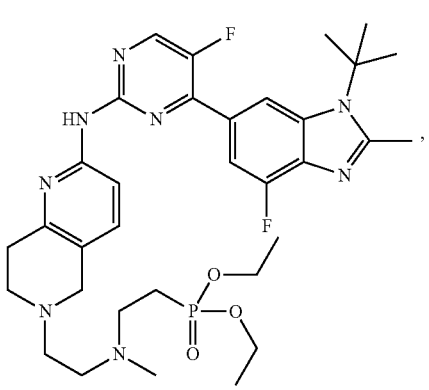
I-198
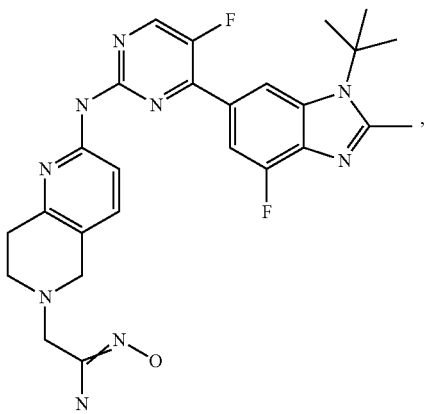
I-199
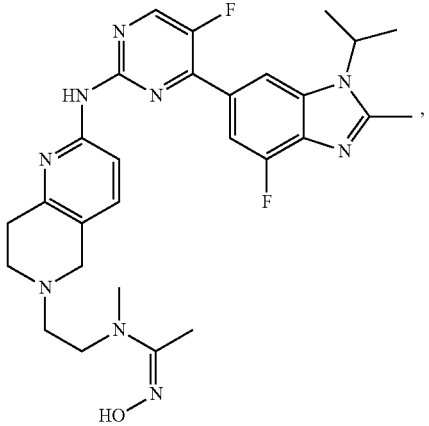
I-200
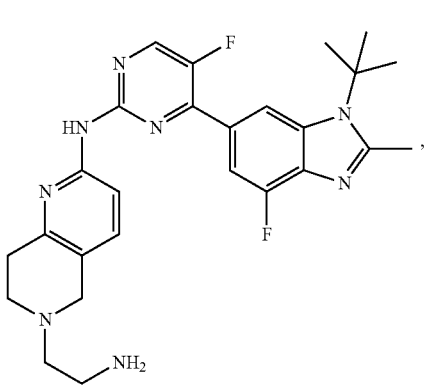
I-202

I-203 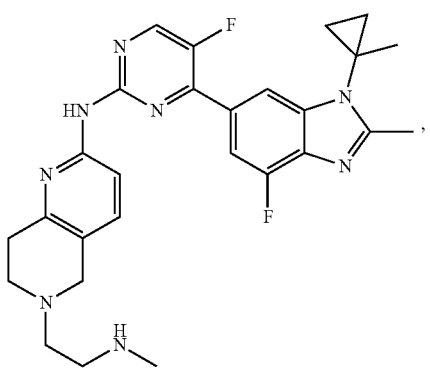
I-207 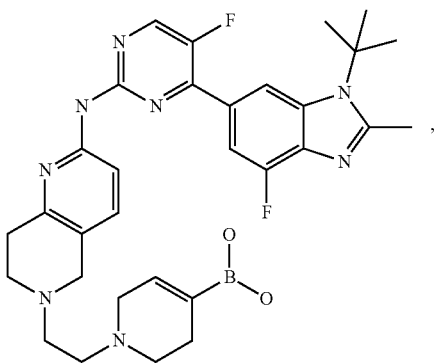
I-204 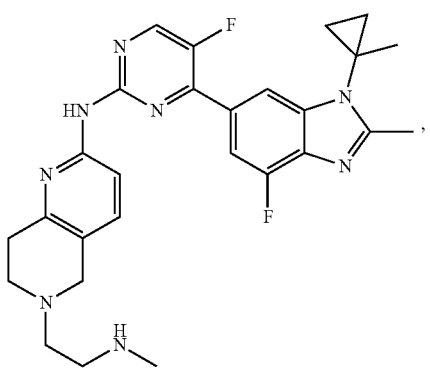
I-208 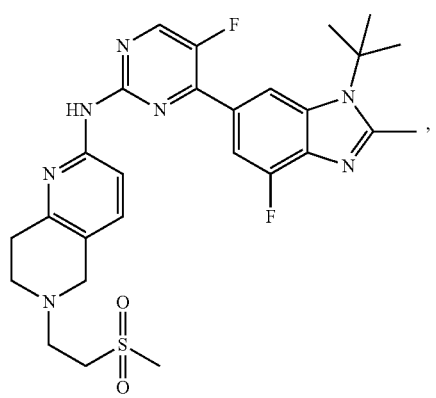
I-205 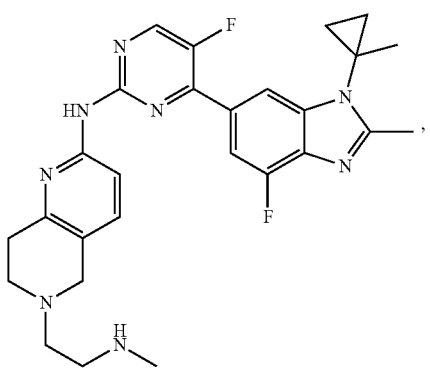
I-209 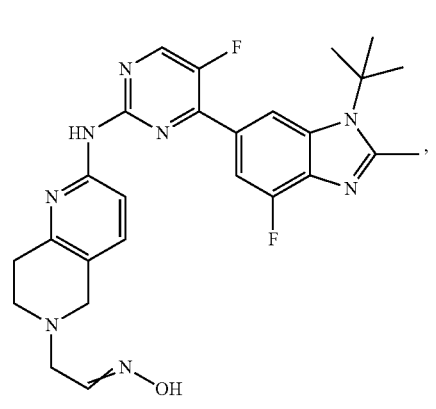
I-206 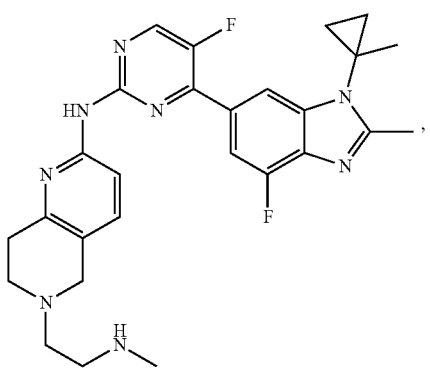
I-210 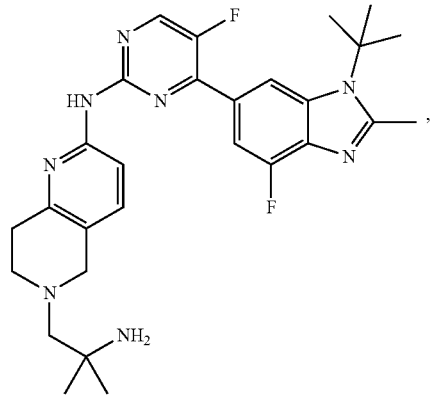

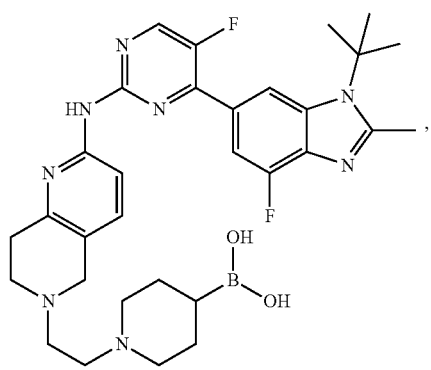
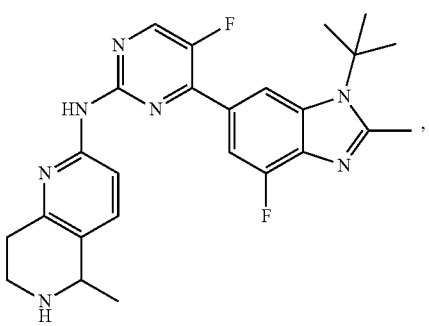

I-219

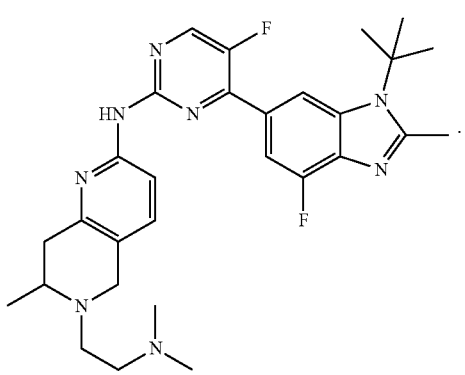

The nitrogen-containing fused heterocyclic compounds involved in the present invention may exhibit tautomerism, structural isomerism and stereoisomerism. The present invention includes any tautomeric or structural isomeric or stereoisomeric forms thereof and mixtures thereof, which have high selectivity and high inhibitory activity on CDK4 and CDK6, at the same time, they have better inhibitory activity against breast cancer cells, which is not limited to any of the isomers or the mixture thereof.

The nitrogen-containing fused heterocyclic compounds in the present invention can be prepared by various methods well-known to those skilled in the field of organic synthesis and medicinal chemistry, or prepared by the methods described below combined with the synthetic methods known in the field of organic chemistry or transformational methods thereof understood by those skilled in the art.

The preparation method for the nitrogen-containing fused heterocyclic compounds can start from readily available starting materials using the following general methods and processes to prepare the compound in the present invention. It will be understood that where typical or preferable process operating conditions (e.g. reaction temperature, time, mole ratio of reactants, solvent, pressure, etc.) are given; other process operating conditions can also be used, unless otherwise specified. Optimum reaction conditions may vary with the specific reactant or solvent used, but these conditions can be determined by those skilled in the art by routine optimization procedures.

The preparation method for the nitrogen-containing fused heterocyclic compounds described herein can be monitored by any suitable method known in the art. For example, the product formation can be monitored by nuclear magnetic resonance, infrared spectroscopy, spectrophotometry or mass spectrometry, HPLC, or thin layer chromatography.

The preparation method for the nitrogen-containing fused heterocyclic compound may involve protection and deprotection of multiple chemical groups. The need for protection and deprotection, as well as the choice of the appropriate protecting group, can be easily determined by those skilled in the art. The chemical process of the protecting group can refer to Greene et al., *Protective Groups in Organic Synthesis*, Second Edition, Wiley & Sons, 1991, which is incorporated herein by reference in its entirety.

The preparation method described herein can be carried out in a suitable solvent, which can be readily selectable by those skilled in the art of organic synthesis. A suitable solvent does not substantially react with the starting materials, intermediates or products at the temperature at which the described reaction is carried out. The temperature at which the reaction is carried out may vary from the solvent's freezing point to the solvent's boiling temperature. The reaction can be carried out in a solvent or a mixture of multiple solvents. Depending on a specific reaction step, the solvent suitable for the specific reaction step can be selected.

On this basis, particularly preferably (but not limited to reagents and solvents in the reaction condition), the present invention further provides a preparation method for the nitrogen-containing fused heterocyclic compound, which is any one of the following methods:

Method 1:

when $R^5$ is hydrogen, the preparation method for the compound represented by formula I comprises conducting Suzuki coupling reaction to give 1C, followed by conducting Buchwald coupling with the compound represented by formula 1C and

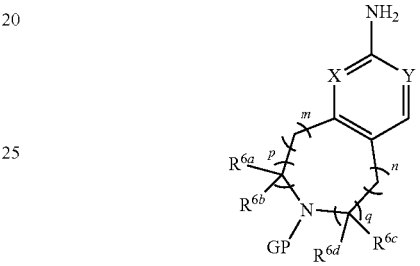

to remove the protecting group and give the compound represented by formula I; the PG in the compound represented by formula 1D is a protecting group;

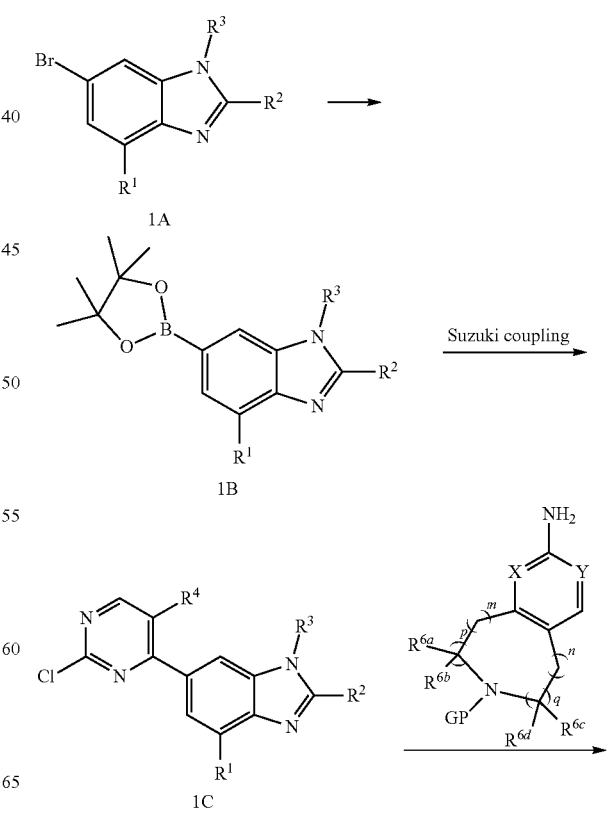

-continued

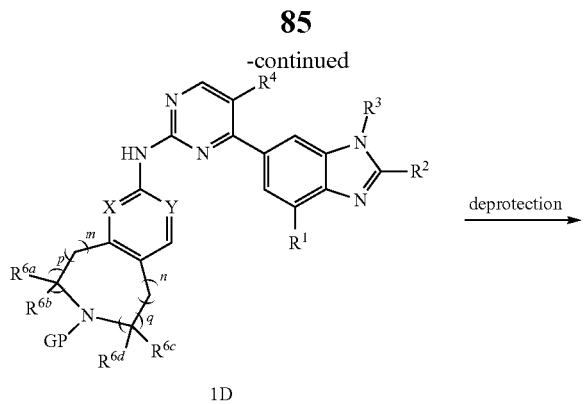

1D

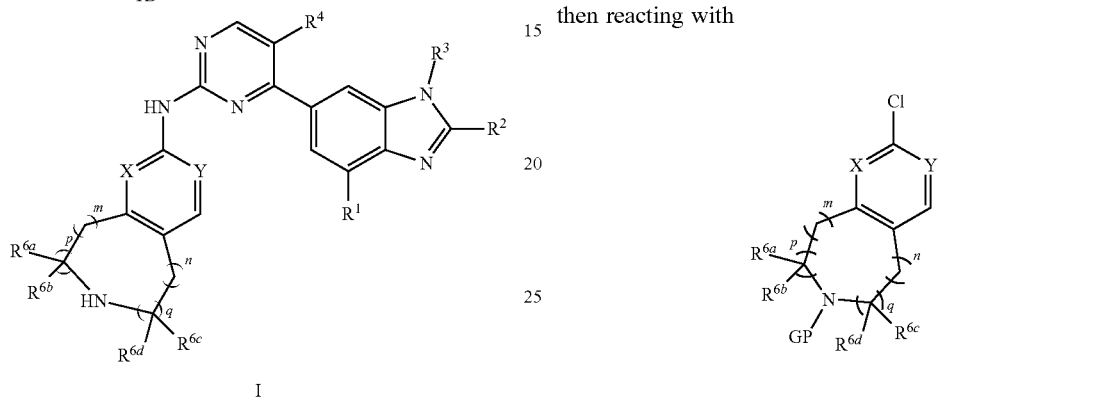

I wherein X, Y, m, n, p, q, $R^1$, $R^2$, $R^3$, $R^4$, $R^6$, $R^{6b}$, $R^{6c}$ and $R^{6d}$ are defined as above;

the PG in the compound represented by formula 1D can be various conventional amino protecting groups in the art, preferably Boc, for the purpose of making certain reactive groups (e.g. amino group) not participate in the reaction when reacts with compound 1C;

the condition of the deprotection reaction can be conventional removal conditions for various protecting groups in the art, e.g. conditions of hydrolysis reaction, conditions of amine hydrolysis reaction, conditions of hydrogenation reaction, and the like;

after the completion of deprotection reaction, preferably further comprising post-treatment; the method and condition of the post-treatment can be conventional methods and conditions for post-reaction treatment in the art, preferably comprising washing the reaction system, drying, filtering, evaporating to dryness; then conducting column chromatography; or, the reaction system is distilled to remove the solvent, washed, filtered; or, the reaction system is distilled to remove the solvent, subjected to thin layer chromatography;

the condition of the substitution reaction or the transition metal catalyzed coupling reaction can be various conventional conditions of such reactions in the art; the substitution reaction may be carried out by heating or pressurizing or acid-base catalyzing etc.;

wherein, the condition of each reaction step in the reaction route can be carried out according to conventional conditions of such reactions in the art;

Method 2:

when $R^5$ is hydrogen, a preparation method for the compound represented by formula I comprises subjecting the 1C obtained according to method 1 to ammonolysis reaction, then reacting with

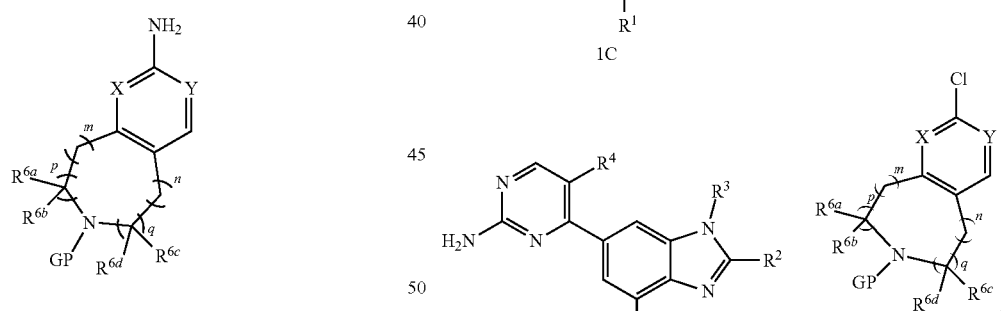

to give 2A, followed by removing the protecting group to give the compound represented by formula I;

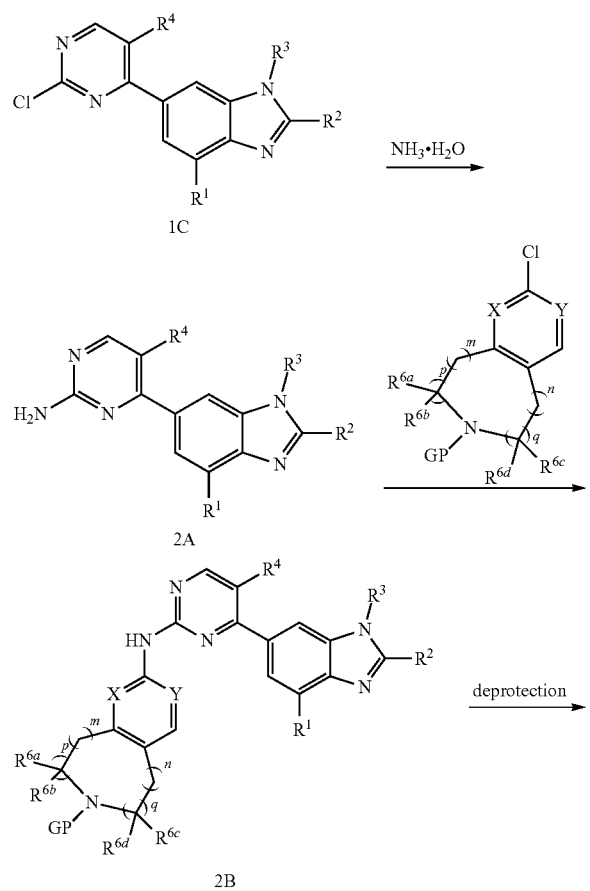

2B

-continued

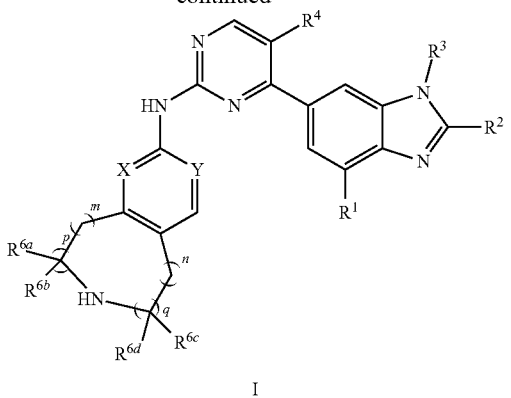

I wherein X, Y, m, n, p, q, $R^1$, $R^2$, $R^3$, $R^4$, $R^{6a}$, $R^{6b}$, $R^{6c}$ and $R^{6d}$ are defined as above;

Method 3:
when $R^5$ is

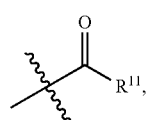

and $R^{11}$ is substituted or unsubstituted $C_1$-$C_6$ alkyl, or substituted or unsubstituted $C_3$-$C_8$ cycloalkyl, the preparation method for the compound represented by formula I comprises that in organic solvent (e.g. selected from the group consisting of 1,4-dioxane, dichloromethane and DMF), in the presence of a condensing agent (e.g. HOBt and EDCI), conducting condensation reaction with compound 3A and

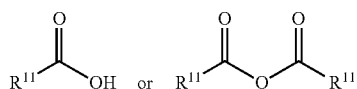

to give compound I; the condition of the condensation reaction can be conventional conditions in the art;

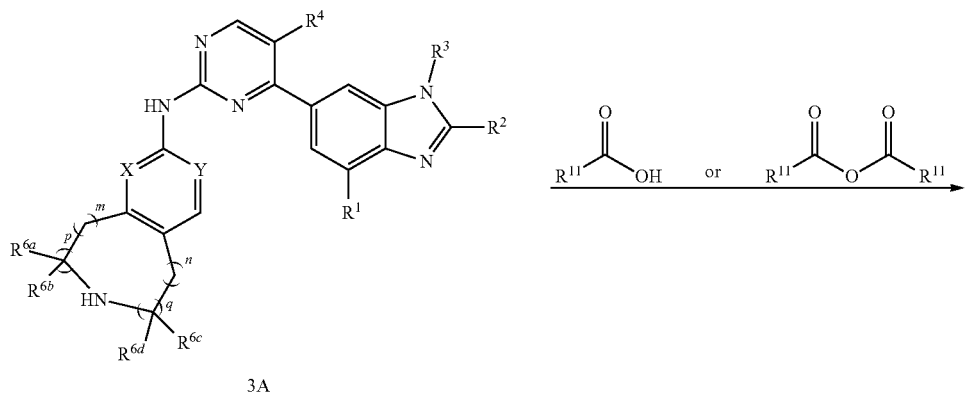

3A

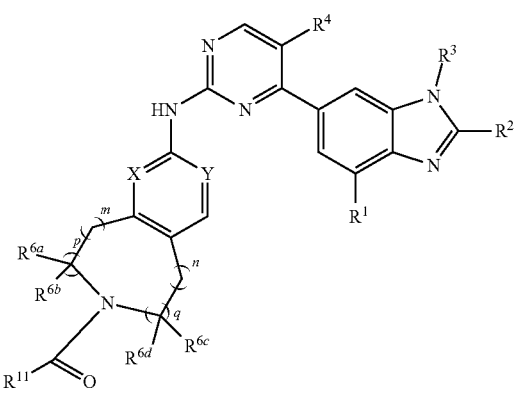

I

X, Y, m, n, p, q, $R^1$, $R^2$, $R^3$, $R^4$, $R^{11}$, $R^{6a}$, $R^{6b}$, $R^{6c}$ and $R^{6d}$ are defined as above;

Method 4:

when $R^5$ is

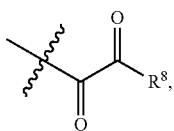

the preparation method for the compound represented by formula I comprises that in organic solvent (e.g. tetrahydrofuran), in the presence of the base (e.g. pyridine), reacting compound 4A with

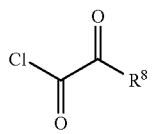

to give compound 4B, followed by conducting hydrolysis reaction to give compound I; the conditions of the amide reaction and the hydrolysis reaction can be conventional conditions in the art;

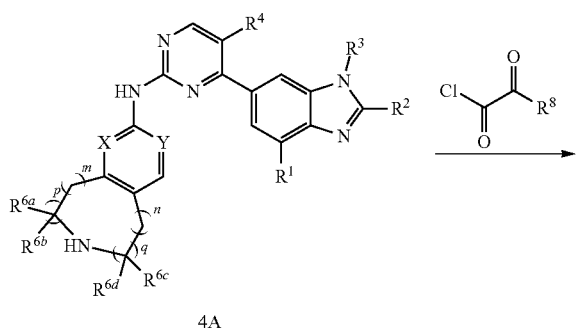

4A

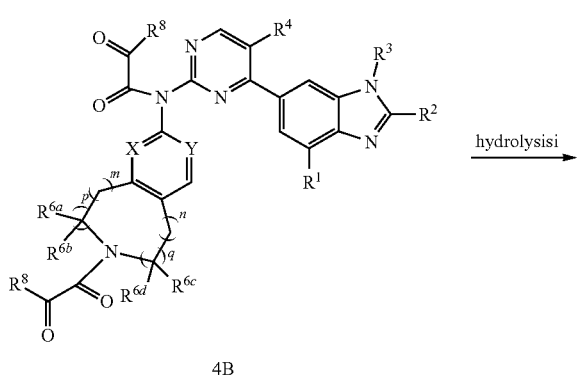

4B

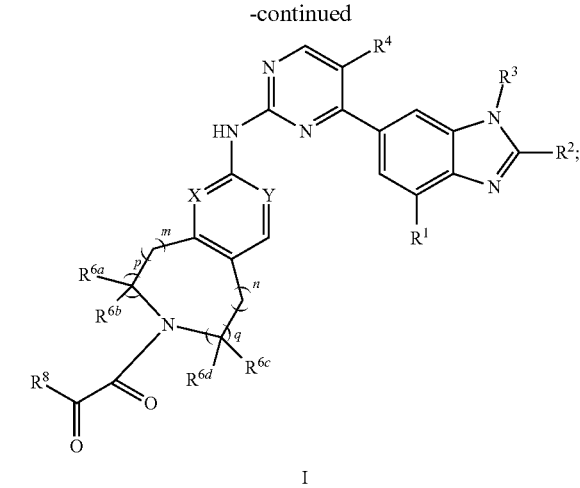

I

X, Y, m, n, p, q, $R^1$, $R^2$, $R^3$, $R^4$, $R^{6a}$, $R^{6b}$, $R^{6c}$, $R^{6d}$ and $R^8$ are defined as above;

Method 5:

when $R^5$ is

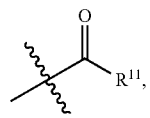

$R^{11}$ is substituted $C_1$-$C_6$ alkyl or $C_3$-$C_8$ cycloalkyl, and the substituent is

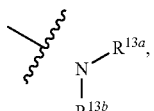

when $R^{13b}$ is H, the preparation method for the compound represented by formula I comprises that in organic solvent (e.g. selected from the group consisting of 1,4-dioxane, dichloromethane and DMF), in the presence of condensing agent (e.g. HOBt and EDCI), reacting compound 5A with

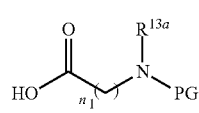

to give compound 5B, then removing the protecting group of the amino group to give compound I; the condition of the amide reaction and the deprotection reaction can be conventional conditions in the art; $R^{13a}NH$—$(CH_2)_{n1}$—$C(=O)$— is $R^5$; —$(CH_2)_{n1}$— is the substituted $C_1$-$C_6$ alkyl or $C_3$-$C_8$ cycloalkyl;

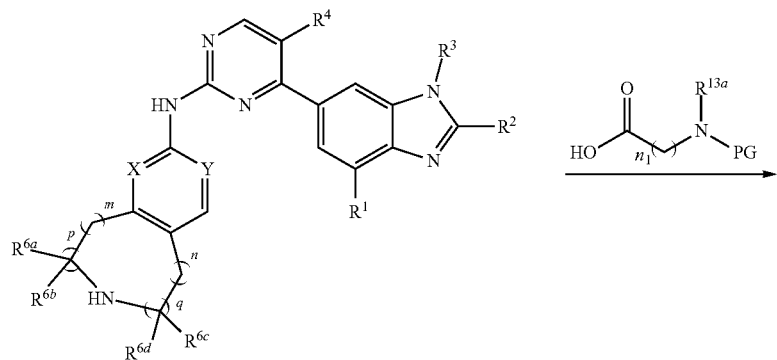

5A

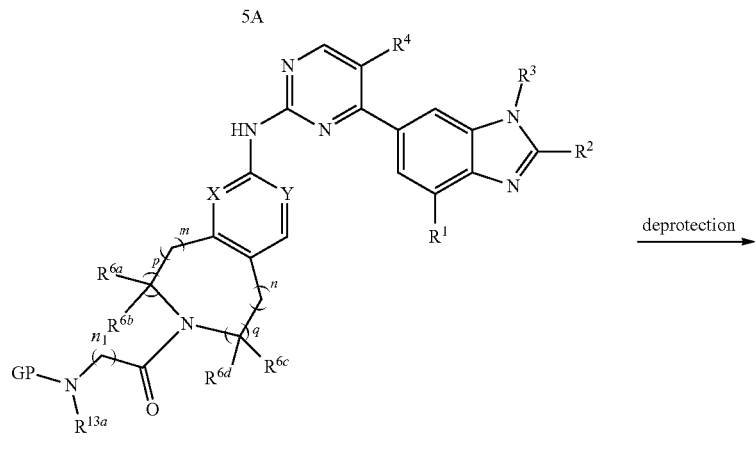

5B deprotection

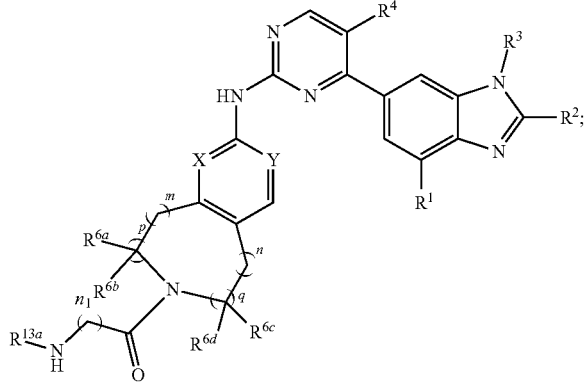

I

X, Y, m, n, p, q, $R^1$, $R^2$, $R^3$, $R^4$, $n_1$, $R^{6a}$, $R^{6b}$, $R^{6c}$, $R^{6d}$ and $R^{13a}$ are defined as above;

PG in the compound represented by formula 5B can be various conventional amino protecting groups in the art, preferably Boc, for the purpose of making certain reactive groups (e.g. amino group) not participate in the reaction when

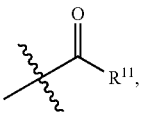

reacts with compound 5A;

Method 6:

when $R^5$ is

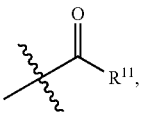

$R^{11}$ is substituted $C_1$-$C_6$ alkyl or $C_3$-$C_8$ cycloalkyl, the substituent is

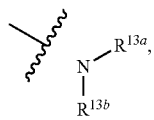

and neither $R^{13a}$ or $R^{13b}$ is H, the preparation method for the compound represented by formula I comprises that in organic solvent (e.g. selected from the group consisting of 1,4-dioxane, dichloromethane and DMF), in the presence of condensing agent (e.g. HOBt and EDCI), reacting compound 6A with

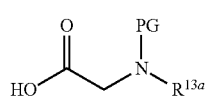

to give compound 6B, then removing the protecting group of the amino group and conducting reductive amination to give compound I; the conditions of the amide reaction, the deprotection reaction and the reductive amination can be conventional conditions in the art;

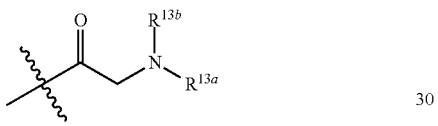

is $R^5$;

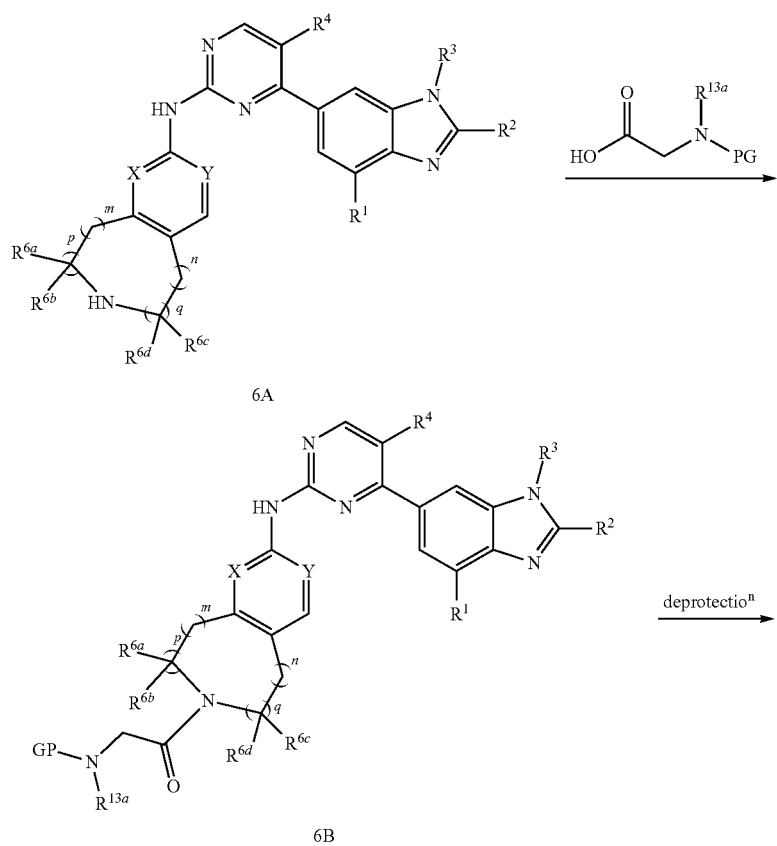

-continued

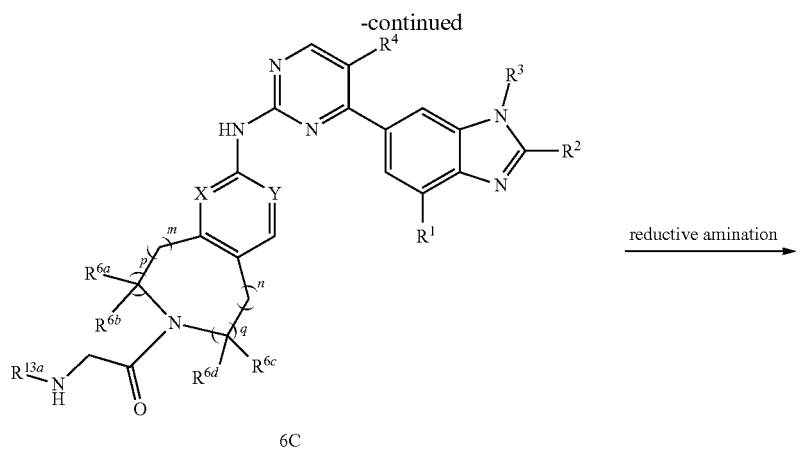

6C reductive amination

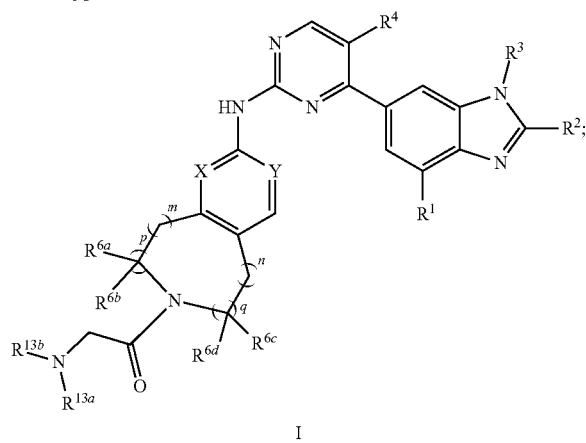

I

X, Y, m, n, p, q, $R^1$, $R^2$, $R^3$, $R^4$, $R^{6a}$, $R^{6b}$, $R^{6c}$, $R^{6d}$, $R^{13a}$ and $R^{13b}$ are defined as above;

PG in the compound represented by formula 6B can be various conventional amino protecting groups in the art, preferably Boc, for the purpose of making certain reactive groups (e.g. amino group) not participate in the reaction when

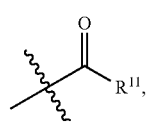

reacts with compound 6A;

Method 7:

when $R^5$ is

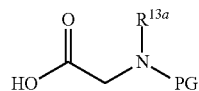

$R^{11}$ is substituted $C_1$-$C_6$ alkyl or $C_3$-$C_8$ cycloalkyl, and the substituent is

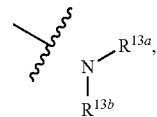

$R^{13b}$ and $R^{13b}$ are the same, the preparation method for the compound represented by formula I comprises that in organic solvent (e.g. selected from the group consisting of 1,4-dioxane, dichloromethane and DMF), in the presence of condensing agent (e.g. HOBt and EDCI), reacting compound 7A with

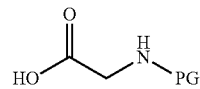

to give compound 7B, then removing the protecting group of the amino group and conducting reductive amination to give compound I; the conditions of the amide reaction, the deprotection reaction and the reductive amination can be conventional conditions in the art;

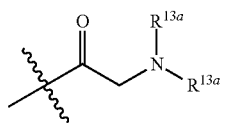
5
is R[5];
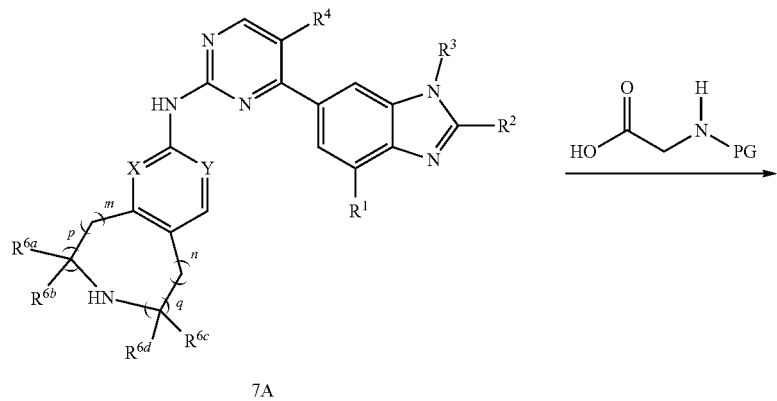
7A
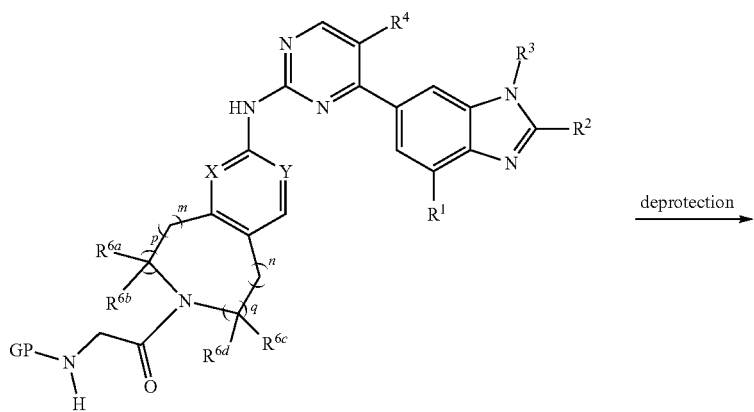
7B
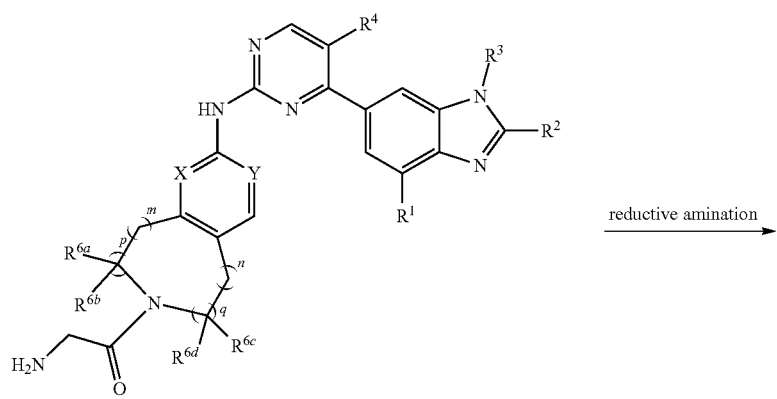
7C

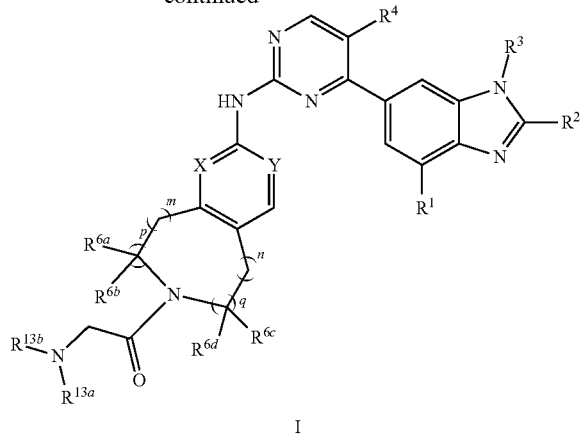

I

X, Y, m, n, p, q, $R^1$, $R^2$, $R^3$, $R^4$, $R^{6a}$, $R^{6b}$, $R^{6c}$, $R^{6d}$ and $R^{13a}$ are defined as above;

PG in the compound represented by formula 7B can be various conventional amino protecting groups in the art, preferably Boc, for the purpose of making certain reactive groups (e.g. amino group) not participate in the reaction when

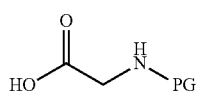

reacts with compound I;

Method 8:

when $R^5$ is substituted or unsubstituted $C_1$-$C_6$ alkyl, substituted or unsubstituted $C_3$-$C_8$ cycloalkyl

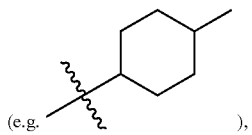

and substituted or unsubstituted $C_3$-$C_8$ heterocycloalkyl, the preparation method for the compound represented by formula I comprises that in organic solvent (e.g. DMF and/or 1,4-dioxane), in the presence of base (e.g. N,N-diisopropylethylamine), conducting substitution reaction with compound 8A and $R^5$—X to give compound I; the conditions of the substitution reaction can be conventional conditions in the art; X is halogen (e.g. bromine) or $CH_3SO_3$—;

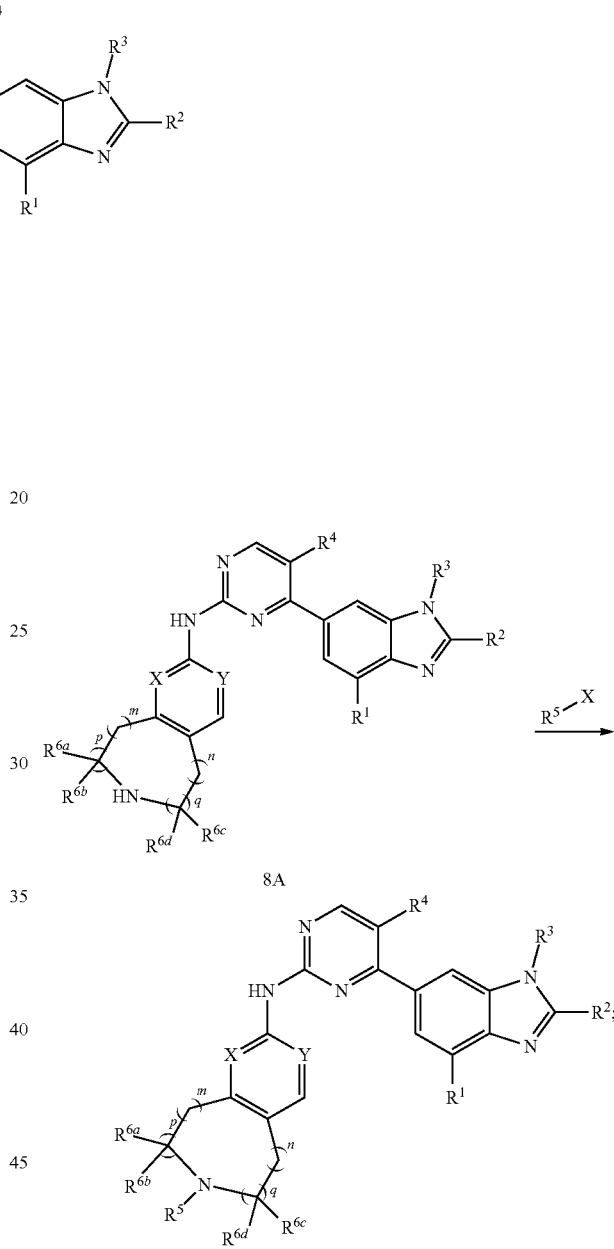

X, Y, m, n, p, q, $R^1$, $R^2$, $R^3$, $R^4$, $R^5$, $R^{6a}$, $R^{6b}$, $R^{6c}$ and $R^{6d}$ are defined as above;

Method 9:

when $R^5$ is substituted or unsubstituted $C_1$-$C_6$ alkyl, substituted or unsubstituted $C_3$-$C_8$ cycloalkyl

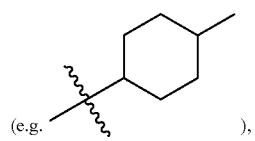

or substituted or unsubstituted $C_3$-$C_8$ heterocycloalkyl, the preparation method for the compound represented by formula I comprises that in organic solvent (e.g. selected from the group consisting of 1,2-dichloroethane, methanol and dioxane), in the presence of reductive agent (e.g. sodium triacetoxyborohydride and/or sodium cyanoborohydride), conducting reductive amination reaction with compound 9A and $R^{5a}$—CHO to give compound I; the condition of the reductive amination reaction can be conventional conditions in the art; $R^{5a}$ CH$_2$— is $R^5$;

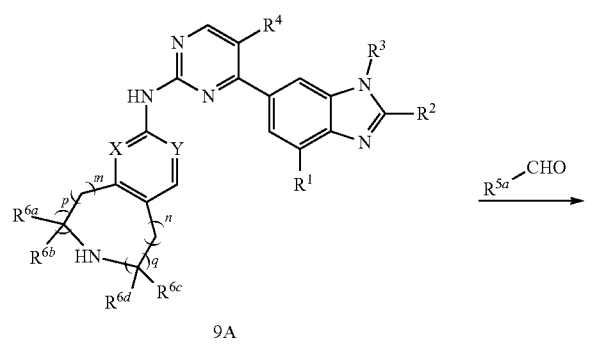

9A

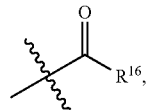

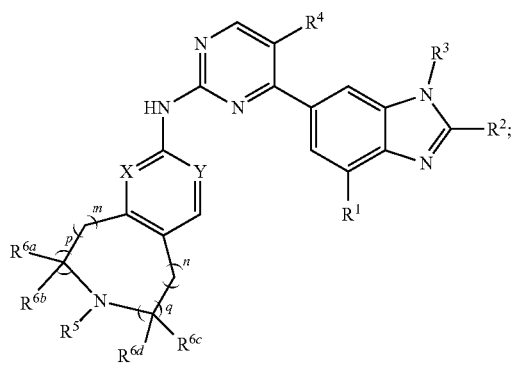

I

X, Y, m, n, p, q, $R^1$, $R^2$, $R^3$, $R^4$, $R^5$, $R^{6a}$, $R^{6b}$, $R^{6c}$ and $R^{6d}$ are defined as above;

Method 10:

when $R^5$ is substituted $C_1$-$C_6$ alkyl, substituted $C_3$-$C_8$ cycloalkyl, or, substituted $C_3$-$C_8$ heterocycloalkyl, the substituent is

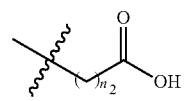

and $R^{16}$ is hydroxyl, the preparation method for the compound represented by formula I comprises that in organic solvent (e.g. selected from the group consisting of DMF, dichloromethane and 1,4-dioxane), in the presence of base (e.g. N,N-diisopropylethylamine), conducting substitution reaction with compound 10A and $R^{5b}$—OC(=O)—(CH$_2$)$_{n2}$—X to give compound I; the condition of the substitution reaction and the hydrolysis reaction can be conventional conditions in the art; X is halogen (e.g. bromine) or CH$_3$SO$_3$—; $R^{5b}$ is $C_1$-$C_6$ alkyl(e.g. methyl); —(CH$_2$)$_{n2}$ is the substituted $C_1$-$C_6$ alkyl(can be branched alkyl or straight alkyl) in $R^5$, substituted $C_3$-$C_8$ cycloalkyl, or, substituted $C_3$-$C_8$ heterocycloalkyl;

is $R^5$;

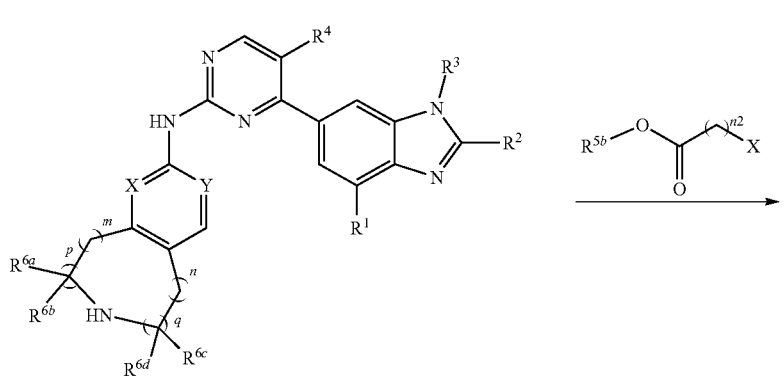

10A

-continued

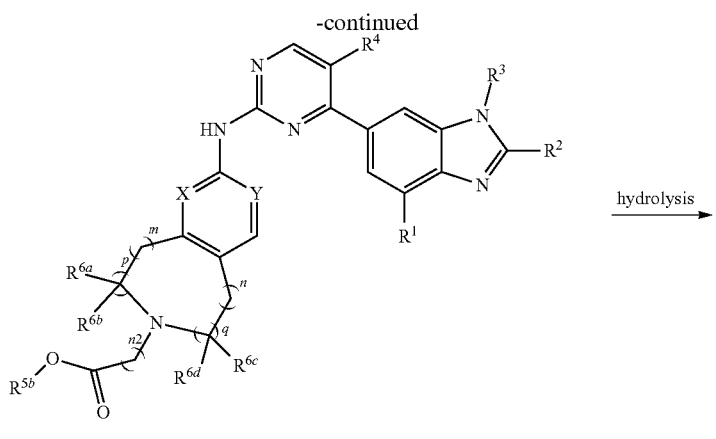

10B

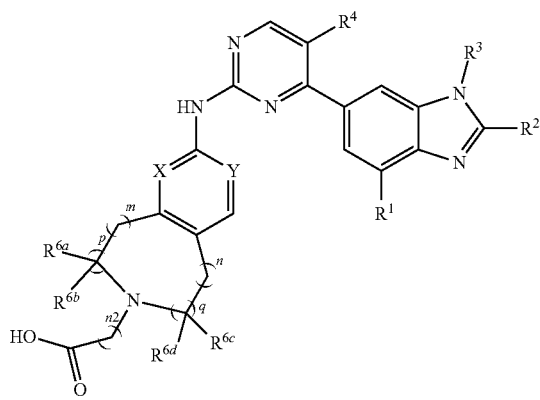

I

X, Y, Z, m, n, p, q, $R^1$, $R^2$, $R^3$, $R^4$, $n_2$, $R^{6a}$, $R^{6b}$, $R^{6c}$ and $R^{6d}$ are defined as above;

Method 11:

when $R^5$ is substituted $C_1$-$C_6$ alkyl, substituted $C_3$-$C_8$ cycloalkyl, the substituent is

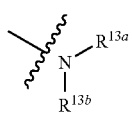

(wherein at least one of $R^{13a}$ and $R^{13b}$ is hydrogen) or hydroxyl, or, unsubstituted $C_3$-$C_8$ heterocycloalkyl, the preparation method for the compound represented by formula I comprises that in organic solvent (e.g. selected from the group consisting of 1,2-dichloroethane, methanol and/or dioxane), in the presence of reductive agent (e.g. sodium triacetoxyborohydride and/or sodium cyanoborohydride), conducting reductive amination reaction with compound 11A and PG-$R^{5c}$—CHO, then removing the protecting group to give compound I; the conditions of the reductive amination reaction and the deprotection reaction can be conventional conditions in the art; $R^{5c}CH_2$— is $R^5$;

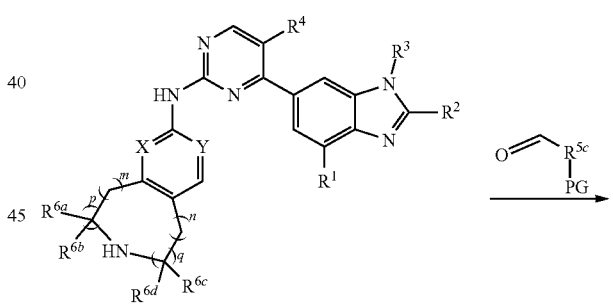

11A

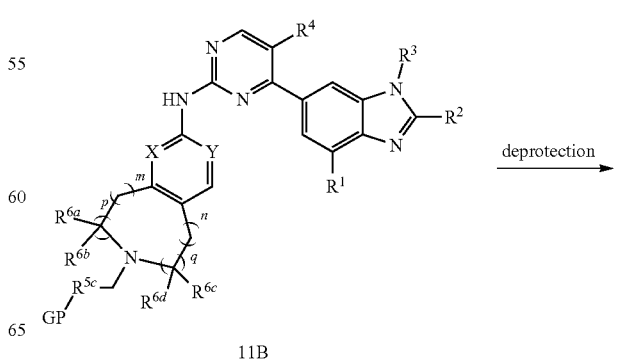

11B

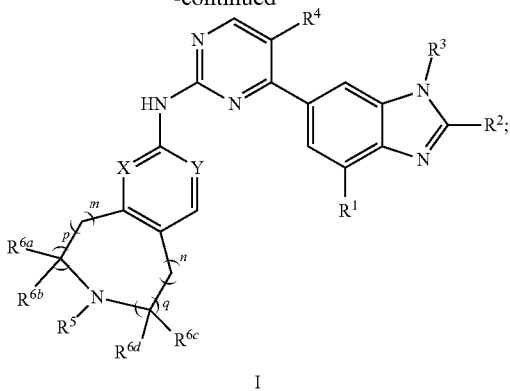

I

X, Y, Z, m, n, p, q, $R^1$, $R^2$, $R^3$, $R^4$, $n_2$, $R^{6a}$, $R^{6b}$, $R^{6c}$ and $R^{6d}$ are defined as above;

PG in the compound represented by formula 11B can be various conventional amino protecting groups in the art, preferably Boc, for the purpose of making certain reactive groups (e.g. amino group) not participate in the reaction when PG-$R^{5c}$—CHO reacts with compound 11A;

Method 12;
when $R^5$ is

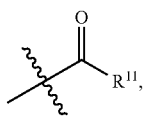

$R^{11}$ is

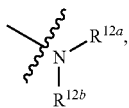

and $R^{12a}$ and $R^{12b}$ are independently substituted or unsubstituted $C_1$-$C_{20}$ alkyl, the preparation method for the compound represented by formula I comprises that in organic solvent, in the presence of triphosgene, conducting condensation reaction with compound 11A and substituted or unsubstituted amino to give compound I; $R^{12a}NR^{12b}$—C(=O)— is $R^5$;

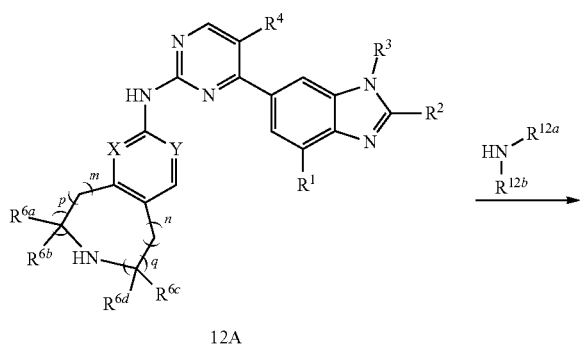

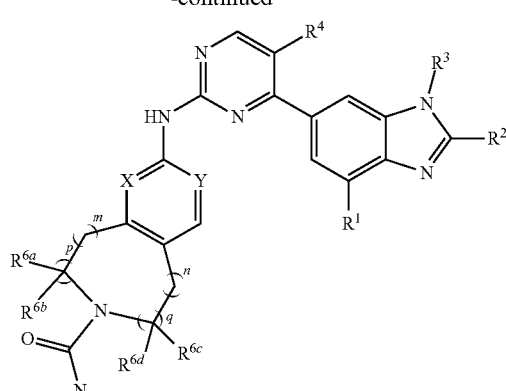

I

X, Y, Z, m, n, p, q, $R^1$, $R^2$, $R^3$, $R^4$, $n_2$, $R^{6a}$, $R^{6b}$, $R^{6c}$ and $R^{6d}$ are defined as above;

Method 13:
when $R^5$ is substituted $C_1$-$C_{20}$ alkyl, or, substituted $C_1$-$C_9$ heterocycloalkyl, the substituent is

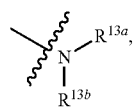

$C_1$-$C_{20}$ alkyl, $C_2$-$C_{20}$ alkenyl, $C_2$-$C_{20}$ alkynyl, substituted $C_1$-$C_9$ heterocycloalkyl, or, $C_3$-$C_{12}$ cycloalkyl, and $R^{13a}$ and $R^{13b}$ are independently hydrogen, $C_1$-$C_{20}$ alkyl, $C_2$-$C_{20}$ alkenyl, $C_2$-$C_{20}$ alkynyl, $C_3$-$C_{12}$ cycloalkyl, borono, phospho, guanidino, thioureido,

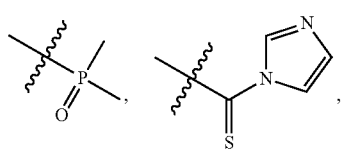

the preparation method for the compound represented by formula I comprises that in organic solvent, in the presence of reductive agent, conducting reductive amination reaction with compound 13A and PG-$NR^{13a}$—$(CH_2)n$-CHO, then removing the protecting group, followed by substitution reaction to give compound I; $R^{13a}NR^{13b}$—$(CH_2)n$- is $R^5$; LG in the formula of the compound is a leaving group;

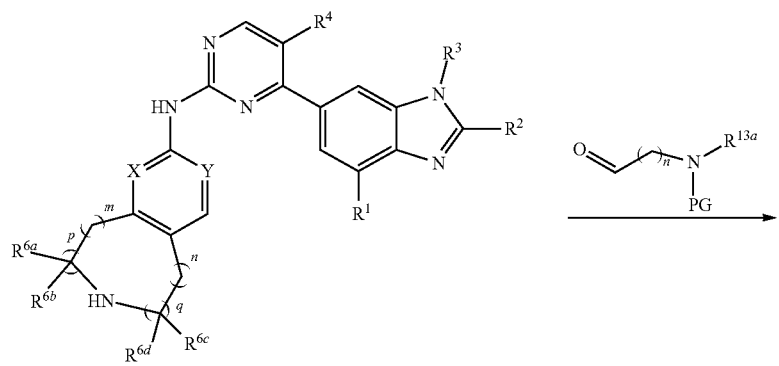
13A
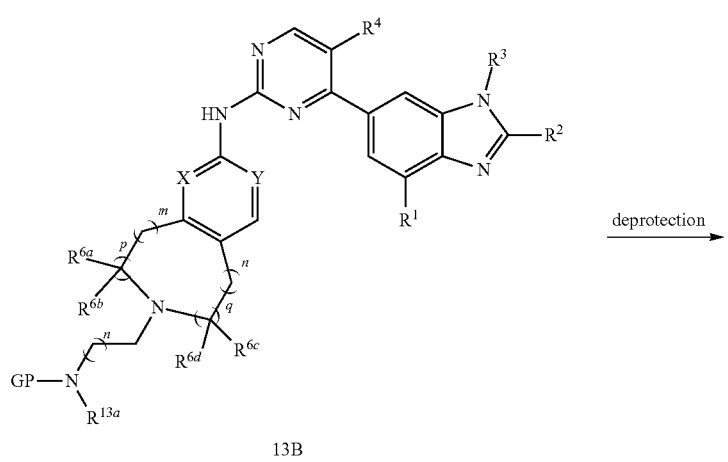
13B
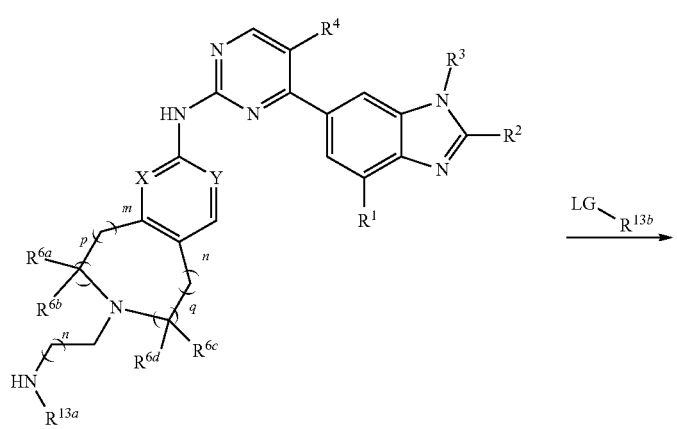
13C

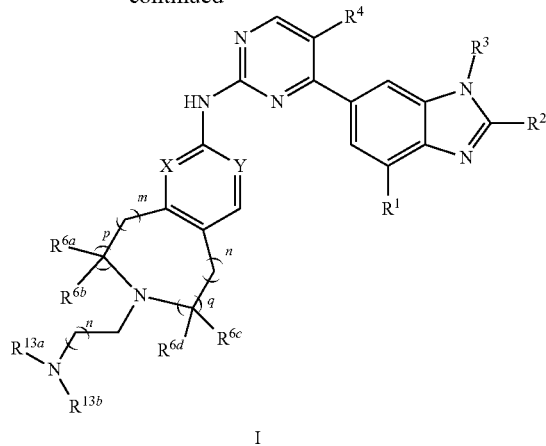

I

X, Y, m, n, p, q, $R^1$, $R^2$, $R^3$, $R^4$, $R^5$, $R^{6a}$, $R^{6b}$, $R^{6c}$ and $R^{6d}$ are defined as above;

Method 14:

when $R^5$ is substituted $C_1$-$C_{20}$ alkyl, or, substituted $C_1$-$C_9$ heterocycloalkyl, the substituent is

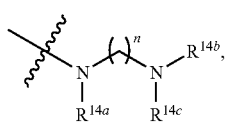

$C_1$-$C_{20}$ alkyl, $C_2$-$C_{20}$ alkenyl, $C_2$-$C_{20}$ alkynyl, substituted $C_1$-$C_9$ heterocycloalkyl, or, $C_3$-$C_{12}$ cycloalkyl, and $R^{14a}$, $R^{14b}$ and $R^{14c}$ are independently hydrogen, $C_1$-$C_{20}$ alkyl, $C_2$-$C_{20}$ alkenyl, $C_2$-$C_{20}$ alkynyl, $C_3$-$C_{12}$ cycloalkyl, borono, phospho, guanidino, thioureido,

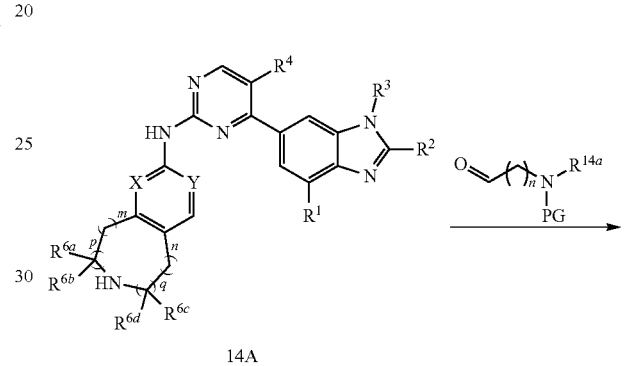

and

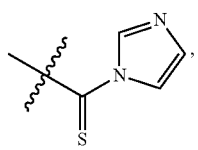 [SMILES: *C(=S)n1ccnc1]

the preparation method for the compound represented by formula I comprises that in organic solvent, in the presence of reductive agent, conducting reductive amination reaction with compound 14A and PG-$NR^{14a}$—$(CH_2)n$-CHO, then removing the protecting group, followed by substitution reaction to give compound I; $R^{14b}NR^{14c}$—$(CH_2)n$-$R^{14a}$ is $R^5$; LG in the formula of compound is a leaving group;

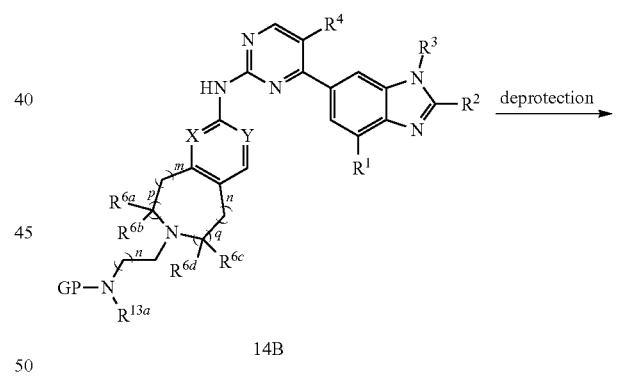

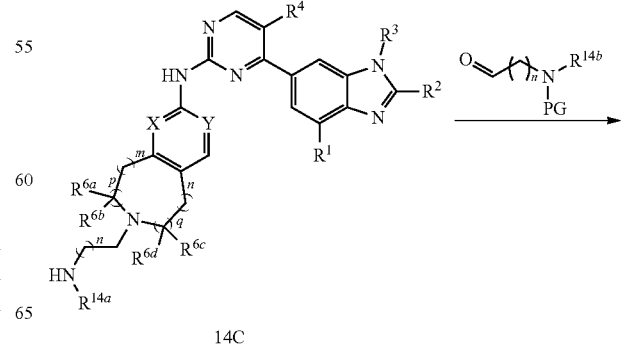

-continued

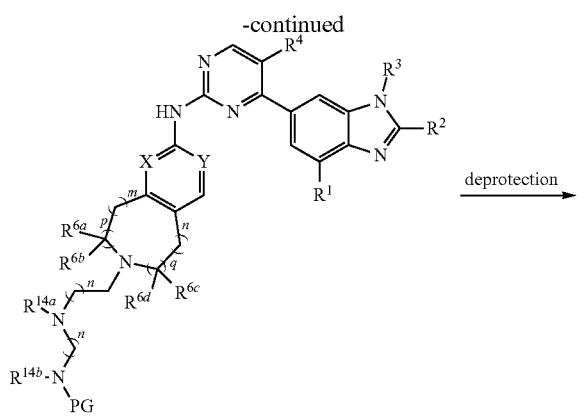

14D

14E

I

X, Y, m, n, p, q, $R^1$, $R^2$, $R^3$, $R^4$, $R^5$, $R^{6a}$, $R^{6b}$, $R^6$ and $R^{6d}$ are defined as above;

Method 15 when $R^5$ is substituted $C_1$-$C_{20}$ alkyl, or, substituted $C_1$-$C_9$ heterocycloalkyl, the substituent is

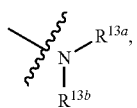

$C_1$-$C_{20}$ alkyl, $C_2$-$C_{20}$ alkenyl, $C_2$-$C_{20}$ alkynyl, substituted $C_1$-$C_9$ heterocycloalkyl, or, $C_3$-$C_{12}$ cycloalkyl, and $R^{13a}$ and $R^{13b}$ are independently hydrogen, $C_1$-$C_{20}$ alkyl, $C_2$-$C_{20}$ alkenyl, $C_2$-$C_{20}$ alkynyl, $C_3$-$C_{12}$ cycloalkyl, borono, phospho, guanidino, thioureido,

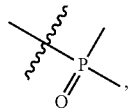 [SMILES: *P(C)(C)=O]

and

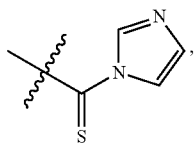 [SMILES: *C(=S)n1ccnc1]

the preparation method for the compound represented by formula I comprises that in organic solvent, in the presence of reductive agent, conducting substitution reaction with compound 15A and LG-(CH$_2$)n-CN, followed by addition reaction to give compound I; LG in the formula compound is a leaving group;

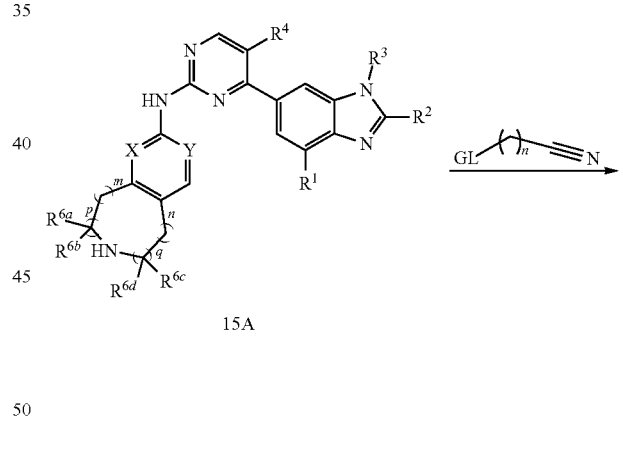

15A

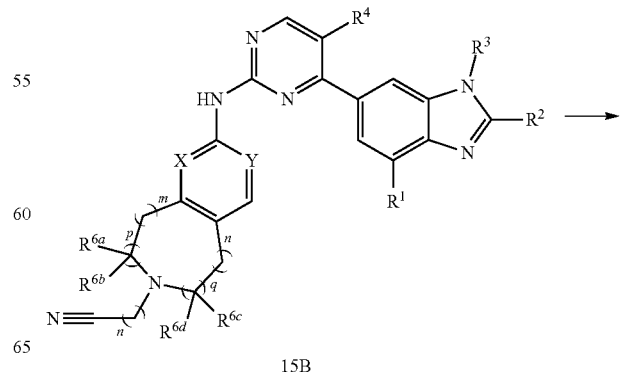

15B

-continued

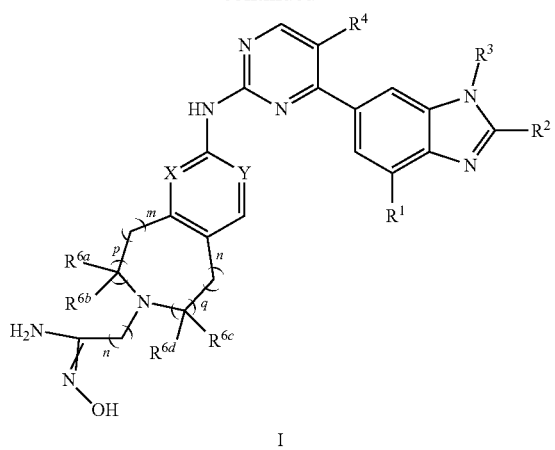

I

X, Y, m, n, p, q, $R^1$, $R^2$, $R^3$, $R^4$, $R^5$, $R^{6a}$, $R^{6b}$, $R^{6c}$ and $R^{6d}$ are defined as above;

after the completing of the preparation method for the nitrogen-containing fused heterocyclic compound, the post-treatment is preferably conducted; the methods and conditions of the post-treatment can be conventional methods and conditions for the post-reaction treatment in the art, preferably comprising washing the reaction system, drying, filtering, evaporating to dryness, then being subjected to column chromatography; or, the reaction system is distilled to remove the solvent, washed, and filtered; or the reaction system is distilled to remove the solvent, subjected to thin layer chromatography.

The present invention also provides a compound II, which is selected from the group consisting of

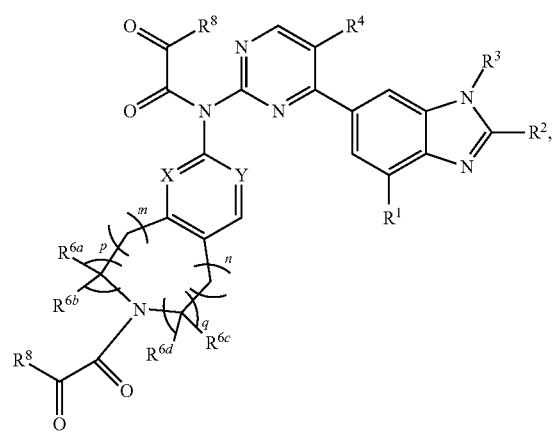

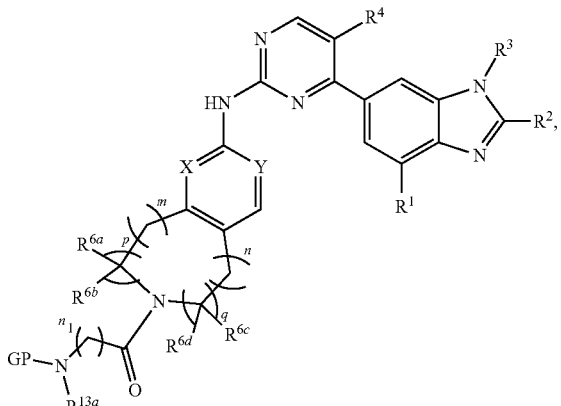

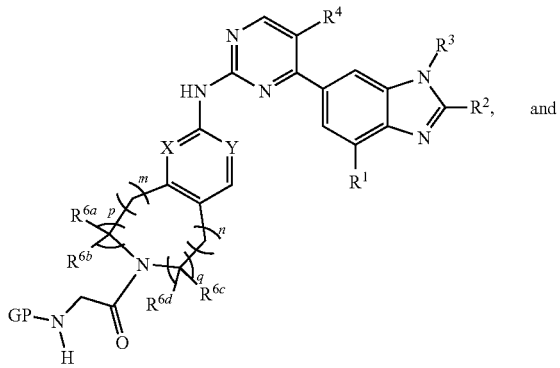

and

11B
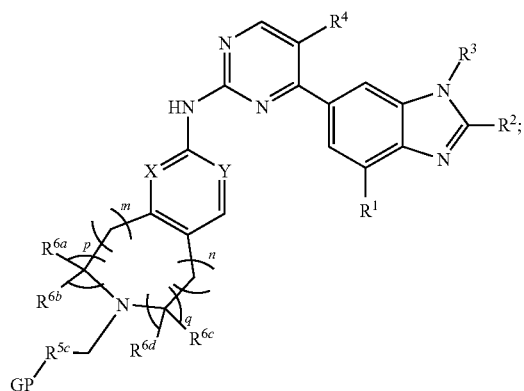
wherein m, n, p, q, X, Y, $R^1$, $R^2$, $R^3$, $R^4$, $R^5$, $R^{5a}$, $R^{5b}$, $R^{5c}$, $R^{6a}$, $R^{6b}$, $R^{6c}$, $R^{6d}$, $R^8$, $R^{13a}$ and PG are defined as above.
Preferably, the compound II is selected from the group consisting of
2-g
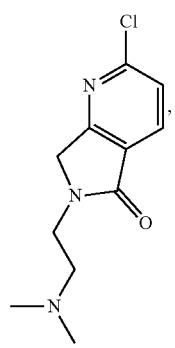
I-4-b
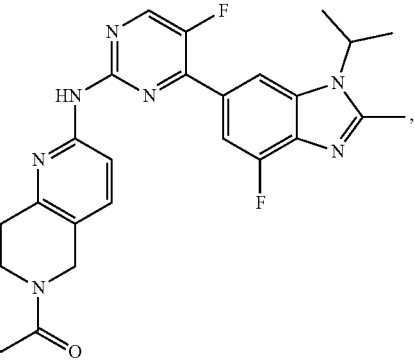
I-10-b
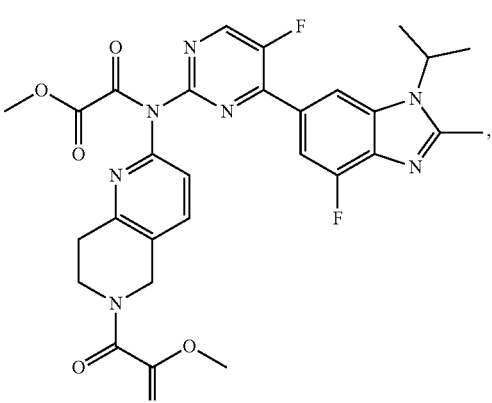
I-15-a
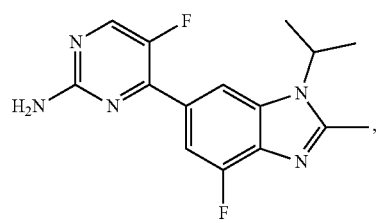
I-16-b
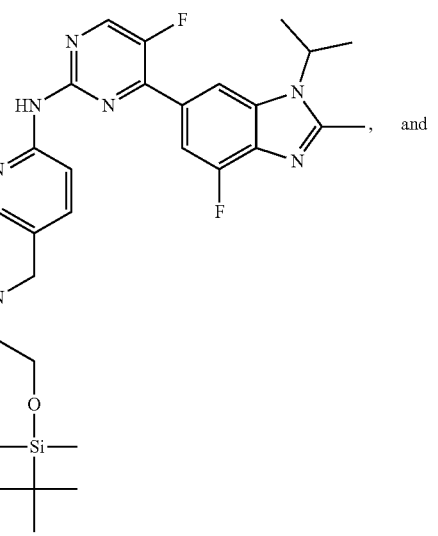
and
I-17-b
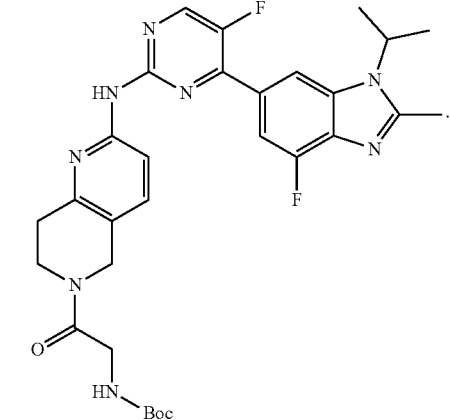
The present invention also provides a use of the nitrogen-containing fused heterocyclic compound, the pharmaceutically acceptable salt, the enantiomer, the diastereomer, the tautomer, the solvate, the metabolite or the drug precursor thereof in manufacturing medicament, the medicament is used for the prevention or the treatment of disorder associated with abnormal cell cycle regulation; the "disorder associated with abnormal cell cycle regulation" is preferably "disorder associated with abnormality of cyclin-dependent kinase (preferably CDK4 and/or CDK6)", more preferably tumor, most preferably malignant tumor (e.g. breast cancer).

The present invention also provides a use of the nitrogen-containing fused heterocyclic compound, the pharmaceutically acceptable salt, the enantiomer, the diastereomer, the tautomer, the solvate, the metabolite or the drug precursor thereof in manufacturing an inhibitor of cyclin-dependent kinase (preferably CDK4 and/or CDK6).

The present invention also provides a use of the nitrogen-containing fused heterocyclic compound, the pharmaceutically acceptable salt, the enantiomer, the diastereomer, the tautomer, the solvate, the metabolite or the drug precursor thereof in manufacturing medicament having tumor cell inhibitory activity; the tumor cell is preferably cancer cell; the cancer cell is preferably breast cancer cell; the breast cancer cell is preferably selected from the group consisting of breast cancer cell MCF-7, T-47D and ZR-75-1.

The present invention also provides a composition, which comprises the nitrogen-containing fused heterocyclic compound, the pharmaceutically acceptable salt, the enantiomer, the diastereomer, the tautomer, the solvate, the metabolite or the drug precursor thereof, and at least a pharmaceutical excipient.

The dose of the nitrogen-containing fused heterocyclic compound, the pharmaceutically acceptable salt, the enantiomer, the diastereomer, the tautomer, the solvate, the metabolite or the drug precursor thereof can be a therapeutically effective dose.

The select of the pharmaceutical excipient varies depending on the route of administration and the characteristic of action, can generally be fillers, diluents, adhesives, wetting agents, disintegrants, lubricants, emulsifiers, suspending agents etc. that are conventional in the art.

The route of administration of the pharmaceutical composition can be oral administration, injection (intravenous, intramuscular, subcutaneous and intracoronary), sublingual administration, buccal administration, rectal administration, transurethral administration, transvaginal administration, nasal administration, inhaled administration or topical administration, preferably oral administration.

In the present invention, unless otherwise specified, the following terms in the description and the claims of the invention have the following meanings:

The term "halogen" is preferably fluorine, chlorine, bromine, iodine, more preferably fluorine.

The term "$C_1$-$C_{20}$ alkyl" refers to a straight chain or branched saturated hydrocarbon group containing 1 to 20 carbon atoms. Alkyl can be optionally substituted with one or more than one substituent described in the present invention. Examples of alkyl include but not limited to methyl (Me, —$CH_3$), ethyl (Et, —$CH_2CH_3$), n-propyl (n-Pr, —$CH_2CH_2CH_3$), isopropyl (i-Pr, —$CH(CH_3)_2$), n-butyl(n-Bu, —$CH_2CH_2CH_2CH_3$), 2-methylpropyl or isobutyl (i-Bu, —$CH_2CH(CH_3)_2$), 1-methylpropyl or sec-butyl (s-Bu, —$CH(CH_3)CH_2CH_3$), tert-butyl (t-Bu, —$C(CH_3)_3$), n-pentyl (—$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl(-$C(CH_3)_2CH_2CH_3$), 3-methyl-2-butyl(-$CH(CH_3)CH(CH_3)_2$), 3-methyl-1-butyl(-$CH_2CH_2CH(CH_3)_2$), 2-methyl-1-butyl(-$CH_2CH(CH_3)CH_2CH_3$), n-hexyl (—$CH_2CH_2CH_2CH_2CH_2CH_3$), 4-methylpentyl(-$CH_2CH_2CH_2CH(CH_3)CH_3$), 3-methylpentyl (—$CH_2CH_2CH(CH_3)CH_2CH_3$), 2-methylpentyl (—$CH_2CH(CH_3)CH_2CH_2CH_3$), 2-hexyl (—$CH(CH_3)CH_2CH_2CH_2CH_3$), 3-hexyl (—$CH(CH_2CH_3)(CH_2CH_2CH_3)$), 3,3-dimethylbutyl (—$CH_2CH_2C(CH_3)_2CH_3$), 2,2-dimethylbutyl (—$CH_2C(CH_3)_2CH_2CH_3$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl(-$C(CH_3)_2CH(CH_3)_2$), 3,3-dimethyl-2-butyl(-$CH(CH_3)C(CH_3)_3$), n-heptyl, n-octyl etc.

In the present invention, the term "alkenyl" refers to a straight, branched, or cyclic non-aromatic hydrocarbon group containing the specified number of carbon atoms and at least one carbon-carbon double bond. Alkenyl is preferably containing one carbon-carbon double bond, and up to four non-aromatic carbon-carbon double bonds can be present. Thus, "$C_{2-12}$ alkenyl" refers to an alkenyl group having 2 to 12 carbon atoms. "$C_{2-6}$ alkenyl" refers to an alkenyl group having 2 to 6 carbon atoms, including vinyl, propenyl, butenyl, 2-methylbutenyl and cyclohexenyl. The straight chain, branched chain or cyclic portion of alkenyl can contain double bond, and if it is substituted alkenyl, the alkenyl can be substituted.

The term "alkynyl" refers to a straight, branched, or cyclic hydrocarbon group containing the specified number of carbon atoms and at least one carbon-carbon triple bond. Up to three carbon-carbon triple bonds can be present. Thus, "$C_{2-12}$ alkynyl" refers to an alkynyl group having 2 to 12 carbon atoms. "$C_{2-6}$ alkynyl" refers to an alkynyl group having 2 to 6 carbon atoms, including but not limited to ethynyl, propynyl, butynyl, and 3-methylbutynyl.

The term "$C_1$-$C_{20}$ alkoxy" refers to $C_1$-$C_{20}$ alkyl connected by the oxygen atom; the $C_1$-$C_{20}$ alkyl is defined as above.

The term "$C_1$-$C_{20}$ alkylthio" refers to $C_1$-$C_{20}$ alkyl connected by the sulfur atom; the $C_1$-$C_{20}$ alkyl is defined as above.

The term "$C_1$-$C_{20}$ silyl" refers to $C_1$-$C_{20}$ alkyl connected by the silicon atom; the $C_1$-$C_{20}$ alkyl is defined as above.

The term "$C_3$-$C_{12}$ cycloalkyl" refers to a cyclic hydrocarbon group that contains 3 to 12 ring-forming carbon atoms, can be saturated or partially unsaturated (contain 1 or 2 double bonds, but none of the rings have a fully conjugated π electron system), and does not contain heteroatom; including a monocycle containing 3 to 12 carbon atoms or a bicycle or tricycle containing 7 to 12 carbon atoms (including spiro ring, bridged ring and fused ring); wherein one or more than one hydrogen atoms in the ring can be independently optionally substituted with one or more than one substituent described herein, and the carbon atoms can be oxidized. A bicyclic carbon ring containing 7 to 12 atoms can be bicyclic[4,5], [5,5], [5,6] or [6,6] system, and a bicyclic carbon ring containing 9 or 10 atoms can be bicyclic[5,6] or [6,6] system. Suitable cycloalkyl group include, but is not limited to, cycloalkyl, cycloalkenyl and cycloalkynyl, e.g. cyclopropyl, cyclobutyl, cyclopentyl, cyclohexyl, 1-cyclopentyl-1-enyl, 1-cyclopentyl-2-enyl, 1-cyclopentyl-3-enyl, cyclohexyl, 1-cyclohexyl-1-enyl, 1-cyclohexyl-2-alkenyl, 1-cyclohexyl-3-enyl, cyclohexadienyl, cycloheptyl, cyclooctyl, cyclononyl, cyclononyl, cycloundecyl, cyclododecyl, adamantyl etc. Depending on the structure, cycloalkyl can be a monovalent or divalent group, i.e. cycloalkylene.

The term "heterocycloalkyl" refers to a 3 to 10 membered monocyclic or polycyclic group (including spiro ring, bridged ring and fused ring) containing 1 to 6 heteroatoms (selected from the group consisting of N, S, B, P, Si, O and Se), wherein each ring can contain one or more than one double bonds, but none of the rings has a fully conjugated π electron system; heteroatom can be substituted or unsubstituted, and N atom can be quaternized. Heterocyclic system can be attached to the main structure via any heteroatom or carbon atom to form a stable compound. One or more than one hydrogen atoms on the ring are independently optionally substituted with one or more than one substituent described herein. For example, 3 to 7 membered monocycle (1 to 6 carbon atoms and 1 to 3 heteroatoms selected from the group consisting of N, O, P, B, Si, S and Se, wherein N, S, B, P or Se is optionally substituted with one or more than one oxygen atoms to form groups like NO, $NO_2$, BOH, SO, $SO_2$, PO, $PO_2$ and SeO, meanwhile —$CH_2$— group can be optionally replaced with —C(=O)—, —C(=S)— or —C(=N)—; —$SH_2$— group can be optionally replaced with —S(=O)—, —S(=O)$_2$—, —S(=N)— or —S(=N)$_2$—; when the ring is a 3 membered ring, there is only one heteroatom), or a bicyclic ring formed by 7 to 10 atoms (4 to 9 carbons atoms and 1 to 3 heteroatoms selected from the group consisting of N, O, P, B, Si and S, wherein N, S, B or P is optionally substituted with one or more than one oxygen atom to form groups like NO, $NO_2$, BOH, SO, $SO_2$, PO, $PO_2$, SeO, meanwhile —$CH_2$— group can be optionally replaced with —C(=O)—. Depending on the structure, the heterocyclic group can be a monovalent or a divalent group, i.e. heterocyclylene. In some embodiments, N atom in the nitrogen-containing heterocycle can be oxidized to form nitrogen oxide.

The term "heteroaryl" refers to a 3 to 10 membered monocyclic or polycyclic aromatic system containing 1 to 6 heteroatoms (selected from the group consisting of N, S, B, P, Si, O and Se, wherein bicyclic heteroaromatic ring, tricyclic heteroaromatic ring or tetracyclic heteroaromatic ring system forms the ring in a fused form, and wherein N, S, B, P or Se is optionally substituted with one or more than one oxygen atom to form groups like NO, $NO_2$, BOH, SO, $SO_2$, PO, $PO_2$ and SeO, N atom can be quaternized, one or more than one hydrogen atom on the ring is independently optionally substituted with one or more than one substituent described herein. Heteroaryl can be attached to the main structure via any heteroatom or carbon atom to form a stable compound. Heteroaryl includes, but is not limited to, monocycle formed by 3 to 7 atoms, or bicyclic ring formed by 7 to 10 atoms, or tricyclic ring formed by 10 to 15 atoms. A bicyclic ring containing 7 to 10 atoms can be bicyclic[4,5], [5,5], [5,6] or [6,6] system, tricyclic ring containing 10 to 15 atoms can be tricyclic[5,5,6], [5,7,6] or [6,5,6] system. Depending on the structure, the heteroaryl can be a monovalent or divalent group, i.e. heteroarylene. Examples of heteroaryl include but not limited to 2-furyl, 3-furyl, N-imidazolyl, 2-imidazolyl, 4-imidazolyl, 5-imidazolyl, 3-isoxazolyl, 4-isoxazolyl, 5-isoxazolyl, 2-oxazolyl, 4-oxazolyl, 5-oxazolyl, 4-methylisoxazol-5-yl, N-pyrrolyl, 2-pyrrolyl, 3-pyrrolyl, 2-pyridyl, 3-pyridyl, 4-pyridyl, 2-pyrimidinyl, 4-pyrimidinyl, pyrimidin-5-yl, pyridazinyl(e.g. 3-pyridazinyl), 2-thiazolyl, 4-thiazolyl, 5-thiazolyl, tetrazolyl (e.g. 5-tetrazolyl), triazolyl (e.g. 2-triazolyl and 5-triazolyl), 2-thienyl, 3-thienyl, pyrazolyl (e.g. 2-pyrazolyl), isothiazolyl, 1,2,3-oxadiazolyl, 1,2,5-oxadiazolyl, 1,2,4-oxadiazolyl, 1,2,3-triazolyl, 1,2,3-thiodiazolyl, 1,3,4-thiodiazolyl, 1,2,5-thiodiazolyl, 1,3,4-thiadiazole-2-yl, pyrazinyl, pyrazin-2-yl, 1,3,5-triazinyl, benzo[d]thiazol-2-yl, imidazo[1,5-a]pyridin-6-yl, benzimidazolyl, benzoxazolyl, quinoxalinyl, 1,8-naphthyridinyl, benzofuranyl, benzothienyl, benzothiazolyl, indolyl (e.g. 2-indolyl), purinyl, quinolyl (2-quinolinyl, 3-quinolinyl, 4-quinolinyl), isoquinolinyl (e.g, 1-isoquinolyl, 3-isoquinolinyl or 4-isoquinolinyl), tetrahydronaphthyl, benzopyrazolyl, acridinyl, benzimidazolyl, benzoindolyl, benzoisoxazinyl, benzo[4,6]imidazo[1,2-a]pyridinyl, benzo[d]imidazo[2,1-b]thiazolyl, benzofuranyl, benzonaphthofuranyl, benzothiadiazolyl, benzothiazolyl, benzothiophenyl, benzotriazolyl, benzothiopyranyl, benzoxazinyl, benzoxazolyl, benzothiazolyl, β-carbolinyl, carbazolyl, o-naphthyridinyl, dibenzofuranyl, imidazopyridyl, imidazothiazolyl, indazolyl, indolizinyl, indolyl, isobenzothienyl, isoindolinyl, isoquinolinyl, isothiazolidinyl, isothiazolyl, naphthyridinyl, decahydroindolyl, decahydroisoindolyl, oxazolidinedionyl, oxazolidinyl, oxazolopyridinyl, oxazolyl, oxiranyl, tea-diazobenzene, phenanthridinyl, phenanthrolinyl, phenarsazinyl, phenazinyl, phenothiazinyl, phenoxazinyl, phthalazinyl, pteridinyl, pyridopyridyl, quinazolinyl, quinoxalinyl, thiophenyl, triazinyl, 2H-pyrrolo[3,4-c]pyridinyl, pyrazolo[2',1':2,3]oxazolo[4,5-c]pyridyl, imidazo[2',1':2,3]thiazolo[4,5-c]pyridyl, imidazo[2',1':2,3]thiazolo[4,5-b]pyridyl, imidazo[2',1':2,3]thiazolo[5,4-b]pyridyl, pyrazolo[2',1':2,3]thiazolo[4,5-b]pyrazinyl, 1H-benzo[4,5]thieno[2,3-d]imidazolyl, 1-methyl-1H-benzo[4,5]thieno[2,3-d]imidazolyl, imidazo[2',1':2,3]thiazolo[4,5-b]pyrazinyl, imidazo[2',1':2,3]thiazolo[5,4-b]pyridyl, imidazo[2',1':2,3]thiazolo[4,5-c]pyridyl, 1H-benzo[f]imidazo[4,5-b][1,4]thiazepine etc.

The term "aryl" refers to monocyclic, bicyclic, and tricyclic carbon ring system, wherein at least one ring system is aromatic, each ring system contains 3 to 7 atoms, one or more than one hydrogen atom on the ring is independently optionally substituted with one or more than one substituent described herein. The term "aryl" can be used interchangeably with the term "aromatic ring", e.g. but not limited to, phenyl, naphthyl and anthracene. Depending on the structure, aryl can be a monovalent group or a divalent group, i.e. arylene.

The term "pharmaceutically acceptable salt" refers to a salt formed by a suitable non-toxic organic acid, inorganic acid, organic base or inorganic base with compound I, which retains the biological activity of compound I. The organic acid can be various conventional organic acids in the art and capable of salt formation, preferably selected from the group consisting of methanesulfonic acid, p-toluenesulfonic acid, maleic acid, fumaric acid, citric acid, tartaric acid, malic acid, lactic acid, formic acid, acetic acid, propionic acid, trifluoroacetic acid, oxalic acid, succinic acid, benzoic acid, isethionic acid, naphthalenesulfonic acid and salicylic acid. The inorganic acid can be various conventional inorganic acid in the art and capable of salt formation, preferably selected from the group consisting of hydrochloric acid, sulfuric acid and phosphoric acid. The organic base can be various conventional organic base in the art and capable of salt formation, preferably selected from the group consisting of pyridines, imidazoles, pyrazines, indoles, purines, tertiary amines and anilines. The tertiary amines organic base is preferably triethylamine and/or N,N-diisopropylethylamine. The anilines organic base is preferably N,N-dimethylaniline. The pyridines organic base is preferably selected from the group consisting of pyridine, methylpyridine, 4-dimethylaminopyridine and 2-methyl-5-ethylpyridine. The inorganic base can be various conventional inorganic base in the art and capable of salt formation, preferably selected from the group consisting of alkali metal hydride, alkali metal hydroxide, alkali metal alkoxide, potassium carbonate, sodium carbonate, lithium carbonate, cesium carbonate, potassium bicarbonate and sodium bicarbonate. The alkali metal hydride is preferably sodium hydride and/or potassium hydride. The alkali metal hydroxide is preferably selected from the group consisting of sodium hydroxide, potassium hydroxide and lithium hydroxide. The alkali metal alkoxide is preferably selected from the group consisting of sodium methoxide, sodium ethoxide, potassium tert-butoxide and sodium tert-butoxide.

In the present invention, the "solvate" refers to a substance formed by the compound I and a suitable solvent. The solvent is preferably water or an organic solvent.

Without violating the common sense in the art, the above preferred conditions can be arbitrarily combined, then preferred embodiments of the present invention are obtained.

The reagents and raw materials used in the present invention are commercially available.

The positive and progressive effect of the present invention is that the compound of the present invention exhibits high selectivity and high inhibitory activity with respect to CDK4 and CDK6 at a molecular level, an excellent inhibitory activity with respect to breast cancer cells at a cellular level, and significant inhibition of tumor cell proliferation associated with cyclin-dependent kinase activity at an animal level. The compound also exhibits good stability with respect to liver microsome of human or mouse etc. without significant inhibition of metabolic enzymes, good in vivo absorption in mice and rats, high bioavailability and good druggability.

DETAILED DESCRIPTION OF THE PREFERRED EMBODIMENT

The structure of all the compound of the present invention can be identified by nuclear magnetic resonance ($^1$H NMR) and/or mass spectrometry (MS). $^1$H NMR chemical shift (δ) is recorded in PPM ($10^{-6}$). NMR was determined on a Bruker AVANCE-400 spectrometer.

LC-MS was determined on Agilent 1200 HPLC/6120 mass spectrometer.

The thin-layer silica gel was Yantai Huanghai HSGF254 or Qingdao GF254 silica gel plate. Column chromatography generally uses Yantai Huanghai 200-300 mesh silica gel as carrier.

Preparation Embodiment 1

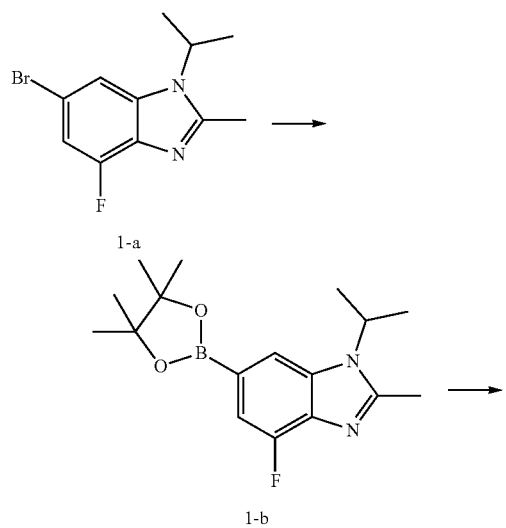

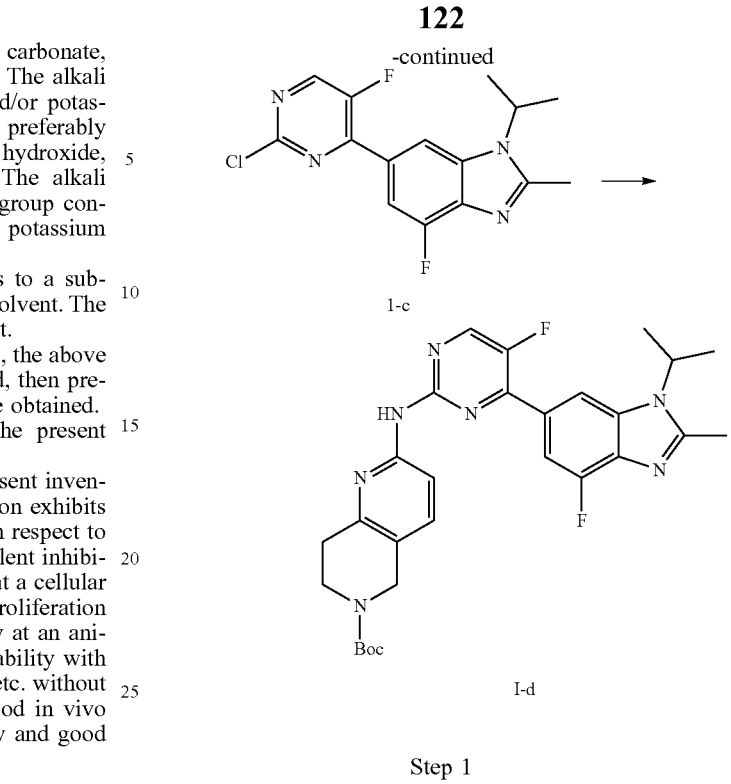

Step 1

6-Bromo-4-fluoro-1-isopropyl-2-methyl-1H-benzimidazole (200 mg, 0.73765 mmol) (compound represented by formula 1-a), bis(pinacolato)diboron (280 mg, 1.1 mmol), tricyclohexylphosphine (37 mg, 0.1320 mmol), potassium acetate (218 mg, 2.221 mmol) and palladium acetate (19 mg, 0.1148 mmol) were added to dimethyl sulfoxide (2 mL), and the mixture was stirred under nitrogen atmosphere at 90° C. for 2 hours. After cooling to room temperature, the reaction solution was diluted with 10 mL ethyl acetate and filtered. The filtrate was washed with saturated brine, dried over anhydrous sodium sulfate. The organic layer was concentrated and purified by silica gel column chromatography (ethyl acetate/n-hexane 0 to 50%) to give compound 4-fluoro-1-isopropyl-2-methyl-6-(4,4,5,5-tetramethyl-1,3,2-dioxaborolan-2-yl)-benzimidazole represented by formula 1-b (180 mg, 0.5657 mmol). LC-MS: m/z: (M+H)$^+$=319.2.

Step 2

2,4-Dichloro-5-fluoropyrimidine (110 mg, 0.65880 mmol) (represented by formula 1-b), 4-fluoro-1-isopropyl-2-methyl-6-(4,4,5,5-tetramethyl-1,3,2-dioxaborolan-2-yl)-benzimidazole (180 mg, 0.5657 mmol), (bis(triphenylphosphine))palladium dichloride (30 mg) were added to 2M sodium carbonate solution (1 mL) and ethylene glycol dimethyl ether (3 mL), and the mixture was stirred under nitrogen atmosphere at 85° C. for 2 hours. After cooling to room temperature, the reaction solution was diluted with 10 mL ethyl acetate, washed with saturated brine, and dried over anhydrous sodium sulfate. The organic phase was concentrated and recrystallized from acetonitrile, filtered to give compound 6-(2-chloro-5-fluoro-pyrimidin-4-yl)-4-fluoro-1-isopropyl-2-methyl-benzimidazole represented by formula 1-c (135 mg, 0.4183 mmol). LC-MS: m/z: (M+H)$^+$=323.2.

Step 3

6-(2-Chloro-5-fluoro-pyrimidin-4-yl)-4-fluoro-1-isopropyl-2-methyl-benzimidazole (110 mg, 0.3409 mmol) (represented by formula 1-c), tert-butyl 2-amino-7,8-dihydro-1,6-naphthyridine-6-carboxylate (85 mg, 0.3410 mmol), cesium carbonate (222 mg, 1.1507 mmol), 4,5-bis(diphenylphosphino)-9,9-dimethylxanthene (17 mg, 0.02938 mmol), tris(dibenzylideneacetone)dipalladium (13 mg) were added to 1,4-dioxane (3 mL), and the mixture was stirred under nitrogen atmosphere at 110° C. for 12 hours. After cooling to room temperature, the reaction solution was diluted with 10 mL ethyl acetate, filtered, and the filtrate was concentrated and purified by silica gel column chromatography (dichloromethane/methanol 0-10%) to give tert-butyl 2-((5-fluoro-4-(7-fluoro-3-isopropyl-2-methyl-benzimidazol-5-yl)pyrimidin-2-yl)amino)-7,8-dihydro-5H-1,6-naphthyridine-6-carboxylate represented by formula 1-d (110 mg, 0.2054 mmol). LC-MS: m/z: (M+H)$^+$=536.2.

Preparation Embodiment 2

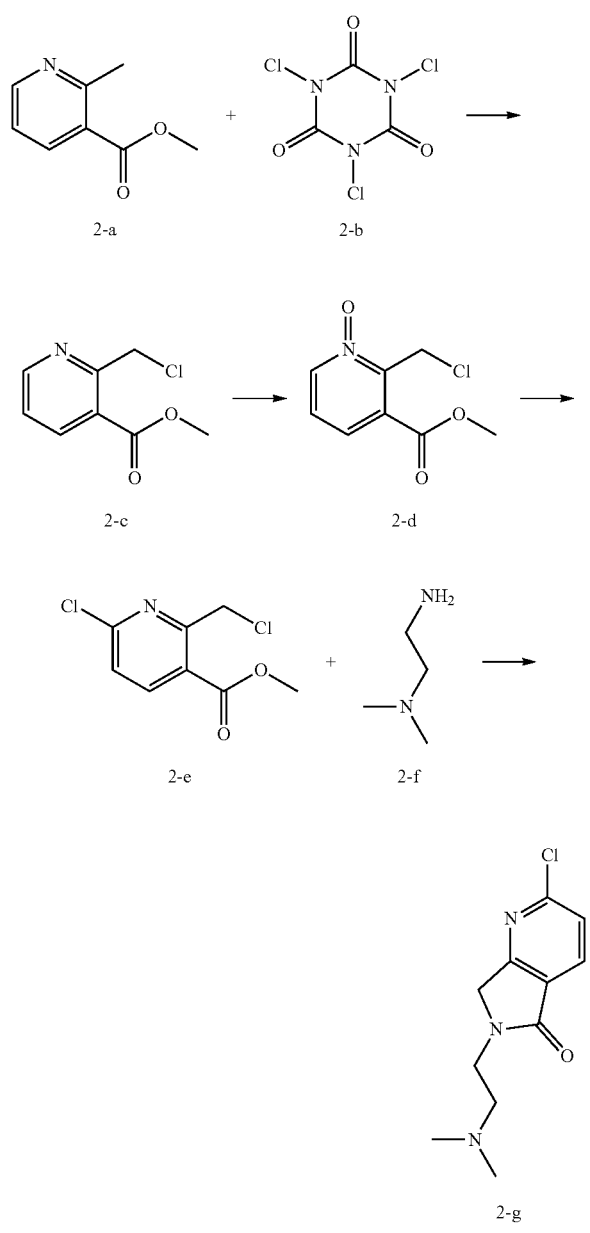

Step 1

Methyl 2-methyl nicotinate (1.9 g, 13.0 mmol) (represented by formula 2-a) and trichloroisocyanuric acid (3.7 g, 16.0 mmol) (represented by formula 2-b) were dissolved in dichloromethane (50 mL), and the mixture was stirred at room temperature for 18 hours. Then saturated aqueous sodium bicarbonate solution was added to the reaction solution, the mixture was extracted with dichloromethane (30 mL×2), the dichloromethane layers were combined, dried over anhydrous sodium sulfate, filtered, and the filtrate was purified by column chromatography (silica gel, petroleum ether/ethyl acetate=100% to 75%) to give methyl 2-(chloromethyl)nicotinate represented by formula 2-c (1.9 g, 10.3 mmol) as a pale yellow solid. LC-MS: m/z: (M+H)$^+$=186.

Step 2

Methyl 2-(chloromethyl)nicotinate (1.9 g, 10 mmol) (represented by formula 2-c) and m-chloroperoxybenzoic acid (2 g, 11.6 mmol) were dissolved in dichloromethane (50 mL), and the mixture was stirred at room temperature for 16 hours. Then saturated aqueous sodium bicarbonate solution was added to the reaction solution, the mixture was extracted with dichloromethane (60 mL×2), the dichloromethane layers were combined, dried over anhydrous sodium sulfate, filtered, and the filtrate was purified by column chromatography (silica gel, petroleum ether/ethyl acetate=100% to 0%) to give methyl 2-(chloromethyl)nicotinate 1-oxide represented by formula 2-d (15 g, 7.4 mmol) as a pale yellow solid. LC-MS: m/z: (M+H)$^+$=202.2.

Step 3

Methyl 2-(chloromethyl)nicotinate 1-oxide (represented by formula 2-d) (1.9 g, 9.4 mmol) was dissolved in phosphorous oxychloride (9 mL), the mixture was stirred under reflux for 5 hours, then cooled and poured into ice water. Then saturated aqueous sodium bicarbonate solution was added, the mixture was extracted with dichloromethane (60 mL×2), and methylene chloride layers were combined, dried over anhydrous sodium sulfate, filtered, and the filtrate was purified by column chromatography (silica gel, petroleum ether/ethyl acetate=100%-0%) to give methyl 6-chloro-2-(chloromethyl)nicotinate represented by formula 2-e (0.88 g, 4.0 mmol) as a pale yellow solid. LC-MS m/z: (M+H)$^+$=240.2.

Step 4

Methyl 6-chloro-2-(chloromethyl) nicotinate (represented by formula 2-e)(70 mg, 0.32 mmol) and N',N'-dimethylethylenediamine (represented by formula 2-f) (50 mg, 0.57 mmol) were dissolved in tetrahydrofuran (10 mL), and the mixture was stirred at room temperature for 16 hours. The reaction solution was concentrated and purified by thin-layer chromatography (silica gel, dichloromethane/methanol=10/1) to give 2-chloro-6-(2-(dimethylamino)ethyl)-6,7-dihydro-5H-pyrrolo[3,4-b]pyridin-5-one represented by formula 2-g (40 mg, 0.17 mmol) as a pale yellow solid. LC-MS: m/z: (M+H)$^+$=240.2.

Preparation Embodiment 3

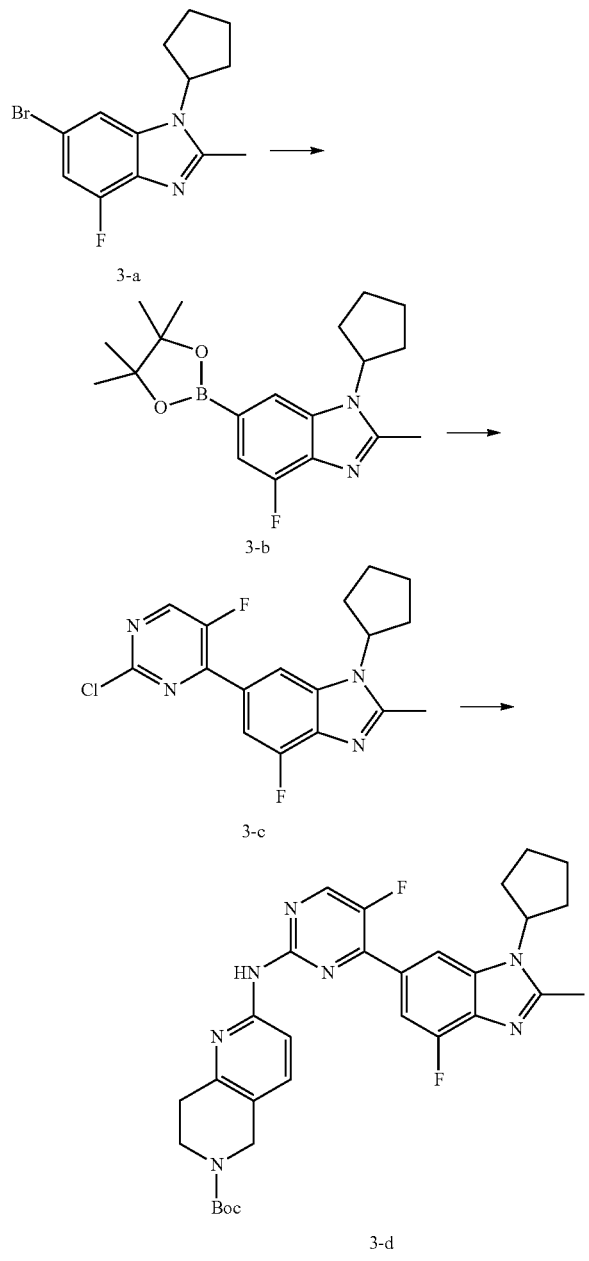

Step 1

6-Bromo-4-fluoro-1-cyclopentyl-2-methyl-benzimidazole (200 mg, 0.6729 mmol) (represented by formula 3-a), bis(pinacolato)diboron (260 mg, 1.1 mmol), tricyclohexylphosphine (37 mg, 0.1320 mmol), potassium acetate (218 mg, 2.221 mmol) and palladium acetate (19 mg, 0.1148 mmol) were added to dimethyl sulfoxide (2 mL), and the mixture was stirred under nitrogen atmosphere at 90° C. for 2 hours. After cooling to room temperature, the reaction solution was diluted with 10 mL ethyl acetate and filtered. The filtrate was washed with saturated brine, dried over anhydrous sodium sulfate. The organic layer was concentrated and purified by silica gel column chromatography (ethyl acetate/n-hexane 0-50%) to give 4-fluoro-1-cyclopentyl-2-methyl-6-(4,4,5,5-tetramethyl-1,3,2-dioxaborolan-2-yl)-benzimidazole represented by formula 3-b (180 mg, 0.523 mmol). LC-MS: m/z: (M+H)$^+$=345.2.

Step 2

2,4-Dichloro-5-fluoropyrimidine (110 mg, 0.65880 mmol), 4-fluoro-1-cyclopentyl-2-methyl-6-(4,4,5,5-tetramethyl-1,3,2-dioxaborolan-2-yl)-benzimidazole (180 mg, 0.523 mmol) (represented by formula 3-b), (bis(triphenylphosphine)palladium dichloride (30 mg) were added to 2M sodium carbonate solution (1 mL) and ethylene glycol dimethyl ether (3 mL), and the mixture was stirred under nitrogen atmosphere at 85° C. for 2 hours. After cooling to room temperature, the reaction solution was diluted with 10 mL ethyl acetate, washed with saturated brine, and dried over anhydrous sodium sulfate. The organic phase was concentrated and recrystallized from acetonitrile to give 6-(2-chloro-5-fluoro-pyrimidine-4-yl)-4-fluoro-1-cyclopentyl-2-methyl-benzimidazole represented by formula 3-c (135 mg, 0.37 mmol). LC-MS: m/z: (M+H)$^+$=349.8.

Step 3

5-(2-Chloro-5-fluoropyrimidin-4-yl)-1-cyclopentyl-7-fluoro-2-methyl-1H-benzo[d]imidazole) (360 mg, 1.03 mmol) (represented by formula 3-c) was dissolved in 5 mL dioxane, tert-butyl 2-amino-7,8-dihydro-1,6-naphthyridine-6(5H)-methylcarboxylate (257 mg, 1.03 mmol), tris(dibenzylideneacetone)dipalladium (94 mg, 0.10 mmol), 4,5-bis(diphenylphosphino)-9,9-dimethylxanthene (119 mg, 0.21 mmol) and cesium carbonate (504 mg, 1.55 mmol) were added, and the mixture was stirred under argon atmosphere at 110° C. for 18 hours. The reaction solution was filtered and evaporated under reduced pressure. The residue was purified by silica gel column chromatography to give the compound represented by formula 3-d as a yellow solid 340 mg, yield 82%. LC-MS: m/z: (M+H)$^+$=548.2.

Preparation Embodiment 4

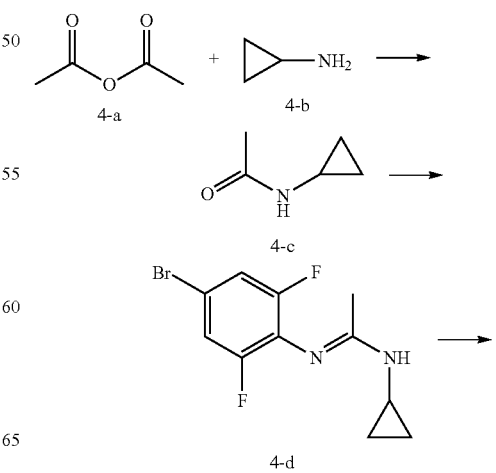

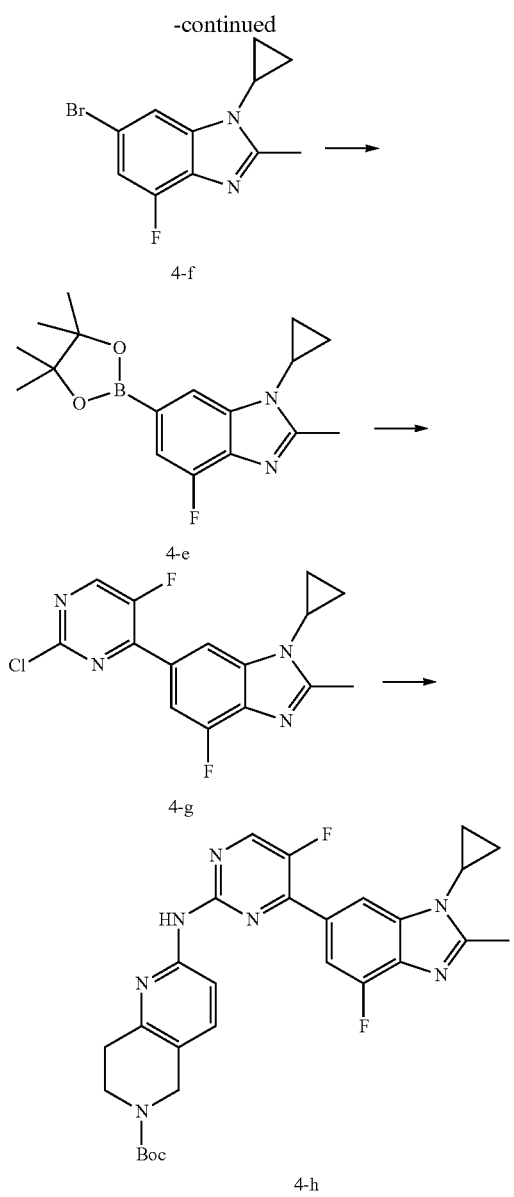

4-f 4-e 4-g 4-h

Step 1

Cyclopropylamine (30 g, 525.5 mmol) and diisopropylacetamide (80 g, 790.6 mmol) were dissolved in dichloromethane (200 mL), the mixture was cooled to 0° C. and acetic anhydride was slowly added dropwise (115 g, 1126 mmol). After the completion of the addition, the mixture was stirred at room temperature for 16 hours, evaporated under reduced pressure, then ethyl acetate and potassium carbonate (144 g, 1050 mmol) were added. The mixture was stirred at room temperature for 16 hours, filtered, and evaporated under reduced pressure to give 55 g N-cyclopropylacetamide represented by formula 4-c.

Step 2

N-cyclopropylacetamide (54 g, 544.7 mmol), 4-bromo-2,6-difluoroaniline (54.6 g, 263 mmol) and N,N-diisopropylethylamine (50.8 g, 393 mmol) were dissolved in toluene (250 mL), then phosphorus oxychloride (40.3 g, 263 mmol) was slowly added. The mixture was stirred at 100° C. for 16 hours, evaporated under reduced pressure, cooled to room temperature, then dichloromethane was added, washed with saturated sodium bicarbonate solution, and the organic layer was dried over anhydrous sodium sulfate, concentrated, slurried with ethyl acetate, filtered, and the solid was dried to give 43.6 g N'-(4-bromo-2,6-difluoro-phenyl)-N-cyclopropyl-acetamidine represented by formula 4-d. LC-MS m/z: $(M+H)^+=289.1, 291.1$.

Step 3

N'-(4-bromo-2,6-difluoro-phenyl)-N-cyclopropyl-acetamidine (43.6 g, 151 mmol) was dissolved in N,N-dimethylformamide (300 mL), potassium tert-butoxide (28 g, 249.5 mmol) was added slowly, and the mixture was stirred at 100° C. for 3 hours, cooled to room temperature. Then 1.5 L water was added, the mixture was filtered, the solid was washed with water and distilled under reduced pressure to remove water, then slurried with a mixed solvent of dichloromethane/petroleum ether=1/2, and filtered to give 35 g 6-bromo-1-cyclopropyl-4-fluoro-2-methyl-benzimidazole represented by formula 4-f. LC-MS m/z: $(M+H)^+=269.1, 271.1$.

Step 4

6-Bromo-1-cyclopropyl-4-fluoro-2-methyl-benzimidazole (15 g, 55.7 mmol), bis(pinacolato)diboron (16 g, 63 mmol), potassium acetate (10 g, 102 mmol), tricyclohexylphosphine (1.5 g, 5.3 mmol) and palladium acetate (1 g, 4.45 mmol) were dissolved in DMSO (60 mL), and the mixture was stirred under argon atmosphere at 80° C. for 16 hours. The reaction solution was cooled to room temperature, filtered, diluted with water and extracted with dichloromethane. The organic layer was dried over anhydrous sodium sulfate and concentrated to give a crude product, which was slurried with ethyl acetate. Partial product was collected by filtration, and the filtrate was concentrated and purified by column chromatography (petroleum ether/ethyl diacid=100% to 25%) to obtain partial product, the product was combined to give 5 g 1-cyclopropyl-4-fluoro-2-methyl-6-(4,4,5,5-tetramethyl-1,3,2-dioxaborolan-2-yl)-benzimidazole represented by formula 4-e. LC-MS m/z: $(M+H)^+=317.2$.

Step 5

1-Cyclopropyl-4-fluoro-2-methyl-6-(4,4,5,5-tetramethyl-1,3,2-dioxaborolan-2-yl)-benzimidazole (5 g, 15.8 mmol), 2,4-dichloro-5-fluoro-pyrimidine (3 g, 18.0 mmol), sodium carbonate (3 g, 28.3 mmol) and dichlorobis(triphenylphosphine)palladium (550 mg, 0.83 mmol) were dissolved in a mixed solution of ethylene glycol dimethyl ether (70 mL) and water (10 mL), the mixture was stirred under argon atmosphere at 80° C. for 16 hours. The reaction solution was cooled to room temperature, filtered, and the ethylene glycol dimethyl ether was distilled off under reduced pressure. The residue was diluted with water and extracted with dichloromethane. The organic layer was dried over anhydrous sodium sulfate, and concentrated to give a crude product, which was slurried with acetonitrile, filtered and dried to give 4.5 g 6-(2-chloro-5-fluoro-pyrimidin-4-yl)-1-cyclopropyl-4-fluoro-2-methyl-benzimidazole represented by 4-g. LC-MS m/z: $(M+H)^+=321.2$.

Step 6

6-(2-Chloro-5-fluoro-pyrimidin-4-yl)-1-cyclopropyl-4-fluoro-2-methyl-benzimidazole (4.5 g, 14 mmol), tert-butyl 2-amino-7,8-dihydro-5H-1,6-naphthyridine-6-carboxylate (3.8 g, 15 mmol), cesium carbonate (9 g, 27.6 mmol), tris(dibenzylideneacetone)dipalladium (900 mg, 0.98 mmol) and 4,5-bis(diphenylphosphino)-9,9-dimethylxanthene (500 mg, 0.86 mmol) were dissolved in dioxane (100 mL), the mixture was stirred under argon atmosphere at 90° C. for 16 hours, then distilled under reduced pressure to remove the solvent, diluted with a mixed solvent of dichloromethane and methanol, filtered. The filtrate was dried over anhydrous sodium sulfate, concentrated, and purified by column chromatography (dichloromethane/methanol=100% to 90%) to give 7 g tert-butyl 2-((5-fluoro-4-(7-fluoro-3-cyclopropyl-2-methyl-benzimidazol-5-yl)pyrimidin-2-yl)amino)-7,8-dihydro-5H-1,6-naphthyridine-6-carboxylate represented by 4-h. LC-MS m/z: $(M+H)^+$=534.2.

Preparation Embodiment 5

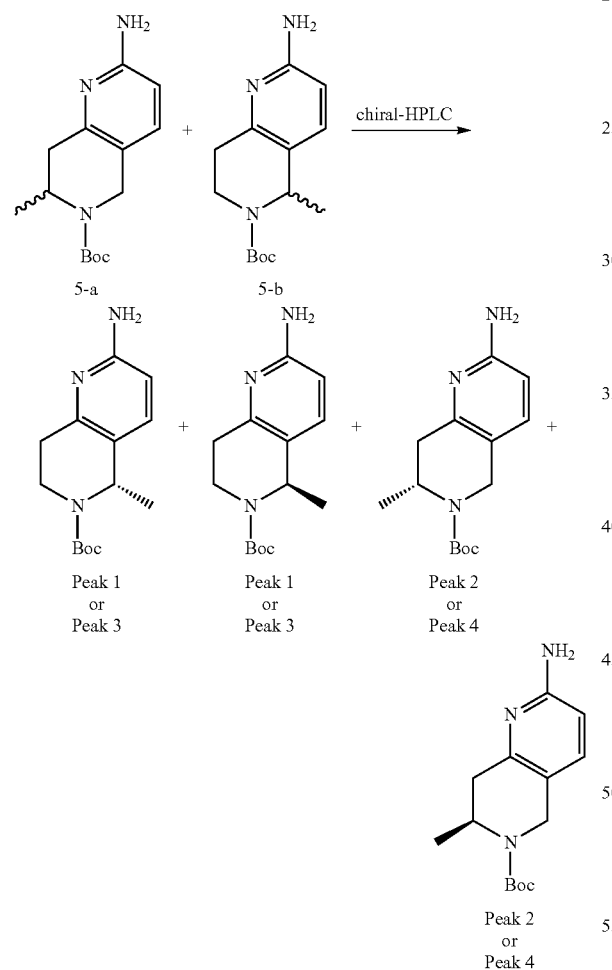

The mixture of tert-butyl 2-amino-7-methyl-7,8-dihydro-5H-1,6-naphthyridine-6-carboxylate and tert-butyl 2-amino-5-methyl-7,8-dihydro-5H-1,6-naphthyridine-6-carboxylate (represented by formula 5-a and 5-b, supplied by KERMANDA) (3.0 g, 11.4 mmol) was isolated via chiral liquid phase preparation to give four isomers, which were tert-butyl 2-amino-5-methyl-7,8-dihydro-5H-1,6-naphthyridine-6-carboxylate (Peak 1, 0.5658 g), tert-butyl 2-amino-5-methyl-7,8-dihydro-5H-1,6-naphthyridine-6-carboxylate (Peak 3, 0.6884 g), tert-butyl 2-amino-7-methyl-7,8-dihydro-5H-1,6-naphthyridine-6-carboxylate (Peak 2, 0.4281 g), tert-butyl 2-amino-7-methyl-7,8-dihydro-5H-1,6-naphthyridine-6-carboxylate (Peak 4, 0.6460 g). LC-MS m/z: $(M+H)^+$=264.2.

Preparation Embodiment 6

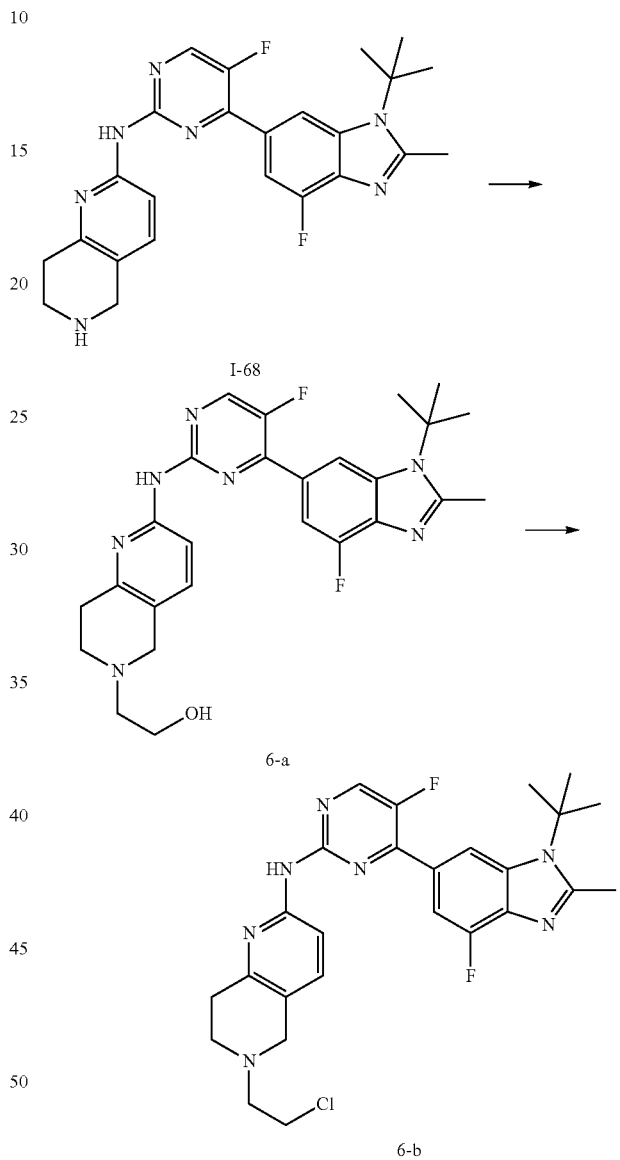

Step 1

DIPEA (1.757 g, 13.59 mmol) and 2-bromoethanol (1.446 g, 11.57 mmol) were added to a suspension of N-(4-(3-tert-butyl-7-fluoro-2-methyl-benzimidazol-5-yl)-5-fluoro-pyrimidin-2-yl)-5,6,7,8-tetrahydro-1,6-naphthyridin-2-amine (1.3 g, 2.892 mmol) (represented by formula I-68) in anhydrous DMF (22 mL) under argon atmosphere at room temperature. The reaction mixture was stirred at 85° C. for 12 hours. TLC monitored that most of the raw materials had already reacted. The reaction mixture was cooled to room temperature and diluted with 20 mL water. The precipitated solid was filtered and the filter cake was washed with water (10 mL×3) and dried in vacuo to give a yellow solid 2-(2-((4-(3-tert-butyl-7-fluoro-2-methyl-benzoimidazol-5-yl)-5-fluoro-pyrimidin-2-yl)amino)-7,8-dihydro-5H-1,6-naphthyridin-6-yl)ethanol represented by formula 3-b (1.1 g, 2.229 mmol) as a pale yellow solid.

$^1$H NMR (400 MHz, Chloroform-d) δ 8.40 (d, J=3.8 Hz, 1H), 8.39 (d, J=1.3 Hz, 1H), 8.23 (d, J=8.4 Hz, 1H), 7.93 (s, 1H), 7.75 (d, J=11.2 Hz, 1H), 7.36 (d, J=8.5 Hz, 1H), 3.78-3.72 (m, 2H), 3.70 (s, 2H), 2.95 (dd, J=10.7, 4.6 Hz, 4H), 2.88 (s, 3H), 2.80-2.75 (m, 2H), 1.91 (s, 9H).

LC-MS m/z: (M+H)$^+$=494.2.

Step 2

Thionyl chloride (7.954 g, 66.86 mmol) was added to a suspension of 2-(2-((4-(3-tert-butyl-7-fluoro-2-methyl-benzimidazol-5-yl)-5-fluoro-pyrimidin-2-yl)amino)-7,8-dihydro-5H-1,6-naphthyridin-6-yl)ethanol (1.1 g, 2.229 mmol) (represented by formula 6-a) in dichloromethane (40 mL) at room temperature under argon atmosphere. The mixture was stirred at room temperature for 16 hours. LCMS monitored the reaction was complete. The solvent was removed by distillation under reduced pressure. The solid residue was dissolved in 100 mL mixed solvent of dichloromethane and methanol (10:1, v/v). The organic phase was washed to neutral with saturated aqueous sodium bicarbonate solution, then washed with saturated brine (50 mL×2). The separated organic phase was evaporated to dryness on a rotary evaporator, the residue was purified by biotage preparative liquid chromatography (methanol/dichloromethane=1% to 5%, v/v, 10 g silica gel column) to give yellow solid N-(4-(3-tert-butyl-7-fluoro-2-methyl-benzimidazol-5-yl)-5-fluoro-pyrimidin-2-yl)-6-(2-chloroethyl)-7,8-dihydro-5H-1,6-naphthyridin-2-amine (600 mg, 1.172 mmol) as a pale yellow solid.

$^1$H NMR (400 MHz, Chloroform-d) δ 8.41-8.36 (m, 2H), 8.22 (d, J=8.5 Hz, 1H), 7.91 (s, 1H), 7.75 (d, J=11.4 Hz, 1H), 7.35 (d, J=8.4 Hz, 1H), 3.72-3.67 (m, 4H), 3.00-2.90 (m, 6H), 2.87 (s, 3H), 1.91 (s, 9H).

LC-MS m/z: (M+H)$^+$=512.2.

Embodiment 3

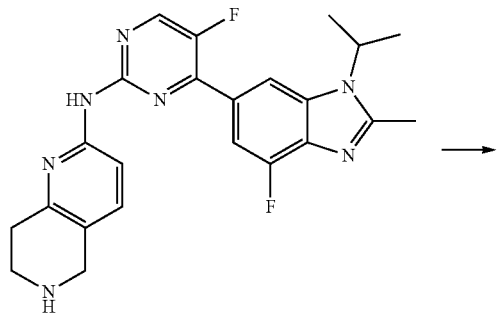

I-1

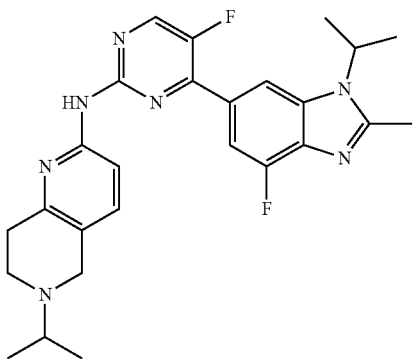

I-3

N-(5-fluoro-4-(7-fluoro-3-isopropyl-2-methyl-benzimidazol-5-yl)pyrimidin-2-yl)-5,6,7,8-tetrahydro-1,6-naphthyridine-2-amine (70 mg, 0.1607 mmol) (represented by formula I-1), 2-bromopropane (40 mg, 0.32523 mmol), N,N-diisopropyl ethylamine (50 mg) were added to 1 mL DMF, and the mixture was stirred at 90° C. for 12 hours. The reaction solution was concentrated and purified by silica gel column chromatography (dichloromethane/methanol 0 to 10%) to give N-(5-fluoro-4-(7-fluoro-3-isopropyl-2-methyl-benzimidazol-5-yl)pyrimidin-2-yl)-6-isopropyl-7,8-dihydro-5H-1,6-naphthyridin-2-amine represented by I-3 (30 mg, 0.06281 mmol). $^1$H-NMR (400 MHz, DMSO-d$_6$) δ 9.90 (s, 1H), 8.68 (d, 1H, J=3.6 Hz), 8.32 (d, 1H, J=1.2 Hz), 8.06 (d, 1H, J=8.4 Hz), 7.69 (d, 1H, J=12.4 Hz), 7.48 (d, 1H, J=1.2 Hz), 4.82-4.89 (m, 1H), 3.63 (s, 2H), 2.81 (br, 4H), 1.97-2.04 (m, 1H), 1.64 (d, 6H, J=6.8 Hz), 1.08 (d, 6H, J=6.0 Hz). LC-MS: m/z: (M+H)$^+$=478.2.

Embodiment 4

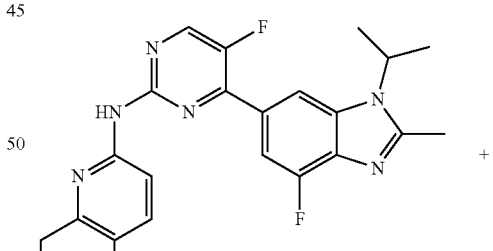

I-1

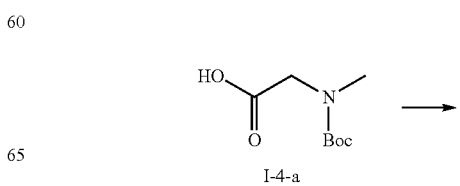

I-4-a

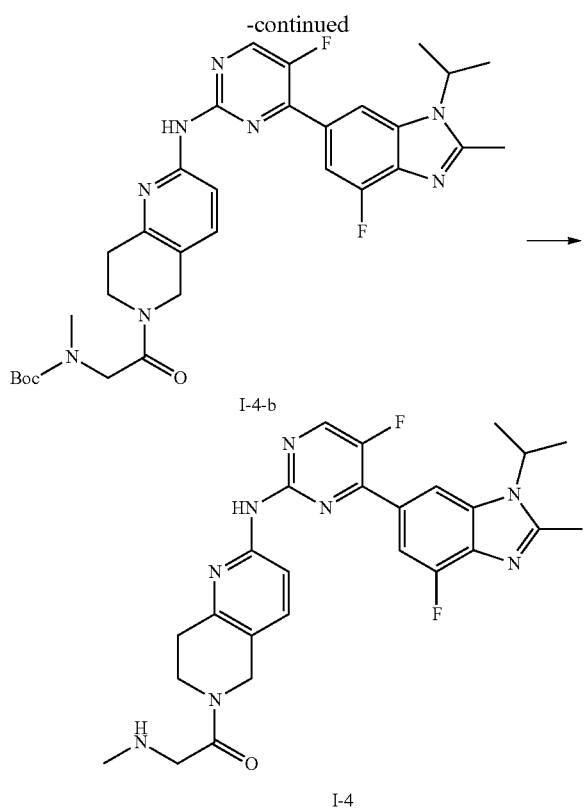

I-4-b

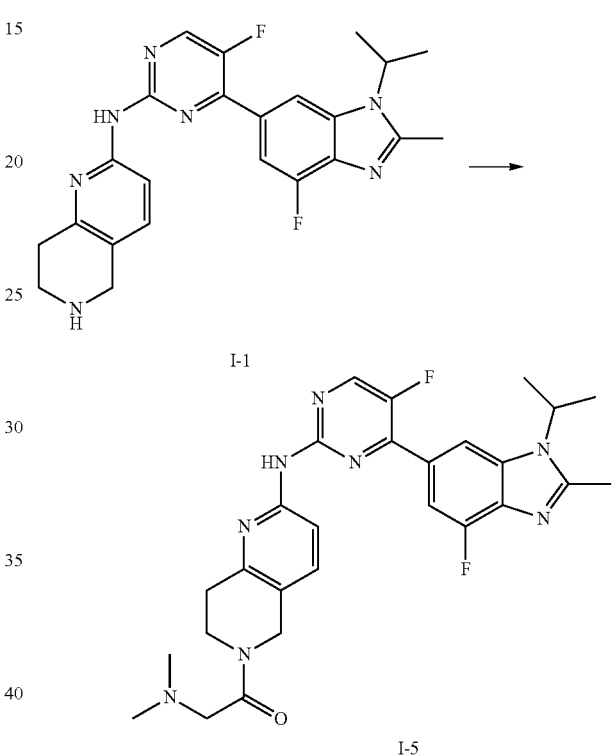

(30 mg, 0.05922 mmol). $^1$H-NMR (400 MHz, CD$_3$OD) δ 8.96-8.97 (m, 1H), 8.62 (s, 1H), 8.22-8.26 (m, 2H), 7.56 (dd, 1H, J=8.8, 2.8 Hz), 5.16-5.23 (m, 1H), 4.87 (s, 1H), 4.78 (s, 1H), 4.32 (s, 1H), 4.27 (s, 1H), 4.08 (t, 1H, J=6.0 Hz), 3.92 (t, 1H, J=6.0 Hz), 3.37-3.38 (m, 2H), 3.24-3.27 (m, 2H), 3.02 (s, 3H), 2.82 (d, 3H, J=2.8 Hz), 1.84 (d, 6H, J=6.8 Hz). LC-MS: m/z: (M+H)$^+$=507.2.

Embodiment 5

Step 1

N-(5-fluoro-4-(7-fluoro-3-isopropyl-2-methyl-benzimidazol-5-yl)pyrimidin-2-yl)-5,6,7,8-tetrahydro-1,6-naphthyridine-2-amine (80 mg, 0.1837 mmol) (represented by formula I-1), N-boc-sarcosine (46 mg, 0.24312 mmol) (represented by formula I-3-a), HOBt (25 mg, 0.18502 mmol), EDCI (36 mg, 0.18779 mmol) were added to 1 mL DMF, and the mixture was stirred at room temperature for 12 hours. The reaction solution was concentrated and purified by silica gel column chromatography (dichloromethane/methanol 0 to 10%) to give tert-butyl N-(2-(2-((5-fluoro-4-(7-fluoro-3-isopropyl-2-methyl-benzimidazol-5-yl)pyrimidin-2-yl)amino)-7,8-dihydro-5H-1,6-naphthyridin-6-yl)-2-oxoethyl)-N-methyl-carbamate represented by formula I-4-b (50 mg, 0.08241 mmol). LC-MS: m/z: (M+H)$^+$=607.2.

Step 2

Tert-butyl N-(2-(2-((5-fluoro-4-(7-fluoro-3-isopropyl-2-methyl-benzimidazol-5-yl)pyrimidin-2-yl)amino)-7,8-dihydro-5H-1,6-naphthyridin-6-yl)-2-oxoethyl)-N-methylcarbamate (50 mg, 0.08241 mmol) (represented by formula I-4-b) was added to 2M HCl/MeOH solution (2 mL), and the mixture was stirred at room temperature for 1 hour. The reaction solution was concentrated to give 1-(2-((5-fluoro-4-(7-fluoro-3-isopropyl-2-methyl-benzimidazol-5-yl)pyrimidine-2-yl)amino)-7,8-dihydro-5H-1,6-naphthyridin-6-yl)-2-(methylamino)ethanone represented by formula I-4 (30 mg, 0.05922 mmol). $^1$H-NMR (400 MHz, CD$_3$OD) δ

N-(5-fluoro-4-(7-fluoro-3-isopropyl-2-methyl-benzimidazol-5-yl)pyrimidin-2-yl)-5,6,7,8-tetrahydro-1,6-naphthyridine-2-amine (80 mg, 0.1837 mmol) (represented by formula I-1), N,N-dimethylglycine (20.5 mg, 0.199 mmol), HOBt (25 mg, 0.18502 mmol), EDCI (36 mg, 0.18779 mmol) were added to 1 mL DMF, and the mixture was stirred at room temperature for 12 hours. The reaction solution was concentrated and purified by silica gel column chromatography (dichloromethane/methanol 0 to 10%) to give 2-(dimethylamino)-1-(2-((5-fluoro-4-(7-fluoro-3-isopropyl-2-methyl-benzimidazol-5-yl)pyrimidin-2-yl)amino)-7,8-dihydro-5H-1,6-naphthyridine-6-yl)ethanone represented by formula I-5 (10 mg, 0.01921 mmol). $^1$H-NMR (400 MHz, CD$_3$OD) δ 8.50 (d, 1H, J=3.6 Hz), 8.26-8.30 (m, 2H), 7.78 (d, 1H, J=12 Hz), 7.56 (d, 1H, J=8.4 Hz), 4.86-4.90 (m, 2H), 4.86 (s, 2H), 4.71 (s, 1H), 3.92 (t, 2H, J=5.6 Hz), 3.00 (t, 1H, J=5.6 Hz), 2.92 (t, 1H, J=5.6 Hz), 2.69 (s, 3H), 2.35 (s, 3H), 2.34 (s, 3H), 1.74 (d, 6H, J=7.2 Hz). LC-MS: m/z: (M+H)$^+$=521.2.

Embodiment 6

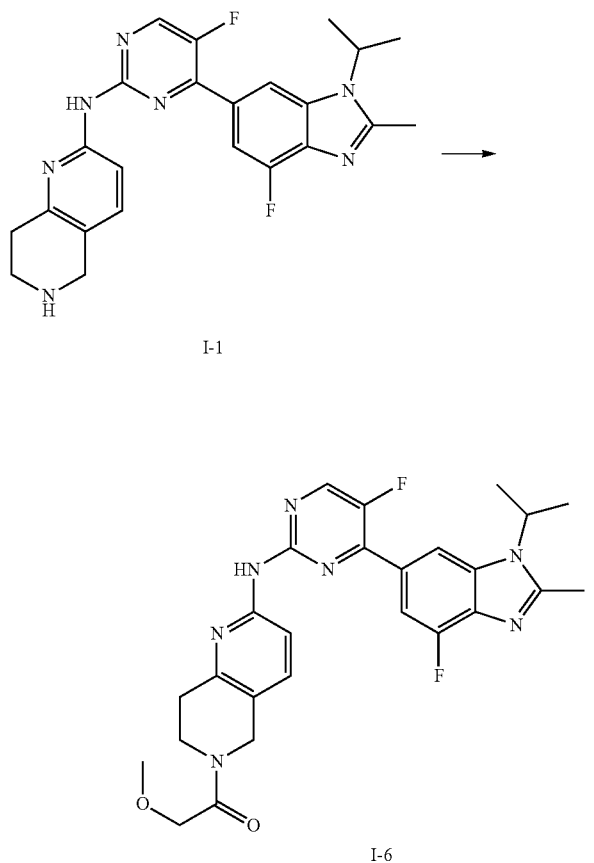

I-1

I-6

N-(5-fluoro-4-(7-fluoro-3-isopropyl-2-methyl-benzimidazol-5-yl)pyrimidin-2-yl)-5,6,7,8-tetrahydro-1,6-naphthyridine-2-amine (80 mg, 0.1837 mmol) (represented by formula I-1), 2-methoxyacetic acid (18 mg, 0.1998 mmol), HOBt (25 mg, 0.18502 mmol), EDCI (36 mg, 0.18779 mmol) were added to 1 mL DMF and the mixture was stirred at room temperature for 12 hours. The reaction solution was concentrated and purified by silica gel column chromatography (dichloromethane/methanol 0 to 10%) to give 1-(2-((5-fluoro-4-(7-fluoro-3-isopropyl-2-methyl-benzimidazol-5-yl)pyrimidin-2-yl)amino)-7,8-dihydro-5H-1,6-naphthyridin-6-yl)-2-methoxyethanone (60 mg, 0.1182 mmol). $^1$H-NMR (400 MHz, CD$_3$OD) δ 8.54 (d, 1H, J=3.6 Hz), 8.33 (s, 1H), 8.23-8.27 (m, 1H), 7.76 (d, 1H, J=11.6 Hz), 7.57 (d, 1H, J=8.4 Hz), 4.87-4.96 (m, 1H), 4.70 (s, 1H), 4.67 (s, 1H), 4.30 (s, 1H), 4.28 (s, 1H), 3.92 (t, 1H, J=5.6 Hz), 3.82 (t, 1H, J=5.6 Hz), 3.46 (s, 1.8H), 3.44 (s, 1.2H), 2.98 (t, 1H, J=5.6 Hz), 2.93 (t, 1H, J=5.6 Hz), 2.71 (s, 3H), 1.73 (d, 6H, J=7.6 Hz). LC-MS: m/z: (M+H)$^+$=508.2.

Embodiment 8

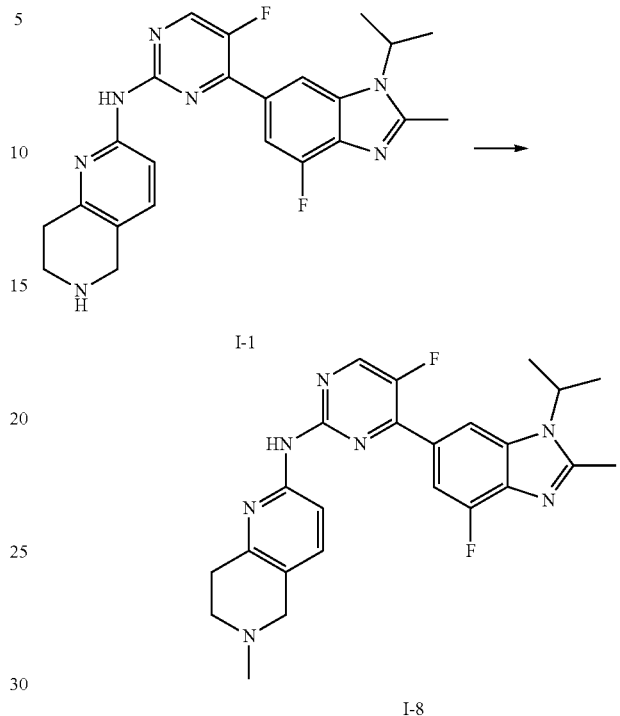

I-1

I-8

N-(5-fluoro-4-(7-fluoro-3-isopropyl-2-methyl-benzimidazol-5-yl)pyrimidin-2-yl)-5,6,7,8-tetrahydro-1,6-naphthyridine-2-amine (80 mg, 0.1837 mmol) (represented by formula I-1), aqueous formaldehyde (20 mg), sodium triacetoxyborohydride (128 mg) were added to 3 mL dioxane, the mixture was stirred at room temperature for 12 hours. The reaction solution was concentrated and purified by silica gel column chromatography (dichloromethane/methanol 0 to 10%) to give N-(5-fluoro-4-(7-fluoro-3-isopropyl-2-methyl-benzoimidazol-5-yl)pyrimidin-2-yl)-6-methyl-7,8-dihydro-5H-1,6-naphthyridin-2-amine represented by formula I-8 (40 mg, 0.08899 mmol). $^1$H-NMR (400 MHz, CD$_3$OD) δ 8.54 (d, 1H, J=4 Hz), 8.33 (d, 1H, J=1.2 Hz), 8.22 (d, 1H, J=8.4 Hz), 7.52 (d, 1H, J=8.4 Hz), 4.85-4.96 (m, 1H), 3.75 (s, 2H), 2.98-3.03 (m, 4H), 2.71 (s, 3H), 2.59 (s, 3H), 1.33 (d, 6H, J=7.2 Hz). LC-MS: m/z: (M+H)$^+$=450.2.

Embodiment 9

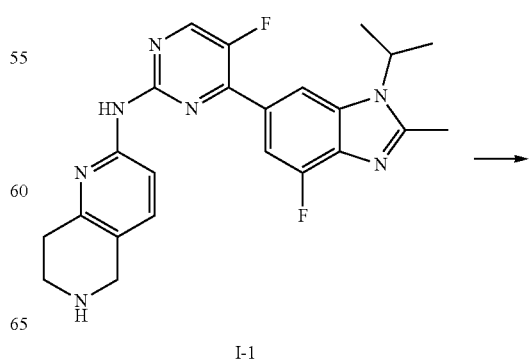

I-1

-continued

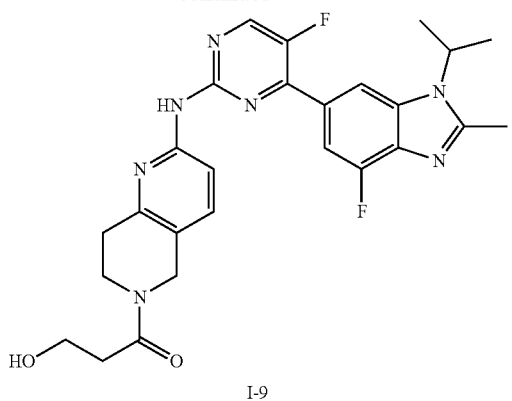

I-9

N-(5-fluoro-4-(7-fluoro-3-isopropyl-2-methyl-benzimidazol-5-yl)pyrimidin-2-yl)-5,6,7,8-tetrahydro-1,6-naphthyridine-2-amine (80 mg, 0.1837 mmol) (represented by formula I-1), 3-hydroxypropionic acid (18 mg, 0.1998 mmol), HOBt (25 mg, 0.18502 mmol), EDCI (36 mg, 0.18779 mmol) were added to 1 mL DMF and the mixture was stirred at room temperature for 12 hours. The reaction solution was concentrated and purified by silica gel column chromatography (dichloromethane/methanol 0 to 10%) to give 1-(2-((5-fluoro-4-(7-fluoro-3-isopropyl-2-methyl-benzimidazol-5-yl)pyrimidin-2-yl)amino)-7,8-dihydro-5H-1,6-naphthyridin-6-yl)-3-hydroxyacetone (8 mg, 0.01576 mmol). $^1$H-NMR (400 MHz, DMSO-d$_6$) δ 10.05 (d, 1H, J=10 Hz), 8.70 (d, 1H, J=4 Hz), 8.32 (s, 1H), 8.13 (m, 1H), 7.71 (d, 1H, J=12.4 Hz), 7.60-7.63 (m, 1H), 4.83-4.89 (m, 1H), 4.69 (s, 1H)), 4.62 (s, 1H), 3.81-3.83 (m, 2H), 3.68-3.69 (m, 2H), 2.91 (t, 1H, J=5.6 Hz), 2.80 (t, 1H, J=5.6 Hz), 2.66 (s, 3H), 2.60-2.63 (m, 2H). LC-MS: m/z: (M+H)$^+$ =508.2.

Embodiment 10

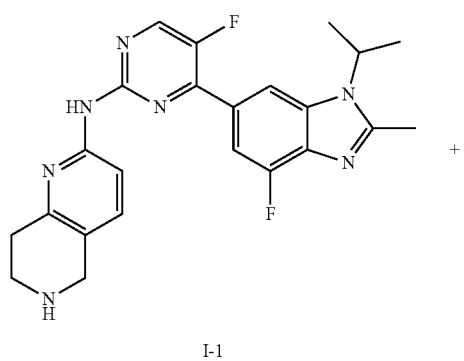

I-1

+

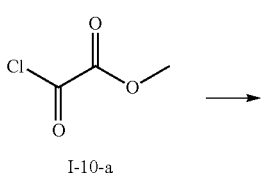

I-10-a

⟶

-continued

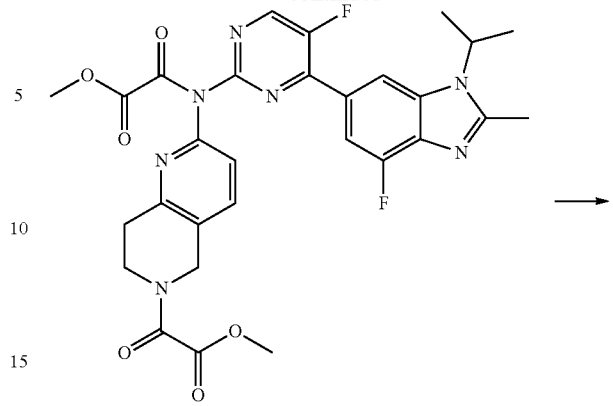

I-10-b

⟶

I-10

Step 1

N-(5-fluoro-4-(7-fluoro-3-isopropyl-2-methyl-benzimidazol-5-yl)pyrimidin-2-yl]-5,6,7,8-tetrahydro-1,6-naphthyridine-2-amine (80 mg, 0.1837 mmol) (represented by formula I-1), pyridine (120 mg, 1.517 mmol), methyl oxalyl chloride (50 mg, 0.40813 mmol) (represented by formula I-10-a) were added to 10 mL THF and the mixture was stirred at room temperature for 12 hours. The reaction solution was concentrated and purified by silica gel column chromatography (dichloromethane/methanol 0 to 10%) to give methyl 2-(2-((5-fluoro-4-(7-fluoro-3-isopropyl-2-methyl-benzimidazol-5-yl)pyrimidin-2-yl)-(2-methoxy-2-oxoacetyl)amino)-7,8-dihydro-5H-1,6-naphthyridin-6-yl)-2-oxoacetate represented by formula I-10-b (100 mg, 0.1646 mmol). LC-MS: m z: (M+H)$^+$=608.2.

Step 2

Methyl 2-(2-((5-fluoro-4-(7-fluoro-3-isopropyl-2-methyl-benzimidazol-5-yl)pyrimidin-2-yl)-(2-methoxy-2-oxoacetyl)amino)-7,8-dihydro-5H-1,6-naphthyridin-6-yl)-2-oxoacetate (100 mg, 0.1646 mmol) (represented by formula I-10-b), lithium hydroxide (40 mg) and water (0.5 mL) were added to 3 mL methanol and the mixture was stirred at room temperature for 12 hours. The reaction solution was concentrated and purified by silica gel column chromatography (dichloromethane/methanol 0 to 10%) to give methyl 2-(2-((5-fluoro-4-(7-fluoro-3-isopropyl-2-methyl-benzimidazol-5-yl)pyrimidin-2-yl]amino]-7,8-dihydro-5H-1,6-naphthyridin-6-yl]-2-oxoacetate represented by formula I-10(70 mg, 0.1342 mmol). ¹H-NMR (400 MHz, DMSO-d₆) δ 10.10 (d, 1H, J=7.2 Hz), 8.69 (d, 1H, J=4 Hz), 8.32 (d, 1H, J=1.2 Hz), 8.14-8.18 (m, 1H), 7.61-7.72 (m, 2H), 4.82-4.89 (m, 1H), 4.68 (s, 1H), 4.60 (s, 1H), 3.87-3.88 (m, 4H), 3.75 (t, 1H, J=5.6 Hz), 2.88-2.92 (m, 2H), 2.65 (s, 3H), 1.64 (d, 6H, J=6.8 Hz). LC-MS: m/z: (M+H)⁺=522.2.

Embodiment 12

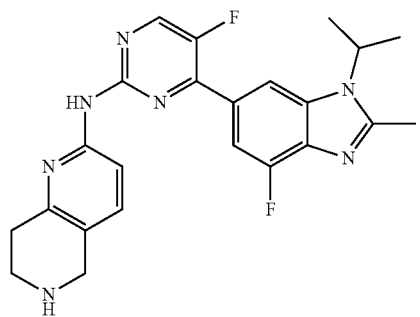

I-1

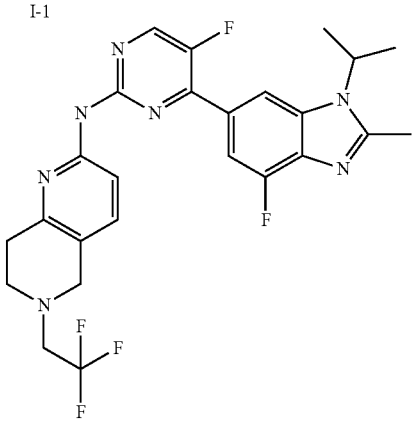

I-12

N-(5-fluoro-4-(4-fluoro-1-isopropyl-2-methyl-1H-benzo[d]imidazol-6-yl)pyrimidin-2-yl)-5,6,7,8-tetrahydro-1,6-naphthyridin-2-amine (80 mg, 0.18 mmol) (represented by formula I-1), 2,2,2-trifluoroethyl methanesulfonate (60 mg, 0.26 mmol) and diisopropylethylamine (60 mg, 0.46 mmol) were dissolved in N,N-dimethylformamide (3 mL) and the mixture was stirred at 90° C. for 16 hours. Then the reaction solution was cooled to room temperature and filtered, the residue was dissolved in dichloromethane, treated with ultrasound for 30 minutes, filtered, rinsed with dichloromethane, and the residue was dissolved in methanol, treated with ultrasound for 30 minutes, then filtered to give N-(5-fluoro-4-(4-fluoro-1-isopropyl-2-methyl-1H-benzo[d]imidazol-6-yl)pyrimidin-2-yl)-6-(2,2,2-trifluoroethyl)-5,6,7,8-tetrahydro-1,6-naphthyridin-2-amine represented by formula I-12 (45 mg) as a pale yellow solid. ¹H-NMR (400 MHz, DMSO-d₆) δ 9.97 (s, 1H), 8.68 (d, 1H, J=4.0 Hz), 8.31 (d, 1H, J=1.2 Hz), 8.08 (d, 1H, J=8.4 Hz), 7.71 (d, 1H, J=12.4 Hz), 7.48 (d, 1H, J=8.4 Hz), 4.83-4.88 (m, 1H), 3.82 (s, 2H), 3.40 (q, 2H, J=10.4 Hz), 3.04 (t, 2H, J=6.0 Hz), 2.86 (t, 2H, J=6.0 Hz), 2.66 (s, 3H), 1.64 (d, 6H, J=6.8 Hz). LC-MS: m/z: (M+H)⁺=518.2.

Embodiment 13

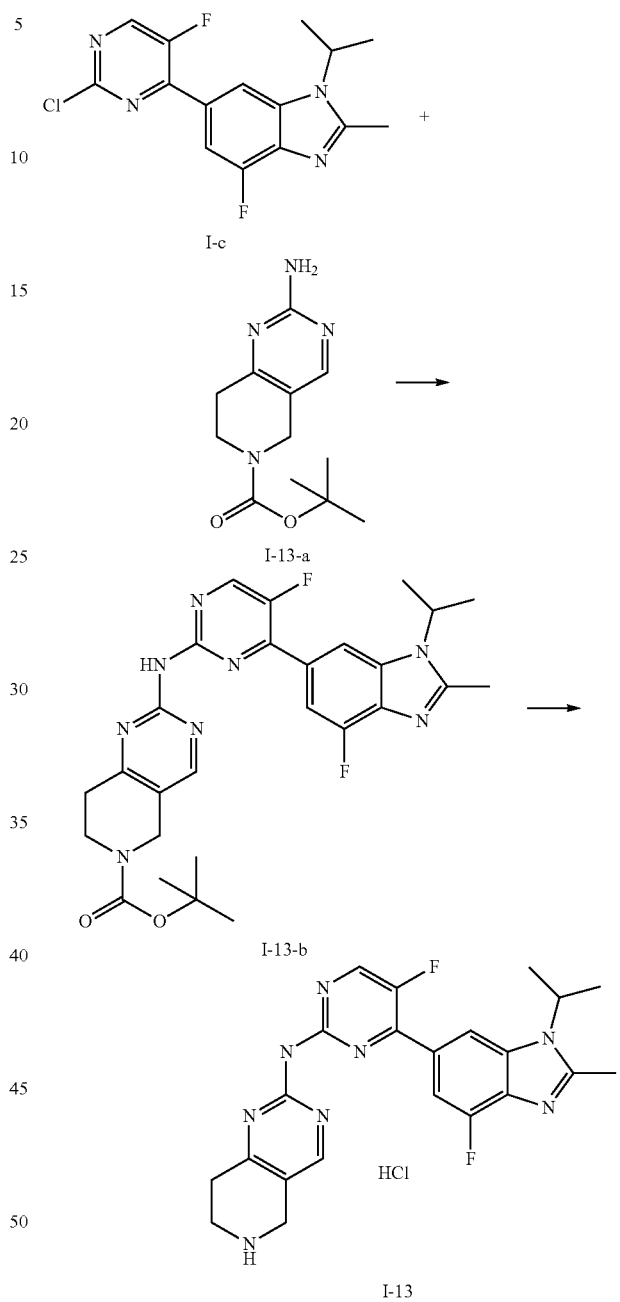

Step 1

6-(2-Chloro-5-fluoro-pyrimidin-4-yl)-4-fluoro-1-isopropyl-2-methyl-1H-benzo[d]imidazole (100 mg, 0.31 mmol) (represented by formula 1-c), tert-butyl 2-amino-7,8-dihydropyrido[4,3-d]pyrimidin-6(5H)-carboxylate (100 mg, 0.4 mmol) (represented by formula I-13-a), tris(dibenzylideneacetone)dipalladium (50 mg, 0.05 mmol), 4,5-bis(diphenylphosphino)-9,9-dimethylxanthene (30 mg, 0.05 mmol) and cesium carbonate (326 mg, 1 mmol) were dissolved in 1,4-dioxane (6 mL) and the mixture was stirred under argon atmosphere at 100° C. for 18 hours. Then the reaction solution was concentrated and purified by column chromatography (dichloromethane/methanol: 0% to 10%) to give tert-butyl 2-((5-fluoro-4-(4-fluoro-1-isopropyl-2-methyl-1H-benzo[d]imidazol-6-yl)pyrimidin-2-yl)amino)-7,8-dihydropyrido[4,3-d]pyrimidine-6(5H)-carboxylate (45 mg) as pale yellow solid. LC-MS: m/z: (M+H)⁺=537.2.

Step 2

Tert-butyl 2-((5-Fluoro-4-(4-fluoro-1-isopropyl-2-methyl-1H-benzo[d]imidazol-6-yl)pyrimidin-2-yl)amino)-7,8-dihydropyrido[4,3-d]pyrimidine-6(5H)-carboxylate (45 mg, 0.08 mmol) (represented by formula I-13-b) was dissolved in tetrahydrofuran (2 mL), hydrochloric acid (4M) in tetrahydrofuran was added, the mixture was stirred at room temperature for 1 hour, then concentrated to give N-(5-fluoro-4-(4-fluoro-1-isopropyl-2-methyl-1H-hydrobenzo[d]imidazol-6-yl)pyrimidin-2-yl)-5,6,7,8-tetrahydropyrido[4,3-d]pyrimidin-2-amine hydrochloride (40 mg) represented by 1-13 as a pale yellow solid. ¹H-NMR (400 MHz, DMSO-d₆) δ 10.67 (s, 1H), 9.59 (s, 1H), 8.78 (d, 1H, J=3.6 Hz), 8.53 (s, 1H), 8.39 (s, 1H), 7.92 (d, 1H, J=11.6 Hz), 4.90-4.94 (m, 1H), 4.29 (t, 2H, J=4.8 Hz), 3.51 (q, 2H, J=6.0 Hz), 3.06 (t, 2H, J=6.4 Hz), 2.75 (s, 3H), 1.65 (d, 6H, J=6.8 Hz). LC-MS m/z: (M+H)⁺=437.2.

Embodiment 14

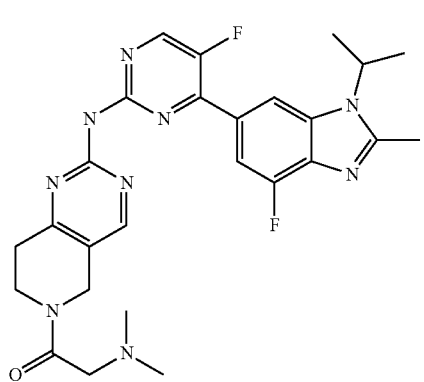

I-14

N-(5-Fluoro-4-(4-fluoro-1-isopropyl-2-methyl-1H-benzo[d]imidazol-6-yl)pyrimidin-2-yl)-5,6,7,8-tetrahydropyrido[4,3-d]pyrimidin-2-amine hydrochloride (30 mg, 0.06 mmol) (represented by formula I-13), N,N-dimethylglycine (8 mg, 0.08 mmol), 1-(3-dimethylaminopropyl)-3-ethylcarbodiimide hydrochloride (30 mg, 0.16 mmol), 1-hydroxybenzotriazole (30 mg, 0.22 mmol) and diisopropylacetamide (100 mg, 0.78 mmol) were dissolved in 1,4-dioxane (4 mL) and the mixture was stirred at room temperature for 16 hours. Then the reaction solution was concentrated, purified with TLC (DCM/CH₃OH=10/1), followed by column chromatography (C18, H₂O/CH₃OH=100% to 5%) to give 2-dimethylamino-1-(2-((5-fluoro-4-(4-fluoro-1-isopropyl-2-methyl-1H-benzo[d]imidazol-6-yl)pyrimidin-2-yl)amino)-7,8-dihydropyrido[4,3-d]pyrimidin-6(5H)-yl)acetamide represented by formula I-14(9 mg) as pale yellow solid. ¹H-NMR (400 MHz, CDCl₃) δ 8.54-8.55 (m, 1H), 8.44 (s, 1H), 8.22-8.25 (m, 1H), 8.15 (s, 1H), 7.90-7.95 (m, 1H), 4.73-4.85 (m, 3H), 3.97 (t, 2H, J=6.0 Hz), 3.24-3.26 (m, 2H), 2.98-3.08 (m, 2H), 2.72 (s, 3H), 2.30-2.33 (m, 6H), 1.73 (d, 6H, J=6.8 Hz). LC-MS: m/z: (M+H)⁺=522.3.

Embodiment 15

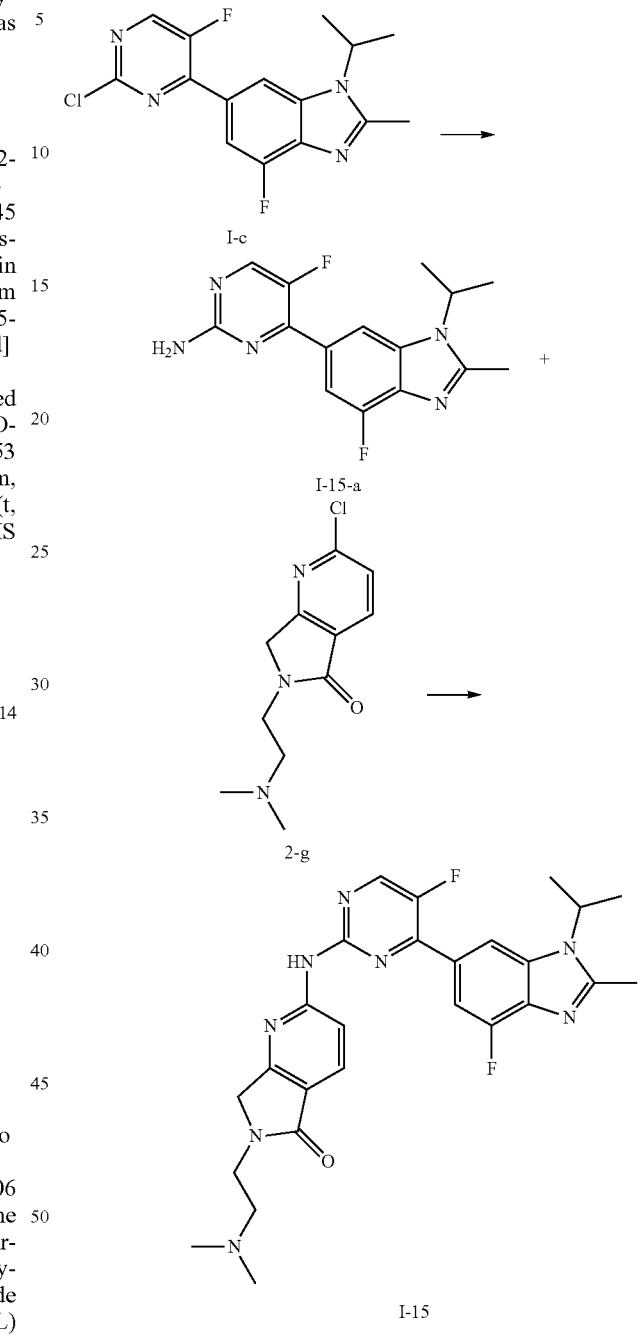

Step 1

6-(2-Chloro-5-fluoro-pyrimidin-4-yl)-4-fluoro-1-isopropyl-2-methyl-benzimidazole (500 mg, 1.55 mmol) (represented by formula 1-c), aqueous ammonia (5 mL, 35%) and 1,4-dioxane (5 mL) were added to a sealed tube and the mixture was stirred at 100° C. for 16 hours, then concentrated and diluted with dichloromethane (30 mL). After 30 minutes under ultrasound, the mixture was filtered, and the residue was rinsed with dichloromethane and dried to give 5-fluoro-4-(4-fluoro-1-isopropyl-2-methyl-1H-benzo[d]

imidazol-6-yl)pyrimidin-2-amine represented by formula I-15-a (280 mg, 0.92 mmol) as a pale yellow solid. LC-MS m/z: (M+H)$^+$=304.2.

Step 2

2-Chloro-6-(2-(dimethylamino)ethyl)-6,7-dihydro-5H-pyrrolo[3,4-b]pyridin-5-one (40 mg, 0.17 mmol) (represented by formula 2-g), 5-fluoro-4-(4-fluoro-1-isopropyl-2-methyl-1H-benzo[d]imidazol-6-yl)pyrimidine-2-amine (60 mg, 0.19 mmol) (represented by formula I-15-a), tris(dibenzylideneacetone)dipalladium (30 mg, 0.03 mmol), 4,5-bis(diphenylphosphino)-9,9-dimethylxanthene (20 mg, 0.04 mmol) and cesium carbonate (120 mg, 0.37 mmol) were dissolved in 1,4-dioxane (6 mL) and the mixture was stirred under argon atmosphere at 100° C. for 18 hours, then concentrated and purified by column chromatography (dichloromethane/methanol 0% to 10%) to give 6-(2-(dimethylamino)ethyl)-2-((5-fluoro-4-(4-fluoro-1-isopropyl-2-methyl-1H-benzo[d]imidazol-6-yl)pyrimidin-2-yl)amino)-6,7-dihydro-5H-pyrrolo[3,4-b]pyridin-5-one (45 mg, 0.09 mmol) represented by formula I-15 as a pale yellow solid. $^1$H-NMR (400 MHz, CDCl$_3$) δ 8.62 (d, 1H, J=8.8 Hz), 8.44 (s, 1H), 8.50 (d, 1H, J=3.6 Hz), 8.40 (s, 1H), 8.24 (d, 1H, J=1.2 Hz), 8.09 (d, 1H, J=11.6 Hz), 7.80 (d, 1H, J=11.6 Hz), 4.74-4.79 (m, 1H), 4.53 (s, 2H), 3.89 (t, 2H, J=7.8 Hz), 2.86 (t, 2H, J=6.4 Hz), 2.72 (s, 3H), 2.51 (s, 6H), 1.75 (d, 6H, J=6.8 Hz). LC-MS m/z: (M+H)$^+$=507.9.

Embodiment 17

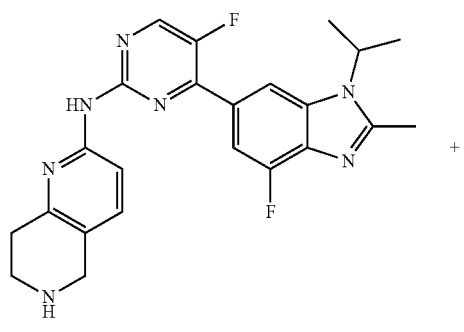

I-1

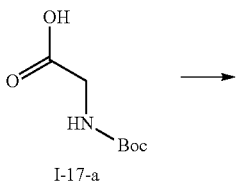

I-17-a

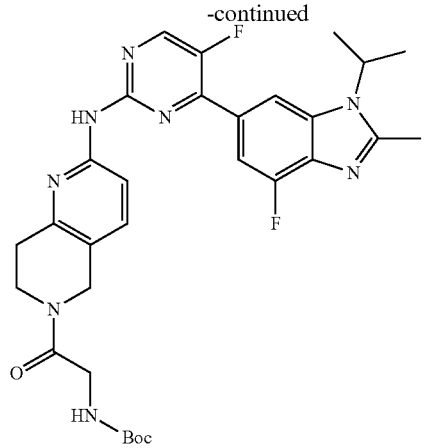

I-17-b

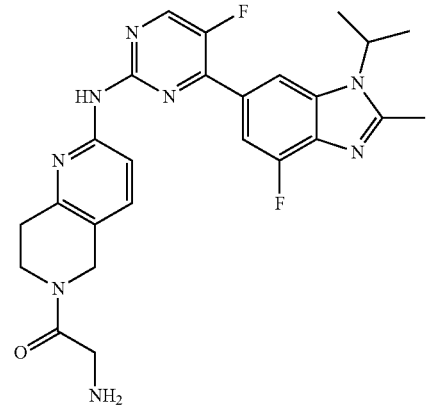

I-17

Step 1

N-(5-fluoro-4-(7-fluoro-1-isopropyl-2-methyl-1H-benzo[d]imidazol-5-yl)pyrimidin-2-yl)-5,6,7,8-tetrahydro-1,6-naphthyridin-2-amine (80 mg, 0.18 mmol) (represented by formula I-1), N-boc-glycine (39 mg, 0.22 mmol) (represented by formula I-17-a), HOBt (30 mg, 0.22 mmol), EDCI (42 mg, 0.22 mmol) were added to 1 mL DMF and the mixture was stirred at room temperature for 12 hours. The reaction solution was concentrated and purified by silica gel column chromatography (dichloromethane/methanol 0-10%) to give the compound represented by formula I-17-b as a yellow solid 43 mg, yield 39%. $^1$H-NMR (400 MHz, CDCl$_3$) δ 8.45 (d, 1H, J=3.6 Hz), 8.34 (dd, 1H, J=8.5, 3.3 Hz), 8.17-8.21 (m, 2H), 7.79 (d, 1H, J=11.7 Hz), 7.48 (d, 0.66H, J=8.6 Hz), 7.43 (d, 0.44H, J=8.6 Hz), 5.57 (s, 1H), 4.76 (s, 1H), 4.71-4.79 (m, 1H), 4.56 (s, 1H), 4.10 (t, 2H, J=3.2 Hz), 3.98 (t, 1H, J=6.0 Hz), 3.75 (t, 1H, J=5.9 Hz), 3.00 (t, 1H, J=6.0 Hz), 2.96 (t, 1H, J=6.0 Hz), 2.71 (s, 3H), 1.73 (d, J=6.9 Hz, 6H), 1.48 (s, 9H). LC-MS: m/z: (M+H)$^+$=593.2.

Step 2

Tert-butyl (2-(2-((5-Fluoro-4-)$_7$-fluoro-1-isopropyl-2-methyl-1H-benzo[d]imidazol-5-yl)pyridin-2-yl)amino)-7,8-dihydro-1,6-naphthyridine-6(5H)-yl)-2-oxoethyl)carbamate (43 mg, 0.23 mmol) (represented by formula I-17-b) was dissolved in 5 mL dioxane, 4N HCl in dioxane (1 mL) was added dropwise, and the mixture was stirred at room temperature for 4 hours. The solvent was evaporated under reduced pressure, saturated sodium bicarbonate solution was added, and the mixture was extracted with dichloromethane. The solvent was evaporated under reduced pressure to give 21 mg the compound represented by formula I-17 as a yellow solid, yield 59%. $^1$H-NMR (400 MHz, CD$_3$OD) δ 8.94 (s, 1H), 8.58 (s, 1H), 8.20 (t, 2H, J=9.3 Hz), 7.56 (d, 1H, J=8.8 Hz), 5.14-5.15 (m, 1H), 4.78 (s, 2H), 4.17 (s, 1H), 4.14 (s, 1H), 4.08 (s, 1H), 3.92 (s, 1H), 3.24 (s, 2H), 2.97 (s, 3H), 1.83 (d, 6H, J=6.9 Hz). LC-MS: m/z: (M+H)$^+$=493.2.

Embodiment 19

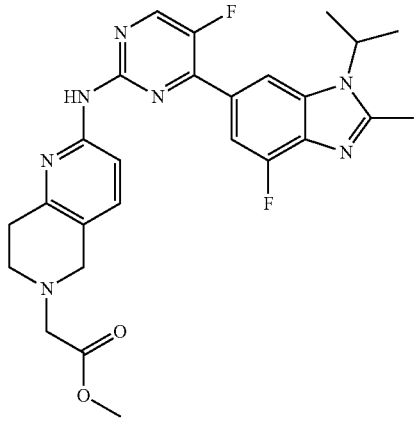

I-19

N-(5-Fluoro-4-(7-fluoro-3-isopropyl-2-methyl-benzimidazol-5-yl)pyrimidin-2-yl)-5,6,7,8-tetrahydro-1,6-naphthyridine-2-amine (200 mg, 0.46 mmol) (represented by formula I-1), methyl bromoacetate (281 mg, 1.837 mmol), N,N-diisopropylethylamine (178 mg) were added to 10 mL 1,4-dioxane, and the mixture was stirred at 90° C. for 12 hours. The reaction solution was concentrated and purified by silica gel column chromatography (dichloromethane/methanol 0 to 10%) to give methyl 2-(2-((5-fluoro-4-(4-fluoro-1-isopropyl-2-methyl-1H-benzo[d]imidazol-6-yl)pyrimidin-2-yl)amino)-7,8-dihydro-1,6-naphthyridin-6(5H)-yl)acetate represented by formula I-19 (130 mg, 0.256 mmol). $^1$H-NMR (400 MHz, CD$_3$OD) δ 8.53 (d, J=3.9 Hz, 1H), 8.32 (s, 1H), 8.16 (d, J=8.5 Hz, 1H), 7.75 (d, J=12.2 Hz, 1H), 7.46 (d, J=8.5 Hz, 1H), 4.89-4.95 (m, 1H), 3.77-3.81 (m, 2H), 3.78 (s, 3H), 3.62 (s, 0.5H), 3.51 (s, 1.5H), 2.97-3.02 (m, 4H), 2.70 (s, 3H), 1.73 (d, 6H, J=6.9 Hz). LC-MS m/z: (M+H)$^+$=508.2.

Embodiment 20

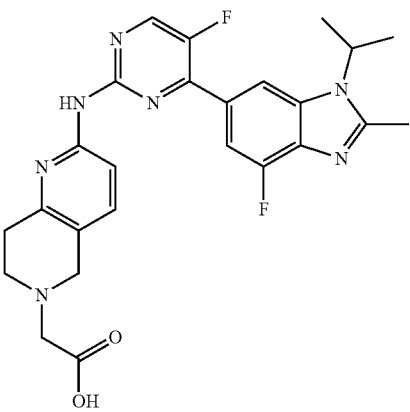

I-20

Methyl 2-(2-((5-fluoro-4-(4-fluoro-1-isopropyl-2-methyl-1H-benzo[d]imidazol-6-yl)pyrimidin-2-yl)amino)-7,8-dihydro-1,6-naphthyridin-6(5H)-yl)acetate (100 mg, 0.197 mmol) (represented by formula I-19), LiOH (42 mg), H$_2$O (10 mL) were added to MeOH (10 mL), the mixtured was stirred at 75° C. for 1 hour. The reaction solution was filtered and washed to give 2-(2-((5-fluoro-4-(4-fluoro-1-isopropyl-2-methyl-1H-benzo[d]imidazol-6-yl)pyrimidin-2-yl)amino)-7,8-dihydro-1,6-naphthyridin-6(5H)-yl)acetic acid represented by formula I-20 (70 mg, 0.14 mmol). $^1$H-NMR (400 MHz, DMSO-d$_6$) δ 10.00 (s, 1H), 8.69 (d, J=4.3 Hz, 1H), 8.32 (s, 1H), 8.09 (d, J=8.7 Hz, 1H), 7.71 (d, J=11.7 Hz, 1H), 7.50 (d, J=8.5 Hz, 1H), 4.83-4.88 (m, 1H), 3.87 (s, 2H), 3.04 (s, 2H), 2.90 (s, 2H), 2.66 (s, 3H), 2.00-2.04 (m, 2H), 1.64 (s, 6H, 6.8 Hz). LC-MS: m/z: (M+H)$^+$=495.2.

Embodiment 21

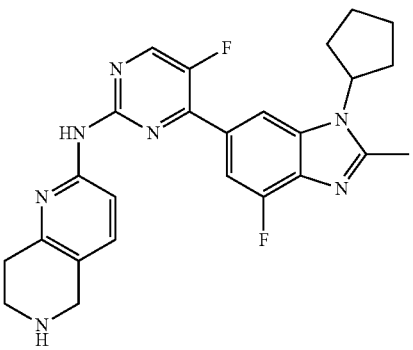

I-21

Tert-butyl 2-((4-(1-Cyclopentyl-7-fluoro-2-methyl-1H-benzo[d]imidazol-5-yl)-5-fluoropyrimidin-2-yl)amino)-7,8-dihydro-1,6-naphthyridine-6(5H)-carboxylate (340 mg, 0.61 mmol) (represented by formula 3-d) were dissolved in 5 mL dioxane, 4N HCl in dioxane (1 mL) was added dropwise and the mixture was stirred at room temperature for 4 hours. Solvent was evaporated under reduced pressure, saturated sodium bicarbonate solution was added, the mixture was extracted with dichloromethane, and the solvent was evaporated under reduced pressure to give 230 mg the compound represented by formula I-21 as a yellow solid, yield 82%. $^1$H-NMR (400 MHz, DMSO-d$_6$) δ 9.83 (s, 1H), 8.67 (d, 1H, J=3.8 Hz), 8.12 (s, 1H), 8.02 (d, 1H, J=7.6 Hz), 7.73 (d, 1H, J=12.1 Hz), 7.39-7.45 (m, 1H), 5.06-4.90 (m, 1H), 4.41 (s, 1H), 3.82 (s, 1H), 3.58 (s, 1H), 3.18 (s, 2H), 3.03 (s, 1H), 2.66 (s, 3H), 2.11-2.20 (m, 4H), 1.96-2.01 (m, 2H), 1.83-1.69 (m, 2H). LC-MS: m/z: (M+H)$^+$=461.9.

Embodiment 22

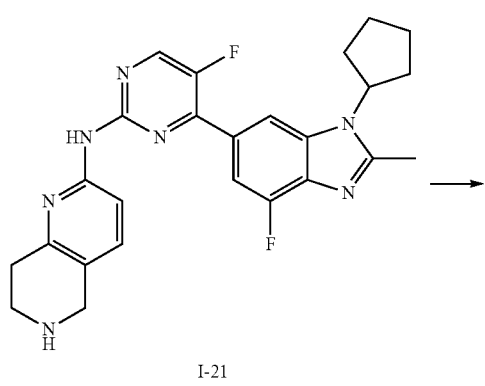

I-21

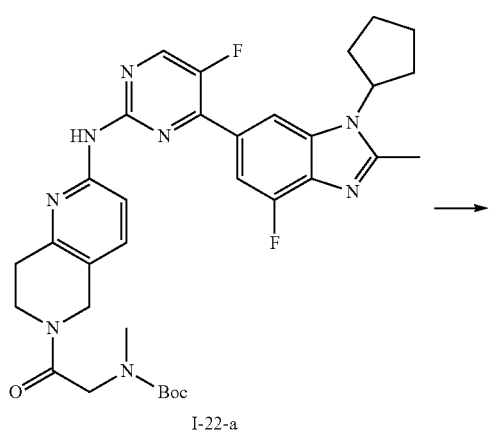

I-22-a

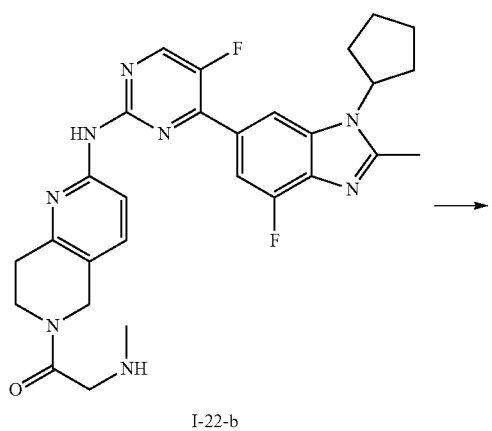

I-22-b

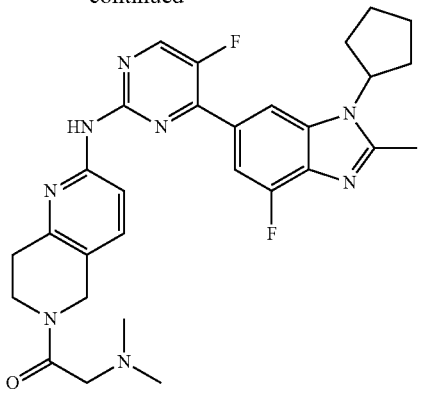

I-22

Step 1

N-(5-Fluoro-4-(7-fluoro-3-cyclopentyl-2-methy-benzimidazol-5-yl)pyrimidin-2-yl]-5,6,7,8-tetrahydro-1,6-naphthyridine-2-amine (90 mg, 0.195 mmol) (represented by formula I-21), N-boc-sarcosine (46 mg, 0.24312 mmol), HOBt (25 mg, 0.18502 mmol), EDCI (36 mg, 0.18779 mmol) were added to 1 mL DMF and the mixture was stirred at room temperature for 12 hours. The reaction solution was concentrated and purified by silica gel column chromatography (dichloromethane/methanol 0 to 10%) to give tert-butyl N-(2-(2-((5-fluoro-4-(7-fluoro-3-cyclopentyl-2-methyl-benzimidazol-5-yl)pyrimidin-2-yl)amino)-7,8-dihydro-5H-1,6-naphthyridine-6-yl)-2-oxoethyl)-N-methyl-carbamate represented by formula I-22-a (100 mg, 0.158 mmol).

Step 2

Tert-butyl N-(2-(2-((5-fluoro-4-(7-fluoro-3-cyclopentyl-2-methyl-benzimidazol-5-yl)pyrimidin-2-yl)amino)-7,8-dihydro-5H-1,6-naphthyridine-6-yl)-2-oxoethyl)-N-methyl-carbamate (100 mg, 0.158 mmol)(represented by formula I-22-a) was add to 2M HCl/MeOH solution (2 mL) and the mixture was stirred at room temperature for 1 hour, then concentrated to give 1-(2-((5-fluoro-4-(7-fluoro-3-cyclopentyl-2-methyl-benzimidazole-5-yl)pyrimidin-2-yl)amino)-7,8-dihydro-5H-1,6-naphthyridin-6-yl)-2-(methylamino)ethanone represented by formula I-22-b (70 mg, 0.1314 mmol).

Step 3

1-(2-((5-Fluoro-4-(7-fluoro-3-cyclopentyl-2-methyl-benzimidazole-5-yl)pyrimidin-2-yl)amino)-7,8-dihydro-5H-1,6-naphthyridin-6-yl)-2-(methylamino)ethanone (70 mg, 0.1314 mmol) (represented by formula I-22-b), aqueous formaldehyde (30 mg) and sodium triacetoxyborohydride (128 mg) were added to 3 mL dioxane and the mixture was stirred at room temperature for 12 hours. The reaction solution was concentrated and purified by silica gel column chromatography (dichloromethane/methanol 0 to 10%) to give 2-(dimethylamino)-1-(2-((5-fluoro-4-(7-fluoro-3-cyclopentyl-2-methyl-benzimidazol-5-yl)pyrimidin-2-yl)amino)-7,8-dihydro-5H-1,6-naphthyridine-6-yl)ethanone represented by formula I-22 (40 mg, 0.08899 mmol). $^1$H-NMR (CD$_3$OD) δ=8.50 (d, 1H, J=3.6 Hz), 8.23-8.27 (m, 1H), 8.17 (s, 1H), 7.77-7.80 (m, 1H), 7.55 (d, 1H, J=8.4 Hz), 4.96-5.02 (m, 2H), 4.77 (s, 1H), 4.70 (s, 1H), 3.90-3.94 (m, 2H), 2.90-3.01 (m, 2H), 2.70 (s, 3H), 2.35 (s, 4H), 2.33 (s, 2H), 2.27 (s, 4H), 2.06-2.09 (m, 2H), 1.87-1.90 (s, 2H). LC-MS: m/z (M+H)$^+$=547.2.

Embodiment 23

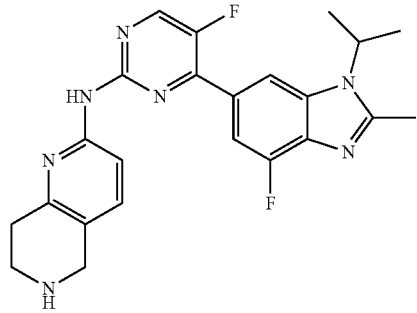

I-1

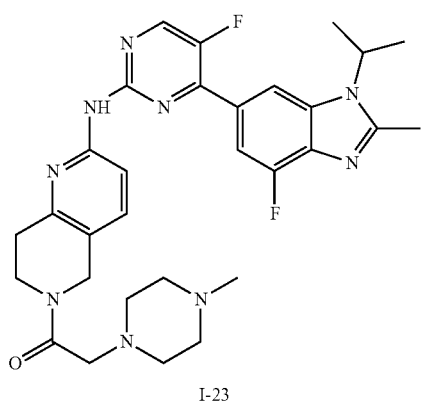

I-23

Embodiment 26

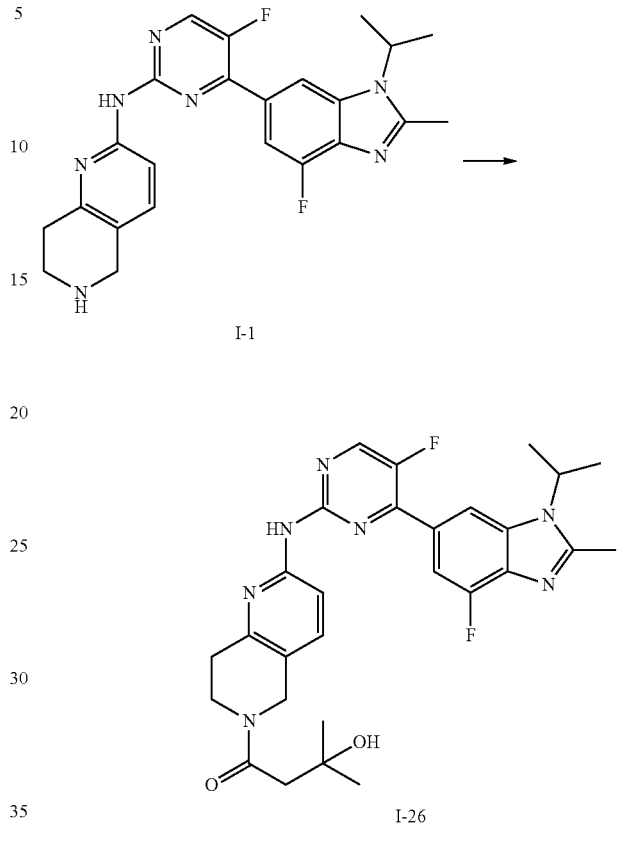

N-(5-Fluoro-4-(7-fluoro-3-isopropyl-2-methyl-benzimidazol-5-yl)pyrimidin-2-yl)-5,6,7,8-tetrahydro-1,6-naphthyridine-2-amine (80 mg, 0.1837 mmol) (represented by formula I-1), 4-methyl-1-piperazineacetic acid (32 mg, 0.20 mmol), HOBt (25 mg, 0.18502 mmol), EDCI (36 mg, 0.18779 mmol) were added to 1 mL DMF and the mixture was stirred at room temperature for 12 hours. The reaction solution was concentrated and purified by silica gel column chromatography (dichloromethane/methanol 0 to 10%) to give 1-(2-((5-fluoro-4-(7-fluoro-3-isopropyl-2-methyl-benzimidazol-5-yl)pyrimidin-2-yl)amino)-7,8-dihydro-5H-1,6-naphthyridin-6-yl)-2-(4-methylpiperazin-1-yl)ethanone (60 mg, 0.104 mmol). $^1$H-NMR (DMSO-d$_6$) δ 9.99-10.02 (m, 1H), 8.69 (d, 1H, J=4 Hz), 8.30 (s, 1H), 8.11-8.16 (m, 1H), 7.70 (d, 1H, J=12 Hz), 7.55-7.72 (m, 1H), 4.81-4.89 (m, 1H), 4.75 (s, 1H), 4.60 (s, 1H), 3.77-3.88 (m, 2H), 3.23-3.25 (m, 2H), 2.90-2.95 (m, 1H), 2.65 (s, 3H), 2.33-2.43 (m, 6H), 2.16 (s, 2H), 2.09 (s, 1H), 1.64 (d, 6H, J=6.8 Hz). LC-MS: m/z (M+H)$^+$=576.2.

N-(5-Fluoro-4-(7-fluoro-3-isopropyl-2-methyl-benzimidazol-5-yl)pyrimidin-2-yl)-5,6,7,8-tetrahydro-1,6-naphthyridine-2-amine (represented by formula I-1) (80 mg, 0.1837 mmol), 3-hydroxy-3-methylbutyric acid (28 mg, 0.237 mmol), HOBt (25 mg, 0.18502 mmol), EDCI (36 mg, 0.18779 mmol) were added to 1 mL DMF and the mixture was stirred at room temperature for 12 hours. The reaction solution was concentrated and purified by silica gel column chromatography (dichloromethane/methanol 0 to 10%) to give 1-(2-((5-fluoro-4-(7-fluoro-3-isopropyl-2-methyl-benzimidazol-5-yl)pyrimidin-2-yl)amino)-7,8-dihydro-5H-1,6-naphthyridin-6-yl)-3-hydroxy-3-methyl-butanone represented by formula I-26 (10 mg, 0.019 mmol). $^1$H-NMR (DMSO-d$_6$) δ 10.06 (d, 1H, J=11.2 Hz), 8.70 (d, 1H, J=4 Hz), 8.32 (s, 1H), 8.12-8.15 (m, 1H), 7.70 (d, 1H, J=12 Hz), 7.57-7.63 (m, 1H), 4.81-4.87 (m, 2H), 4.73 (s, 1H), 4.65 (s, 1H), 3.82-3.88 (m, 2H), 2.89-2.92 (m, 1H), 2.79-2.82 (m, 1H), 2.66 2.57-2.59 (m, 3H), 1.64 (d, 6H, J=6.8 Hz), 1.21 (s, 3H), 1.19 (s, 3H). LC-MS: m/z (M+H)$^+$=536.2.

Embodiment 27

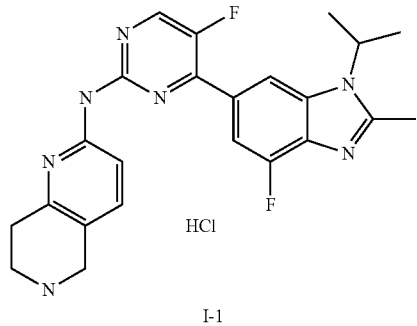

I-1

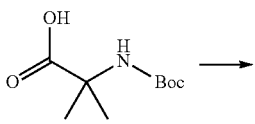

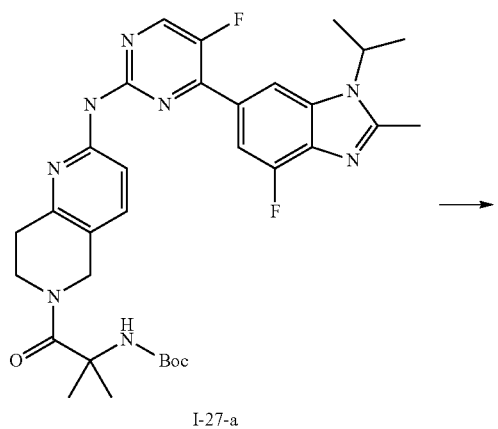

I-27-a

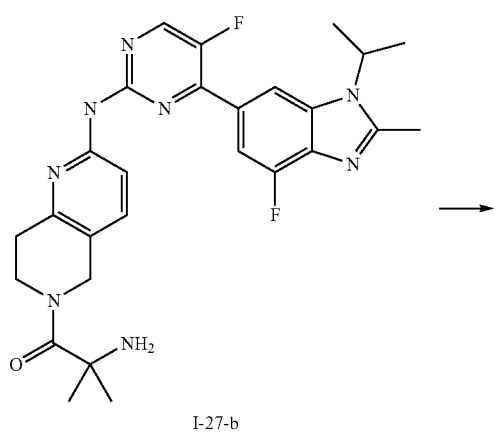

I-27-b

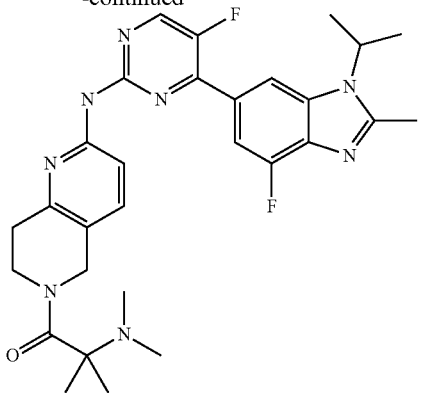

I-27

Step 1

N-(5-Fluoro-4-(7-fluoro-3-isopropyl-2-methyl-benzimidazol-5-yl)pyrimidin-2-yl)-5,6,7,8-tetrahydro-1,6-naphthyridin-2-amine (110 mg, 0.2 mmol) (represented by formula I-1), N-tert-butoxycarbonyl-2-methylalanine (100 mg, 0.49 mmol), EDCI (60 mg, 0.31 mmol), HOBt: (40 mg, 0.29 mmol) and diisopropylacetamide (500 mg, 3.87 mmol) were dissolved in DMF (4 mL) and the mixture was stirred at room temperature for 16 hours. The reaction solution was concentrated and purified by silica gel column chromatography (DCM/CH$_3$H 0 to 10%) to give tert-butyl (1-(2-((5-fluoro-4-(4-fluoro-1-isopropyl-2-methyl-1H-benzo[d]imidazol-6-yl)pyrimidin-2-yl)amino)-7,8-dihydro-1,6-naphthyridin-6(5H)-yl)<sub>2</sub>-methyl-1-oxopropan-2-yl) carbamate represented by formula I-27-a (70 mg) as a pale yellow solid. LC-MS m/z: (M+H)$^+$=621.1.

Step 2

Tert-butyl (1-(2-((5-fluoro-4-(4-fluoro-1-isopropyl-2-methyl-1H-benzo[d]imidazol-6-yl)pyrimidin-2-yl)amino)-7,8-dihydro-1,6-naphthyridin-6(5N)-yl)<sub>2</sub>-methyl-1-oxopropan-2-yl)carbamate (70 mg, 0.11 mmol) (represented by formula I-27-a) was dissolved in 1,4-dioxane (4 mL), a solution of hydrochloride (4M) in 1,2-dioxane was added, then the mixture was stirred at room temperature for 16 hours, filtered, the cake was dissolved in water. After adjusting the pH to 7 by adding aqueous sodium bicarbonate solution, the mixture was extracted with a mixed solution of dichloromethane and methanol, and the organic layer was concentrated to give 2-amino-1-(2-((5-fluoro-4-(4-fluoro-1-isopropyl-2-methyl-1H-benzo[d]imidazol-6-yl)pyrimidin-2-yl)amino)-7,8-dihydro-1,6-naphthyridine-6(5H)-yl)-2-methylpropyl-1-one represented by formula I-27-b (40 mg). LC-MS m/z: (M+H)$^+$=521.2.

Step 3

2-Amino-1-(2-((5-fluoro-4-(4-fluoro-1-isopropyl-2-methyl-1H-benzo[d]imidazol-6-yl)pyrimidin-2-yl)amino)-7,8-dihydro-1,6-naphthyridine-6(5H)-yl)-2-methylpropyl-1-one (40 mg, 0.077 mmol) (represented by formula I-27-b) was dissolved in dioxane (4 mL), aqueous formaldehyde solution (10 mg, 0.33 mmol) was slowly added dropwise and the mixture was stirred at room temperature for 1 hour, then sodium triacetoxyborohydride (60 mg, 0.28 mmol) was added and stirred for 16 hours. The reaction was quenched with water, then aqueous sodium bicarbonate was added to adjust the pH to 7, the mixture was extracted with dichloromethane, the organic layer was dried over anhydrous sodium sulfate, and purified by thin-layer chromatography (DCM/CH₃OH=10/1) to give a crude product, which was dissolved in dimethyl sulfoxide, filtered, and the residue was rinsed with methanol and dried to give 2-(methylamino)-1-(2-((5-fluoro-4-(4-fluoro-1-isopropyl-2-methyl-1H-hydrobenzo[d]imidazol-6-yl)pyrimidin-2-yl)amino)-7,8-dihydro-1,6-naphthyridine-6(5H)-yl)-2-methylpropyl-1-one (15 mg) as a yellow solid. ¹H-NMR (CDCl₃) δ 8.44 (d, 1H, J=4.0 Hz), 8.29 (d, 1H, J=6.8 Hz), 8.22 (s, 1H), 7.92-8.01 (m, 1H), 7.81 (d, 1H, J=11.6 Hz), 7.42-7.50 (m, 1H), 5.40-5.44 (m, 1H), 4.73-4.81 (m, 2H), 4.51-4.54 (m, 1H), 3.96-3.98 (m, 1H), 2.96 (t, 2H, J=4.4 Hz), 2.72 (s, 3H), 2.18-2.26 (m, 6H), 1.74 (d, 6H, J=7.2 Hz), 1.28-1.32 (m, 6H). LC-MS m/z: (M+H)⁺=548.9.

Embodiment 28

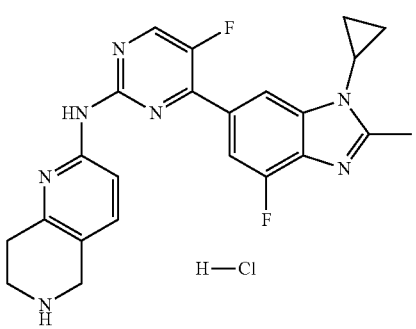

I-28

Tert-butyl 2-((5-fluoro-4-(7-fluoro-3-cyclopropyl-2-methyl-benzimidazol-5-yl)pyrimidin-2-yl)amino)-7,8-dihydro-5H-1,6-naphthyridine-6-carboxylate (7 g, 13.1 mmol) was dissolved in dioxane (40 mL) and a solution of hydrochloric acid (2M, 30 mL) in dioxane was added, the mixture was stirred at room temperature for 16 hours, concentrated, and slurried with dichloromethane to give N-(5-fluoro-4-(7-fluoro-3-cyclopropyl-2-methyl-benzimidazole-5-yl)pyrimidin-2-yl)-5,6,7,8-tetrahydro-1,6-naphthyridin-2-amino hydrochloride represented by formula I-28 (5.5 g). ¹H-NMR (DMSO-d₆) δ 11.0 (s, 1H), 10.0 (s, 2H), 8.87 (d, 1H, J=3.2 Hz), 8.29 (s, 1H), 8.08 (d, 1H, J=8.8 Hz), 7.92-7.95 (m, 2H), 4.29 (s, 2H), 3.55-3.60 (m, 1H), 3.46-3.49 (m, 2H), 3.19 (t, 2H, J=6.0 Hz), 2.82 (s, 3H), 1.31-1.36 (m, 2H), 1.20-1.22 (m, 2H). LC-MS m/z: (M+H)⁺=434.2.

Embodiment 29

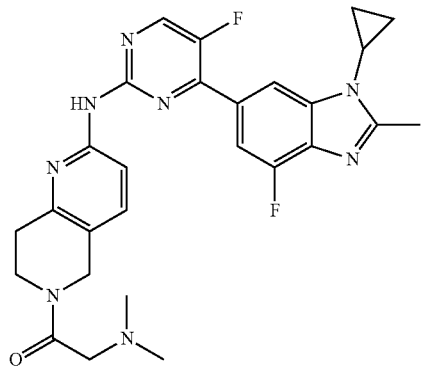

I-29

N-(5-Fluoro-4-(7-fluoro-3-cyclopropyl-2-methyl-benzimidazol-5-yl)pyrimidin-2-yl)-5,6,7,8-tetrahydro-1,6-naphthyridin-2-amine (100 mg, 0.25 mmol) (represented by formula I-28), N,N-dimethylglycine (100 mg, 0.49 mmol), EDCI (60 mg, 0.31 mmol), HOBt (40 mg, 0.29 mmol) and diisopropylacetamide (500 mg, 3.87 mmol) were dissolved in a mixed solution of DMF (4 mL) and dichloromethane (4 mL) and the mixture was stirred at 60° C. for 16 hours. The reaction solution was concentrated and purified by silica gel column chromatography (DCM/CH₃OH/NH₃.CH₃OH=100/10/1) to give (1-(2-((4-(3-cyclopropyl-7-fluoro-2-methyl-benzimidazol-5-yl)-5-fluoro-pyrimidin-2-yl)amino-7,8-dihydro-5H-1,6-naphthyridine-6-yl)-2-(dimethylamino)-ethanone represented by formula I-29 (70 mg) as a pale yellow solid. ¹H-NMR (CDCl₃+CD₃OD) δ 8.37 (s, 1H), 8.23 (d, 1H, J=8.0 Hz), 8.11 (s, 1H), 7.72 (d, 1H, J=11.2 Hz), 7.44-7.46 (m, 1H), 4.64-4.67 (m, 2H), 3.82-3.85 (m, 2H), 3.25-3.31 (m, 4H), 2.86-2.92 (m, 2H), 2.66 (s, 3H), 2.31 (s, 6H), 1.28-1.35 (m, 2H), 1.08-1.10 (m, 2H). LC-MS m/z: (M+H)⁺=519.2.

Embodiment 30

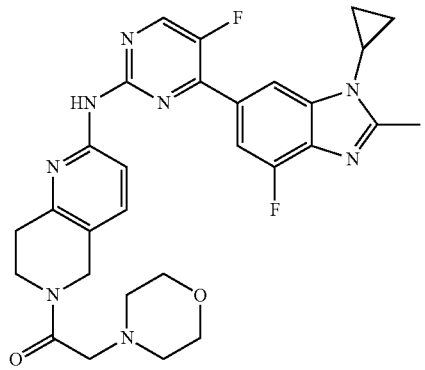

I-30

N-(5-Fluoro-4-(7-fluoro-3-cyclopropyl-2-methyl-benzimidazol-5-yl)pyrimidin-2-yl)-5,6,7,8-tetrahydro-1,6-naphthyridin-2-amine (100 mg, 0.25 mmol) (represented by formula I-28), N,N-morpholin-4-yl acetic acid (100 mg, 0.49 mmol), EDCI (60 mg, 0.31 mmol), HOBt (40 mg, 0.29 mmol) and diisopropylacetamide (500 mg, 3.87 mmol) were dissolved in DMF (4 mL) and the mixture was stirred at room temperature for 16 hours. The reaction solution was concentrated and purified by silica gel column chromatography (DCM/CH$_3$OH=100% to 90%) to give (1-(2-((4-(3-cyclopropyl-7-fluoro-2-methyl))-benzimidazol-5-yl)-5-fluoro-pyrimidin-2-yl)amino-7,8-dihydro-5H-1,6-naphthyridin-6-yl)-2-morpholine-ethanone represented by formula I-30 (20 mg) as a pale yellow solid. $^1$H-NMR (CDCl$_3$) δ 8.44-8.46 (m, 1H), 8.30-8.33 (m, 1H), 8.16-8.18 (m, 1H), 8.09 (s, 1H), 7.78-7.82 (m, 1H), 7.50-7.52 (m, 1H), 4.74-4.79 (m, 2H), 3.92-3.95 (m, 2H), 3.75-3.77 (m, 2H), 3.67-3.72 (m, 1H), 3.31-3.35 (m, 3H), 2.94-3.05 (m, 2H), 2.76 (s, 3H), 2.55-2.57 (m, 4H), 1.33-1.38 (m, 2H), 1.13-1.17 (m, 2H). LC-MS m/z: (M+H)$^+$=561.2.

Embodiment 31

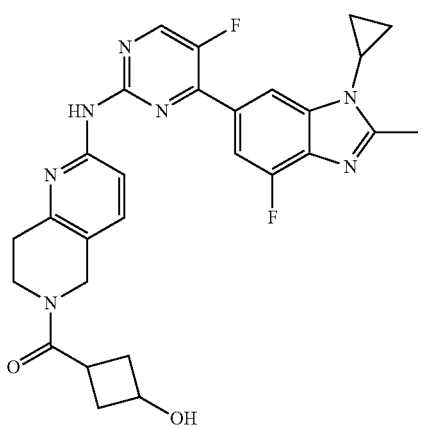

I-31

3-Hydroxycyclobutylcarboxylic acid (26 mg, 0.22391 mmol), N-(5-fluoro-4-(7-fluoro-3-isopropyl-2-methyl-benzimidazol-5-yl)pyrimidine-2-yl)-5,6,7,8-tetrahydro-1,6-naphthyridin-2-amine (80 mg, 0.1837 mmol) (represented by formula I-28), 1-hydroxybenzotriazole (25 mg, 0.185 mmol), 1-(3-dimethylaminopropyl)-3-ethylcarbodiimide hydrochloride (36 mg, 0.18779 mmol) were added to 1 mL DMF and the mixture was stirred at room temperature for 12 hours. The reaction solution was concentrated and purified by silica gel column chromatography (dichloromethane/methanol 0 to 10%) to give (2-((5-fluoro-4-(7-fluoro-3-isopropyl-2-methyl-benzimidazol-5-yl)pyrimidin-2-yl)amino)-7,8-dihydro-5H-1,6-naphthyridin-6-yl)-(3-hydroxycyclobutyl)methanone (50 mg, 0.09370 mmol). $^1$H-NMR (DMSO-d$_6$) δ 10.05 (d, 1H, J=12 Hz), 8.69 (d, 1H, J=3.6 Hz), 8.32 (s, 1H), 8.13 (d, 1H, J=8.4 Hz), 7.71 (d, 1H, J=12.4 Hz), 7.60 (d, 1H, J=16.4 Hz), 5.07 (s, 1H), 4.84-4.88 (m, 1H), 4.57-4.61 (m, 2H), 3.99 (s, 1H), 3.71-3.81 (m, 2H), 2.83-2.90 (m, 3H), 2.68 (s, 3H), 2.38-2.42 (m, 2H), 1.93-2.03 (m, 2H), 1.64 (d, 6H, J=6.8 Hz). LC-MS: m/z: (M+H)$^+$=534.2.

Embodiment 32

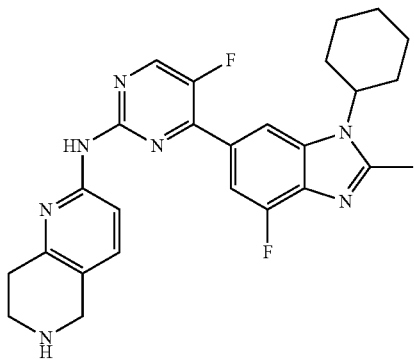

I-32

3-Hydroxycyclobutylcarboxylic acid (26 mg, 0.22391 mmol), N-(5-fluoro-4-(7-fluoro-3-isopropyl-2-methyl-benzimidazol-5-yl)pyrimidine-2-yl)-5,6,7,8-tetrahydro-1,6-naphthyridin-2-amine (80 mg, 0.1837 mmol) (represented by formula I-28), 1-hydroxybenzotriazole (25 mg, 0.185 mmol), 1-(3-dimethylaminopropyl)-3-ethylcarbodiimide hydrochloride (36 mg, 0.18779 mmol) were added to 1 mL DMF and the mixture was stirred at room temperature for 12 hours. The reaction solution was concentrated and purified by silica gel column chromatography (dichloromethane/methanol 0 to 10%) to give (2-((5-fluoro-4-(7-fluoro-3-isopropyl-2-methyl-benzimidazol-5-yl)pyrimidin-2-yl)amino)-7,8-dihydro-5H-1,6-naphthyridin-6-yl)-(3-hydroxycyclobutyl)methanone (50 mg, 0.09370 mmol). $^1$H-NMR (DMSO-d$_6$) δ 10.05 (d, 1H, J=12 Hz), 8.69 (d, 1H, J=3.6 Hz), 8.32 (s, 1H), 8.13 (d, 1H, J=8.4 Hz), 7.71 (d, 1H, J=12.4 Hz), 7.60 (d, 1H, J=16.4 Hz), 5.07 (s, 1H), 4.84-4.88 (m, 1H), 4.57-4.61 (m, 2H), 3.99 (s, 1H), 3.71-3.81 (m, 2H), 2.83-2.90 (m, 3H), 2.68 (s, 3H), 2.38-2.42 (m, 2H), 1.93-2.03 (m, 2H), 1.64 (d, 6H, J=6.8 Hz). LC-MS: m/z: (M+H)$^+$=534.2.

Embodiment 37

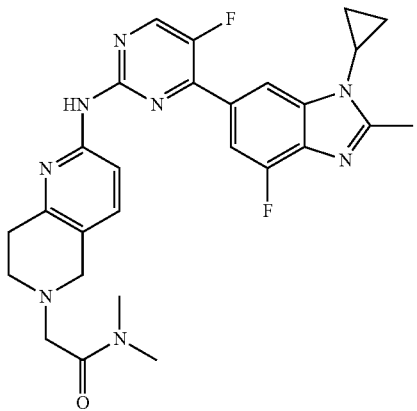

I-37

N-(5-Fluoro-4-(7-fluoro-3-cyclopropyl-2-methyl-benzimidazol-5-yl)pyrimidin-2-yl)-5,6,7,8-tetrahydro-1,6-naphthyridin-2-amine (100 mg, 0.23 mmol) (represented by formula I-28), 2-bromo-N,N-dimethylacetamide (50 mg, 0.30 mmol), diisopropylacetamide (200 mg, 1.55 mmol) were dissolved in DMF (2 mL) and the mixture was stirred at 90° C. for 16 hours. The reaction solution was cooled and diluted with water, extracted with ethyl acetate. The organic layer was concentrated and purified by silica gel thin-layer chromatography (DCM/CH₃OH=10/1). The crude product was slurried with ethyl acetate to give (2-(2-((4-(3-cyclopropyl-7-fluoro-2-methyl-benzimidazol-5-yl)-5-fluoro-pyrimidin-2-yl)amino)-7,8-dihydro-5H-1,6-naphthyridin-6-yl)-acetamide represented by formula I-37 (5 mg) as a pale yellow solid. ¹H-NMR (CDCl₃) δ 8.43 (d, 1H, J=3.6 Hz), 8.23 (d, 1H, J=8.4 Hz), 8.19 (s, 1H), 8.06 (s, 1H), 7.80 (d, 1H, J=12.0 Hz), 7.40 (d, 1H, J=8.0 Hz), 3.75 (s, 2H), 3.43 (s, 2H), 3.32-3.33 (m, 1H), 3.15 (s, 3H), 2.96-3.01 (m, 6H), 2.76 (s, 3H), 1.33-1.38 (m, 2H), 1.13-1.17 (m, 2H). LC-MS m/z: (M+H)⁺=519.2.

Embodiment 52

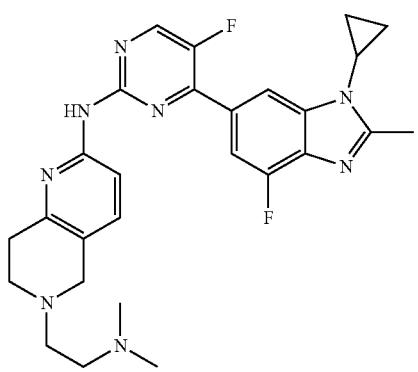

I-52

N-(5-Fluoro-4-(7-fluoro-3-cyclopropyl-2-methyl-benzimidazol-5-yl)pyrimidin-2-yl)-5,6,7,8-tetrahydro-1,6-naphthyridin-2-amine (1 g, 2.3 mmol) (represented by formula I-28), 2-(dimethylamino)acetaldehyde (600 mg, 6.9 mmol) were dissolved in dichloromethane, sodium triacetoxyborohydride (1.5 g, 7.1 mmol) was slowly added, and the mixture was stirred under reflux for 16 hours. The reaction solution was concentrated and purified by silica gel column chromatography (DCM/CH₃OH/NH₃.CH₃OH=100/10/2) to give N-(4-(3-cyclopropyl-7-fluoro-2-methyl-benzimidazol-5-yl)-5-fluoro-pyrimidin-2-yl)₆-(2-dimethylaminoethyl)-7,8-dihydro-5H-1,6-naphthyridin-2-amine represented by formula I-52 (1.1 g) as a pale yellow solid. H-NMR (CDCl₃) δ 8.43 (d, 1H, J=3.6 Hz), 8.26 (d, 1H, J=8.8 Hz), 8.19 (s, 1H), 7.80 (d, 1H, J=11.6 Hz), 7.42 (d, 1H, J=8.4 Hz), 3.72 (s, 2H), 3.31-3.34 (m, 1H), 3.10 (t, 2H, J=6.4 Hz), 2.92-2.98 (m, 6H), 2.76 (s, 3H), 2.74 (s, 6H), 1.33-1.38 (m, 2H), 1.13-1.17 (m, 2H). LC-MS m/z: (M+H)⁺=505.2.

Embodiment 61

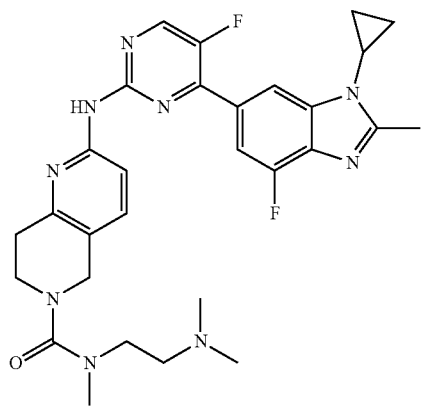

I-61

N-(5-Fluoro-4-(7-fluoro-3-cyclopropyl-2-methyl-benzimidazol-5-yl)pyrimidin-2-yl)-5,6,7,8-tetrahydro-1,6-naphthyridin-2-amine (100 mg, 0.23 mmol) (represented by formula I-28), bis(trichloromethyl)carbonate (40 mg, 0.13 mmol) and DIPEA (120 mg, 0.93 mmol) were dissolved in dichloromethane and the mixture was stirred at room temperature for 1 hour, then N,N,N'-trimethylethylenediamine (50 mg, 0.49 mmol) was added and stirred at room temperature for 16 hours. The reaction solution was concentrated, diluted with dichloromethane and water, partitioned, and the aqueous layer was concentrated and purified by column chromatography (C18, H₂O/CH₃OH=100% to 90%) and then purified by thin layer chromatography (DCM/CH₃OH=10/1) to give 2-((4-(3-cyclopropyl-7-fluoro-2-methyl-benzimidazol-5-yl)-5-fluoro-pyrimidine-)₂-yl)amino)-N-(2-dimethylaminoethyl)-N-methyl-7,8-dihydro-5H-1,6-naphthyridine-6-carboxamide represented by formula I-61 (10 mg) as a pale yellow solid. ¹H-NMR (400M Hz, CD₃OD) δ 8.45 (d, 1H, J=4.4 Hz), 7.93 (d, 1H, J=8.0 Hz), 7.79 (s, 1H), 7.43 (d, 1H, J=12.0 Hz), 7.27 (d, 1H, J=8.0 Hz), 4.28 (s, 2H), 3.52-3.55 (m, 4H), 3.24-3.27 (m, 1H), 3.04-3.07 (m, 5H), 2.80-8.83 (m, 2H), 2.72 (s, 6H), 2.58 (s, 3H), 1.22-1.24 (m, 2H), 0.95-0.98 (m, 2H). LC-MS m/z: (M+H)⁺=562.3.

Embodiment 62

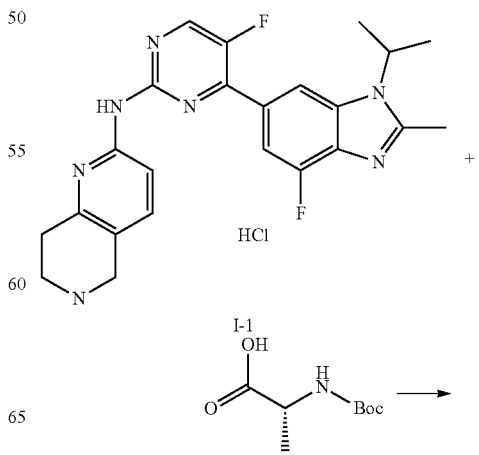

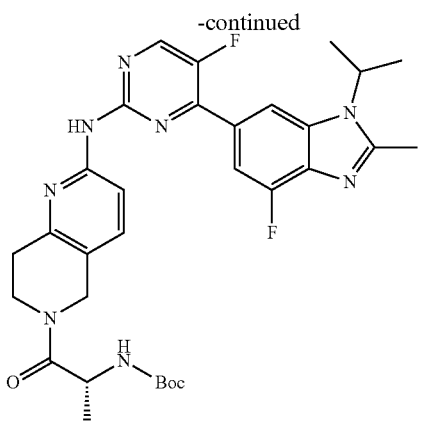

I-62-a

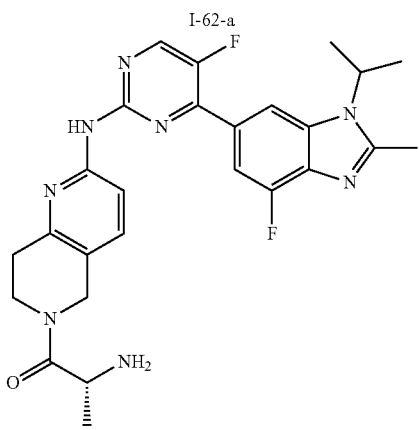

I-62-b

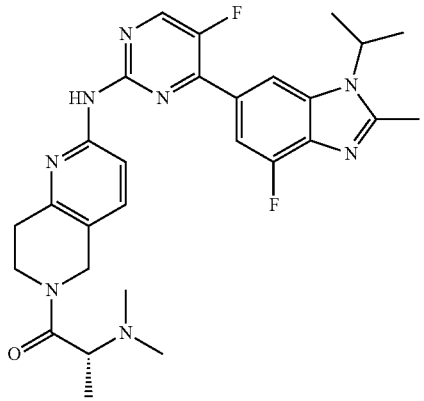

I-62

Step 1

N-(5-fluoro-4-(7-fluoro-3-cyclopropyl-2-methyl-benzimidazol-5-yl)pyrimidin-2-yl)-5,6,7,8-tetrahydro-1,6-naphthyridin-2-amine (110 mg, 0.23 mmol) (represented by formula I-1), Boc-N-methyl-D-alanine (60 mg, 0.29 mmol), EDCI (60 mg, 0.31 mmol), HOBt (50 mg, 0.37 mmol) and diisopropylacetamide (100 mg, 0.77 mmol) were dissolved in DMF (4 mL) and the mixture was stirred at room temperature for 16 hours. The reaction solution was purified by silica gel column chromatography (DCM/CH$_3$OH 0 to 10%) to give tert-butyl N-((1R)-(2-(2-((5-fluoro-4-(7-fluoro-3-isopropyl-2-methyl-benzimidazol-5-yl)pyrimidin-2-yl)amino)-7,8-dihydro-5H-1,6-naphthyridine-6-yl)-1-methyl-2-oxo-ethyl)-N-methylcarbamate represented by formula I-62-a (130 mg) as a pale yellow solid. LC-MS m/z: (M+H)$^+$=607.2.

Step 2

Tert-butyl N-((1R)-(2-(2-((5-fluoro-4-(7-fluoro-3-isopropyl-2-methyl-benzimidazol-5-yl)pyrimidin-2-yl)amino)-7,8-dihydro-5H-1,6-naphthyridine-6-yl)-1-methyl-2-oxo-ethyl)-N-methylcarbamate (120 mg, 0.19 mmol) (represented by formula I-62-a) was dissolved in 1,4-dioxane (4 mL), a solution of hydrochloride (4M) in 1,2-dioxane was added, the mixture was stirred at room temperature for 16 hours, filtered, dissolved in water. After adjusting the pH to 7 by adding aqueous sodium bicarbonate solution, the mixture was extracted with a mixed solution of dichloromethane and methanol, and the organic solvent was concentrated to give (2R)-1-(2-((5-fluoro-4-(7-fluoro-3-isopropyl-2-methyl-benzimidazol-5-yl)pyrimidin-2-yl)amino)-7,8-dihydro-1,6-naphthyridin-6-yl)-2-(methylamino)propyl-1-one represented by the formula I-62-b (110 mg). LC-MS m/z: (M+H)$^+$=507.2.

Step 3

(2R)-1-(2-((5-Fluoro-4-(7-fluoro-3-isopropyl-2-methyl-benzimidazol-5-yl)pyrimidin-2-yl)amino)-7,8-dihydro-1,6-naphthyridin-6-yl)-2-(methyl amino)propyl-1-one (110 mg, 0.21 mmol) (represented by the formula I-62-b) was dissolved in methanol (4 mL), aqueous formaldehyde solution (10 mg, 0.33 mmol) was slowly added dropwise and the mixture was stirred at room temperature for 1 hour, then sodium cyanoborohydride (50 mg, 0.44 mmol) was added and stirred for 16 hours. The reaction solution was concentrated and purified by column chromatography (DCM/CH$_3$OH/NH$_3$.CH$_3$OH=10/1/0.2) to give a crude product, which was then purified by preparative liquid chromatography to give (2R)-2-(methylamino)-1-(2-((5-fluoro-4-(7-fluoro-3-isopropyl-2-methyl-benzimidazol-5-yl)pyrimidin-2-yl)amino)-7,8-dihydro-5H-1,6-naphthyridin-6-yl)propyl-1-ketone represented by formula I-62 (30 mg) as a yellow solid. H-NMR (400M Hz, CD$_3$OD) δ 8.55 (d, 1H, J=3.6 Hz), 8.33 (d, 1H, J=1.2 Hz), 8.28 (t, 1H, J=7.2 Hz), 7.80 (d, 1H, J=12.0 Hz), 7.61-7.64 (m, 1H), 4.88-4.96 (m, 2H), 4.66-4.75 (m, 1H), 4.45-4.49 (m, 1H), 3.85-4.11 (m, 2H), 3.03-3.11 (m, 1H), 2.95-2.98 (m, 1H), 2.84 (d, 6H, J=3.6 Hz), 2.71 (s, 3H), 1.74 (d, 6H, J=6.8 Hz), 1.50-1.56 (m, 3H). LC-MS m/z: (M+H)$^+$=535.2.

Embodiment 72

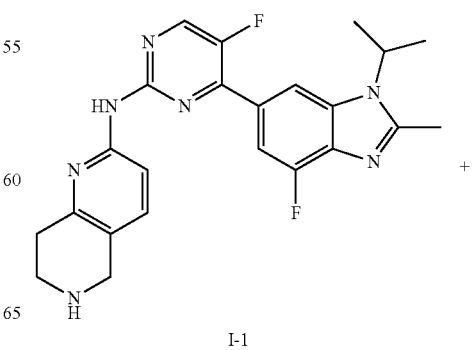

I-1

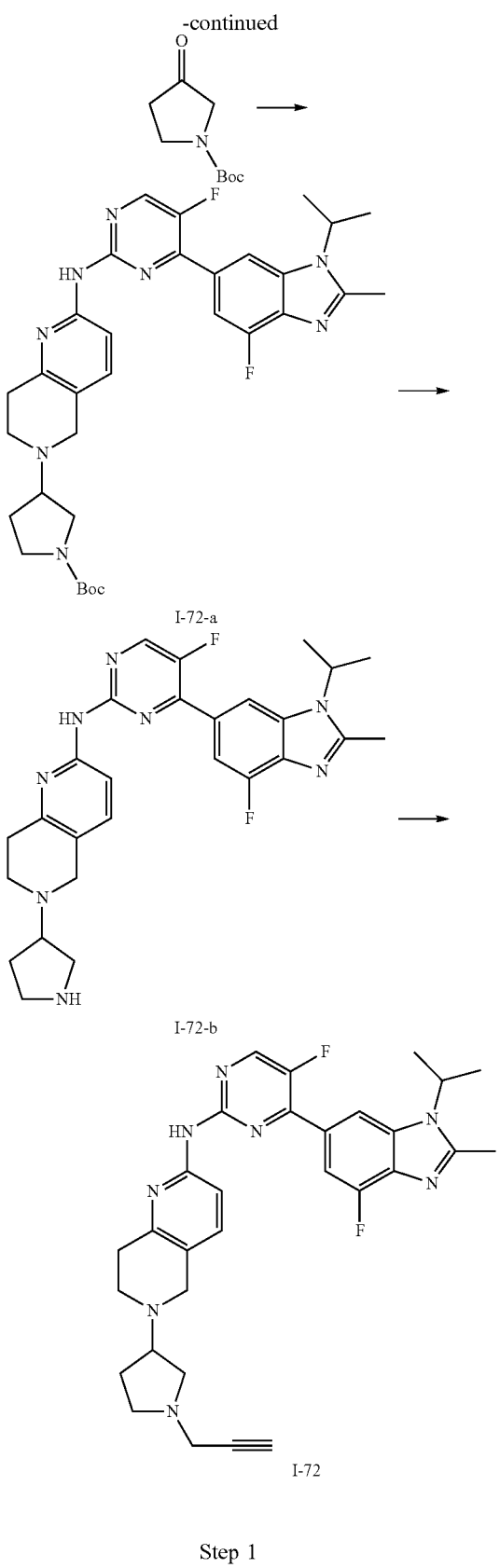

I-72-a

I-72-b

I-72

Step 1

N-(5-Fluoro-4-(7-fluoro-1-isopropyl-2-methyl-1H-benzo[d]imidazol-5-yl)pyrimidin-2-yl)-5,6,7,8-tetrahydro-1,6-naphthyridin-2-amine (200 mg, 0.46 mmol) (represented by formula I-1) was dissolved in 5 mL methanol, 1-tert-butoxycarbonyl-3-pyrrolidone (170 mg, 0.92 mmol) and sodium triacetoxyborohydride (146 mg, 0.92 mmol) were added, the mixture was stirred at room temperature for 16 hours. Solvent was evaporated under reduced pressure, saturated sodium bicarbonate solution was added, the mixture was extracted with dichloromethane, evaporated under reduced pressure. The residue was purified by silica gel column chromatography to give the compound represented by formula I-72-a as a yellow solid (170 mg), yield 61%. LC-MS: 604.9[M+H]+.

Step 2

Tert-butyl 3-(2-((5-fluoro-4-(4-fluoro-1-isopropyl-2-methyl-1H-benzo[d]imidazol-6-yl)pyrimidin-2-yl)amino)-7,8-dihydro-1,6-naphthyridine-6(5H)-yl)pyrrolidine-1-carboxylate (represented by formula I-72-a) (170 mg, 0.28 mmol) was dissolved in 5 mL dioxane, a solution of 4N HCl in dioxane (1 mL) was added dropwise, and the mixture was stirred at room temperature for 4 hours. Solvent was evaporated under reduced pressure, saturated sodium bicarbonate solution was added, and the mixture was extracted with dichloromethane. The solvent was evaporated under reduced pressure to give the compound represented by the formula I-72-b as a yellow solid (138 mg), yield 97%. LC-MS: 504.9 [M+H]$^+$.

Step 3

N-(5-Fluoro-4-(4-fluoro-1-isopropyl-2-methyl-1H-benzo[d]imidazol-6-yl)pyrimidin-2-yl)-6-(pyrrolidine-3-yl)-5,6,7,8-tetrahydro-1,6-naphthyridin-2-amine (represented by formula I-72-b) (138 mg, 0.27 mmol) was dissolved in 5 mL dioxane, sodium hydroxide (55 mg, 1.37 mmol) and bromopropyne (32 mg, 0.27 mmol) were added and the mixture was stirred at room temperature for 2 hours. Solvent was evaporated under reduced pressure, and the residue was purified by silica gel column chromatography to give the compound represented by formula I-72 as a yellow solid, 55 mg, 38% yield. $^1$H NMR (400 MHz, CDCl$_3$) δ 8.43 (d, J=3.8 Hz, 1H), 8.23 (dd, J=9.2, 4.8 Hz, 2H), 7.99 (s, 1H), 7.80 (d, J=12.2 Hz, 1H), 7.39 (d, J=8.5 Hz, 1H), 4.75 (dt, J=14.0, 7.0 Hz, 1H), 3.69 (s, 2H), 3.49 (d, J=2.2 Hz, 2H), 3.27-3.05 (m, 2H), 3.00 (d, J=7.9 Hz, 2H), 2.97-2.75 (m, 4H), 2.74-2.68 (m, 3H), 2.28 (t, J=2.3 Hz, 1H), 2.20 (dd, J=13.0, 6.3 Hz, 1H), 1.92 (dd, J=12.9, 6.4 Hz, 2H), 1.73 (d, J=7.0 Hz, 6H). LC-MS: m/z: (M+H)$^+$=542.9.

Embodiment 73

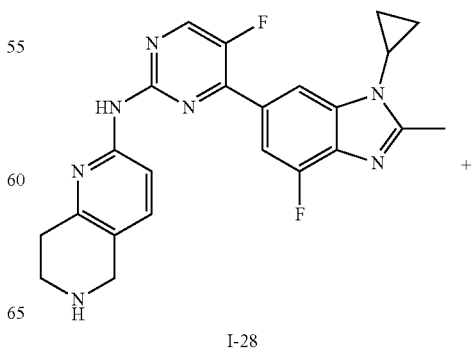

I-28

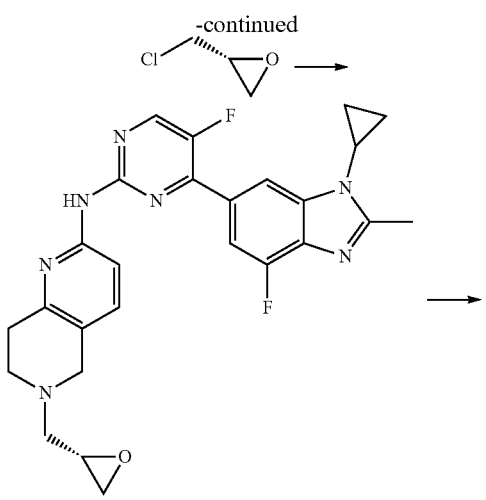

I-73-a

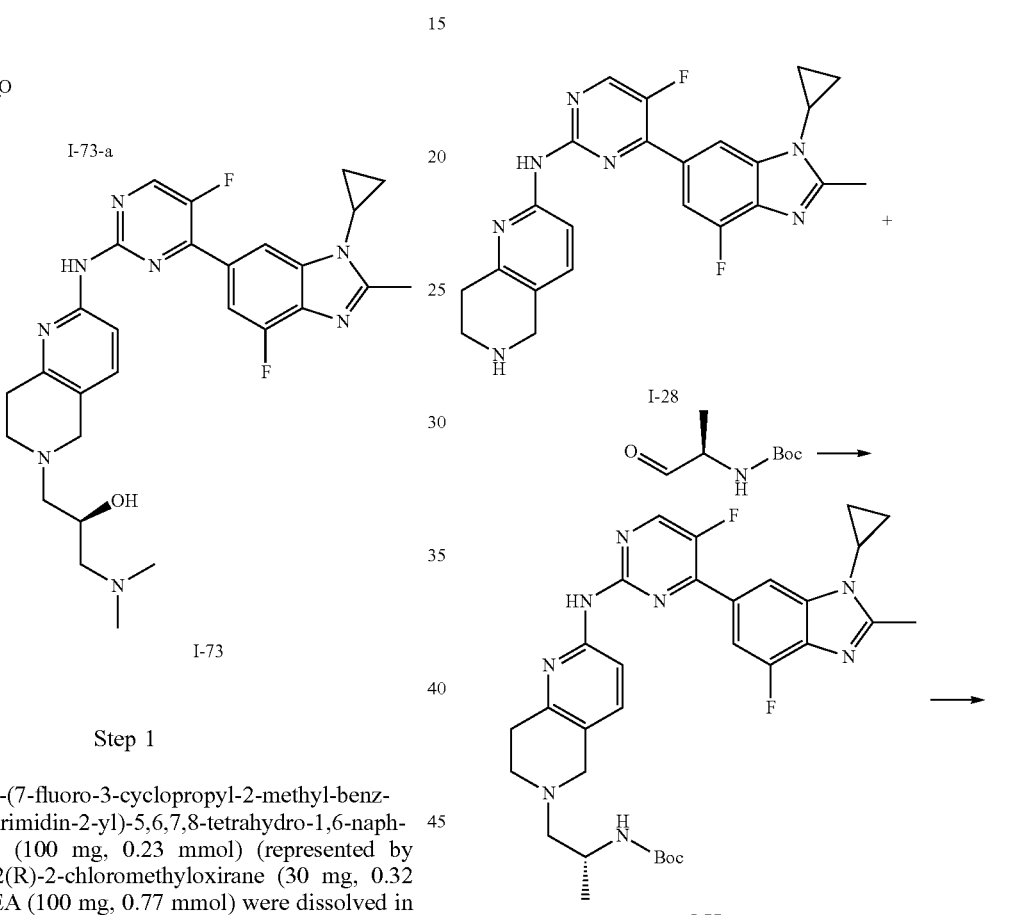

I-73

Step 1

N-(5-Fluoro-4-(7-fluoro-3-cyclopropyl-2-methyl-benzimidazol-5-yl)pyrimidin-2-yl)-5,6,7,8-tetrahydro-1,6-naphthyridin-2-amine (100 mg, 0.23 mmol) (represented by formula I-28), 2(R)-2-chloromethyloxirane (30 mg, 0.32 mmol) and DIPEA (100 mg, 0.77 mmol) were dissolved in N,N-dimethylformamide (4 mL), the mixture was stirred at 80° C. for 16 hours. The reaction solution was concentrated and purified by silica gel column chromatography (DCM/CH$_3$OH=10/1) to give (S)—N-(4-(1-cyclopropyl-4-fluoro-2-methyl-1H-benzimidazol-6-yl)-5-fluoropyrimidin-2-yl)-6-(epoxy-2-ylmethyl)-5,6,7,8-tetrahydro-1,6-naphthyridin-2-amine represented by formula I-73-a (30 mg) as a pale yellow solid. LC-MS m/z: (M+H)$^+$=490.2.

Step 2

(S)—N-(4-(1-cyclopropyl-4-fluoro-2-methyl-1H-benzimidazol-6-yl)-5-fluoropyrimidin-2-yl)-6-(epoxy-2-ylmethyl)-5,6,7,8-tetrahydro-1,6-naphthyridin-2-amine (30 mg, 0.06 mmol)(represented by formula I-73-a), dimethylamine (10 mg, 0.22 mmol) were dissolved in ethanol (5 mL), the mixture was stirred at 60° C. for 4 hours. The reaction solution was concentrated and purified by silica gel column chromatography (DCM/CH$_3$OH=10/1) to give (S)-1-(2-((4-(1-cyclopropyl-4-fluoro-2-methyl-1H-benzimidazol-6-yl)-5-fluoropyrimidin-2-yl)amino)-7,8-dihydro-1,6-naphthyridine-6(5H)-yl)-3-(dimethylamino)propyl-2-ol represented by formula I-73 (10 mg) as a pale yellow solid. $^1$H NMR (400 MHz, CDCl$_3$) δ 8.37 (d, J=3.7 Hz, 1H), 8.19 (d, J=8.5 Hz, 1H), 8.13 (s, 1H), 7.77-7.70 (m, 1H), 7.40 (d, J=8.6 Hz, 1H), 4.35 (m, 1H), 3.77 (s, 2H), 3.23 (d, J=15.2 Hz, 2H), 3.06-2.91 (m, 5H), 2.87 (s, 6H), 2.72-2.62 (m, 5H), 1.34-1.29 (m, 2H), 1.10 (t, J=8.0 Hz, 2H). LC-MS m/z: (M+H)$^+$=534.9.

Embodiment 77

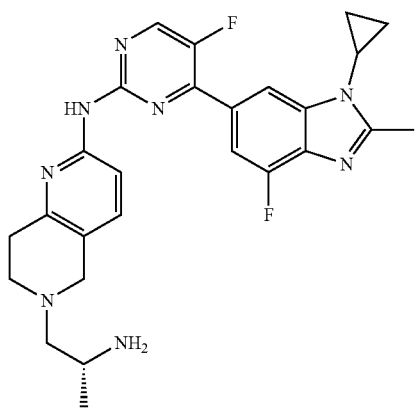

I-77

Step 1

N-(5-Fluoro-4-(7-fluoro-3-cyclopropyl-2-methyl-benzoimidazol-5-yl)pyrimidin-2-yl)-5,6,7,8-tetrahydro-1,6-naphthyridin-2-amine (100 mg, 0.23 mmol) (represented by formula I-28), N-boc-D-alanal (100 mg, 0.58 mmol) were dissolved in dichloromethane, sodium triacetoxyborohydride (200 mg, 0.94 mmol) was added slowly, the mixture was stirred under reflux for 16 hours. The reaction solution was concentrated and purified by silica gel column chromatography (DCM/CH$_3$OH/NH$_3$.CH$_3$OH=100/10/2) to give N-(4-(3-tert-butyl-N-((1R)-2-(2-((4-(3-cyclopropyl-7-fluoro-2-methyl-benzoimidazol-5-yl)-5-fluoro-pyrimidin-2-yl)amino)-7,8-dihydro-5H-1,6-naphthyridin-6-yl)-1-methyl-ethyl)carbonate represented by formula I-77-a (60 mg) as a pale yellow solid. LC-MS m/z: (M+H)$^+$=591.2.

Step 2

Tert-butyl N-((1R)-2-(2-((4-(3-cyclopropyl-7-fluoro-2-methyl-benzimidazol-5-yl)-5-fluoro-pyrimidine 2-yl) amino)-7,8-dihydro-5H-1,6-naphthyridin-6-yl)-1-methylethyl)carbonate (60 mg, 0.2 mmol) (represented by formula I-77-a) was dissolved in dichloromethane (4 mL), a solution of hydrochloric acid in 1,2-dioxane (4M, 1 mL) was added, and the mixture was stirred at room temperature for 4 hours. The reaction solution was concentrated and dissolved in dichloromethane and stirred at room temperature for 30 min, then filtered and dried to give 6-((2R)-aminopropyl)-N-(4-(3-cyclopropyl-7-fluoro-2-yl-benzimidazol-5-yl)-5-fluoro-pyrimidin-2-yl)-7,8-dihydro-5H-1,6-naphthyridin-2-amino hydrochloride (60 mg) as a pale yellow solid. $^1$H NMR (400 MHz, CD$_3$OD) δ 8.98 (d, J=3.3 Hz, 1H), 8.58 (s, 1H), 8.27 (d, J=11.2 Hz, 1H), 8.22 (d, J=9.1 Hz, 1H), 7.59 (d, J=9.0 Hz, 1H), 4.75-4.44 (m, 2H), 4.08 (M, 1H), 3.95-3.82 (m, 1H), 3.80-3.73 (m, 2H), 3.67-3.48 (m, 4H), 3.04 (s, 3H), 1.54 (M, 5H), 1.42-1.34 (m, 2H). LC-MS: m/z: (M+H)$^+$=490.9.

Embodiment 80

6-((2R)-Aminopropyl)-N-(4-(3-cyclopropyl-7-fluoro-2-methyl-benzimidazol-5-yl)-5-fluoro-pyrimidine-2-yl)-7,8-dihydro-5H-1,6-naphthyridin-2-amine (50 mg, 0.21 mmol) (represented by formula I-77) was dissolved in methanol (6 mL), aqueous formaldehyde (20 mg, 0.67 mmol) was slowly added dropwise, followed by addition of sodium triacetoxyborohydride (50 mg, 0.24 mmol), the mixture was stirred at 60° C. for 16 hours. The reaction solution was concentrated and purified by column chromatography (DCM/CH$_3$OH/NH$_3$.CH$_3$OH=10/1/0.2) to give a crude product, which was purified by preparative liquid phase to give N-(4-(3-cyclopropyl-7-fluoro-2-methyl-benzoimidazol-5-yl)-5-fluoro-pyrimidin-2-yl)-6-((2R)-2-(dimethylaminopropyl)-7,8-dihydro-5H-1,6-naphthyridin-2-amine represented by formula I-80(25 mg) as a pale yellow solid. $^1$H NMR (400 MHz, CD$_3$OD) δ 8.52 (d, J=3.9 Hz, 1H), 8.26 (s, 1H), 8.18 (d, J=8.5 Hz, 1H), 7.80 (d, J=12.1 Hz, 1H), 7.52 (d, J=8.6 Hz, 1H), 3.87 (d, J=14.7 Hz, 1H), 3.78-3.65 (m, 2H), 3.46 (m, 1H), 3.14-3.04 (m, 1H), 3.02-2.88 (m, 4H), 2.80 (s, 6H), 2.75 (s, 3H), 2.68 (m, 1H), 1.36 (d, J=7.0 Hz, 2H), 1.31 (d, J=6.6 Hz, 3H), 1.21-1.14 (m, 2H). LC-MS: m/z: (M+H)$^+$=519.0.

Embodiment 95

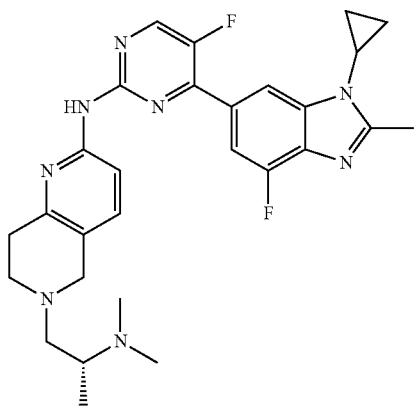

I-80

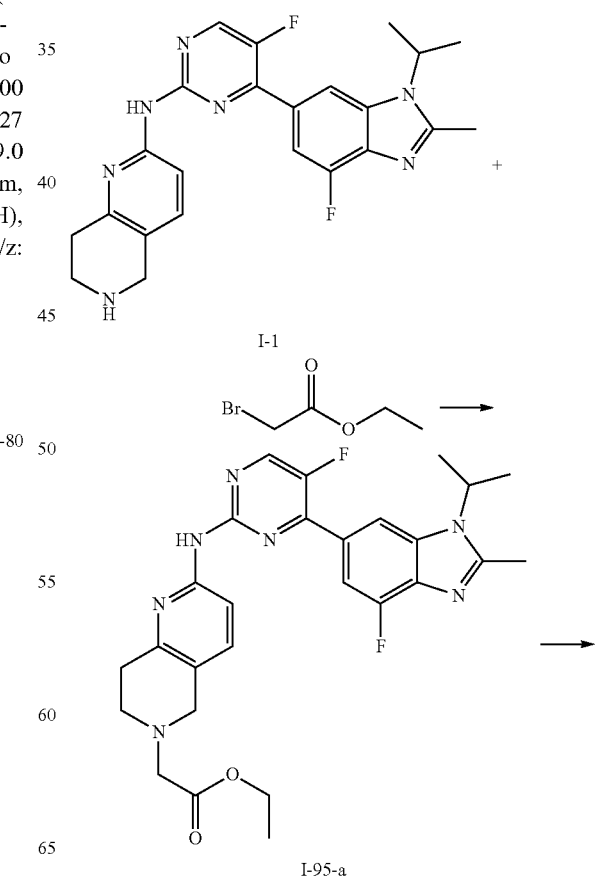

I-1

I-95-a

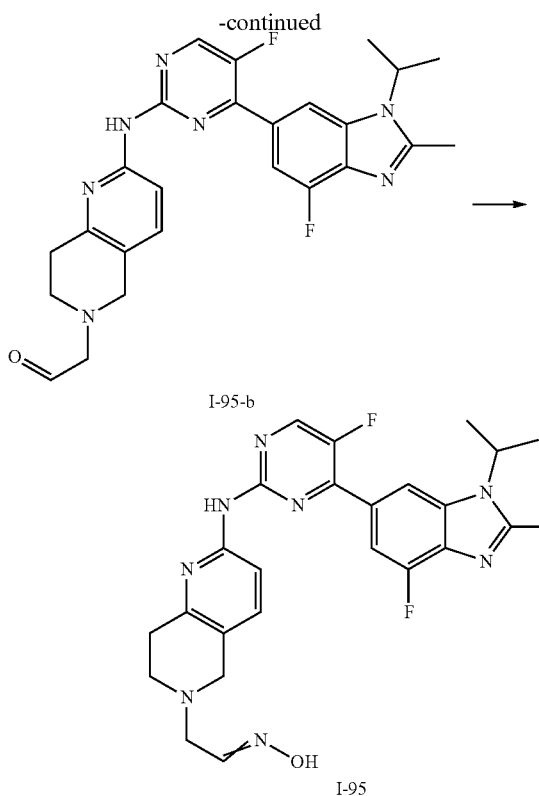

I-95-b

I-95

Step 1

Potassium carbonate (75 mg, 0.55 mmol) and N-(5-fluoro-4-(4-fluoro-1-isopropyl-2-methyl-1H-benzo[d]imidazol-6-yl)pyrimidine-2-yl)-5,6,7,8-tetrahydro-1,6-naphthyridin-2-amine (120 mg, 0.275 mmol) was added to 15 mL N,N-dimethylformamide, followed by the addition of ethyl bromoacetate (75 mg, 0.45 mmol), the mixture was stirred at room temperature overnight. The reaction solution was evaporated to dryness under reduced pressure and purified by silica gel column chromatography to give 2-(2-((5-fluoro-4-(4-fluoro-1-isopropyl-2-methyl-1H-benzo[d]imidazol-6-yl)pyrimidin-2-yl)amino)-7,8-dihydro-1,6-naphthyridin-6(5H)-yl)ethyl acetate represented by the formula I-95-a (100 mg) as a pale yellow solid.

Step 2

Ethyl 2-(2-((5-Fluoro-4-(4-fluoro-1-isopropyl-2-methyl-1H-benzo[d]imidazol-6-yl)pyrimidin-2-yl)amino)-7,8-dihydro-1,6-naphthyridin-6(5H)-yl) acetate was dissolved in 15 mL dry dichloromethane, and 2 mL DIBAL-H (1 mol/L in toluene) was added at −78° C., the mixture was stirred at this temperature for 3 h. Then the reaction was quenched with methanol, 2 mL saturated ammonium chloride was added and the mixture was stirred at room temperature for 10 minutes. The organic layer was dried over sodium sulfate and then concentrated to give 2-(2-((5-fluoro-4-(4-fluoro-1-isopropyl-2-methyl-1H-benzo[d]imidazol-6-yl)pyrimidin-2-yl)amino)-7,8-dihydro-1,6-naphthyridin-6(5H)-yl)acetaldehyde represented by formula I-95-b, which was used in the next step without further purification. LC-MS: m/z: $(M+H)^+=478$.

Step 3

2-(2-((5-Fluoro-4-(4-fluoro-1-isopropyl-2-methyl-1H-benzo[d]imidazol-6-yl)pyrimidin-2-yl)amino)-7,8-dihydro-1,6-naphthyridin-6(5H)-yl)acetaldehyde (80 mg, 0.167 mmol), sodium acetate (100 mg, 0.73 mmol) and hydroxylamine hydrochloride (70 mg, 1 mmol) were added to 15 mL ethanol and the mixture was stirred at 80° C. for 2 h. The reaction solution was evaporated to dryness under reduced pressure and then purified by silica gel column chromatography to give 2-(2-((5-fluoro-4-(4-fluoro-1-isopropyl-2-methyl-1H-benzo[d]imidazol-6-yl)pyrimidin-2-yl)amino)-7,8-dihydro-1,6-naphthyridin-6(5H)-yl)acetaldehyde represented by formula I-95(28 mg) as a light yellow solid. H NMR (400 MHz, CD$_3$OD) δ 8.48 (d, J=3.8 Hz, 1H), 8.28 (d, J=0.9 Hz, 1H), 8.22 (d, J=8.5 Hz, 1H), 7.78 (d, J=11.9 Hz, 1H), 7.55-7.42 (m, 1.44H), 6.90 (t, J=4.5 Hz, 0.3H), 4.89-4.83 (m, 1H), 3.71 (d, J=10.8 Hz, 2H), 3.58 (d, J=4.5 Hz, 1H), 3.36 (d, J=6.1 Hz, 2H), 3.06-2.89 (m, 4H), 2.69 (s, 3H), 1.74 (t, J=6.5 Hz, 6H). LC-MS: m/z: $(M+H)^+=493$.

Embodiment 97

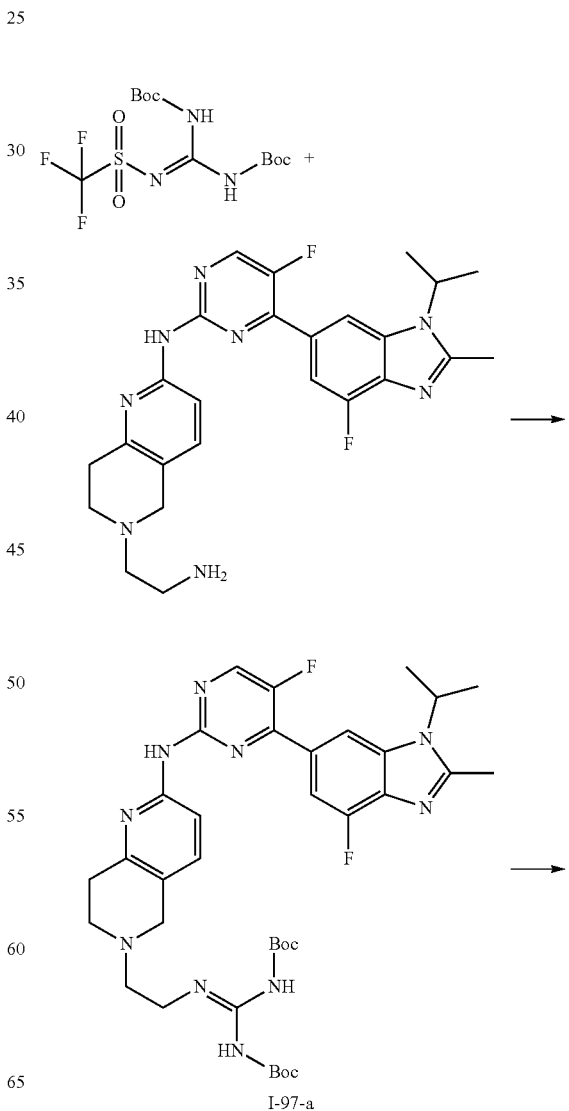

I-97-a

-continued

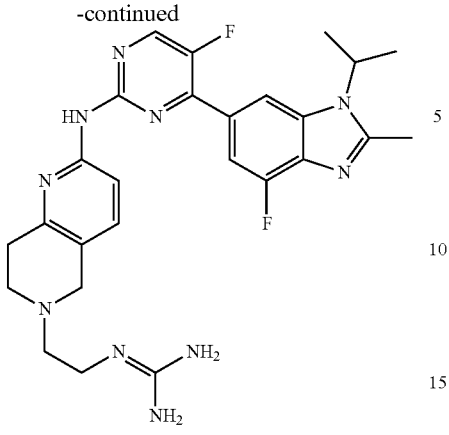

I-97

Step 1

Tert-butyl-N—(N-tert-butoxycarbonyl-N'-(trifluoromethylsulfonyl)carbamimidoyl)carbamate (80 mg, 0.21 mmol), 6-(2-aminoethyl)-N-(5-fluoro-4-(4-fluoro-1-isopropyl-2-methyl-1H-benzo[d]imidazol-6-yl)pyrimidin-2-yl)-5,6,7,8-tetrahydro-1,6-naphthyridin-2-amine hydrochloride (100 mg, 0.21 mol) and triethylamine (0.5 ml) were added to 15 mL N,N-dimethylformamide and the mixture was stirred at room temperature overnight. The reaction solution was evaporated to dryness under reduced pressure and then purified by silica gel column chromatography to give tert-butyl-N—(N-tert-butoxycarbonyl-N'-(2-(2-((5-fluoro-4-(7-fluoro-3-isopropyl-2-methylbenzimidazol-5-yl)pyrimidin-2-yl)amino)-7,8-dihydro-5H-1,6-naphthyridin-6-yl)ethyl)carbamimidoyl)carbamic acid represented by the formula I-97-a (130 mg) as a pale yellow solid. LC-MS: m/z: $(M+H)^+=721$.

Step 2

Tert-butyl-N—(N-tert-butoxycarbonyl-N'-(2-(2-((5-fluoro-4-(7-fluoro-3-isopropyl-2-methylbenzimidazol-5-yl)pyrimidin-2-yl)amino)-7,8-dihydro-5H-1,6-naphthyridin-6-yl)ethyl)carbamimidoyl)carbamic acid (120 mg, 0.166 mmol) was added to 5 mL dichloromethane and 5 mL trifluoroacetic acid was added under an ice bath. The mixture was stirred at room temperature for 3 h, then evaporated to dryness under reduced pressure and purified by preparative HPLC to give 2-(2-(2-((5-fluoro-4-(4-fluoro-1-isopropyl-2-methyl-1H-benzo[d]imidazol-6-yl)pyrimidin-2-yl)amino)-7,8-dihydro-1,6-naphthyridine-6(5H)-yl)ethyl) guanidine represented by formula I-97 (50 mg) as a light yellow solid. $^1$H NMR (400 MHz, CD$_3$OD) δ 8.53 (d, J=3.9 Hz, 1H), 8.32 (d, J=1.2 Hz, 1H), 8.26 (s, 1H), 8.16 (d, J=8.5 Hz, 1H), 7.77 (d, J=12.8 Hz, 1H), 7.50 (d, J=8.6 Hz, 1H), 4.93 (d, J=6.9 Hz, 1H), 3.73 (s, 2H), 3.48-3.41 (m, 2H), 2.97 (s, 4H), 2.84 (t, J=5.7 Hz, 2H), 2.71 (s, 3H), 1.73 (d, J=6.9 Hz, 6H). LC-MS: m/z: $(M+H)^+=521$.

Embodiment 107

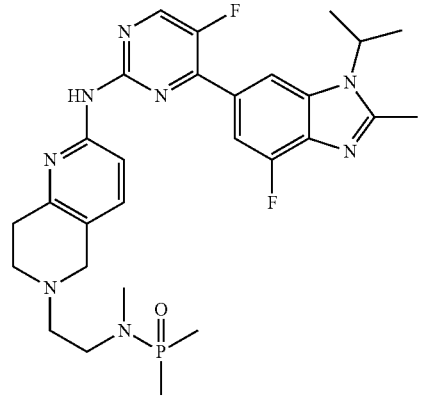

I-107

Triethylamine (0.5 mL) and N-(5-fluoro-4-(4-fluoro-1-isopropyl-2-methyl-1H-benzo[d]imidazol-6-yl)pyrimidine-2-yl)-6-(2-(methylamino)ethyl)-5,6,7,8-tetrahydro-1,6-naphthyridin-2-amine hydrochloride (100 mg, 0.203 mmol) were added to 15 mL dry dichloromethane, then dimethylphosphine chloride (30 mg, 0.2667 mmol) was added and the mixture was stirred at room temperature for 3 h. The reaction solution was evaporated to dryness under reduced pressure and purified by silica gel column chromatography (DCM/CH$_3$OH/NH$_3$. CH$_3$OH=10/1/0.2) to give N-(2-(2-((5-fluoro-4-(4-fluoro-1-isopropyl-2-methyl-1H-benzo[d]imidazol-6-yl)pyrimidin-2-yl)amino)-7,8-dihydro-1,6-naphthyridin-6(5H)-yl)ethyl)-N,P,P-dimethylphosphinic amide represented by formula I-107 (40 mg) as a pale yellow solid. $^1$H NMR (400 MHz, CDCl$_3$) δ 8.44 (d, J=3.8 Hz, 1H), 8.22 (dd, J=17.5, 9.9 Hz, 3H), 7.78 (d, J=11.6 Hz, 1H), 7.39 (d, J=8.5 Hz, 1H), 4.83-4.67 (m, 1H), 3.77 (s, 2H), 3.29 (dd, J=15.9, 7.0 Hz, 2H), 3.00 (s, 4H), 2.83-2.77 (m, 2H), 2.72 (d, J=11.8 Hz, 6H), 1.74 (t, J=9.7 Hz, 6H), 1.50 (d, J=13.2 Hz, 6H). LC-MS: m/z: $(M+H)^+=569$.

Embodiment 110

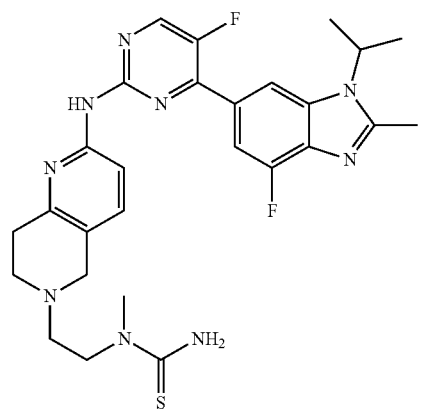

I-110

N-(5-Fluoro-4-(4-fluoro-1-isopropyl-2-methyl-1H-benzo[d]imidazol-6-yl)pyrimidin-2-yl)-6-(2-(methylamino)ethyl)-5,6,7,8-tetrahydro-1,6-naphthyridin-2-amine hydrochloride (100 mg, 0.2 mmol), diisopropylethylamine (0.5 mL) and thiocarbonyldiimidazole (74 mg, 0.41 mmol) were added to 15 mL N,N-dimethylformamide, the mixture was stirred at 50° C. for 3 h. The reaction solution was cooled to room temperature, 10 mL aqueous ammonia was added to the above reaction solution, and the mixture was stirred overnight at room temperature. The reaction solution was evaporated to dryness under reduced pressure, then purified by silica gel column chromatography to give 1-(2-(2-((5-fluoro-4-(4-fluoro-1-isopropyl-2-methyl-1H-benzo[d]imidazol-6-yl)pyrimidin-2-yl)amino)-7,8-dihydro-1,6-naphthyridine-6(5H)-yl)ethyl)-1-methylthiourea represented by formula I-110 (24 mg) as a pale yellow solid. $^1$H NMR (400 MHz, DMSO-$d_6$) δ 9.95 (s, 1H), 8.68 (d, J=3.9 Hz, 1H), 8.32 (s, 1H), 8.07 (d, J=8.5 Hz, 1H), 7.70 (d, J=12.0 Hz, 1H), 7.45 (d, J=8.5 Hz, 1H), 7.25 (s, 1H), 4.85 (dt, J=13.9, 7.0 Hz, 1H), 3.64 (s, 2H), 3.11 (d, J=19.9 Hz, 2H), 2.86 (d, J=11.9 Hz, 4H), 2.72 (t, J=6.5 Hz, 2H), 2.65 (s, 3H), 1.64 (d, J=6.9 Hz, 6H). LC-MS: m/z: (M+H)$^+$=552.

Embodiment 132

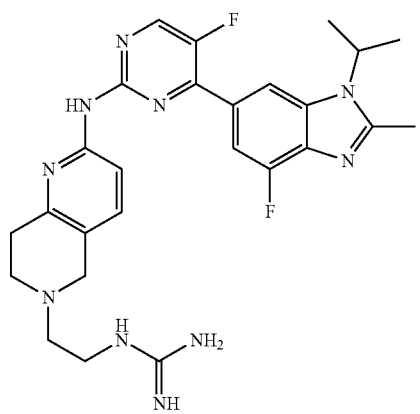

A-132

6-(2-Aminoethyl)-N-(5-fluoro-4-(4-fluoro-1-isopropyl-2-methyl-1H-benzo[d]imidazol-6-yl)pyrimidine-2-yl)-5,6,7,8-tetrahydro-1,6-naphthyridin-2-amine hydrochloride (120 mg, 0.25 mol) and 1H-pyrazole-1-carboxamidine hydrochloride (73 mg, 0.5 mmol) were dissolved in N,N-dimethylformamide (5 ml), then diisopropylethylamine (350 mg, 2.7 mmol) was added and the mixture was stirred at room temperature overnight. The reaction solution was evaporated under reduced pressure, and then purified by preparative HPLC to give 1-(2-(2-((5-fluoro-4-(4-fluoro-1-isopropyl-2-methyl-1H-benzo[d]imidazol-6-yl)pyrimidin-2-yl)amino)-7,8-dihydro-1,6-naphthyridine-6(5H)-yl)ethyl)guanidine (28 mg) as a pale yellow solid. $^1$H NMR (400 MHz, CD$_3$OD) δ 8.51 (d, J=4.0 Hz, 1H), 8.38 (s, 2H), 8.29 (d, J=1.1 Hz, 1H), 8.13 (d, J=8.5 Hz, 1H), 7.71 (d, J=12.7 Hz, 1H), 7.44 (d, J=8.5 Hz, 1H), 4.93 (d, J=7.0 Hz, 0H), 3.69 (s, 0H), 3.45 (t, J=5.6 Hz, 2H), 2.93 (s, 4H), 2.82 (t, J=5.6 Hz, 2H), 2.69 (s, 3H), 1.72 (d, J=6.9 Hz, 6H). LC-MS: m/z: (M+H)$^+$=521.

Embodiment 133

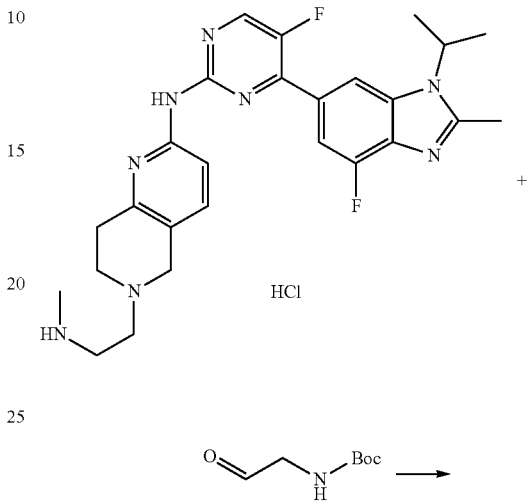

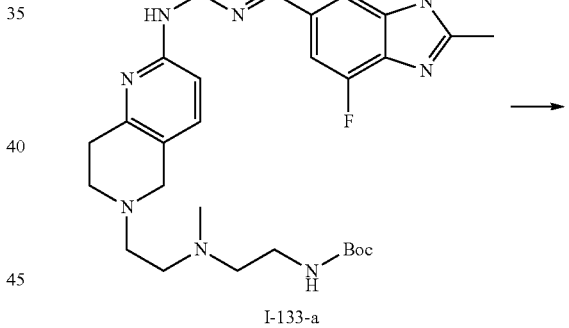

I-133-a

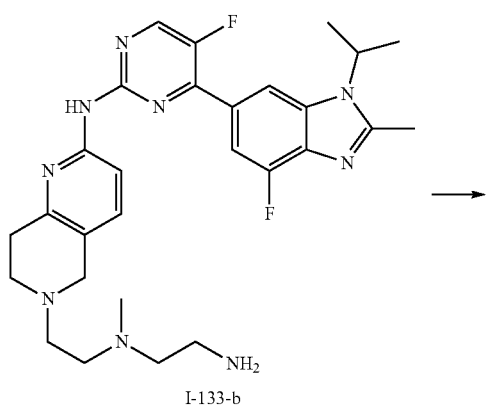

I-133-b

-continued

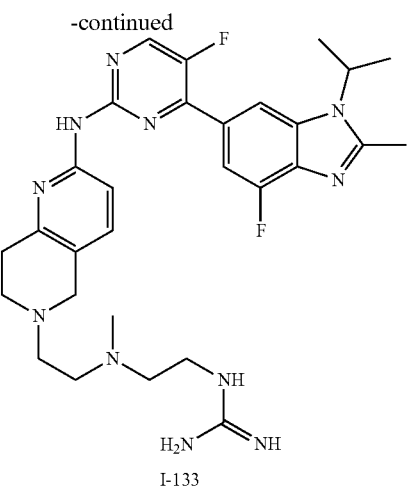

I-133

Step 1

N-(5-Fluoro-4-(4-fluoro-1-isopropyl-2-methyl-1H-benzo[d]imidazol-6-yl)pyrimidin-2-yl)-6-(2-(methylamino)ethyl)-5,6,7,8-tetrahydro-1,6-naphthyridin-2-amine hydrochloride (90 mg, 0.15 mmol), tert-butyl (2-oxoethyl)carbamic acid (50 mg, 0.3 mmol) and triethylamine (1 mL) were added to 25 mL dichloromethane, followed by the addition of sodium triacetoxyborohydride (65 mg, 0.3 mmol). The mixture was stirred at room temperature overnight. The reaction solution was evaporated to dryness under reduced pressure and the residue was purified by silica gel column chromatography to give tert-butyl(2-((2-(2-((5-fluoro-4-(4-fluoro-1-isopropyl-2-methyl-1H-benzo[d]imidazol-6-yl)pyrimidin-2-yl)amino)-7,8-dihydro-1,6-naphthyridine-6(5H)-yl)ethyl)(methyl)amino)ethyl)carbamate represented by formula I-133-a (80 mg) as a pale yellow solid. LC-MS: m/z: (M+H)$^+$=636.

Step 2

Tert-butyl(2-((2-(2-((5-Fluoro-4-(4-fluoro-1-isopropyl-2-methyl-1H-benzo[d]imidazol-6-yl)pyrimidin-2-yl)amino)-7,8-dihydro-1,6-naphthyridine-6(5H)-yl)ethyl)(methyl)amino)ethyl)carbamate (90 mg, 0.14 mmol) was dissolved in methanol (3 mL), 4 mL solution of 4 mol/L hydrochloride in 1,4-dioxane was added, and the resulting solution was stirred at room temperature for 2 h. The reaction mixture was evaporated to dryness under reduced pressure to give N$^1$-(2-(2-((5-fluoro-4-(4-fluoro-1-isopropyl-2-methyl-1H-benzo[d]imidazol-6-yl)pyrimidin-2-yl)amino)-7,8-dihydro-1,6-naphthyridine-6(5H)-yl)ethyl)-N$^1$-methylethane-1,2-diamine hydrochloride represented by formula I-133-b (80 mg) as a white solid. LC-MS: m/z: (M+H)$^+$=536.

Step 3

N$^1$-(2-(2-((5-Fluoro-4-(4-fluoro-1-isopropyl-2-methyl-1H-benzo[d]imidazol-6-yl)pyrimidin-2-yl)amino)-7,8-dihydro-1,6-naphthyridine-6(5H)-yl)ethyl)-N$^1$-methylethane-1,2-diamine hydrochloride (80 mg, 0.15 mmol) and 1H-pyrazole-1-carboxamidine hydrochloride (45 mg, 0.3 mmol) were dissolved in N,N-dimethylformamide (5 mL) and diisopropylethylamine (350 mg, 2.7 mmol) was added. The mixture was stirred at room temperature overnight, then evaporated to dryness under reduced pressure and purified by preparative HPLC to give 1-(2-((2-(2-((5-fluoro-4-(4-fluoro-1-isopropyl-2-methyl-1H-benzo[d]imidazol-6-yl)pyrimidin-2-yl)amino)-7,8-dihydro-1,6-naphthyridine-6(5H)-yl)ethyl)(methyl)amino)ethyl)guanidine (29 mg) as a pale yellow solid. H NMR (400 MHz, CD$_3$OD) δ 8.54 (d, J=3.9 Hz, 1H), 8.40 (s, 1H), 8.31 (d, J=1.0 Hz, 1H), 8.22 (d, J=8.5 Hz, 1H), 7.78 (d, J=12.0 Hz, 1H), 7.54 (d, J=8.6 Hz, 1H), 4.93 (d, J=6.9 Hz, 1H), 3.97 (s, 2H), 3.37 (t, J=5.7 Hz, 2H), 3.21 (t, J=6.0 Hz, 2H), 3.07 (t, J=5.7 Hz, 2H), 3.02 (t, J=6.2 Hz, 2H), 2.86 (t, J=6.1 Hz, 2H), 2.77 (t, J=5.7 Hz, 2H), 2.71 (s, 3H), 2.42 (s, 3H), 1.73 (d, J=6.9 Hz, 6H). LC-MS: m/z: (M+H)$^+$=578.

Embodiment 135

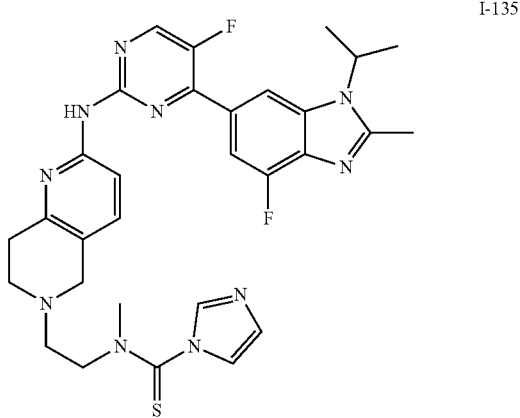 [SMILES: Cc1nc2c(F)cc(-c3nc(Nc4ccc5c(n4)CCN(CCN(C)C(=S)n4ccnc4)C5)ncc3F)cc2n1C(C)C]

I-135

N-(5-Fluoro-4-(4-fluoro-1-isopropyl-2-methyl-1H-benzo[d]imidazol-6-yl)pyrimidin-2-yl)-6-(2-(methylamino)ethyl)-5,6,7,8-tetrahydro-1,6-naphthyridin-2-amine hydrochloride (100 mg, 0.2 mmol), diisopropylethylamine (0.5 mL) and thiocarbonyldiimidazole (74 mg, 0.41 mmol) were added to 15 mL N,N-dimethylformamide and the mixture was stirred at 50° C. for 3 hours. The reaction mixture was cooled to room temperature and 30 mL methanol was added. The mixture was stirred overnight at room temperature, then evaporated to dryness under reduced pressure, and purified by silica gel column chromatography to give N-(2-(2-((5-fluoro-4-(4-fluoro-1-isopropyl-2-methyl-1H-benzo[d]imidazol-6-yl)pyrimidin-2-yl)amino)-7,8-dihydro-1,6-naphthyridine-6(5H)-yl)ethyl)-N-methyl-1H-imidazole-1-carbothioamide represented by formula I-135 (21 mg) as a pale yellow solid. $^1$H NMR (400 MHz, DMSO-d$_6$) δ 10.09 (s, 1H), 8.71 (d, J=3.9 Hz, 1H), 8.31 (s, 1H), 8.16 (d, J=8.6 Hz, 1H), 7.88 (s, 1H), 7.70 (d, J=12.2 Hz, 1H), 7.45 (d, J=8.3 Hz, 1H), 7.23 (s, 1H), 7.00 (s, 1H), 5.37 (s, 2H), 4.90-4.76 (m, 1H), 3.89-3.75 (m, 2H), 3.55 (d, J=3.7 Hz, 4H), 3.05-2.95 (m, 5H), 2.65 (s, 3H), 1.60 (d, J=6.9 Hz, 6H). LC-MS: m/z: (M+H)$^+$=603.

Embodiment 137

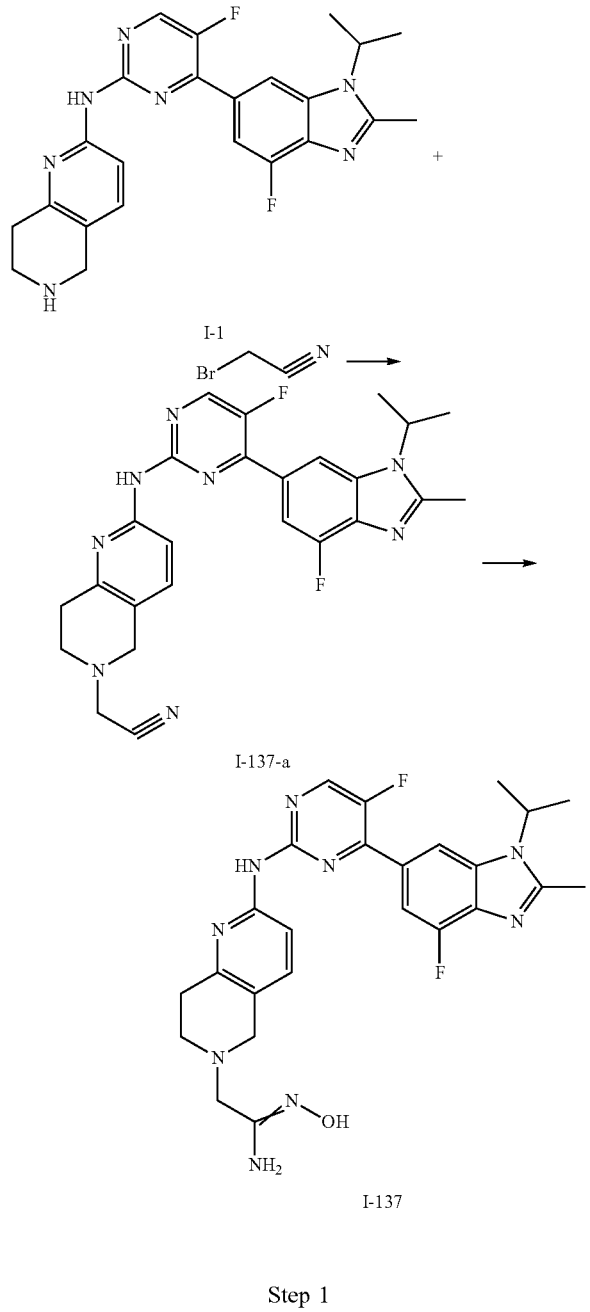

Step 1

Diisopropylethylamine (0.5 mL) and N-(5-fluoro-4-(4-fluoro-1-isopropyl-2-methyl-1H-benzo[d]imidazol-6-yl)pyrimidin-2-yl)-5,6,7,8-tetrahydro-1,6-naphthyridin-2-amine (132 mg, 0.3 mmol) were added to 15 mL N,N-dimethylformamide, bromoacetonitrile (72 mg, 0.6 mmol) was added and the mixture was stirred at room temperature for 2 h. The reaction solution was evaporated to dryness under reduced pressure and then purified by silica gel column chromatography to give 2-(2-((5-fluoro-4-(4-fluoro-1-isopropyl-2-methyl-11H-benzo[d]imidazol-6-yl)pyrimidin-2-yl)amino)-7,8-dihydro-1,6-naphthyridin-6(5H)-yl)acetonitrile represented by formula I-137-a (120 mg) as a pale yellow solid. LC-MS: m/z: (M+H)$^+$=475.

Step 2

2-(2-((5-Fluoro-4-(4-fluoro-1-isopropyl-2-methyl-1H-benzo[d]imidazol-6-yl)pyrimidin-2-yl)amino)-7,8-dihydro-1,6-naphthyridin-6(5H)-yl)acetonitrile (120 mg, 0.253 mmol) was added to a mixed solvent of 20 mL ethanol and 20 mL tetrahydrofuran, then 0.5 mL 50% aqueous hydroxylamine solution was added and the mixture was stirred at 80° C. overnight. The reaction solution was evaporated to dryness under reduced pressure and then purified by silica gel column chromatography to give 2-(2-((5-fluoro-4-(4-fluoro-1-isopropyl-2-methyl-1H-benzo[d]imidazol-6-yl)pyrimidin-2-yl)amino)-7,8-dihydro-1,6-naphthyridine-6(5H)-yl)-N'-hydroxyacetimidamide represented by formula I-137 (85 mg) as a pale yellow solid. $^1$H NMR (400 MHz, CD$_3$OD) δ 8.47 (d, J=3.9 Hz, 1H), 8.27 (d, J=0.9 Hz, 1H), 8.19 (d, J=8.5 Hz, 1H), 7.75 (d, J=11.5 Hz, 1H), 7.43 (d, J=8.5 Hz, 1H), 4.87 (d, J=7.0 Hz, 1H), 3.64 (s, 2H), 3.20 (s, 2H), 2.96 (d, J=5.2 Hz, 2H), 2.88 (t, J=5.6 Hz, 2H), 2.69 (s, 3H), 1.73 (d, J=6.9 Hz, 6H). LC-MS: m/z: (M+H)$^+$=508.

Embodiment 153

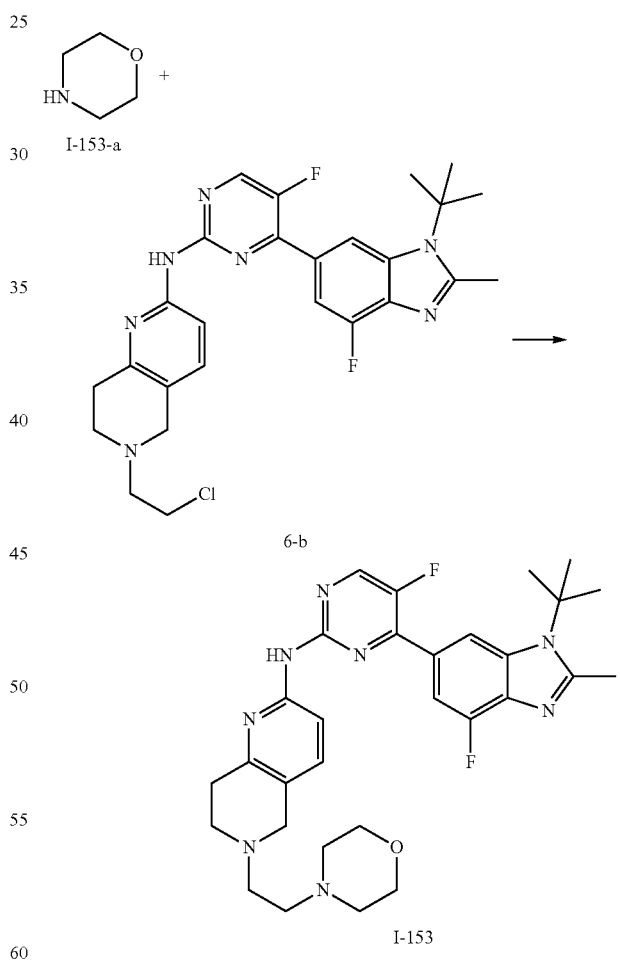

N-(4-(3-Tert-butyl-7-fluoro-2-methyl-benzimidazol-5-yl)-5-fluoro-pyrimidine-2-yl)-6-(2-chloroethyl)-7,8-dihydro-5H-1,6-naphthyridin-2-amine (50 mg, 0.09766 mmol) (represented by formula 6-b), anhydrous acetonitrile (1 mL) and morpholine (85 mg, 0.9766 mmol) were successively added to a dry flask at room temperature under argon atmosphere. The reaction mixture was stirred at 80° C. for 12 hours. LCMS monitored the reaction was complete. The reaction mixture was cooled to room temperature and concentrated by a rotary evaporator. The residue was purified by preparative TLC (silica gel, dichloromethane/methanol=10:1, v/v) to give N-(4-(3-tert-butyl-7-fluoro-2-methyl-benzimidazol-5-yl)-5-fluoro-pyrimidin-2-yl)-6-(2-diethylaminoethyl)-7,8-dihydro-5H-1,6-naphthyridin-2-amine represented by formula I-153 (12.8 mg, 0.0227 mmol) as a pale yellow solid. $^1$H NMR (400 MHz, Chloroform-d) δ 8.41 (d, J=3.8 Hz, 1H), 8.38 (d, J=1.2 Hz, 1H), 8.32 (br.s, 1H), 8.24 (d, J=8.5 Hz, 1H), 7.74 (d, J=11.3 Hz, 1H), 7.35 (d, J=8.5 Hz, 1H), 3.84-3.68 (m, 6H), 3.02-2.93 (m, 4H), 2.87 (s, 3H), 2.85-2.79 (m, 2H), 2.75-2.69 (m, 2H), 2.66-2.59 (m, 4H), 1.90 (s, 9H). LC-MS m/z: (M+H)$^+$=563.40.

Embodiment 155

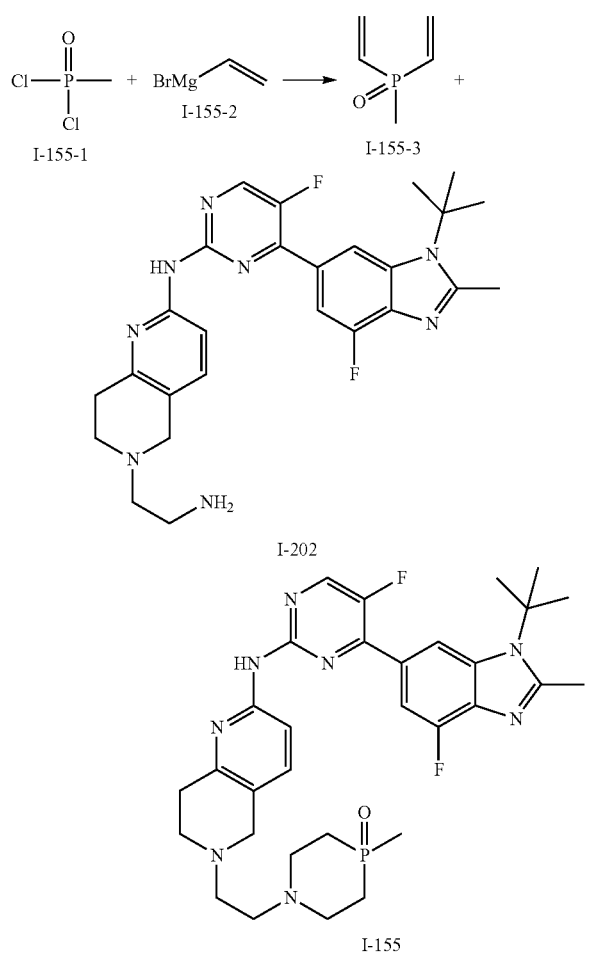

Step 1

Vinylmagnesium bromide (25 mL, 0.7 mmol/L) was added to a solution of methylphosphonic dichloride (1 g, 7.52 mmol) in tetrahydrofuran at −78° C. in more than half an hour. The mixture was stirred at this temperature for 3.5 hours, then warmed to 0° C. and stirred for 1 hour. The reaction was quenched with 20 mL saturated ammonium chloride solution. The mixture was filtered through a pad of silica gel and eluted with 10% 7M methanolic ammonia in dichloromethane. The filtrate was concentrated to give a crude product (0.1 g) as colorless viscous liquid, yield 10%, which was directly used in the next step.

Step 2

Methyl divinyl phosphine oxide (20 mg, 0.17 mmol) and 6-(2-aminoethyl)-N-(4-(1-(tert-butyl)-4-fluoro-2-methyl-1H-benzo[d]imidazol-6-yl)-5-fluoropyrimidin-2-yl)-5,6,7,8-tetrahydro-1,6-naphthyridin-2-amine (50 mg, 0.1 mmol) were added to a mixed solvent of tetrahydrofuran (6 mL) and water (2 mL), then 0.5 mL triethylamine was added and the mixture was stirred under reflux overnight. The reaction mixture was evaporated to dryness under reduced pressure and purified by column chromatography (methanol:dichloromethane=0-20%) to give a crude product, which was purified by preparative HPLC to give 1-(2-(2-((4-(1-(tert-butyl)-4-fluoro-2-methyl-1H-benzo[d]imidazol-6-yl)-5-fluoropyrimidin-2-yl)amino)-7,8-dihydro-1,6-naphthyridin-6(5H)-yl)ethyl)-4-methyl-1,4-azaphosphinane 4-oxide (8 mg) as a yellow solid, yield 12%. $^1$H NMR (400 MHz, CDCl$_3$) δ 8.43 (d, J=8.2 Hz, 2H), 8.26 (d, J=8.1 Hz, 1H), 7.77 (d, J=10.9 Hz, 1H), 7.42 (d, J=8.6 Hz, 1H), 3.74 (s, 2H), 2.98 (s, 6H), 2.83 (m, 9H), 1.95 (t, 13H), 1.57 (d, J=12.9 Hz, 3H). LC-MS m/z: (M+H)$^+$=609.

Embodiment 187

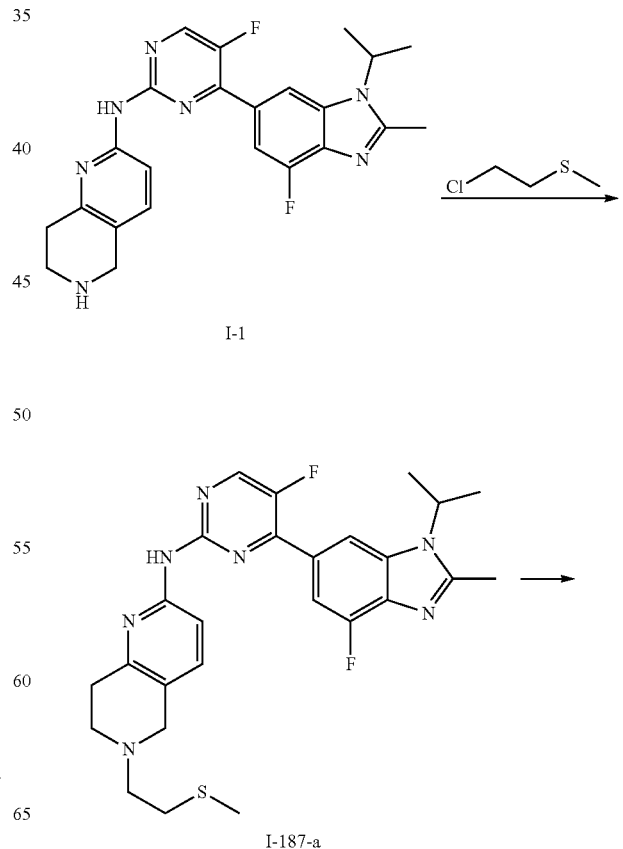

179

-continued

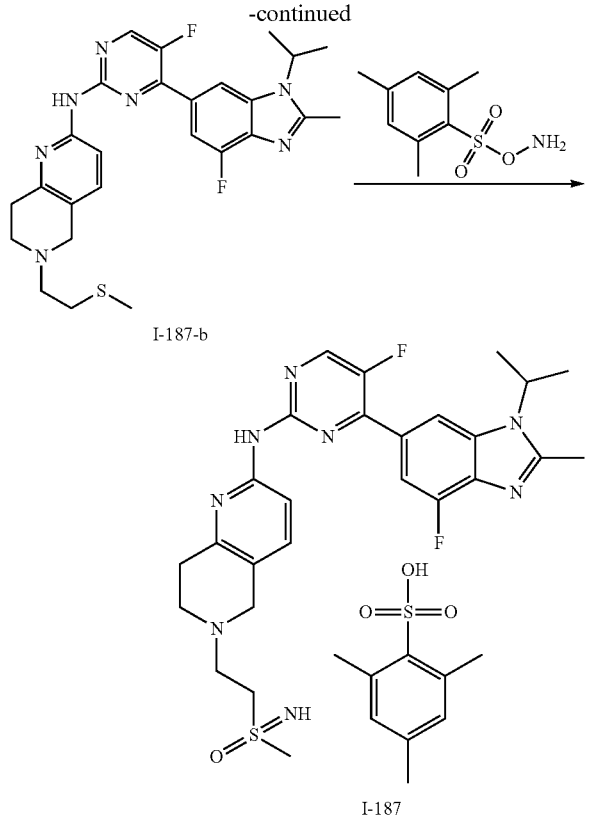

I-187-b

I-187

Step 1

N-(5-Fluoro-4-(4-fluoro-1-isopropyl-2-methyl-1H-benzo[d]imidazol-6-yl)pyrimidin-2-yl)-5,6,7,8-tetrahydro-1,6-naphthyridin-2-amine (400 mg, 0.918 mmol) and diisopropylethylamine (1 ml) were added to a mixed solvent of 10 mL N,N-dimethylformamide and 20 mL acetonitrile, then 2-chloroethyl methyl sulfide (0.6 mL) was added and the mixture was stirred at 70° C. overnight. Additional 2-chloroethyl methylsulfide (0.6 mL) was added and stirred at 70° C. overnight. The mixture was concentrated under reduced pressure and purified by silica gel column chromatography to give N-(5-fluoro-4-(4-fluoro-1-isopropyl-2-methyl-1H-benzo[d]imidazol-6-yl)pyrimidin-2-yl)-6-(2-(methylthio)ethyl)-5,6,7,8-tetrahydro-1,6-naphthyridine-2-amine (210 mg) as a yellow solid. LC-MS: m/z: (M+H)$^+$=510.

Step 2

N-(5-Fluoro-4-(4-fluoro-1-isopropyl-2-methyl-1H-benzo[d]imidazol-6-yl)pyrimidin-2-yl)-6-(2-(methylthio)ethyl)-5,6,7,8-tetrahydro-1,6-naphthyridine-2-amine (100 mg, 0.1962 mmol) was added to 10 mL dichloromethane, then m-chloroperbenzoic acid (42 mg, 0.188 mmol) was added and the mixture stirred overnight at room temperature. The mixture was concentrated under reduced pressure and purified by silica gel column chromatography to give N-(5-fluoro-4-(4-fluoro-1-isopropyl-2-methyl-1H-benzo[d]imidazol-6-yl)pyrimidin-2-yl)-6-(2-(methylsulfonyl)ethyl)-5,6,7,8-tetrahydro-1,6-naphthyridine-2-amine represented by the formula I-187-b (80 mg) as a pale yellow solid. LC-MS: m/z: (M+H)$^+$=526.

180

Step 3

N-(5-Fluoro-4-(4-fluoro-1-isopropyl-2-methyl-1H-benzo[d]imidazol-6-yl)pyrimidin-2-yl)-6-(2-(methylsulfonyl)ethyl)-5,6,7,8-tetrahydro-1,6-naphthyridine-2-amine (90 mg, 0.17 mmol) and 2-((aminooxy)sulfonyl)-1,3,5-trimethylbenzene (60 mg, 0.28 mmol) were added to a mixed solvent of 10 mL dichloromethane and 10 mL acetonitrile, the mixture was stirred at room temperature overnight. The solvent was evaporated under reduced pressure and the crude product was purified by preparative HPLC to give N-(5-fluoro-4-(7-fluoro-3-isopropyl-2-methyl-benzimidazol-5-yl)pyrimidin-2-yl)-6-(2-(methylsulfonyl)ethyl]-7,8-dihydro-5H-1,6-naphthyridine-2-amine 2,4,6-trimethylbenzenesulfonate represented by formula I-187 (30 mg) as a pale yellow solid. $^1$H NMR (400 MHz, CD$_3$OD) δ 8.56 (d, J=3.8 Hz, 1H), 8.40-8.29 (m, 2H), 7.79 (d, J=11.8 Hz, 1H), 7.60 (d, J=8.8 Hz, 1H), 6.88 (s, 2H), 4.92 (d, J=6.9 Hz, 2H), 4.78 (s, 1H), 4.07 (s, 4H), 3.76-3.61 (m, 1H), 3.52-3.39 (m, 2H), 3.28 (dd, J=14.5, 9.5 Hz, 1H), 2.82 (d, J=3.3 Hz, 3H), 2.71 (s, 3H), 2.63 (s, 6H), 2.24 (s, 3H), 1.73 (d, J=6.9 Hz, 6H). LC-MS: m/z: (M+H)$^+$=541.

Embodiment 197

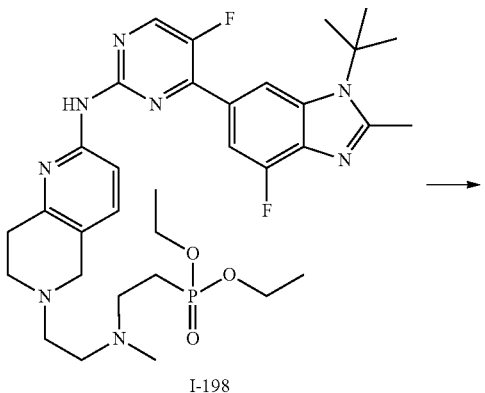

I-198

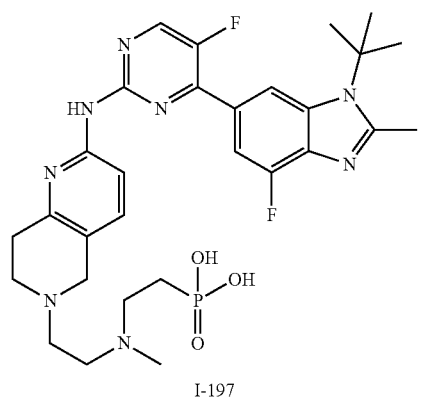

I-197

-continued

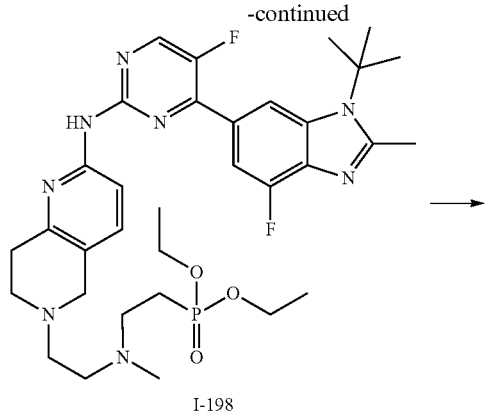

I-198

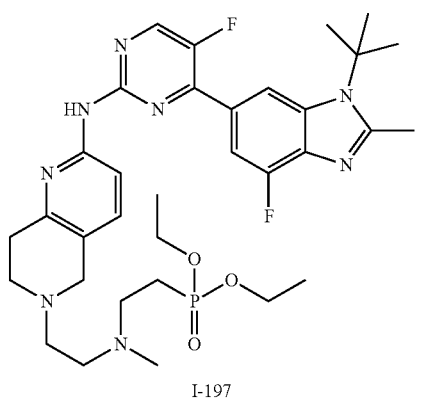

I-197

Diethyl (2-((2-(2-((4-(1-(tert-butyl)-4-fluoro-2-methyl-1H-benzo[d]imidazol-6-yl)-5-fluoropyrimidin-2(5H)-yl)ethyl)(methyl)amino)ethyl)phosphonate (100 mg, 0.15 mmol) was added to 10 mL dichloromethane, followed by the addition of trimethylsilyl iodide (0.2 mL). The mixture was stirred at room temperature overnight. The reaction mixture was evaporated to dryness under reduced pressure and the crude product was purified by preparative HPLC to give (2-((2-(2-((4-(1-(tert-butyl)-4-fluoro-2-methyl-1H-benzo[d]imidazol-6-yl)-5-fluoropyrimidin-2-yl)amino)-7,8-dihydro-1,6-naphthyridin-6(5H)-yl)ethyl)(methyl)amino)ethyl)phosphonic acid (50 mg) as a pale yellow solid, yield 54%. $^1$H NMR (400 MHz, MeOD) δ 8.47 (d, J=3.8 Hz, 1H), 8.41 (d, J=1.1 Hz, 1H), 8.17 (d, J=8.6 Hz, 1H), 8.08 (s, 1H), 7.75 (d, J=11.5 Hz, 1H), 7.51 (d, J=8.6 Hz, 1H), 3.87 (s, 2H), 3.24 (m, 4H), 3.13-3.00 (m, 6H), 2.85 (s, 3H), 2.80 (s, 3H), 2.04-1.82 (m, 12H). LC-MS: m/z: (M+H)$^+$=615.

Embodiment 204

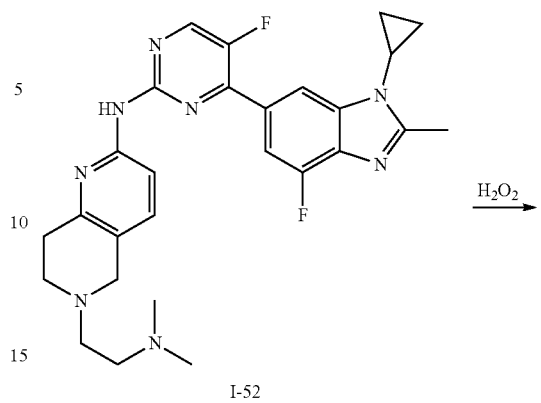

I-52

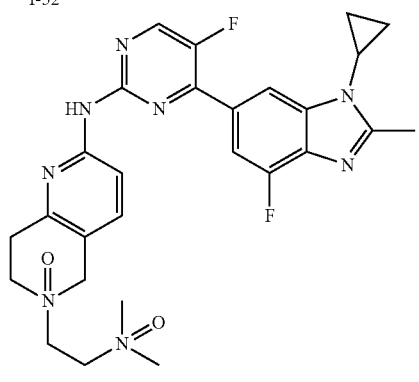

I-204

N-(4-(3-cyclopropyl-7-fluoro-2-methyl-benzimidazol-5-yl)-5-fluoro-pyrimidin-2-yl)-6-(2-dimethylaminoethyl)-7,8-dihydro-5H-1,6-naphthyridin-2-amine (100 mg, 0.198 mmol) was dissolved in hydrogen peroxide (5 mL), the mixture was stirred at room temperature for about 1 hour, then quenched by adding aqueous sodium sulfite solution. Water was distilled off under reduced pressure. The solid was dissolved in a mixed solvent of dichloromethane and methanol, then filtered and the filtrate was purified by HPLC to give 2-(2-((4-(3-cyclopropyl-7-fluoro-2-methyl-benzimidazol-5-yl)-5-fluoro-pyrimidin-2-yl)amino)6-oxo-7,8-dihydro-5H-1,6-naphthyridine-6-yl)-N,N-dimethyl-ethylaminooxy represented by formula I-205(30 mg) as a pale yellow solid. $^1$H NMR (400 MHz, MeOD) δ 8.61-8.47 (br, 2H), 8.02 (s, 1H), 7.52-7.30 (br, 2H), 4.60-4.40 (br, 4H), 4.14-3.85 (m, 2H), 3.56-3.70 (br, 4H), 3.48-3.35 (m, 2H), 3.02-2.85 (m, 1H), 2.55 (s, 3H), 1.30-1.15 (m, 2H), 1.05-0.84 (m, 2H). LC-MS: m/z: (M+H)$^+$=537.

Embodiment 205

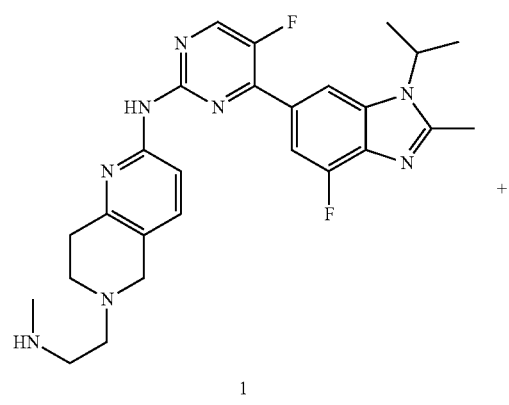

1

-continued

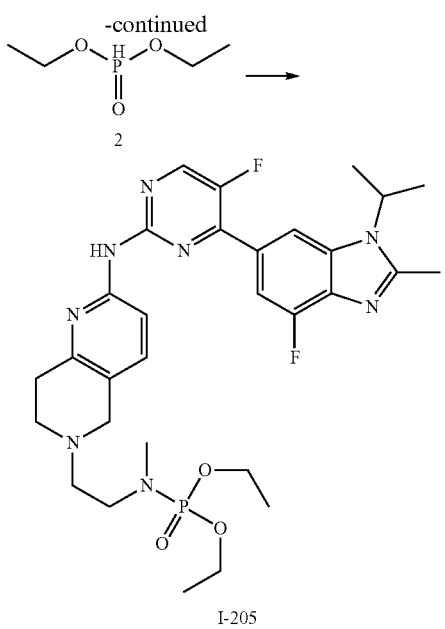

I-205

Diethyl phosphonate (50 mg, 0.36 mmol), triethylamine (0.5 ml) and N-(5-fluoro-4-(4-fluoro-1-isopropyl-2-methyl-1H-benzo[d]imidazol-6-yl)pyrimidin-2-yl)-6-(2-(methylamino)ethyl)-5,6,7,8-tetrahydro-1,6-naphthyridine-2-amine (120 mg, 0.24 mmol) were added to a mixed solvent of 10 mL acetonitrile, 10 mL carbon tetrachloride and 5 mL dichloromethane, and the mixture was stirred at room temperature overnight. The reaction mixture was filtered and the filtrate was evaporated to dryness under reduced pressure to give a crude product, which was purified by preparative HPLC to give (2-(2-((5-fluoro-4-(4-fluoro-1-isopropyl-2-methyl-1H-benzo[d]imidazol-6-yl)pyrimidine-2-yl)amino)-7,8-dihydro-1,6-naphthyridin-6(5H)-yl)ethyl)(methyl)phosphoramidate (90 mg) as a pale yellow solid, yield 58%. $^1$H NMR (400 MHz, CDCl$_3$) δ 8.44 (d, J=3.8 Hz, 1H), 8.28 (d, J=8.5 Hz, 1H), 8.23 (d, J=1.1 Hz, 1H), 7.80 (d, J=11.7 Hz, 1H), 7.42 (d, J=8.6 Hz, 1H), 4.76 (dd, J=13.9, 6.9 Hz, 1H), 4.10-3.99 (m, 4H), 3.94 (dt, J=14.2, 6.8 Hz, 2H), 3.83 (s, 2H), 3.38 (m, 2H), 3.05 (s, 3H), 2.86 (t, J=6.9 Hz, 2H), 2.76-2.69 (m, 5H), 1.74 (d, J=7.1 Hz, 6H), 1.37-1.27 (t, 6H). LC-MS m/z: (M+H)$^+$=607.

TABLE 1

| Embodiment | Structure | Analytic data | Method |
|---|---|---|---|
| 24 | 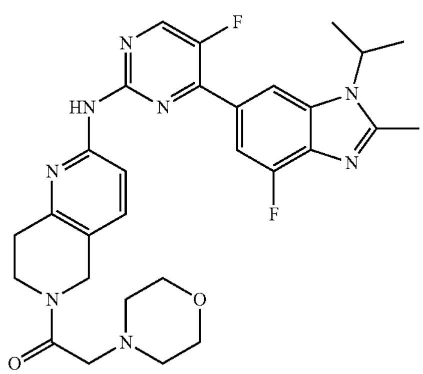 [SMILES: Cc1nc2c(F)cc(-c3nc(Nc4ccc5c(n4)CCN(C(=O)CN4CCOCC4)C5)ncc3F)cc2n1C(C)C] | White powder. $^1$HNMR (400 MHz, DMSO-d$_6$) δ 10.05 (d, J = 6.7 Hz, 1H), 8.69 (s, 1H), 8.31 (s, 1H), 8.14 (t, J = 11.4 Hz, 1H), 7.71 (d, J = 11.9 Hz, 1H), 7.65-7.56 (m, 1H), 4.86 (t, J = 5.4 Hz, 1H), 4.68 (d, J = 40.6 Hz, 2H), 3.90-3.80 (m, 2H), 3.62 (d, J = 18.6 Hz, 4H), 3.42 (d, J = 40.8 Hz, 4H), 2.88 (d, J = 55.2 Hz, 3H), 2.66 (s, 4H), 1.65 (d, J = 6.9 Hz, 7H). LC-MS: m/z: (M + H)$^+$ = 563.2. | I-5 |
| 25 | 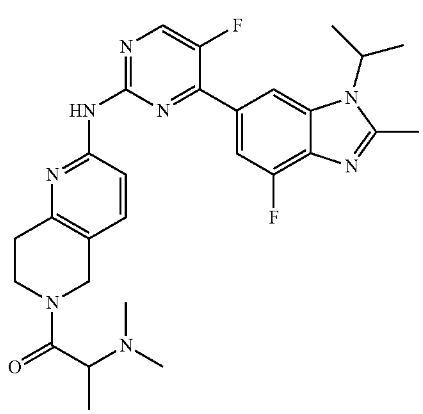 [SMILES: Cc1nc2c(F)cc(-c3nc(Nc4ccc5c(n4)CCN(C(=O)C(C)N(C)C)C5)ncc3F)cc2n1C(C)C] | Yellow powder. 1H NMR (400 MHz, CD$_3$OD) δ 8.47 (d, J = 51.2 Hz, 2H), 8.27 (s, 1H), 7.81 (d, J = 12.6 Hz, 1H), 7.64 (d, J = 8.5 Hz, 1H), 4.80-4.58 (m, 1H), 4.42 (s, 1H), 4.15-3.80 (m, 2H), 3.41 (d, J = 25.8 Hz, 2H), 3.00 (d, J = 31.7 Hz, 2H), 2.82 (s, 6H), 2.75 (s, 3H), 1.53 (s, 2H), 1.33 (d, J = 20.5 Hz, 3H), 1.19 (s, 2H). LC-MS: m/z (M + H)$^+$ = 533.2 | I-22 |

TABLE 1-continued

List of embodiments

| Embodiment | Structure | Analytic data | Method |
|---|---|---|---|
| 33 | 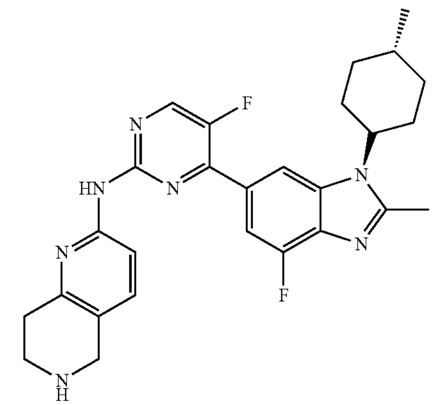 | Yellow solid, yield 98%<br>$^1$H-NMR (400 MHz, DMSO-d$_6$) δ 8.78 (d, J = 3.3 Hz, 1H), 8.37 (s, 1H), 8.06 (d, J = 8.7 Hz, 1H), 7.89 (d, J = 11.5 Hz, 1H), 7.74 (d, J = 8.7 Hz, 1H), 4.50 (s, 1H), 4.28 (s, 2H), 3.50 (t, J = 6.1 Hz, 2H), 3.11 (t, J = 6.3 Hz, 2H), 2.79 (s, 3H), 2.22 (d, J = 10.4 Hz, 2H), 2.07-1.95 (m, 2H), 1.86 (d, J = 12.2 Hz, 2H), 1.52 (d, J = 22.4 Hz, 1H), 1.27 (d, J = 12.2 Hz, 2H), 0.96 (d, J = 6.4 Hz, 3H).<br>LC-MS: m/z: (M + H)$^+$ = 489.9. | Preparation embodiment 4 |
| 34 | 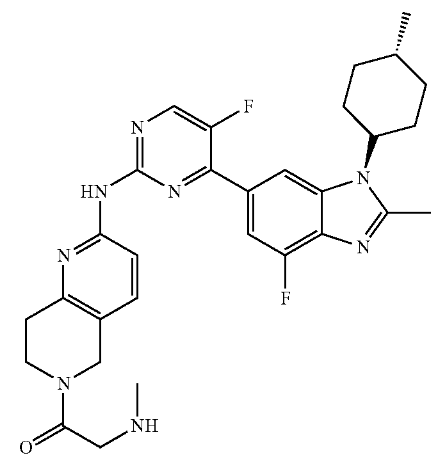 | Yellow solid, yield 94%<br>$^1$H NMR (400 MHz, DMSO-d$_6$) δ 9.01 (br, 2H), 8.70 (d, J = 3.8 Hz, 1H), 8.29 (s, 1H), 8.17 (d, J = 8.6 Hz, 1H), 7.78-7.51 (m, 2H), 4.64 (d, J = 32.0 Hz, 2H), 4.39 (s, 1H), 4.17 (d, J = 19.2 Hz, 2H), 3.80 (dt, J = 56.6, 5.8 Hz, 2H), 2.91 (d, J = 44.2 Hz, 2H), 2.66 (s, 3H), 2.58 (d, J = 3.1 Hz, 3H), 2.24 (d, J = 12.0 Hz, 2H), 1.92 (dd, J = 28.7, 12.4 Hz, 3H), 1.52 (s, 1H), 1.34-1.21 (m, 2H), 1.04-0.90 (m, 3H).<br>LC-MS: m/z: (M + H)$^+$ = 560.9. | I-4 |
| 35 | 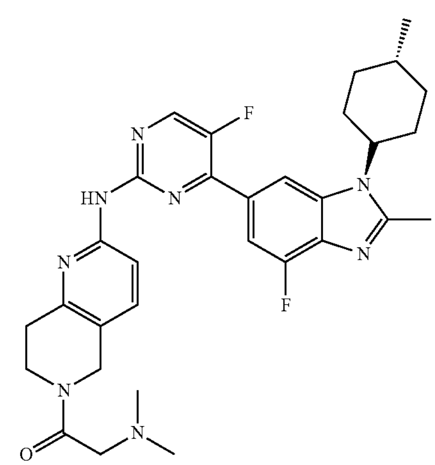 | Solid.<br>$^1$H-NMR (400 MHz, DMSO-d$_6$) δ = 10.08-10.10 (m, 1H), 8.70 (d, 1H, J = 4 Hz), 8.29 (s, 1H), 8.13-8.17 (m, 1H), 7.68 (d, 1H, J = 12.4 Hz), 7.54-7.59 (m, 1H), 4.73 (s, 1H), 4.61 (s, 1H), 4.35-4.38 (m, 1H), 3.79-3.87 (m, 2H), 2.90-2.94 (m, 1H), 2.79-2.82 (m, 1H), 2.66 (s, 4H), 2.22-2.29 (m, 8H), 1.86-1.97 (m, 4H), 1.21-1.29 (m, 3H), 0.95-0.99 (m, 3H).<br>LC-MS: m/z: (M + H)$^+$ = 575.2. | I-5 |

TABLE 1-continued

List of embodiments

| Embodiment | Structure | Analytic data | Method |
|---|---|---|---|
| 36 | 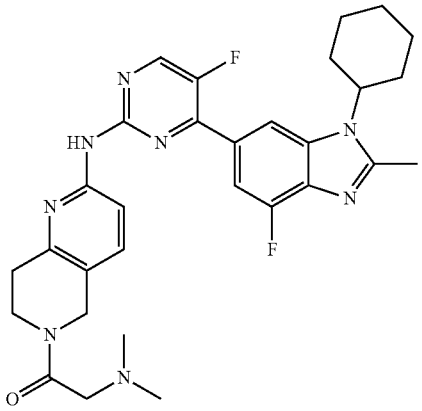 [SMILES: Cc1nc2c(F)cc(-c3nc(Nc4ccc5c(n4)CCN(C(=O)CN(C)C)C5)ncc3F)cc2n1C1CCCCC1] | Solid.<br>$^1$H-NMR (400 MHz, CDCl$_3$) 8.44 (d, 1H, J = 3.6 Hz), 8.31 (d, 1H, J = 8.4 Hz), 8.20-8.22 (m, 1H), 7.98-8.03 (m, 1H), 7.76-7.81 (m, 1H), 7.46-7.50 (m, 1H), 4.74-4.80 (m, 2H), 4.22-4.29 (m, 1H), 3.92-3.98 (m, 2H), 3.29 (s, 2H), 2.94-3.02 (m, 2H), 2.72 (s, 3H), 2.37 (s, 6H), 2.22-2.33 (m, 2H), 2.02-2.08 (m, 4H), 1.86-1.92 (m, 1H), 1.53-1.59 (m, 2H).<br>LC-MS: m/z: (M + H)$^+$ = 561.2. | I-5 |
| 38 | 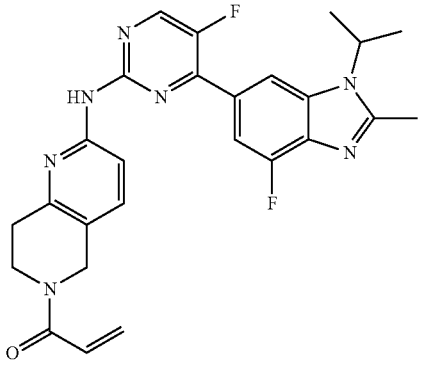 [SMILES: C=CC(=O)N1CCc2nc(Nc3ncc(F)c(-c4cc(F)c5nc(C)n(C(C)C)c5c4)n3)ccc2C1] | Solid.<br>$^1$H-NMR (400 MHz, DMSO-d$_6$) δ = 10.12-10.14 (m, 1H), 8.70 (d, 1H, J = 4 Hz), 8.32 (s, 1H), 8.14 (d, 1H, J = 8 Hz), 7.58-7.72 (m, 2H), 6.90-6.98 (m, 1H), 6.18 (dd, 1H, J = 16.8 Hz, 2 Hz), 5.75 (dd, 1H, J = 10.4 Hz, 2.4 Hz), 4.82-4.88 (m, 1H), 4.68-4.79 (m, 2H), 3.87-3.92 (m, 2H), 2.84-2.92 (m, 2H), 2.66 (s, 3H), 1.64 (d, 6H, J = 7.2 Hz), 1.24 (s, 3H).<br>LC-MS: m/z: (M + H)$^+$ = 490.2. | I-10 |
| 39 | 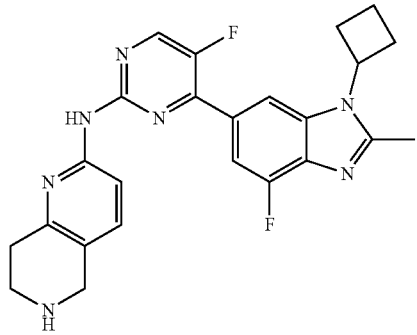 [SMILES: Cc1nc2c(F)cc(-c3nc(Nc4ccc5c(n4)CCNC5)ncc3F)cc2n1C1CCC1] | Yellow solid 760 mg, yield 98%.<br>$^1$H NMR (400 MHz, DMSO-d$^6$) δ 9.82 (s, 2H), 8.83 (d, J = 3.4 Hz, 1H), 8.41 (s, 1H), 8.12 (d, J = 8.7 Hz, 1H), 7.92 (d, J = 11.6 Hz, 1H), 7.80 (d, J = 8.7 Hz, 1H), 5.27-5.12 (m, 1H), 4.27 (s, 2H), 3.48 (s, 2H), 3.14 (d, J = 5.9 Hz, 2H), 2.93-2.82 (m, 2H), 2.76 (s, 3H), 2.71-2.61 (m, 2H), 2.07-1.89 (m, 3H).<br>LC-MS: m/z: (M + H)$^+$ = 447.9. | I-28 |

TABLE 1-continued

List of embodiments

| Embodiment | Structure | Analytic data | Method |
|---|---|---|---|
| 40 | 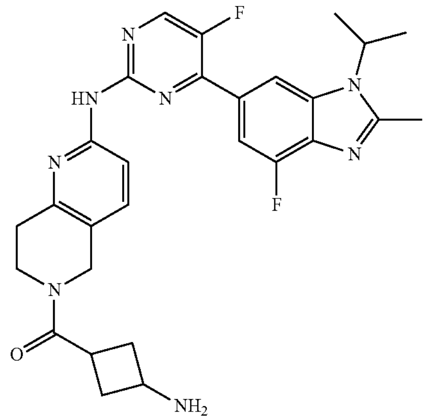 [SMILES: Cc1nc2c(F)cc(-c3nc(Nc4ccc5c(n4)CCN(C(=O)C4CC(N)C4)C5)ncc3F)cc2n1C(C)C] | Solid.<br>$^1$H NMR (400 MHz, DMSO-$d_6$) δ 10.05 (d, J = 11.9 Hz, 1H), 8.69 (d, J = 3.4 Hz, 1H), 8.31 (s, 1H), 8.13 (d, J = 8.3 Hz, 1H), 7.81-7.51 (m, 2H), 5.00-4.78 (m, 1H), 4.59 (d, J = 25.3 Hz, 2H), 3.76 (d, J = 39.2 Hz, 2H), 3.65-3.46 (m, 2H), 2.83 (d, J = 25.6 Hz, 2H), 2.65 (s, 3H), 2.46 (d, J = 8.6 Hz, 2H), 2.25 (dd, J = 22.7, 9.9 Hz, 2H), 1.64 (d, J = 6.7 Hz, 6H).<br>LC-MS: m/z: (M + H)$^+$ = 532.9. | I-4 |
| 41 | 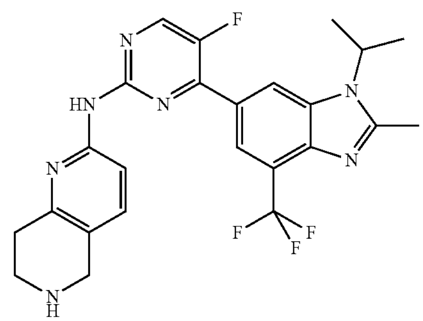 [SMILES: Cc1nc2c(C(F)(F)F)cc(-c3nc(Nc4ccc5c(n4)CCNC5)ncc3F)cc2n1C(C)C] | Solid.<br>$^1$H NMR (400 MHz, DMSO-$d_6$) δ 10.90 (s, 1H), 9.88 (br, 1H), 8.93-8.72 (m, 2H), 8.31 (s, 1H), 8.11 (d, J = 8.7 Hz, 1H), 7.83 (d, J = 8.8 Hz, 1H), 5.00 (s, 1H), 4.28 (s, 2H), 3.47 (s, 2H), 3.14 (s, 2H), 2.79 (s, 3H), 1.68 (d, J = 6.9 Hz, 6H).<br>LC-MS: m/z: (M + H)$^+$ = 485.9. | I-28 |
| 42 | 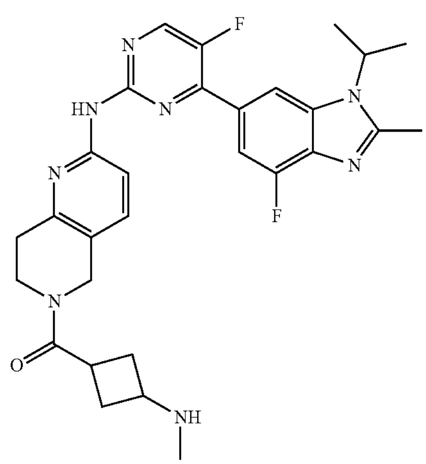 [SMILES: CNC1CC(C(=O)N2CCc3nc(Nc4ncc(F)c(-c5cc(F)c6nc(C)n(C(C)C)c6c5)n4)ccc3C2)C1] | Yellow solid 5 mg, yield 11%.<br>$^1$H-NMR (400 MHz, CD$_3$OD) δ 8.93 (s, 1H), 8.57 (s, 1H), 8.26-8.15 (m, 2H), 7.55 (s, 1H), 5.14 (s, 2H), 3.99 (d, J = 31.3 Hz, 2H), 3.74 (d, J = 26.0 Hz, 2H), 2.97 (s, 3H), 2.73 (s, 2H), 2.64 (s, 3H), 2.44 (s, 2H), 2.21 (d, J = 7.5 Hz, 1H), 2.04 (s, 1H), 1.83 (d, J = 6.4 Hz, 6H), 1.61 (s, 1H).<br>LC-MS: m/z: (M + H)$^+$ = 547.3. | I-4 |

TABLE 1-continued

List of embodiments

| Embodiment | Structure | Analytic data | Method |
|---|---|---|---|
| 43 | 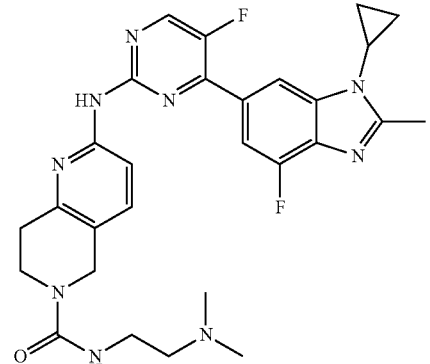 | Yellow solid.<br>¹H NMR (400 MHz, CD₃OD) δ 8.55 (d, J = 3.9 Hz, 1H), 8.44 (s, 1H), 8.33-8.20 (m, 2H), 7.84 (d, J = 12.2 Hz, 1H), 7.61 (d, J = 8.8 Hz, 1H), 4.61 (s, 2H), 3.79 (t, J = 5.9 Hz, 2H), 3.55 (t, J = 5.7 Hz, 2H), 3.44-3.48 (m, 1H), 3.21 (t, J = 5.7 Hz, 2H), 2.95 (t, J = 5.7 Hz, 2H), 2.90 (s, 6H), 2.76 (s, 3H), 1.37 (d, J = 5.3 Hz, 2H), 1.20 (s, 2H).<br>LC-MS: m/z: (M + H)⁺ = 548. | I-61 |
| 44 | 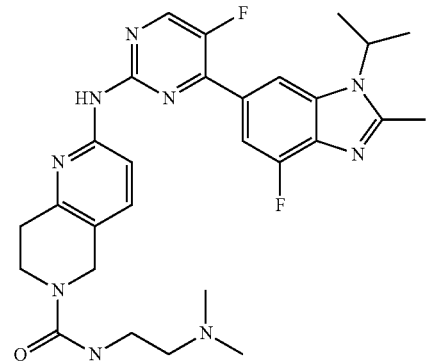 | Yellow solid.<br>¹H NMR (400 MHz, CD₃OD) δ 8.55 (d, J = 3.9 Hz, 1H), 8.43 (s, 1H), 8.33 (s, 1H), 8.26 (d, J = 8.5 Hz, 1H), 7.81 (d, J = 11.9 Hz, 1H), 7.58 (d, J = 8.7 Hz, 1H), 5.02-4.88 (m, 1H), 4.60 (s, 2H), 3.79 (t, J = 5.9 Hz, 2H), 3.57 (t, J = 5.6 Hz, 2H), 3.23 (t, J = 6 Hz, 3H), 2.95 (t, J = 5.9 Hz, 3H), 2.92 (s, 6H), 2.71 (s, 3H), 1.74 (d, J = 6.9 Hz, 6H).<br>LC-MS: m/z: (M + H)⁺ = 550. | I-61 |
| 45 | 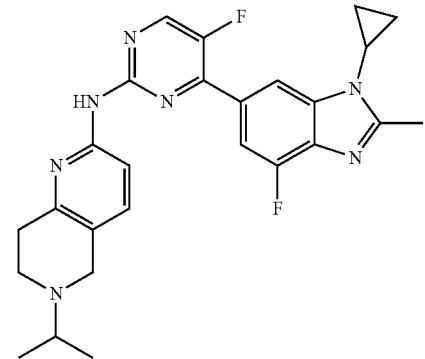 [SMILES: Cc1nc2c(F)cc(-c3nc(Nc4ccc5c(n4)CCN(C(C)C)C5)ncc3F)cc2n1C1CC1] | Pale yellow solid.<br>¹H-NMR (400 MHz, CDCl₃) δ 8.44 (d, 1H, J = 3.6 Hz), 8.19-8.35 (m, 3H), 7.81 (d, 1H, J = 12.0 Hz), 7.46 (d, 1H, J = 8.4 Hz), 3.95 (s, 2H), 3.32-3.39 (m, 1H), 3.21-3.31 (m, 1H), 3.12 (s, 4H), 2.76 (s, 3H), 1.35-1.37 (m, 2H), 1.30 (d, 6H, J = 6.4 Hz), 1.13-1.17 (m, 2H).<br>LC-MS m/z: (M + H)⁺ = 476.2 | I-3 |
| 46 | 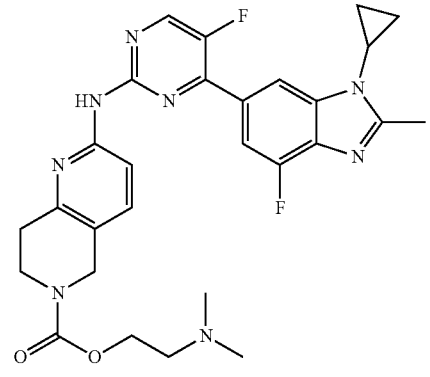 [SMILES: Cc1nc2c(F)cc(-c3nc(Nc4ccc5c(n4)CCN(C(=O)OCCN(C)C)C5)ncc3F)cc2n1C1CC1] | Solid.<br>¹H-NMR (400 MHz, DMSO-d₆) δ = 9.99 (s, 1H), 8.70 (d, 1H, J = 4 Hz), 8.22 (s, 1H), 8.16 (s, 1H), 8.12 (d, 1H, J = 8.4 Hz), 4.56 (s, 2H), 4.15 (t, 2H, J = 11.6 Hz), 3.71-3.75 (m, 2H), 3.41-3.49 (m, 2H), 2.82-2.86 (m, 2H), 2.67 (s, 4H), 2.53-2.56 (m, 3H), 2.22 (s, 6H), 1.24-1.28 (m, 3H), 1.12-1.15 (m, 2H).<br>LC-MS: m/z: (M + H)⁺ = 549.2. | I-61 |

TABLE 1-continued

List of embodiments

| Embodiment | Structure | Analytic data | Method |
|---|---|---|---|
| 47 | 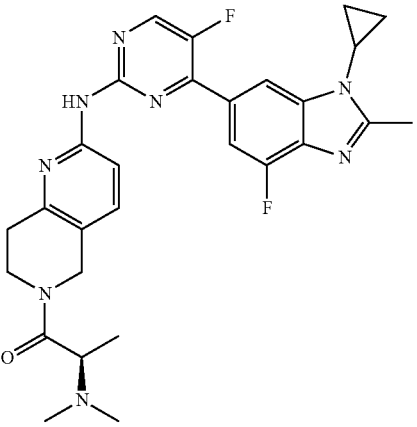 [SMILES: Cc1nc2c(F)cc(-c3nc(Nc4ccc5c(n4)CCN(C(=O)[C@@H](C)N(C)C)C5)ncc3F)cc2n1C1CC1] | Solid.<br>$^1$H-NMR (400 MHz, DMSO-$d_6$) δ = 9.97 (d, 1H, J = 7.2 Hz), 8.69 (d, 1H, J = 4 Hz), 8.21 (s, 1H), 8.10 (d, 1H, J = 8.8 Hz), 7.75 (d, 1H, J = 12 Hz), 7.61-7.66 (m, 1H), 4.56-4.86 (m, 2H), 3.66-3.94 (m, 3H), 3.44-3.48 (m, 1H), 2.79-2.91 (m, 2H), 2.67 (s, 3H), 2.17 (d, 1H, J = 14.4 Hz), 1.26-1.30 (m, 2H), 1.13 (s, 2H), 1.05 (d, 3H, J = 6.4 Hz). LC-MS: m/z: (M + H)$^+$ = 533.2. | I-22 |
| 48 | 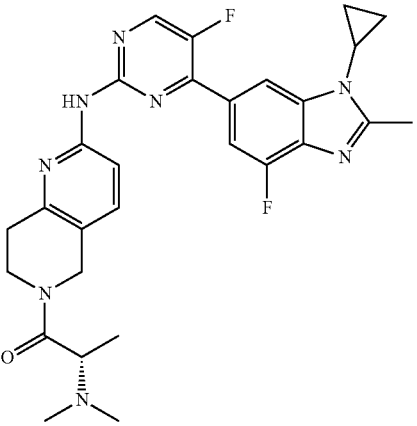 | Yellow powder.<br>$^1$H NMR (400 MHz, CD$_3$OD) δ 8.97 (s, 1H), 8.57 (s, 1H), 8.25 (t, J = 8.6 Hz, 2H), 7.57 (d, J = 14.1 Hz, 1H), 5.04-4.94 (m, 2H), 4.64 (s, 2H), 4.07 (d, J = 31.7 Hz, 1H), 3.68 (d, J = 47.0 Hz, 2H), 3.04 (s, 3H), 2.73 (d, J = 17.8 Hz, 4H), 1.56 (dd, J = 18.3, 6.7 Hz, 7H).<br>LC-MS: m/z: (M + H)$^+$ = 519.2. | I-22 |
| 49 | 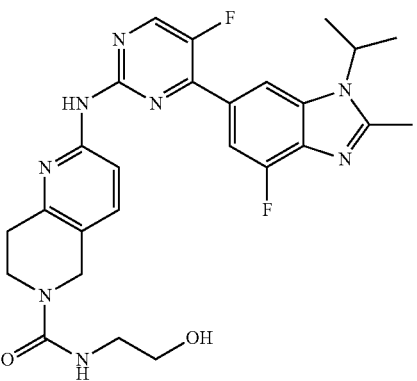 [SMILES: Cc1nc2c(F)cc(-c3nc(Nc4ccc5c(n4)CCN(C(=O)NCCO)C5)ncc3F)cc2n1C(C)C] | Solid.<br>$^1$H NMR (400 MHz, CD$_3$OD) δ 8.55 (s, 1H), 8.35 (s, 1H), 8.24 (d, J = 8.2 Hz, 1H), 7.81 (d, J = 11.8 Hz, 1H), 7.58 (d, J = 8.2 Hz, 1H), 5.36 (s, 1H), 3.77 (t, J = 5.6 Hz, 2H), 3.64 (t, J = 5.8 Hz, 2H), 3.18-2.88 (m, 4H), 2.71 (s, 3H), 2.14 (d, J = 62.1 Hz, 4H), 1.74 (d, J = 6.9 Hz, 6H). LC-MS: m/z: (M + H)$^+$ = 522.9. | I-61 |

TABLE 1-continued

List of embodiments

| Embodiment | Structure | Analytic data | Method |
|---|---|---|---|
| 50 | 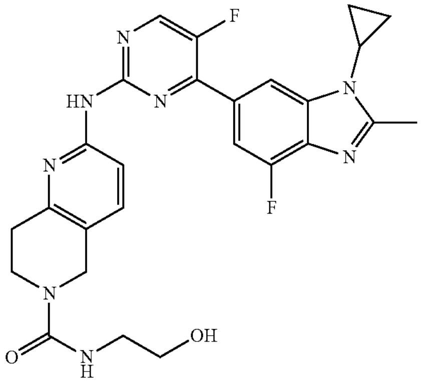 [SMILES: Cc1nc2c(F)cc(-c3nc(Nc4ccc5c(n4)CCN(C(=O)NCCO)C5)ncc3F)cc2n1C1CC1] | Solid.<br>$^1$H NMR (400 MHz, DMSO-d$_6$) δ 9.96 (s, 1H), 8.69 (d, J = 3.9 Hz, 1H), 8.22 (s, 1H), 8.11 (d, J = 8.4 Hz, 1H), 7.75 (d, J = 11.7 Hz, 1H), 7.57 (d, J = 8.5 Hz, 1H), 6.63 (s, 1H), 5.33 (s, 1H), 4.56 (d, J = 54.3 Hz, 4H), 3.67 (t, J = 5.7 Hz, 2H), 3.14 (d, J = 5.8 Hz, 2H), 2.81 (s, 2H), 2.67 (s, 3H), 2.14-1.79 (m, 4H).<br>LC-MS: m/z: (M + H)$^+$ = 520.9. | I-61 |
| 51 | 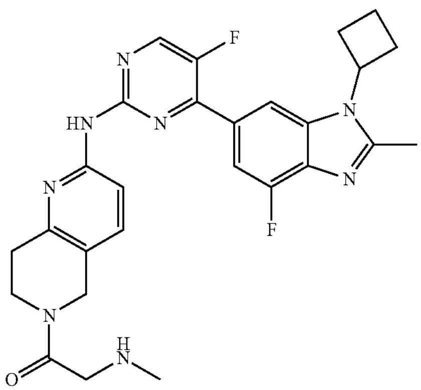 [SMILES: CNCC(=O)N1CCc2nc(Nc3ncc(F)c(-c4cc(F)c5nc(C)n(C6CCC6)c5c4)n3)ccc2C1] | Solid.<br>$^1$H NMR (400 MHz, DMSO-d$_6$) δ 9.07 (s, 2H), 8.88 (t, J = 3.2 Hz, 1H), 8.38 (s, 1H), 8.09 (dd, J = 8.8, 3.4 Hz, 1H), 7.94 (dd, J = 45.3, 10.2 Hz, 2H), 5.22-5.13 (m, 1H), 4.69 (d, J = 25.5 Hz, 2H), 4.20 (dd, J = 17.8, 12.4 Hz, 2H), 3.83 (dt, J = 52.4, 5.7 Hz, 2H), 3.04 (d, J = 51.3 Hz, 2H), 2.82 (dd, J = 20.4, 10.6 Hz, 2H), 2.73 (s, 3H), 2.65 (dd, J = 16.9, 7.9 Hz, 2H), 2.58 (d, J = 5.3 Hz, 3H), 1.99 (dd, J = 23.4, 10.6 Hz, 2H).<br>LC-MS: m/z: (M + H)$^+$ = 518.9. | I-4 |
| 53 | 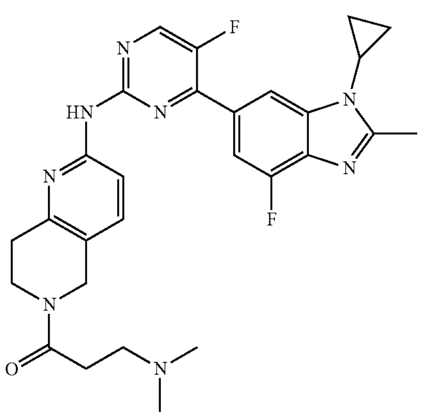 [SMILES: Cc1nc2c(F)cc(-c3nc(Nc4ccc5c(n4)CCN(C(=O)CCN(C)C)C5)ncc3F)cc2n1C1CC1] | Solid.<br>$^1$H NMR (400 MHz, DMSO-d$^6$) δ 10.00 (d, J = 10.1 Hz, 1H), 8.70 (s, 1H), 8.18 (d, J = 29.5 Hz, 2H), 7.87-7.57 (m, 2H), 4.67 (d, J = 23.5 Hz, 2H), 3.82 (s, 2H), 3.47 (s, 2H), 3.33 (s, 5H), 2.88 (d, J = 49.8 Hz, 6H), 2.67 (s, 3H), 1.27 (s, 2H), 1.13 (s, 2H).<br>LC-MS: m/z: (M + H)$^+$ = 532.9. | I-6 |

TABLE 1-continued

List of embodiments

| Embodiment | Structure | Analytic data | Method |
|---|---|---|---|
| 54 | 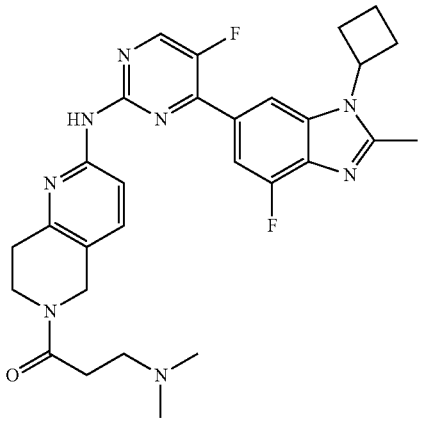 | Solid.<br>$^1$H-NMR (400 MHz, DMSO-d$_6$)<br>δ = 10.02-10.04 (m, 1H), 8.70 (d, 1H, J = 3.6 Hz), 8.35 (s, 1H), 8.11-8.15 (m, 1H), 7.73 (d, 1H, J = 12 Hz), 7.58-7.61 (m, 1H), 5.32-5.35 (m, 1H), 5.07-5.12 (m, 1H), 4.61-4.72 (m, 2H), 3.80-3.86 (m, 2H), 2.81-2.93 (m, 4H), 2.30 (s, 6H), 1.95-2.04 (m, 6H), 1.44-1.48 (m, 2H), 0.84-0.88 (m, 2H).<br>LC-MS: m/z: (M + H)$^+$ = 533.2. | I-5 |
| 55 | 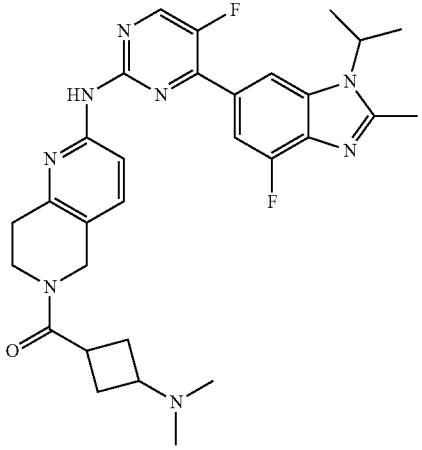 [SMILES: Cc1nc2c(F)cc(-c3nc(Nc4ccc5c(n4)CCN(C(=O)C4CC(N(C)C)C4)C5)ncc3F)cc2n1C(C)C] | Solid.<br>$^1$H NMR (400 MHz, DMSO-d$_6$)<br>δ 10.06 (d, J = 16.5 Hz, 1H), 8.70 (d, J = 3.8 Hz, 1H), 8.31 (s, 1H), 8.19-8.05 (m, 1H), 7.86-7.52 (m, 2H), 4.96-4.76 (m, 1H), 4.62 (dd, J = 20.8, 13.4 Hz, 2H), 3.77 (d, J = 33.9 Hz, 2H), 3.20 (d, J = 9.0 Hz, 2H), 2.84 (d, J = 32.0 Hz, 2H), 2.65 (s, 3H), 2.56 (s, 6H), 2.46-2.18 (m, 4H), 1.64 (d, J = 6.8 Hz, 6H).<br>LC-MS: m/z: (M + H)$^+$ = 560.9. | I-22 |
| 57 | 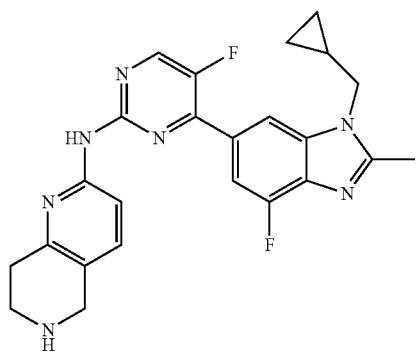 [SMILES: Cc1nc2c(F)cc(-c3nc(Nc4ccc5c(n4)CCNC5)ncc3F)cc2n1CC1CC1] | Yellow powder.<br>$^1$H NMR (400 MHz, CD$_3$OD) δ 8.97 (d, J = 3.0 Hz, 1H), 8.58 (s, 1H), 8.25 (dd, J = 21.3, 10.1 Hz, 2H), 7.63 (d, J = 9.1 Hz, 1H), 4.59-4.46 (m, 4H), 3.75 (t, J = 6.1 Hz, 2H), 3.53 (t, J = 6.0 Hz, 2H), 3.03 (s, 3H), 1.51-1.42 (m, 1H), 0.83-0.73 (m, 2H), 0.67 (q, J = 5.1 Hz, 2H).<br>LC-MS: m/z: (M + H)$^+$ = 448.2. | I-28 |

TABLE 1-continued

List of embodiments

| Embodiment | Structure | Analytic data | Method |
|---|---|---|---|
| 58 | 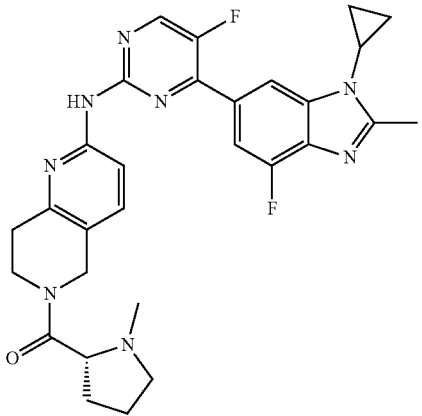 [SMILES: Cc1nc2c(F)cc(-c3nc(Nc4ccc5c(n4)CCN(C(=O)[C@H]4CCCN4C)C5)ncc3F)cc2n1C1CC1] | Yellow solid.<br>$^1$H NMR (400 MHz, CD$_3$OD) δ 8.53 (s, 1H), 8.42 (d, J = 16.9 Hz, 1H), 7.93 (d, J = 30.5 Hz, 1H), 7.72 (d, J = 27.6 Hz, 1H), 7.51-7.08 (m, 2H), 4.62 (s, 2H), 3.90 (d, J = 32.8 Hz, 1H), 3.77 (d, J = 39.8 Hz, 2H), 3.17 (d, J = 22.1 Hz, 2H), 2.91 (d, J = 12.1 Hz, 3H), 2.73 (s, 2H), 2.55 (d, J = 36.5 Hz, 3H), 2.16 (d, J = 72.2 Hz, 4H), 1.19 (s, 2H), 1.05-0.69 (m, 2H).<br>LC-MS: m/z: (M + H)$^+$ = 544.9. | I-22 |
| 59 | 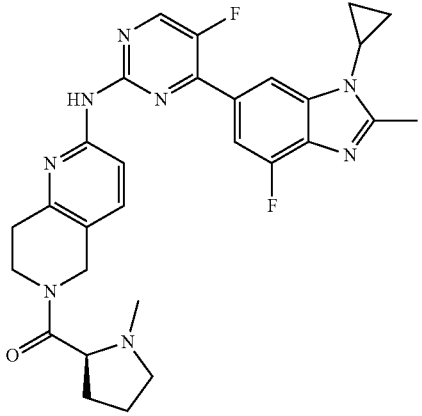 [SMILES: Cc1nc2c(F)cc(-c3nc(Nc4ccc5c(n4)CCN(C(=O)[C@@H]4CCCN4C)C5)ncc3F)cc2n1C1CC1] | Solid.<br>$^1$H-NMR (400 MHz, DMSO-d$_6$) δ 9.98-10.00 (m, 1H), 8.69 (d, 1H, J = 4 Hz), 8.20-8.21 (m, 2H), 8.12 (d, 1H, J = 8.8 Hz), 7.75 (d, 1H, J = 12.4 Hz), 7.62-7.67 (m, 1H), 4.55-4.82 (m, 2H), 3.80-4.04 (m, 2H), 3.33-3.48 (m, 3H), 3.02-3.06 (m, 1H), 2.80-2.90 (m, 2H), 2.67 (s, 3H), 2.28-2.33 (m, 4H), 1.79 (s, 2H), 1.24-1.30 (m, 3H), 1.12-1.14 (m, 2H).<br>LC-MS: m/z: (M + H)$^+$ = 545.2. | I-22 |
| 60 | 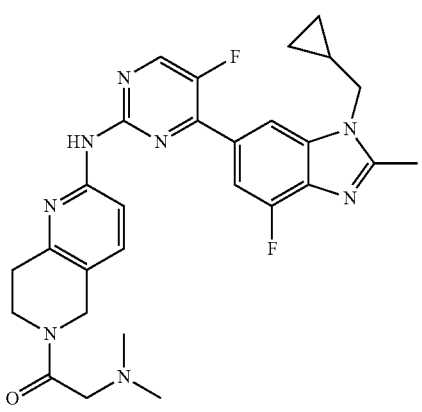 [SMILES: Cc1nc2c(F)cc(-c3nc(Nc4ccc5c(n4)CCN(C(=O)CN(C)C)C5)ncc3F)cc2n1CC1CC1] | Yellow powder.<br>$^1$H NMR (400 MHz, CD$_3$OD) δ 8.49 (d, J = 33.2 Hz, 1H), 8.19 (d, J = 29.6 Hz, 1H), 7.79 (s, 1H), 7.60 (s, 1H), 4.92 (d, J = 13.2 Hz, 1H), 4.70 (d, J = 33.6 Hz, 2H), 4.18 (d, J = 41.1 Hz, 4H), 3.88 (d, J = 63.1 Hz, 2H), 2.98 (d, J = 36.9 Hz, 2H), 2.85 (s, 6H), 2.71 (s, 3H), 0.74-0.42 (m, 4H).<br>LC-MS: m/z: (M + H)$^+$ = 533.2. | I-5 |

| Embodiment | Structure | Analytic data | Method |
|---|---|---|---|
| 63 | 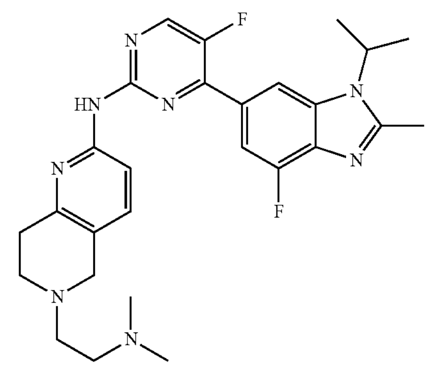 [SMILES: Cc1nc2c(F)cc(-c3nc(Nc4ccc5c(n4)CCN(CCN(C)C)C5)ncc3F)cc2n1C(C)C] | Solid.<br>¹H-NMR (DMSO-d₆) δ 9.92 (s, 1H), 8.68 (d, 1H, J = 4 Hz), 8.31 (d, 1H, J = 1.2 Hz), 8.06 (d, 1H, J = 8.4 Hz), 7.70 (d, 1H, J = 12 Hz), 7.45 (d, 1H, J = 8.4 Hz), 4.82-4.87 (m, 1H), 3.58 (s, 2H), 2.80-2.84 (m, 4H), 2.65 (s, 3H), 2.58-2.63 (m, 3H), 2.22 (s, 6H), 1.64 (d, 6H, J = 6.8 Hz).<br>LC-MS: m/z: (M + H)⁺ = 507.9. | I-52 |
| 64 | 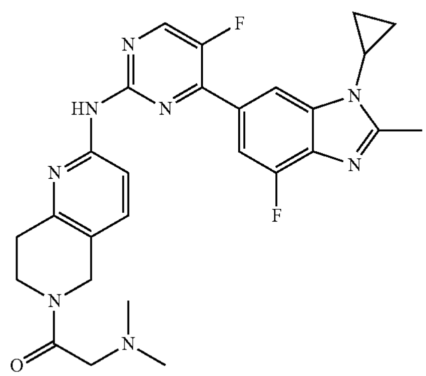 [SMILES: Cc1nc2c(F)cc(-c3nc(Nc4ccc5c(n4)CCN(C(=O)CN(C)C)C5)ncc3F)cc2n1C1CC1] | Pale yellow solid.<br>¹H-NMR (400 MHz, CD₃OD) δ 8.44-8.45 (m, 1H), 8.35-8.39 (m, 1H), 7.93 (s, 1H), 7.59-7.62 (m, 1H), 7.52 (s, 1H), 4.65-4.74 (m, 2H), 3.80-3.98 (m, 4H), 3.37-3.38 (m, 1H), 2.94-3.03 (m, 2H), 2.75 (s, 6H), 2.71 (s, 3H), 1.30-1.34 (m, 2H), 1.15-1.17 (m, 2H).<br>LC-MS: m/z: (M + H)⁺ = 517.2. | I-5 |
| 65 | 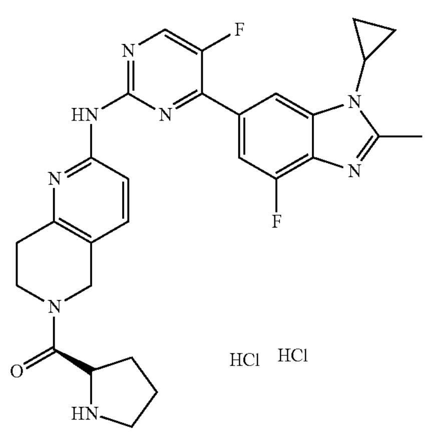 | Solid.<br>¹H NMR (400 MHz, CD₃OD) δ 8.97 (t, J = 3.2 Hz, 1H), 8.58 (s, 1H), 8.25 (dd, J = 12.0, 9.0 Hz, 2H), 7.57 (dd, J = 8.7, 4.8 Hz, 1H), 4.97 (dd, J = 17.2, 6.6 Hz, 2H), 4.81 (d, J = 17.6 Hz, 1H), 4.18 (dd, J = 108.9, 17.0 Hz, 2H), 3.86 (dd, J = 30.6, 26.8 Hz, 2H), 3.57-3.40 (m, 2H), 3.28 (s, 1H), 3.05 (s, 3H), 2.76-1.90 (m, 4H), 1.67-1.48 (m, 2H), 1.35 (d, J = 30.5 Hz, 2H).<br>LC-MS: m/z: (M + H)⁺ = 530.9. | I-4 |

TABLE 1-continued

List of embodiments

| Embodiment | Structure | Analytic data | Method |
|---|---|---|---|
| 66 | 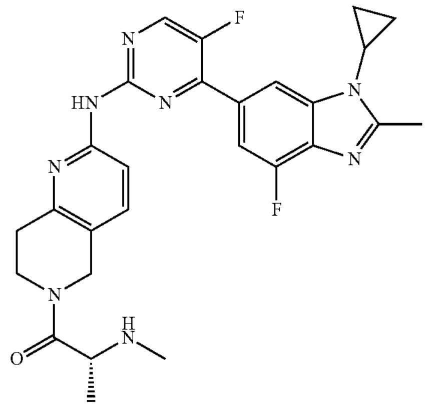 [SMILES: CN[C@H](C)C(=O)N1CCc2nc(Nc3ncc(F)c(-c4cc(F)c5nc(C)n(C6CC6)c5c4)n3)ccc2C1] | White powder.<br>¹H NMR (400 MHz, CD₃OD) δ 8.97 (s, 1H), 8.57 (s, 1H), 8.25 (t, J = 8.6 Hz, 2H), 7.57 (d, J = 14.1 Hz, 1H), 5.04-4.94 (m, 2H), 4.64 (s, 2H), 4.07 (d, J = 31.7 Hz, 1H), 3.68 (d, J = 47.0 Hz, 2H), 3.04 (s, 3H), 2.73 (d, J = 17.8 Hz, 4H), 1.56 (dd, J = 18.3, 6.7 Hz, 7H).<br>LC-MS: m/z: (M + H)⁺ = 519.2. | I-4 |
| 67 | 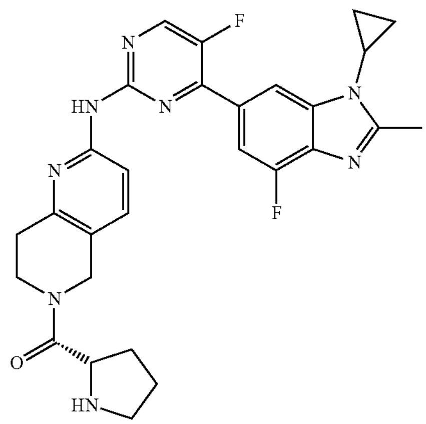 | Solid.<br>¹H NMR (400 MHz, CD₃OD) δ 8.54 (dd, J = 9.3, 7.7 Hz, 2H), 8.29 (d, J = 7.9 Hz, 1H), 7.82 (d, J = 12.3 Hz, 1H), 7.65 (dd, J = 8.7, 4.6 Hz, 1H), 4.74 (dd, J = 33.1, 18.6 Hz, 4H), 4.00-3.82 (m, 2H), 3.51-3.43 (m, 2H), 3.04 (d, J = 6.2 Hz, 1H), 2.96 (s, 1H), 2.75 (s, 3H), 2.16-1.91 (m, 4H), 1.41-1.30 (m, 4H).<br>LC-MS: m/z: (M + H)⁺ = 530.9. | I-4 |
| 68 | 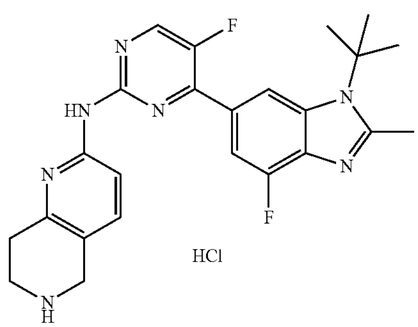 [SMILES: Cc1nc2c(F)cc(-c3nc(Nc4ccc5c(n4)CCNC5)ncc3F)cc2n1C(C)(C)C ; Cl] | Pale yellow solid.<br>¹H NMR (400 MHz, CD₃OD) δ 8.96 (d, J = 2.9 Hz, 1H), 8.76 (s, 1H), 8.22 (dd, J = 9.6, 7.2 Hz, 2H), 7.65 (d, J = 8.9 Hz, 1H), 4.52 (s, 2H), 3.75 (s, 2H), 3.53 (s, 2H), 3.16 (s, 3H), 2.07 (s, 9H).<br>LC-MS: m/z: (M + H)⁺ = 449.9. | I-28 |
| 69 | 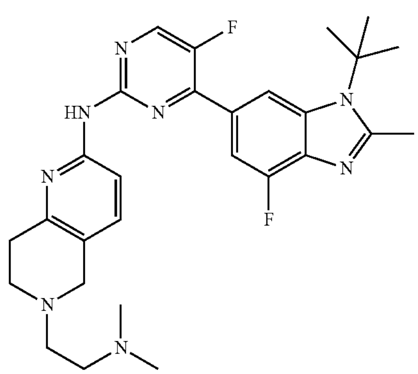 [SMILES: Cc1nc2c(F)cc(-c3nc(Nc4ccc5c(n4)CCN(CCN(C)C)C5)ncc3F)cc2n1C(C)(C)C] | Pale yellow solid.<br>¹H NMR (400 MHz, CDCl₃) δ 8.45-8.39 (m, 2H), 8.24 (d, J = 8.4 Hz, 1H), 7.94 (s, 1H), 7.77 (d, J = 11.5 Hz, 1H), 7.37 (d, J = 8.5 Hz, 1H), 3.70 (s, 2H), 2.99 (t, J = 5.8 Hz, 2H), 2.94-2.88 (m, 5H), 2.82 (d, J = 6.0 Hz, 2H), 2.77-2.69 (m, 2H), 2.46 (s, 6H), 1.94 (s, 9H).<br>LC-MS: m/z: (M +30 H)⁺ = 521.0. | I-52 |

TABLE 1-continued

List of embodiments

| Embodiment | Structure | Analytic data | Method |
|---|---|---|---|
| 70 | 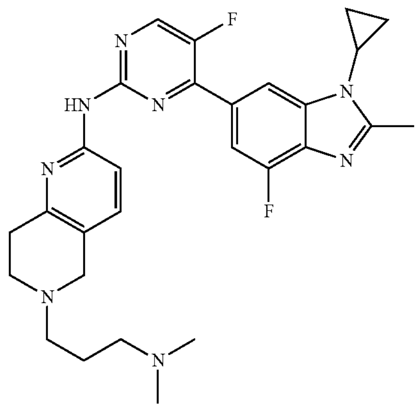 [SMILES: Cc1nc2c(F)cc(-c3nc(Nc4ccc5c(n4)CCN(CCCN(C)C)C5)ncc3F)cc2n1C1CC1] | Yellow powder.<br>¹H NMR (400 MHz, CDCl₃) δ 8.40 (d, J = 3.7 Hz, 1H), 8.23-8.15 (m, 2H), 7.95 (s, 1H), 7.79 (d, J = 11.7 Hz, 1H), 7.39 (d, J = 8.5 Hz, 1H), 3.62 (s, 2H), 3.35-3.26 (m, 1H), 2.95 (d, J = 5.8 Hz, 2H), 2.84 (t, J = 5.9 Hz, 2H), 2.73 (s, 3H), 2.62 (dd, J = 12.8, 6.0 Hz, 4H), 2.43 (s, 6H), 1.91 (dd, J = 14.9, 7.4 Hz, 2H), 1.36-1.31 (m, 2H), 1.14 (d, J = 7.2 Hz, 2H).<br>LC-MS: m/z: (M + H)⁺ = 519.3. | I-3 |
| 71 | 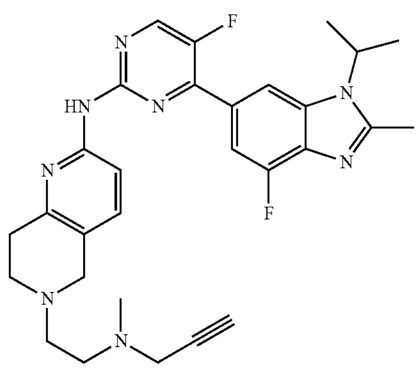 [SMILES: C#CCN(C)CCN1CCc2nc(Nc3ncc(F)c(-c4cc(F)c5nc(C)n(C(C)C)c5c4)n3)ccc2C1] | Solid.<br>¹H NMR (400 MHz, CDCl₃) δ 8.43 (d, J = 3.8 Hz, 1H), 8.23 (t, J = 5.1 Hz, 2H), 7.99 (s, 1H), 7.80 (d, J = 11.6 Hz, 1H), 7.38 (d, J = 8.5 Hz, 1H), 4.75 (dt, J = 14.0, 7.0 Hz, 1H), 3.75 (d, J = 15.3 Hz, 2H), 3.53-3.46 (m, 2H), 3.00 (d, J = 5.2 Hz, 2H), 2.96 (d, J = 5.1 Hz, 2H), 2.77 (s, 4H), 2.71 (s, 3H), 2.42 (s, 3H), 2.28 (t, J = 2.3 Hz, 1H), 1.73 (d, J = 7.0 Hz, 6H).<br>LC-MS: m/z: (M + H)⁺ = 530.9. | I-52 |
| 74 | 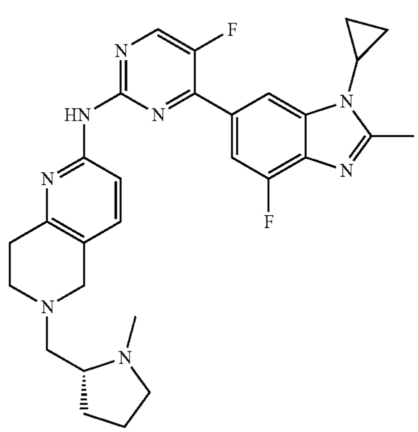 [SMILES: Cc1nc2c(F)cc(-c3nc(Nc4ccc5c(n4)CCN(C[C@H]4CCCN4C)C5)ncc3F)cc2n1C1CC1] | Yellow solid.<br>¹H NMR (400 MHz, CD₃OD) δ 8.53 (d, J = 3.9 Hz, 1H), 8.27 (s, 1H), 8.18 (d, J = 8.6 Hz, 1H), 7.81 (d, J = 12.0 Hz, 1H), 7.54 (d, J = 8.5 Hz, 1H), 3.76 (dd, J = 35.1, 14.8 Hz, 4H), 3.62-3.56 (m, 1H), 3.46 (m, 1H), 3.15-3.06 (m, 2H), 3.02-2.93 (m, 5H), 2.93-2.85 (m, 2H), 2.81-2.73 (m, 3H), 2.35 (m, 1H), 2.22-2.00 (m, 2H), 1.88-1.75 (m, 1H), 1.37 (m, 2H), 1.22-1.16 (m, 2H).<br>LC-MS m/z: (M + H)⁺ = 530.9. | I-3 |

TABLE 1-continued

List of embodiments

| Embodiment | Structure | Analytic data | Method |
|---|---|---|---|
| 75 | 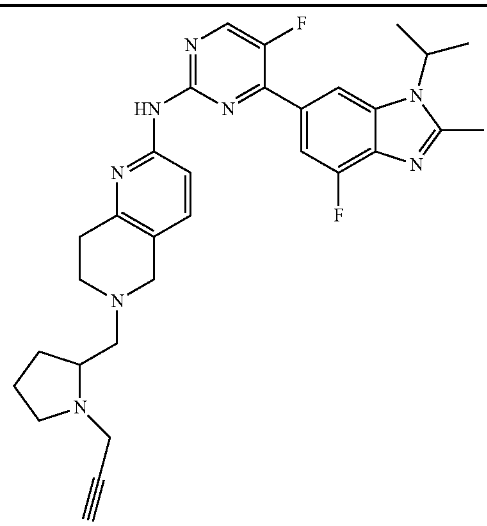 | Yellow solid.<br>$^1$H NMR (400 MHz, CDCl$_3$) δ 8.39 (d, J = 3.8 Hz, 1H), 8.21 (d, J = 8.5 Hz, 2H), 7.89 (s, 1H), 7.78 (d, J = 12.0 Hz, 1H), 7.36 (d, J = 8.4 Hz, 1H), 4.71 (m, 1H), 3.65 (s, 4H), 2.93 (d, J = 3.7 Hz, 2H), 2.86 (d, J = 11.6 Hz, 2H), 2.69 (s, 3H), 2.61 (s, 2H), 2.21 (d, J = 12.0 Hz, 1H), 2.00 (s, 1H), 1.71 (d, J = 6.9 Hz, 6H), 1.30 (d, J = 11.4 Hz, 6H).<br>LC-MS: m/z: (M + H)$^+$ = 557.3. | I-72 |
| 76 | 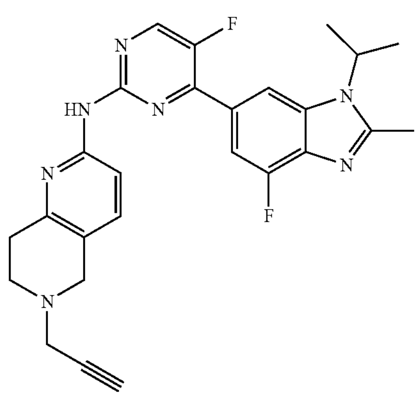 [SMILES: C#CCN1CCc2nc(Nc3ncc(F)c(-c4cc(F)c5nc(C)n(C(C)C)c5c4)n3)ccc2C1] | Yellow powder.<br>$^1$H NMR (400 MHz, DMSO-d$_6$) δ 9.93 (s, 1H), 8.68 (d, J = 3.9 Hz, 1H), 8.31 (s, 1H), 8.07 (d, J = 8.5 Hz, 1H), 7.70 (d, J = 12.2 Hz, 1H), 7.50 (d, J = 8.5 Hz, 1H), 4.96-4.78 (m, 1H), 3.65 (d, J = 3.5 Hz, 2H), 3.51 (d, J = 2.0 Hz, 2H), 3.23 (s, 1H), 2.85 (dd, J = 10.4, 4.3 Hz, 4H), 2.65 (s, 3H), 1.64 (d, J = 6.9 Hz, 6H).<br>LC-MS: m/z: (M + H)$^+$ = 473.9. | I-3 |
| 78 | 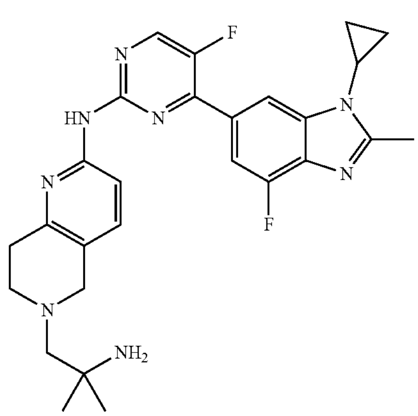 [SMILES: Cc1nc2c(F)cc(-c3nc(Nc4ccc5c(n4)CCN(CC(C)(C)N)C5)ncc3F)cc2n1C1CC1] | Yellow solid.<br>$^1$H NMR (400 MHz, CD$_3$OD) δ 8.97 (s, 1H), 8.58 (s, 1H), 8.28 (s, 1H), 8.15 (s, 1H), 7.51 (s, 1H), 4.10 (s, 2H), 3.64 (dt, J = 9.4, 4.4 Hz, 4H), 3.37 (s, 2H), 3.02 (d, J = 24.1 Hz, 4H), 1.50 (d, J = 35.2 Hz, 4H), 1.42-1.27 (m, 6H).<br>LC-MS: m/z: (M + H)$^+$ = 504.9. | I-77 |

TABLE 1-continued

List of embodiments

| Embodiment | Structure | Analytic data | Method |
|---|---|---|---|
| 79 | 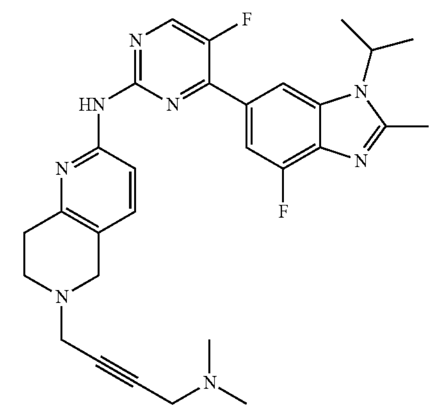 [SMILES: Cc1nc2c(F)cc(-c3nc(Nc4ccc5c(n4)CCN(CC#CCN(C)C)C5)ncc3F)cc2n1C(C)C] | Yellow solid.<br>$^1$H NMR (400 MHz, CD$_3$OD) δ 8.52 (d, J = 3.9 Hz, 1H), 8.29 (s, 1H), 8.15 (d, J = 8.5 Hz, 1H), 7.72 (d, J = 11.7 Hz, 1H), 7.45 (d, J = 8.4 Hz, 1H), 4.91 (d, J = 7.1 Hz, 1H), 3.75 (s, 2H), 3.60 (s, 2H), 3.40 (s, 2H), 2.97 (s, 4H), 2.69 (s, 3H), 2.38 (s, 6H), 1.72 (d, J = 6.9 Hz, 6H).<br>LC-MS: m/z: (M + H)$^+$ = 530.9. | I-3 |
| 81 | 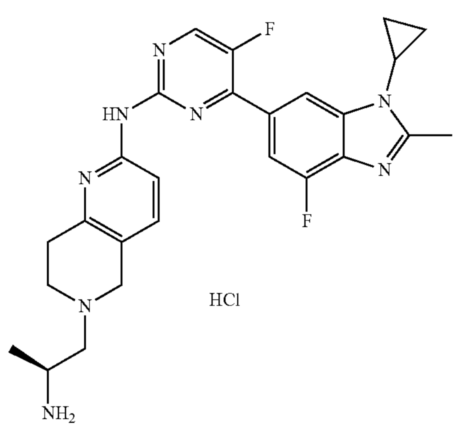 [SMILES: Cc1nc2c(F)cc(-c3nc(Nc4ccc5c(n4)CCN(C[C@H](C)N)C5)ncc3F)cc2n1C1CC1 ; Cl] | Yellow solid.<br>$^1$H NMR (400 MHz, CD$_3$OD) δ 8.95 (d, J = 3.1 Hz, 1H), 8.55 (s, 1H), 8.23 (t, J = 8.1 Hz, 1H), 8.18-8.13 (m, 1H), 7.55 (d, J = 8.9 Hz, 1H), 4.29 (s, 2H), 3.90 (s, 1H), 3.72 (s, 2H), 3.51 (s, 4H), 3.02 (s, 3H), 1.52 (d, J = 7.2 Hz, 2H), 1.45 (d, J = 6.3 Hz, 2H), 1.35 (s, 3H), 1.29 (s, 1H).<br>LC-MS: m/z: (M + H)$^+$ = 491.2. | I-52 |
| 82 | 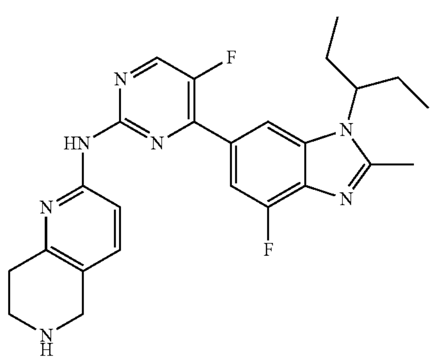 [SMILES: CCC(CC)n1c(C)nc2c(F)cc(-c3nc(Nc4ccc5c(n4)CCNC5)ncc3F)cc21] | Solid.<br>$^1$H NMR (400 MHz, DMSO-d$_6$) δ 9.95 (s, 1H), 8.67 (d, J = 3.8 Hz, 1H), 8.26 (s, 1H), 8.05 (d, J = 8.5 Hz, 1H), 7.71 (d, J = 12.0 Hz, 1H), 7.43 (d, J = 8.4 Hz, 1H), 4.35 (s, 1H), 3.88 (s, 2H), 3.09 (t, J = 5.6 Hz, 2H), 2.76 (t, J = 5.8 Hz, 2H), 2.64 (s, 4H), 2.20-2.07 (m, 2H), 2.06-1.93 (m, 2H), 0.74 (t, J = 7.3 Hz, 7H).<br>LC-MS: m/z: (M + H)$^+$ = 464.9. | I-39 |

TABLE 1-continued

List of embodiments

| Embodiment | Structure | Analytic data | Method |
|---|---|---|---|
| 83 | 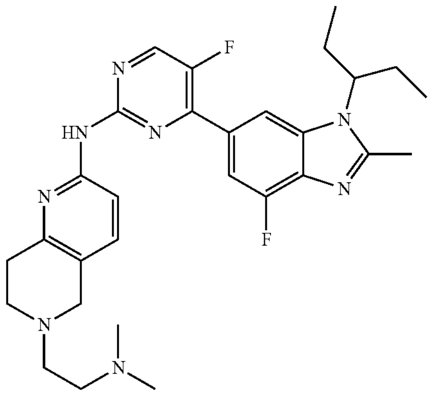 [SMILES: CCC(CC)n1c(C)nc2c(F)cc(-c3nc(Nc4ccc5c(n4)CCN(CCN(C)C)C5)ncc3F)cc21] | Pale yellow solid.<br>$^1$H NMR (400 MHz, DMSO-$d_6$) δ 9.95 (s, 1H), 8.67 (d, J = 3.9 Hz, 1H), 8.26 (s, 1H), 8.05 (d, J = 8.4 Hz, 1H), 7.70 (d, J = 12.4 Hz, 1H), 7.44 (d, J = 8.5 Hz, 1H), 4.39-4.28 (m, 1H), 3.58 (s, 2H), 2.82 (dd, J = 9.4, 4.2 Hz, 5H), 2.66-2.57 (m, 7H), 2.22 (s, 7H), 2.13 (dd, J = 16.9, 7.2 Hz, 3H), 2.06-1.95 (m, 3H), 0.74 (t, J = 7.3 Hz, 7H).<br>LC-MS: m/z: (M + H)$^+$ = 535.0. | I-52 |
| 84 | 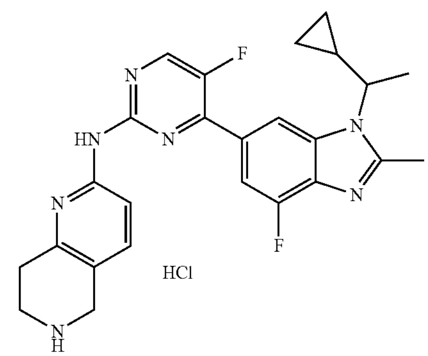 [SMILES: Cc1nc2c(F)cc(-c3nc(Nc4ccc5c(n4)CCNC5)ncc3F)cc2n1C(C)C1CC1 ; Cl] | White solid.<br>$^1$H NMR (400 MHz, CD$_3$OD) δ 8.88 (d, J = 3.3 Hz, 1H), 8.66 (s, 1H), 8.20 (d, J = 11.1 Hz, 1H), 8.07 (d, J = 8.9 Hz, 1H), 7.79 (d, J = 8.9 Hz, 1H), 4.48 (s, 2H), 4.38-4.25 (m, 1H), 3.71 (dd, J = 10.9, 4.8 Hz, 2H), 3.44 (d, J = 6.0 Hz, 2H), 2.95 (s, 3H), 1.84 (t, J = 7.0 Hz, 3H), 1.78 (dd, J = 11.8, 5.4 Hz, 1H), 0.93 (m, 1H), 0.82-0.74 (m, 1H), 0.69-0.60 (m, 1H), 0.50-0.38 (m, 1H).<br>LC-MS: m/z: (M + H)$^+$ = 462.0. | I-28 |
| 85 | 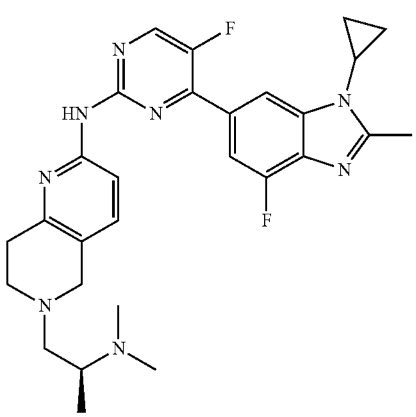 [SMILES: Cc1nc2c(F)cc(-c3nc(Nc4ccc5c(n4)CCN(C[C@H](C)N(C)C)C5)ncc3F)cc2n1C1CC1] | Yellow powder.<br>$^1$H NMR (400 MHz, CDCl$_3$) δ 8.53 (s, 1H), 8.43 (s, 1H), 8.24 (d, J = 8.5 Hz, 1H), 8.19 (s, 1H), 7.80 (d, J = 11.6 Hz, 1H), 7.41 (d, J = 8.5 Hz, 1H), 3.70 (s, 2H), 3.40 (dt, J = 10.5, 8.3 Hz, 2H), 2.99-2.95 (m, 4H), 2.76 (s, 3H), 2.69 (s, 6H), 2.60-2.50 (m, 1H), 1.40-1.35 (m, 2H), 1.32 (s, 3H), 1.27 (s, 1H), 1.15 (s, 2H).<br>LC-MS: m/z: (M + H)$^+$ = 519.3. | I-80 |

TABLE 1-continued

List of embodiments

| Embodiment | Structure | Analytic data | Method |
|---|---|---|---|
| 86 | 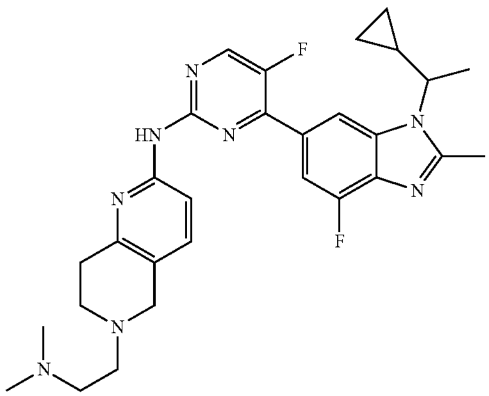 | Pale yellow solid.<br>$^1$H NMR (400 MHz, CD$_3$OD) δ 8.54 (d, J = 3.9 Hz, 1H), 8.40 (d, J = 1.1 Hz, 1H), 8.18 (d, J = 8.5 Hz, 1H), 7.81 (d, J = 11.9 Hz, 1H), 7.50 (d, J = 8.5 Hz, 1H), 4.00 (dq, J = 14.0, 7.0 Hz, 1H), 3.74 (s, 2H), 3.03-2.95 (m, 6H), 2.85 (t, J = 6.6 Hz, 2H), 2.67 (s, 3H), 2.62 (s, 6H), 1.77 (d, J = 7.0 Hz, 3H), 1.75-1.67 (m, 1H), 0.86 (m, 1H), 0.65 (m, 1H), 0.61-0.53 (m, 1H), 0.37-0.28 (m, 1H).<br>LC-MS: m/z: (M + H)$^+$ = 533.3. | I-52 |
| 87 | 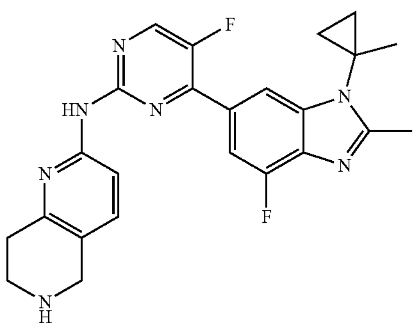 [SMILES: Cc1nc2c(F)cc(-c3nc(Nc4ccc5c(n4)CCNC5)ncc3F)cc2n1C1(C)CC1] | yellow solid.<br>$^1$H NMR (400 MHz, DMSO-d$_6$) δ 9.88 (s, 1H), 8.68 (d, J = 3.9 Hz, 1H), 8.23 (s, 1H), 8.06 (d, J = 8.4 Hz, 1H), 7.73 (d, J = 12.1 Hz, 1H), 7.44 (d, J = 8.4 Hz, 1H), 3.83 (s, 2H), 3.04 (t, J = 5.8 Hz, 2H), 2.73 (t, J = 5.6 Hz, 2H), 2.69 (s, 3H), 1.56 (s, 3H), 1.38-1.13 (m, 4H).<br>LC-MS: m/z: (M + H)$^+$ = 447.9. | I-28 |
| 88 | 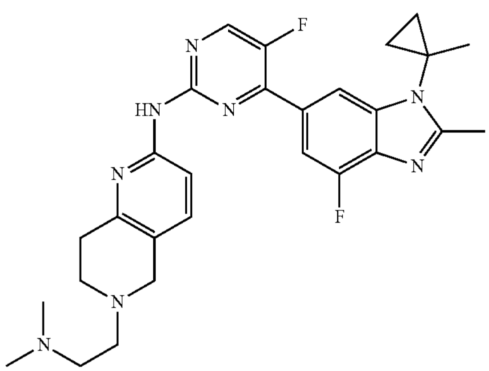 | Pale yellow solid.<br>$^1$H NMR (400 MHz, DMSO-d$_6$) δ 9.93 (s, 1H), 8.69 (d, J = 3.9 Hz, 1H), 8.23 (s, 1H), 8.08 (d, J = 8.4 Hz, 1H), 7.74 (d, J = 12.1 Hz, 1H), 7.48 (d, J = 8.5 Hz, 1H), 3.59 (s, 2H), 2.92-2.77 (m, 4H), 2.69 (s, 3H), 2.61 (dd, J = 15.2, 5.8 Hz, 4H), 2.28 (s, 6H), 1.56 (s, 3H), 1.23 (d, J = 11.8 Hz, 4H).<br>LC-MS: m/z: (M + H)$^+$ = 518.9. | I-52 |
| 89 | 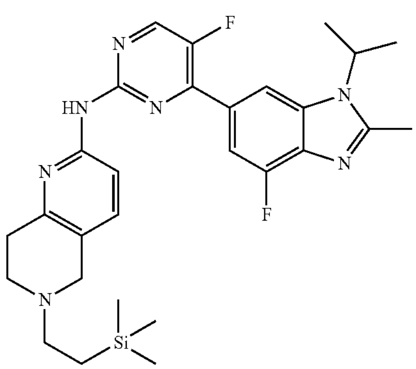 [SMILES: Cc1nc2c(F)cc(-c3nc(Nc4ccc5c(n4)CCN(CC[Si](C)(C)C)C5)ncc3F)cc2n1C(C)C] | Yellow solid.<br>$^1$H NMR (400 MHz, CD$_3$OD + CDCl$_3$) δ 8.52 (d, J = 3.8 Hz, 1H), 8.31 (d, J = 8.6 Hz, 1H), 8.28 (d, J = 1.1 Hz, 1H), 7.77 (d, J = 11.2 Hz, 1H), 7.58 (d, J = 8.7 Hz, 1H), 4.89 (d, J = 6.9 Hz, 1H), 4.25 (s, 2H), 3.49 (t, J = 6.0 Hz, 2H), 3.20 (dd, J = 10.9, 5.4 Hz, 4H), 2.70 (s, 3H), 1.73 (d, J = 6.9 Hz, 6H), 1.18-1.04 (m, 2H), 0.14 (d, J = 3.3 Hz, 9H).<br>LC-MS: m/z: (M + H)$^+$ = 536.0. | I-3 |

TABLE 1-continued

List of embodiments

| Embodiment | Structure | Analytic data | Method |
|---|---|---|---|
| 90 | 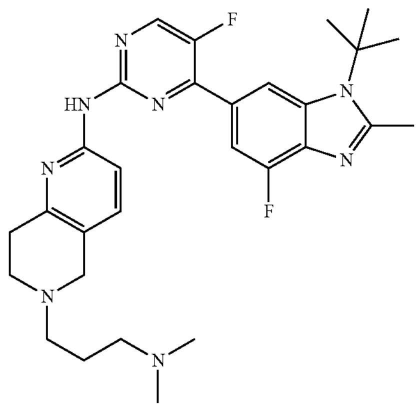 [SMILES: Cc1nc2c(F)cc(-c3nc(Nc4ccc5c(n4)CCN(CCCN(C)C)C5)ncc3F)cc2n1C(C)(C)C] | Tawney solid.<br>¹H NMR (400 MHz, CD₃OD) δ 8.57 (d, J = 3.9 Hz, 1H), 8.51 (s, 1H), 8.21 (d, J = 8.5 Hz, 1H), 7.79 (d, J = 11.6 Hz, 1H), 7.61 (d, J = 8.4 Hz, 1H), 4.03 (s, 2H), 3.25-3.29 (m, 4H), 3.10-3.12 (m, 2H), 3.04-2.97 (m, 2H), 2.95 (s, 6H), 2.89 (s, 3H), 2.23-2.11 (m, 2H), 1.96 (s, 9H).<br>LC-MS m/z: (M + H)⁺ = 534.9. | I-3 |
| 91 | 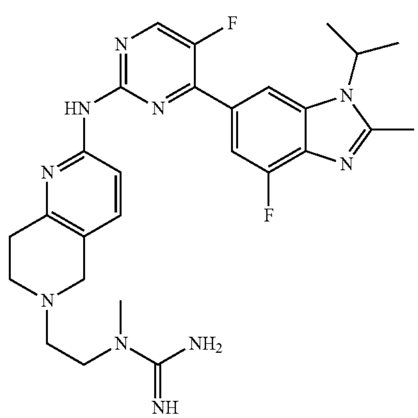 [SMILES: Cc1nc2c(F)cc(-c3nc(Nc4ccc5c(n4)CCN(CCN(C)C(=N)N)C5)ncc3F)cc2n1C(C)C] | Yellow solid.<br>¹H NMR (400 MHz, CD₃OD) + CDCl₃) δ 8.52 (s, 1H), 8.50 (d, J = 3.9 Hz, 1H), 8.28 (d, J = 1.0 Hz, 1H), 8.18 (d, J = 8.5 Hz, 1H), 7.76 (d, J = 11.9 Hz, 1H), 7.47 (d, J = 8.6 Hz, 1H), 4.90 (d, J = 6.9 Hz, 1H), 3.74 (s, 2H), 3.60 (t, J = 5.2 Hz, 2H), 3.10 (s, 3H), 2.97 (s, 4H), 2.85 (t, J = 5.3 Hz, 2H), 2.70 (s, 3H), 1.73 (d, J = 6.9 Hz, 6H).<br>LC-MS: m/z: (M + H)⁺ = 535.0. | I-72 |
| 92 | 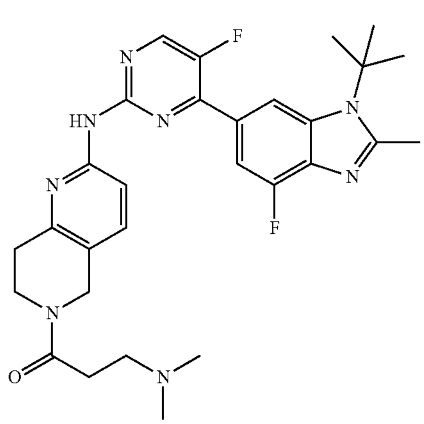 [SMILES: Cc1nc2c(F)cc(-c3nc(Nc4ccc5c(n4)CCN(C(=O)CCN(C)C)C5)ncc3F)cc2n1C(C)(C)C] | Pale yellow solid.<br>¹H NMR (400 MHz, CD₃OD) δ 8.56-8.52 (m, 1H), 8.51 (s, 1H), 8.25 (dd, J = 12.0, 8.6 Hz, 1H), 7.75 (d, J = 11.7 Hz, 1H), 7.63-7.54 (m, 1H), 4.72 (d, J = 10.2 Hz, 2H), 3.95-3.86 (m, 2H), 2.98 m, 3H), 2.91-2.80 (m, 6H), 2.52 (d, J = 7.3 Hz, 6H), 1.96 (d, J = 3.3 Hz, 9H).<br>LC-MS m/z: (M + H)⁺ = 548.9. | I-5 |

TABLE 1-continued

List of embodiments

| Embodiment | Structure | Analytic data | Method |
|---|---|---|---|
| 93 | 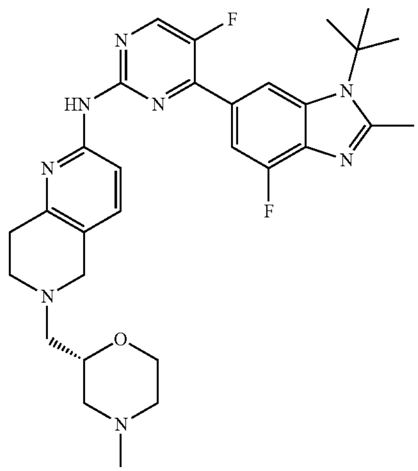 [SMILES: Cc1nc2c(F)cc(-c3nc(Nc4ccc5c(n4)CCN(C[C@H]4CN(C)CCO4)C5)ncc3F)cc2n1C(C)(C)C] | Pale yellow solid.<br>$^1$H NMR (400 MHz, CD$_3$OD) δ 8.54 (m, 2H), 8.21 (d, J = 8.4 Hz, 1H), 7.79 (d, J = 11.6 Hz, 1H), 7.51 (d, J = 8.6 Hz, 1H), 3.98-3.83 (m, 2H), 3.77 (d, J = 1.5 Hz, 2H), 3.70 (td, J = 11.7, 2.2 Hz, 2H), 3.04-2.98 (m, 5H), 2.2-2.89 (m, 4H), 2.84-2.71 (m, 2H), 2.66 (dd, J = 13.3, 4.1 Hz, 1H), 2.38 (s, 3H), 2.25 (td, J = 11.8, 3.3 Hz, 1H), 1.97 (s, 9H).<br>LC-MS m/z: (M + H)$^+$ = 563.3. | I-22 |
| 94 | 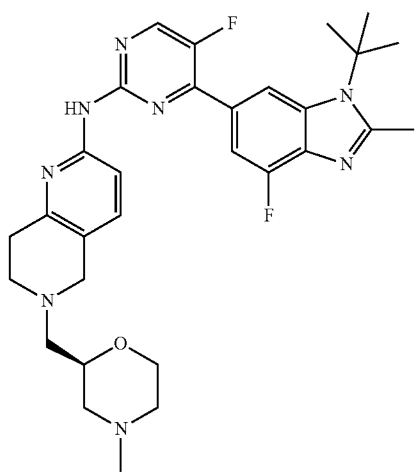 [SMILES: Cc1nc2c(F)cc(-c3nc(Nc4ccc5c(n4)CCN(C[C@@H]4CN(C)CCO4)C5)ncc3F)cc2n1C(C)(C)C] | Pale yellow solid.<br>$^1$H NMR (400 MHz, CD$_3$OD) δ 8.53 (d, J = 4.0 Hz, 1H), 8.51 (d, J = 1.1 Hz, 1H), 8.20 (d, J = 8.5 Hz, 1H), 7.76 (d, J = 11.7 Hz, 1H), 7.50 (d, J = 8.6 Hz, 1H), 4.01 (dd, J = 12.5, 2.7 Hz, 1H), 3.96-3.90 (m, 1H), 3.86 (s, 2H), 3.75 (td, J = 11.9, 2.2 Hz, 1H), 3.10-3.07 (m, 3H), 3.04-3.0 (m, 3H), 2.95 (d, J = 12.7 Hz, 1H), 2.89 (s, 3H), 2.87-2.82 (m, 1H), 2.79-2.76 (m, 1H), 2.54-2.35 (m, 4H), 1.96 (s, 9H).<br>LC-MS m/z: (M + H)$^+$ = 563.3. | I-22 |
| 96 | 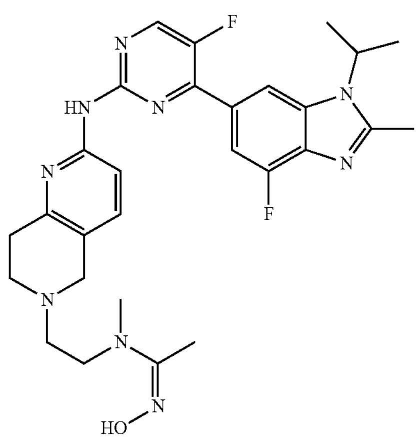 [SMILES: C/C(=N/O)N(C)CCN1CCc2nc(Nc3ncc(F)c(-c4cc(F)c5nc(C)n(C(C)C)c5c4)n3)ccc2C1] | Pale yellow solid.<br>$^1$H NMR (400 MHz, CD$_3$OD) δ 8.47 (d, J = 3.8 Hz 1H), 8.27 (d, J = 1.4 Hz, 1H), 8.21 (d, J = 8.5 Hz, 1H), 7.81-7.74 (m, 1H), 7.45 (d, J = 8.6 Hz, 1H), 4.85 (p, J = 6.9 Hz, 1H), 3.69 (s, 2H), 3.42 (t, J = 7.2 Hz, 2H), 2.98-2.89 (m, 4H), 2.83 (s, 3H), 2.73-2.68 (m, 2H), 2.68 (s, 3H), 2.04 (s, 3H), 1.73 (s, 3H), 1.71 (s, 3H).<br>LC-MS m/z: (M + H)$^+$ = 550.3. | I-95 |

TABLE 1-continued

List of embodiments

| Embodiment | Structure | Analytic data | Method |
|---|---|---|---|
| 98 | 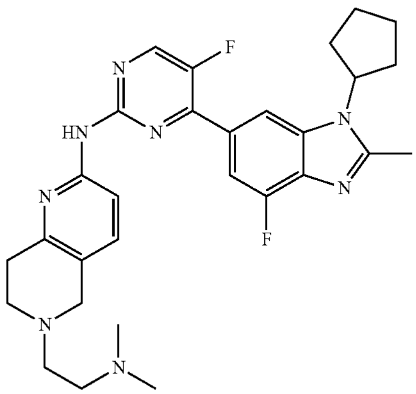 [SMILES: Cc1nc2c(F)cc(-c3nc(Nc4ccc5c(n4)CCN(CCN(C)C)C5)ncc3F)cc2n1C1CCCC1] | Pale yellow solid.<br>$^1$H NMR (400 MHz, CD$_3$OD) δ 8.52 (d, J = 3.9 Hz, 1H), 8.19 (s, 1H), 8.16 (d, J = 8.4 Hz, 1H), 7.78 (d, J = 12.0 Hz, 1H), 7.48 (d, J = 8.5 Hz, 1H), 5.05 (dd, J = 17.6, 8.8 Hz, 1H), 3.70 (s, 2H), 2.95 (dd, J = 10.0, 4.4 Hz, 4H), 2.78 (s, 4H), 2.70 (s, 3H), 2.44 (s, 6H), 2.31-2.22 (m, 4H), 2.08 (td, J = 12.9, 6.7 Hz, 2H), 1.90 (dt, J = 9.6, 3.4 Hz, 2H).<br>LC-MS m/z: (M + H)$^+$ = 533.3. | I-52 |
| 101 | HCl<br>or<br>HCl<br>Peak 1 | White solid.<br>$^1$H NMR (400 MHz, CD$_3$OD) δ 8.98 (d, J = 3.2 Hz, 1H), 8.76 (s, 1H), 8.34 (d, J = 9.2 Hz, 1H), 8.24 (d, J = 10.8 Hz, 1H), 7.65 (d, J = 9.1 Hz, 1H), 4.84-4.79 (m, 1H), 3.83 (dt, J = 11.0, 5.7 Hz, 1H), 3.74-3.66 (m, 1H), 3.62-3.49 (m, 2H), 3.17 (s, 3H), 2.07 (s, 9H), 1.81 (d, J = 6.8 Hz, 3H).<br>LC-MS m/z: (M + H)$^+$ = 464.3. | I-28 |
| 102 | 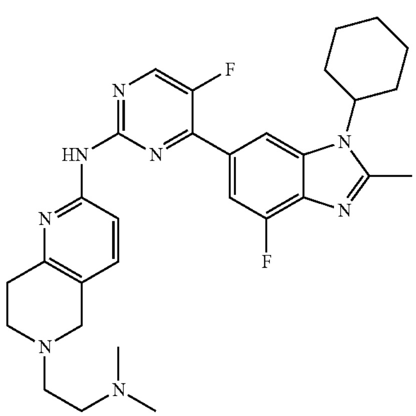 [SMILES: Cc1nc2c(F)cc(-c3nc(Nc4ccc5c(n4)CCN(CCN(C)C)C5)ncc3F)cc2n1C1CCCCC1] | Yellow solid.<br>$^1$H NMR (400 MHz, CD$_3$OD) δ 8.52 (d, J = 4.0 Hz, 1H), 8.32 (s, 1H), 8.15 (d, J = 8.4 Hz, 1H), 7.72 (d, J = 12.1 Hz, 1H), 7.44 (d, J = 8.2 Hz, 1H), 4.42 (t, J = 12.6 Hz, 1H), 3.66 (s, 2H), 2.92 (dd, J = 13.7, 4.3 Hz, 4H), 2.78-2.68 (m, 7H), 2.40 (s, 6H), 2.31-2.22 (m, 2H), 2.02 (d, J = 11.2 Hz, 4H), 1.84 (d, J = 14.7 Hz, 1H), 1.67-1.57 (m, 2H), 1.42-1.27 (m, 2H).<br>LC-MS m/z: (M + H)$^+$ = 547.3. | I-52 |

TABLE 1-continued

List of embodiments

| Embodiment | Structure | Analytic data | Method |
|---|---|---|---|
| 103 | 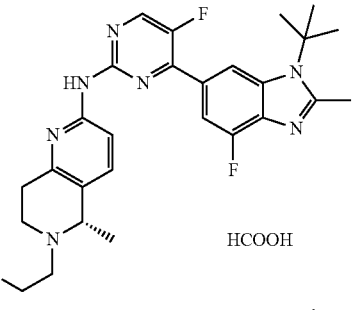 HCOOH  <br> 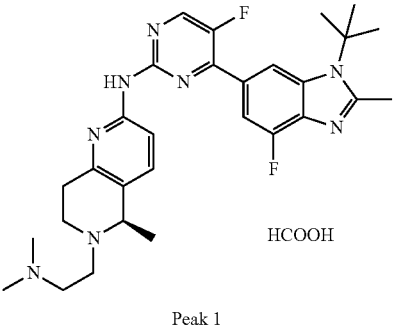 HCOOH  <br> Peak 1 | White solid. <br> $^1$H NMR (400 MHz, CD$_3$OD) δ 8.54 (d, J = 3.9 Hz, 1H), 8.51 (s, 1H), 8.39 (s, 1H), 8.20 (d, J = 8.6 Hz, 1H), 7.78 (d, J = 11.6 Hz, 1H), 7.57 (d, J = 8.6 Hz, 1H), 4.04 (q, J = 6.6 Hz, 1H), 3.39-3.35 (m, 1H), 3.30-3.23 (m, 1H), 3.12-2.95 (m, 5H), 2.93 (s, 6H), 2.89 (s, 3H), 2.84-2.76 (m, 1H), 1.96 (s, 9H), 1.43 (d, J = 6.7 Hz, 3H). <br> LC-MS m/z: (M + H)$^+$ = 535.3. | I-52 |
| 104 | 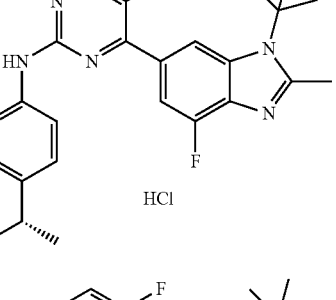 HCl  <br> 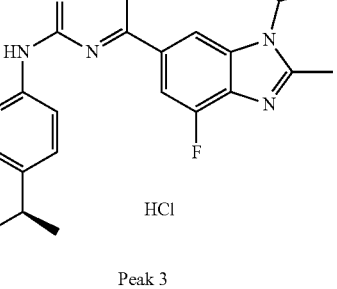 HCl  <br> Peak 3 | Yellow solid. <br> $^1$H NMR (400 MHz, CD$_3$OD) δ 8.98 (d, J = 3.2 Hz, 1H), 8.76 (s, 1H), 8.34 (d, J = 9.2 Hz, 1H), 8.24 (d, J = 10.8 Hz, 1H), 7.65 (d, J = 9.1 Hz, 1H), 4.84-4.79 (m, 1H), 3.83 (dt, J = 11.0, 5.7 Hz, 1H), 3.74-3.66 (m, 1H), 3.62-3.49 (m, 2H), 3.17 (s, 3H), 2.07 (s, 9H), 1.81 (d, J = 6.8 Hz, 3H). <br> LC-MS m/z: (M + H)$^+$ = 464.3. | I-28 |

TABLE 1-continued

List of embodiments

| Embodiment | Structure | Analytic data | Method |
|---|---|---|---|
| 106 | 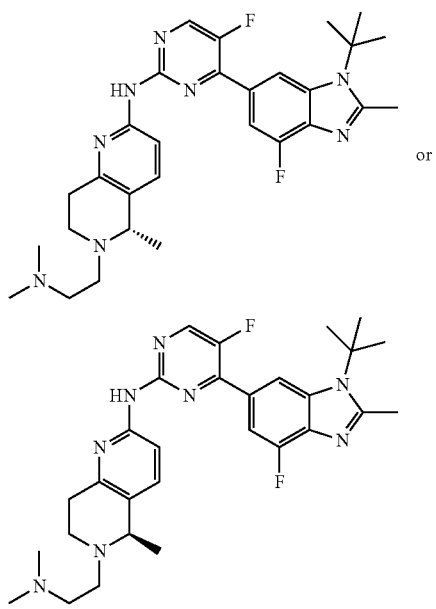 or 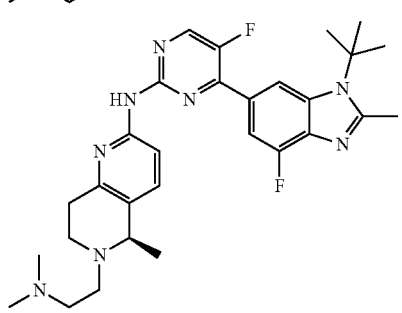<br>Peak 3 | Yellow solid.<br>$^1$H NMR (400 MHz, CD$_3$OD) δ 8.53 (d, J = 4.0 Hz, 1H), 8.51 (d, J = 1.1 Hz, 1H), 8.20 (d, J = 8.5 Hz, 1H), 7.78 (d, J = 11.5 Hz, 1H), 7.57 (d, J = 8.6 Hz, 1H), 4.02 (q, J = 6.6 Hz, 1H), 3.29-3.22 (m, 1H), 3.17 (dd, J = 9.6, 5.9 Hz, 2H), 3.00 (m, 4H), 2.89 (s, 3H), 2.85-2.81 (m, 1H), 2.78 (s, 6H), 1.96 (s, 9H), 1.42 (d, J = 6.7 Hz, 3H).<br>LC-MS m/z: (M + H)$^+$ = 535.3. | I-52 |
| 108 | 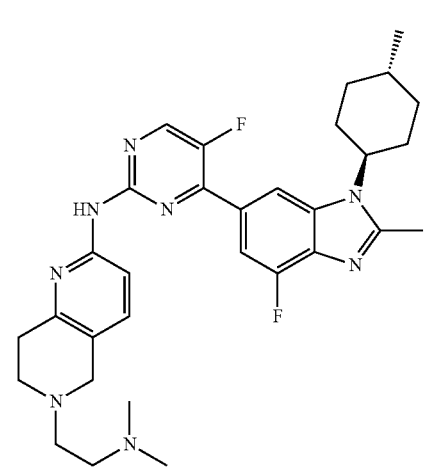 [SMILES: Cc1nc2c(F)cc(-c3nc(Nc4ccc5c(n4)CCN(CCN(C)C)C5)ncc3F)cc2n1[C@H]1CC[C@H](C)CC1] | Yellow solid.<br>$^1$H NMR (400 MHz, CD$_3$OD) δ 8.54 (d, J = 3.8 Hz, 1H), 8.36 (s, 1H), 8.21 (d, J = 8.4 Hz, 1H), 7.78 (d, J = 11.6 Hz, 1H), 7.50 (d, J = 8.2 Hz, 1H), 4.43 (t, J = 13.2 Hz, 1H), 3.74 (s, 2H), 3.03-2.95 (m, 6H), 2.86 (t, J = 6.5 Hz, 2H), 2.71 (s, 3H), 2.63 (s, 6H), 2.38 (dd, J = 24.7, 10.6 Hz, 2H), 2.09-1.94 (m, 4H), 1.67-1.50 (m, 1H), 1.44-1.27 (m, 2H), 1.05 (d, J = 6.4 Hz, 3H).<br>LC-MS m/z: (M + H)$^+$ = 561.3. | I-52 |

TABLE 1-continued
List of embodiments
| Embodiment | Structure | Analytic data | Method |
|---|---|---|---|
| 109 | 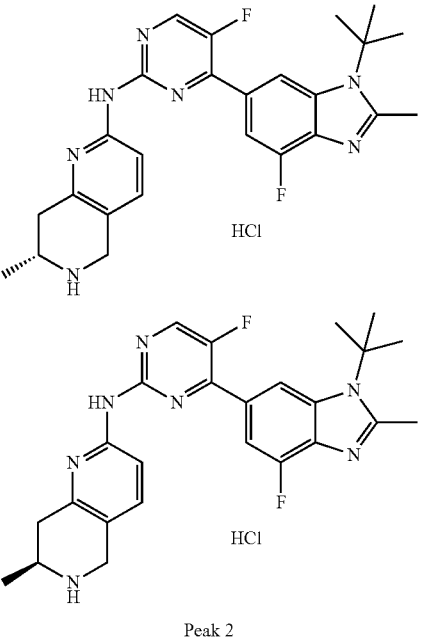<br>or<br>Peak 2 | White solid.<br>$^1$H NMR (400 MHz, CD$_3$OD) δ 8.96 (s, 1H), 8.76 (s, 1H), 8.23 (d, J = 10.1 Hz, 2H), 7.63 (d, J = 8.5 Hz, 1H), 4.94 (s, 1H), 4.64-4.48 (m, 2H), 3.93 (s, 1H), 3.62-3.59 (m, 1H), 3.16 (s, 3H), 2.07 (s, 9H), 1.63 (d, J = 2.1 Hz, 3H).<br>LC-MS m/z: (M + H)$^+$ = 464.3. | I-28 |
| 111 | 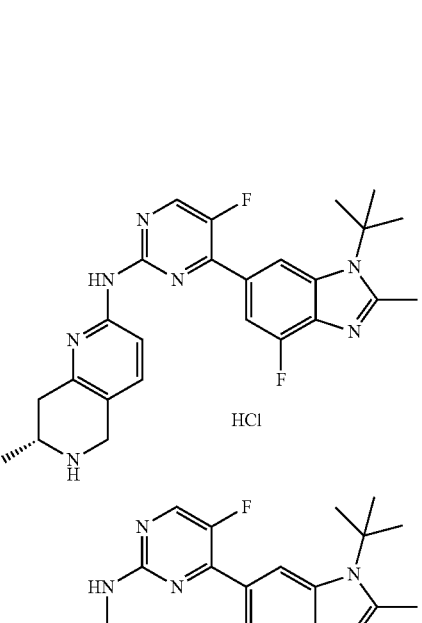<br>or<br>Peak 4 | Yellow solid.<br>$^1$H NMR (400 MHz, CD$_3$OD) δ 8.97 (d, J = 3.2 Hz, 1H), 8.77 (s, 1H), 8.26 (s, 1H), 8.23 (d, J = 2.9 Hz, 1H), 7.62 (d, J = 9.0 Hz, 1H), 4.63-4.50 (m, 2H), 3.99-3.88 (m, 1H), 3.64-3.60 (m, 1H), 3.41-3.35 (m, 1H), 3.17 (s, 3H), 2.07 (s, 9H), 1.64 (d, J = 6.4 Hz, 3H).<br>LC-MS m/z: (M + H)$^+$ = 464.2. | I-28 |

TABLE 1-continued

List of embodiments

| Embodiment | Structure | Analytic data | Method |
|---|---|---|---|
| 112 | 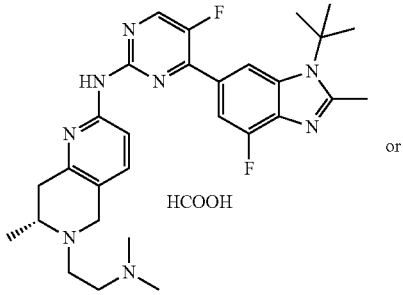 HCOOH <br> or <br> 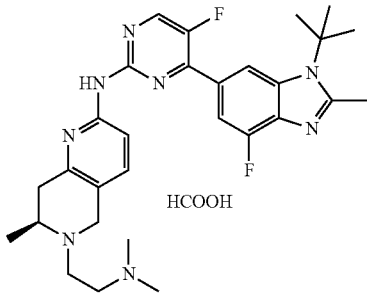 HCOOH <br> Peak 2 | White solid. <br> $^1$H NMR (400 MHz, CD$_3$OD) δ 8.55 (d, J = 3.9 Hz, 1H), 8.52 (d, J = 1.2 Hz, 1H), 8.47 (s, 1H), 8.22 (d, J = 8.4 Hz, 1H), 7.80 (d, J = 12.0 Hz, 1H), 7.54 (d, J = 8.5 Hz, 1H), 3.88 (s, 2H), 3.41-3.37 (m, 2H), 3.28 (dd, J = 8.2, 4.8 Hz, 1H), 3.01-2.97 (m, 2H), 2.91 (m, 10H), 2.69 (dd, J = 17.2, 4.9 Hz, 1H), 1.97 (s, 9H), 1.21 (d, J = 6.6 Hz, 3H). <br> LC-MS m/z: (M + H)$^+$ = 535.3. | I-52 |
| 114 | 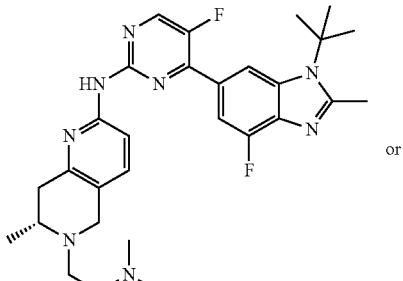 <br> or <br> 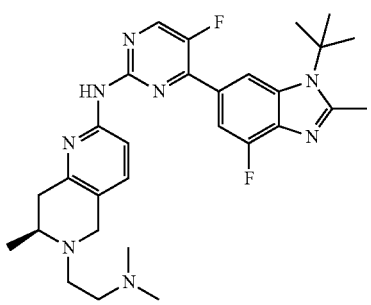 <br> Peak 4 | Yellow solid. <br> $^1$H NMR (400 MHz, CD$_3$OD) δ 8.55 (d, J = 4.0 Hz, 1H), 8.52 (d, J = 1.1 Hz, 1H), 8.20 (d, J = 8.5 Hz, 1H), 7.79 (d, J = 11.6 Hz, 1H), 7.56 (d, J = 8.5 Hz, 1H), 3.89 (s, 2H), 3.42-3.35 (m, 3H), 3.17 (dd, J = 17.2, 5.3 Hz, 1H), 3.00 (td, J = 5.2, 1.4 Hz, 2H), 2.93 (s, 6H), 2.90 (s, 3H), 2.69 (dd, J = 17.2, 4.7 Hz, 1H), 1.97 (s, 9H), 1.21 (d, J = 6.6 Hz, 3H). <br> LC-MS m/z: (M + H)$^+$ = 535.3. | I-52 |

TABLE 1-continued

List of embodiments

| Embodiment | Structure | Analytic data | Method |
|---|---|---|---|
| 126 | 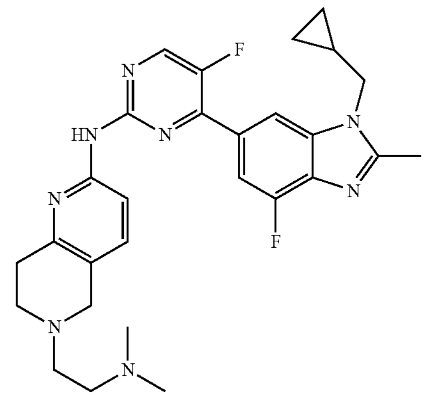 [SMILES: Cc1nc2c(F)cc(-c3nc(Nc4ccc5c(n4)CCN(CCN(C)C)C5)ncc3F)cc2n1CC1CC1] | Yellow powder.<br>¹H NMR (400 MHz, CD₃OD) δ 8.52 (s, 1H), 8.15 (d, J = 7.7 Hz, 2H), 7.80 (d, J = 12.3 Hz, 1H), 7.52 (d, J = 6.0 Hz, 1H), 4.23 (d, J = 6.8 Hz, 2H), 3.70 (s, 2H), 2.94 (d, J = 9.3 Hz, 4H), 2.79 (s, 3H), 2.69 (s, 4H), 2.47 (s, 6H), 0.89 (t, J = 7.4 Hz, 1H), 0.66 (d, J = 3.0 Hz, 2H), 0.51 (d, J = 10.7 Hz, 2H).<br>LC-MS: m/z: (M + H)⁺ = 519.3. | I-52 |
| 127 | 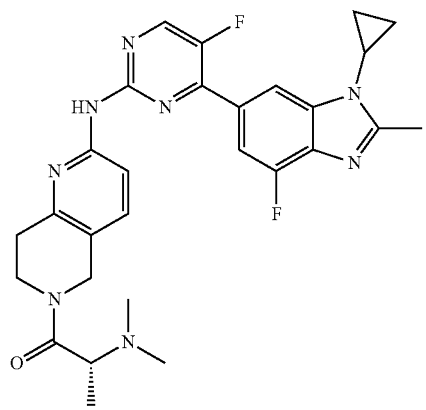 [SMILES: Cc1nc2c(F)cc(-c3nc(Nc4ccc5c(n4)CCN(C(=O)[C@@H](C)N(C)C)C5)ncc3F)cc2n1C1CC1] | Yellow powder.<br>¹H NMR (400 MHz, CD₃OD) δ 8.47 (d, J = 51.2 Hz, 2H), 8.27 (s, 1H), 7.81 (d, J = 12.6 Hz, 1H), 7.64 (d, J = 8.5 Hz, 1H), 4.80-4.58 (m, 1H), 4.42 (s, 1H), 4.15-3.80 (m, 2H), 3.41 (d, J = 25.8 Hz, 2H), 3.00 (d, J = 31.7 Hz, 2H), 2.82 (s, 6H), 2.75 (s, 3H), 1.53 (s, 2H), 1.33 (d, J = 20.5 Hz, 3H), 1.19 (s, 2H).<br>LC-MS: m/z (M + H)⁺ = 533.2. | I-22 |
| 129 | 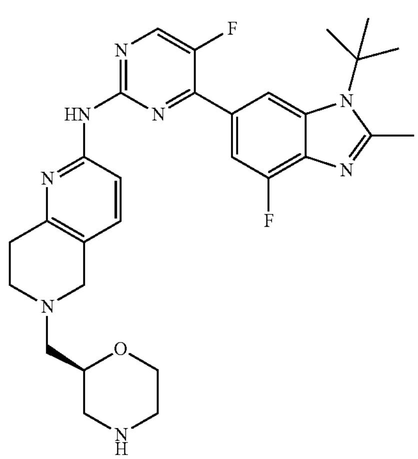 [SMILES: Cc1nc2c(F)cc(-c3nc(Nc4ccc5c(n4)CCN(C[C@@H]4CNCCO4)C5)ncc3F)cc2n1C(C)(C)C] | Yellow solid.<br>¹H NMR (400 MHz, CD₃OD) δ 8.56-8.47 (m, 2H), 8.17 (d, J = 8.5 Hz, 1H), 7.75 (d, J = 11.9 Hz, 1H), 7.47 (d, J = 8.5 Hz, 1H), 3.94 (d, J = 13.4 Hz, 1H), 3.84 (m, 1H), 3.76-3.63 (m, 3H), 3.07-2.85 (m, 10H), 2.65 (m, 3H), 1.95 (s, 9H).<br>LC-MS m/z: (M + H)⁺ = 549.3. | I-77 |

TABLE 1-continued

List of embodiments

| Embodiment | Structure | Analytic data | Method |
|---|---|---|---|
| 130 | 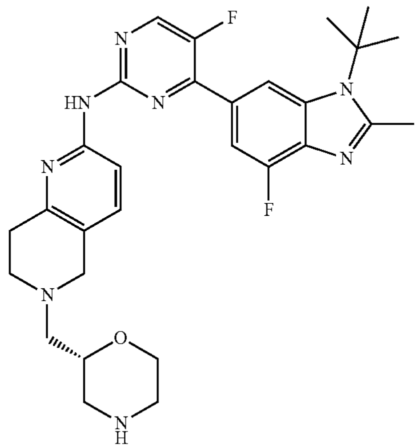 [SMILES: Cc1nc2c(F)cc(-c3nc(Nc4ccc5c(n4)CCN(C[C@H]4CNCCO4)C5)ncc3F)cc2n1C(C)(C)C] | Yellow solid.<br>¹H NMR (400 MHz, CD₃OD) δ 8.56-8.47 (m, 2H), 8.17 (d, J = 8.5 Hz, 1H), 7.75 (d, J = 11.9 Hz, 1H), 7.47 (d, J = 8.5 Hz, 1H), 3.94 (d, J = 13.4 Hz, 1H), 3.84 (m, 1H), 3.76-3.63 (m, 3H), 3.07-2.85 (m, 10H), 2.65 (m, 3H), 1.95 (s, 9H).<br>LC-MS m/z: $(M + H)^+$ = 549.3. | I-71 |
| 131 | 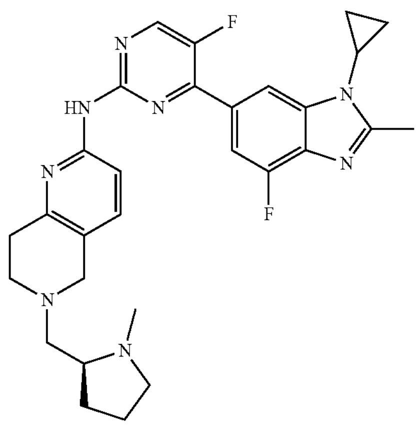 [SMILES: Cc1nc2c(F)cc(-c3nc(Nc4ccc5c(n4)CCN(C[C@@H]4CCCN4C)C5)ncc3F)cc2n1C1CC1] | Yellow solid.<br>¹H NMR (400 MHz, CDCl₃) δ 8.40 (d, J = 3.7 Hz, 1H), 8.26-8.10 (m, 2H), 7.99 (s, 1H), 7.78 (d, J = 11.9 Hz, 1H), 7.38 (d, J = 8.4 Hz, 1H), 3.69 (q, J = 14.6 Hz, 2H), 3.61-3.52 (m, 1H), 3.30 (t, J = 5.3 Hz, 1H), 3.12 (dd, J = 13.2, 7.4 Hz, 1H), 2.94 (s, 3H), 2.86 (d, J = 5.7 Hz, 1H), 2.74 (d, J = 4.0 Hz, 5H), 2.62 (ddd, J = 33.3, 13.4, 7.3 Hz, 2H), 1.97-1.76 (m, 3H), 1.39-1.29 (m, 3H), 1.25 (s, 2H), 1.13 (t, J = 8.0 Hz, 2H).<br>LC-MS: m/z: $(M + H)^+$ = 531.3. | I-3 |
| 134 | 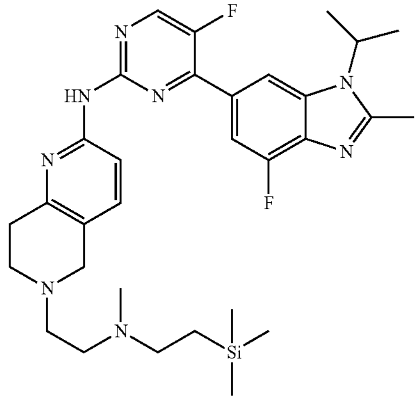 [SMILES: Cc1nc2c(F)cc(-c3nc(Nc4ccc5c(n4)CCN(CCN(C)CC[Si](C)(C)C)C5)ncc3F)cc2n1C(C)C] | Pale yellow solid.<br>¹H NMR (400 MHz, CD₃OD) δ 8.54 (d, J = 3.9 Hz, 1H), 8.49 (s, 1H), 8.33 (s, 1H), 8.19 (d, J = 8.5 Hz, 1H), 7.80 (d, J = 11.8 Hz, 1H), 7.52 (d, J = 8.6 Hz, 1H), 4.94 (s, 1H), 3.76 (s, 2H), 3.38 (d, J = 5.5 Hz, 2H), 3.30-3.23 (m, 2H), 3.02-2.93 (m, 6H), 2.90 (s, 3H), 2.71 (s, 3H), 1.74 (d, J = 6.9 Hz, 6H), 1.11-0.99 (m, 2H), 0.11 (s, 9H).<br>LC-MS m/z: $(M + H)^+$ = 593. | I-3 |

TABLE 1-continued

List of embodiments

| Embodiment | Structure | Analytic data | Method |
|---|---|---|---|
| 136 | 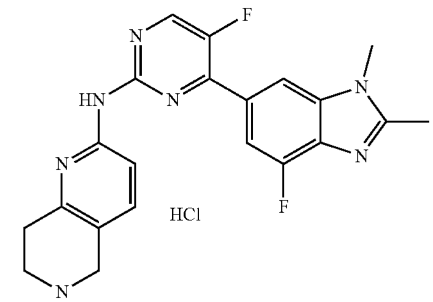 [SMILES: Cc1nc2c(F)cc(-c3nc(Nc4ccc5c(n4)CCNC5)ncc3F)cc2n1C ; Cl] | Pale yellow solid.<br>$^1$H NMR (400 MHz, D$_2$O) δ 8.34 (s, 1H), 7.81 (d, J = 3.8 Hz, 1H), 7.12 (s, 2H), 6.90 (s, 1H), 6.77 (d, J = 12.1 Hz, 1H), 4.82 (s, 3H), 4.12 (s, 2H), 3.45 (t, J = 6.0 Hz, 2H), 2.85 (s, 2H), 2.20 (s, 3H).<br>LC-MS m/z: (M + H)$^+$ = 408.2. | I-21 |
| 138 | 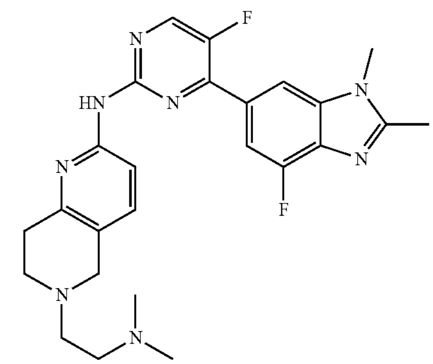 [SMILES: Cc1nc2c(F)cc(-c3nc(Nc4ccc5c(n4)CCN(CCN(C)C)C5)ncc3F)cc2n1C] | Yellow solid.<br>$^1$H NMR (400 MHz, CD$_3$OD) δ 8.49 (d, J = 3.8 Hz, 1H), 8.10 (d, J = 7.1 Hz, 1H), 8.00 (s, 1H), 7.75 (d, J = 11.6 Hz, 1H), 7.48 (d, J = 8.4 Hz, 1H), 3.83 (s, 3H), 3.71 (s, 2H), 3.01 (t, J = 6.3 Hz, 2H), 2.94 (s, 4H), 2.85 (t, J = 6.5 Hz, 2H), 2.64 (s, 9H).<br>LC-MS m/z: (M + H)$^+$ = 479.3. | I-52 |
| 139 | 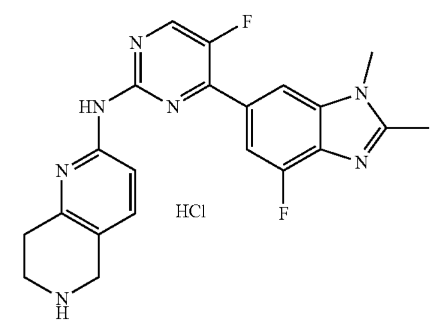 | Yellow solid.<br>$^1$H NMR (400 MHz, CD$_3$OD) δ 8.97 (d, J = 3.3 Hz, 1H), 8.56 (s, 1H), 8.23 (dd, J = 16.0, 10.1 Hz, 2H), 7.63 (d, J = 9.0 Hz, 1H), 4.67 (q, J = 7.3 Hz, 2H), 4.52 (s, 2H), 3.75 (t, J = 6.3 Hz, 2H), 3.53 (t, J = 6.1 Hz, 2H), 3.00 (s, 3H), 1.61 (t, J = 7.3 Hz, 3H).<br>LC-MS m/z: (M + H)$^+$ = 422.2. | I-21 |
| 140 | 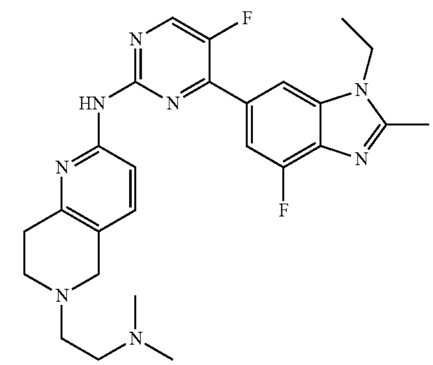 [SMILES: CCn1c(C)nc2c(F)cc(-c3nc(Nc4ccc5c(n4)CCN(CCN(C)C)C5)ncc3F)cc21] | Pale yellow solid.<br>$^1$H NMR (400 MHz, CD$_3$OD) δ 8.52 (d, J = 3.9 Hz, 1H), 8.13 (d, J = 8.5 Hz, 1H), 8.10 (s, 1H), 7.78 (d, J = 12.0 Hz, 1H), 7.51 (d, J = 8.6 Hz, 1H), 4.37 (q, J = 7.2 Hz, 2H), 3.77 (s, 2H), 3.44-3.39 (m, 2H), 2.97 (m, 12H), 2.69 (s, 3H), 1.48 (t, J = 7.3 Hz, 3H).<br>LC-MS m/z: (M + H)$^+$ = 493.3. | I-52 |

TABLE 1-continued

List of embodiments

| Embodiment | Structure | Analytic data | Method |
|---|---|---|---|
| 141 | 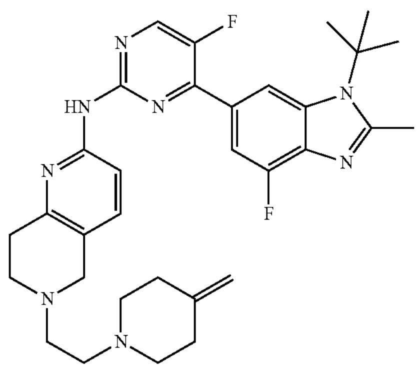 [SMILES: C=C1CCN(CCN2CCc3nc(Nc4ncc(F)c(-c5cc(F)c6nc(C)n(C(C)(C)C)c6c5)n4)ccc3C2)CC1] | Pale yellow solid.<br>LC-MS m/z: (M + H)$^+$ = 573.2. | I-52 |
| 142 | 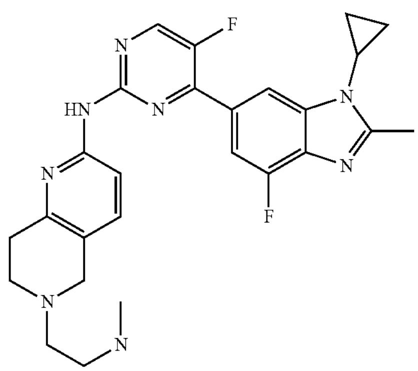 [SMILES: CNCCN1CCc2nc(Nc3ncc(F)c(-c4cc(F)c5nc(C)n(C6CC6)c5c4)n3)ccc2C1] | Pale yellow solid.<br>$^1$H NMR (400 MHz, DMSO-d$_6$) δ 9.91 (s, 1H), 8.68 (d, J = 3.9 Hz, 1H), 8.22 (s, 1H), 8.06 (d, J = 8.5 Hz, 1H), 7.75 (d, J = 12.5 Hz, 1H), 7.51 (d, J = 8.4 Hz, 1H), 3.52 (d, J = 40.3 Hz, 4H), 3.33 (s, 17H), 2.75 (dt, J = 70.0, 16.4 Hz, 14H), 2.59-2.35 (m, 20H), 2.35 (s, 1H), 2.32 (s, 3H), 1.28 (s, 2H), 1.20 (d, J = 53.8 Hz, 3H).<br>LC-MS m/z: (M + H)$^+$ = 491.2. | I-77 |
| 143 | 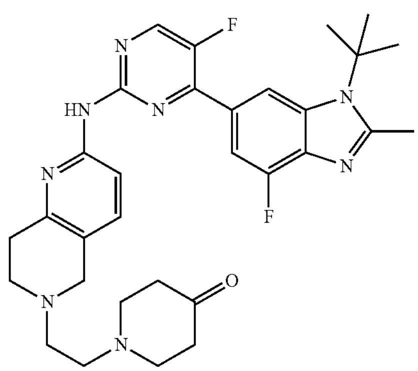 [SMILES: Cc1nc2c(F)cc(-c3nc(Nc4ccc5c(n4)CCN(CCN4CCC(=O)CC4)C5)ncc3F)cc2n1C(C)(C)C] | Pale yellow solid.<br>LC-MS m/z: (M + H)$^+$ = 575.2. | I-52 |
| 145 | 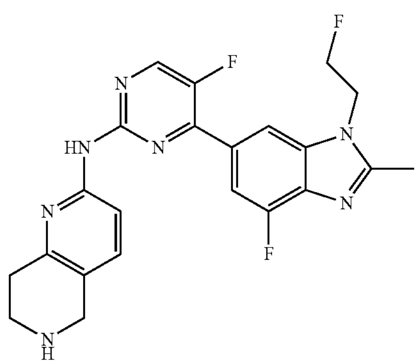 [SMILES: Cc1nc2c(F)cc(-c3nc(Nc4ccc5c(n4)CCNC5)ncc3F)cc2n1CCF] | Pale yellow solid.<br>LC-MS m/z: (M + H)$^+$ = 440.2. | Preparation embodiment 4 |

TABLE 1-continued

List of embodiments

| Embodiment | Structure | Analytic data | Method |
|---|---|---|---|
| 146 | 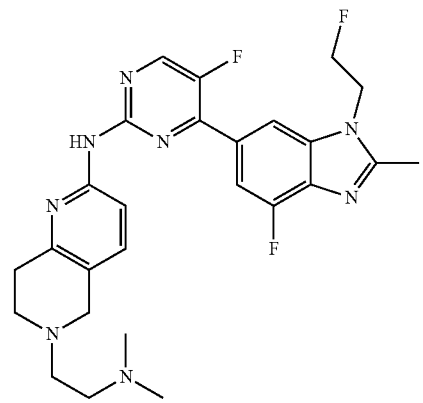 [SMILES: Cc1nc2c(F)cc(-c3nc(Nc4ccc5c(n4)CCN(CCN(C)C)C5)ncc3F)cc2n1CCF] | Pale yellow solid.<br>LC-MS m/z: (M + H)+ = 511.3. | I-52 |
| 147 | 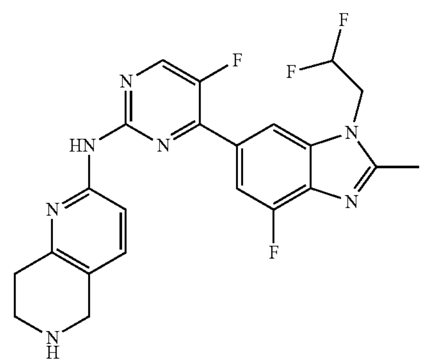 [SMILES: Cc1nc2c(F)cc(-c3nc(Nc4ccc5c(n4)CCNC5)ncc3F)cc2n1CC(F)F] | Pale yellow solid.<br>LC-MS m/z: (M + H)+ = 458.2. | Preparation embodiment 4 |
| 148 | 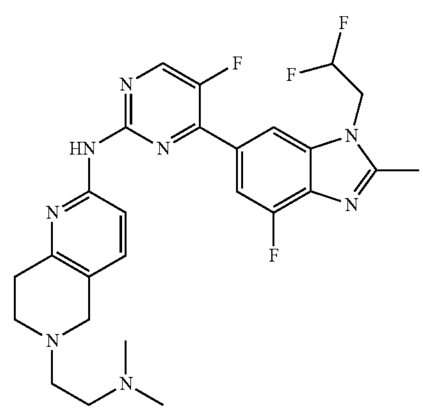 [SMILES: Cc1nc2c(F)cc(-c3nc(Nc4ccc5c(n4)CCN(CCN(C)C)C5)ncc3F)cc2n1CC(F)F] | Pale yellow solid.<br>LC-MS m/z: (M + H)+ = 529.3. | I-52 |
| 149 | 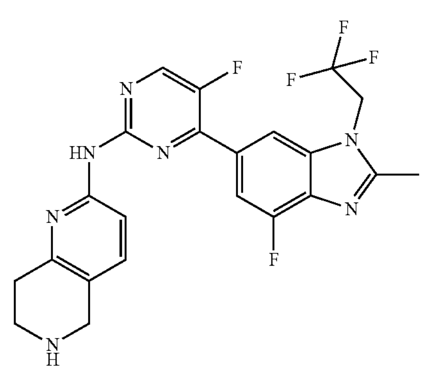 [SMILES: Cc1nc2c(F)cc(-c3nc(Nc4ccc5c(n4)CCNC5)ncc3F)cc2n1CC(F)(F)F] | Pale yellow solid.<br>LC-MS m/z: (M + H)+ = 476.2. | Preparation embodiment 4 |

TABLE 1-continued
List of embodiments
| Embodiment | Structure | Analytic data | Method |
|---|---|---|---|
| 150 | 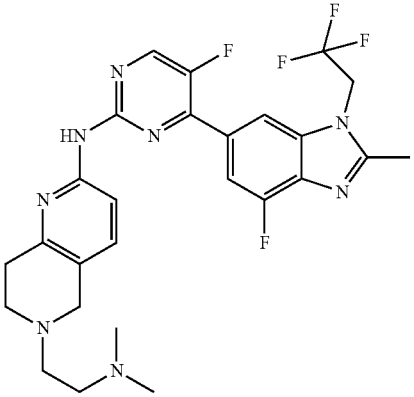 [SMILES: Cc1nc2c(F)cc(-c3nc(Nc4ccc5c(n4)CCN(CCN(C)C)C5)ncc3F)cc2n1CC(F)(F)F] | Pale yellow solid.<br>LC-MS m/z: (M + H)$^+$ = 547.2. | I-52 |
| 151 | 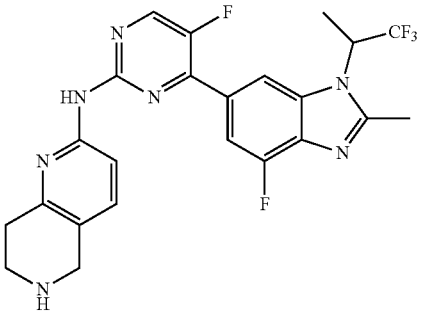 [SMILES: Cc1nc2c(F)cc(-c3nc(Nc4ccc5c(n4)CCNC5)ncc3F)cc2n1C(C)C(F)(F)F] | Pale yellow solid.<br>LC-MS m/z: (M + H)$^+$ = 490.3. | Preparation embodiment 4 |
| 152 | 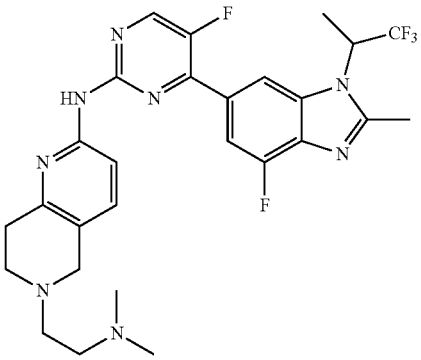 [SMILES: Cc1nc2c(F)cc(-c3nc(Nc4ccc5c(n4)CCN(CCN(C)C)C5)ncc3F)cc2n1C(C)C(F)(F)F] | Pale yellow solid.<br>LC-MS m/z: (M + H)$^+$ = 561.3. | I-52 |
| 154 | 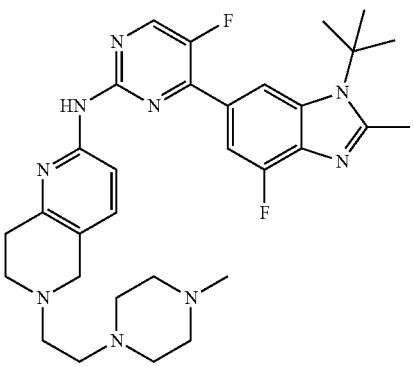 [SMILES: Cc1nc2c(F)cc(-c3nc(Nc4ccc5c(n4)CCN(CCN4CCN(C)CC4)C5)ncc3F)cc2n1C(C)(C)C] | Pale yellow solid.<br>$^1$H NMR (400 MHz, CD$_3$OD) δ 8.53 (d, J = 4.0 Hz, 1H), 8.48 (d, J = 1.0 Hz, 1H), 8.43 (s, 1H), 8.20 (d, J = 8.5 Hz, 1H), 7.73 (d, J = 11.6 Hz, 1H), 7.50 (d, J = 8.6 Hz, 1H), 3.93 (s, 2H), 3.15 (dd, J = 17.9, 12.0 Hz, 6H), 3.07-2.97 (m, 5H), 2.94-2.84 (m, 8H), 2.72 (s, 3H), 1.95 (s, 9H).<br>LC-MS m/z: (M + H)$^+$ = 576.3. | I-52 |

TABLE 1-continued

List of embodiments

| Embodiment | Structure | Analytic data | Method |
|---|---|---|---|
| 156 | 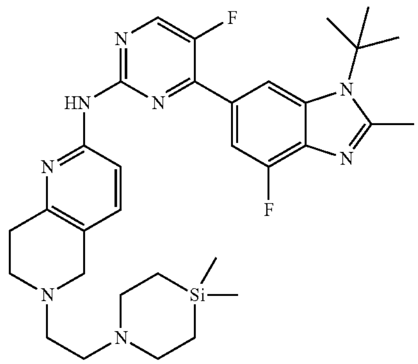 | Pale yellow solid.<br>LC-MS m/z: (M + H)+ = 490.3. | I-52 |
| 157 | 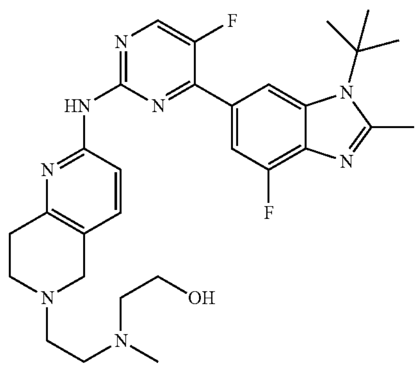 [SMILES: Cc1nc2c(F)cc(-c3nc(Nc4ccc5c(n4)CCN(CCN(C)CCO)C5)ncc3F)cc2n1C(C)(C)C] | Pale yellow solid.<br>$^1$H NMR (400 MHz, CD$_3$OD) δ 8.51 (d, J = 4.0 Hz, 1H), 8.48 (d, J = 1.2 Hz, 1H), 8.17 (d, J = 8.5 Hz, 1H), 7.73 (d, J = 11.5 Hz, 1H), 7.47 (dd, J = 8.5, 4.5 Hz, 1H), 3.84 (t, J = 5.3 Hz, 2H), 3.79 (s, 1H), 3.71 (dd, J = 10.1, 5.3 Hz, 1H), 3.35 (s, 2H), 3.19-3.14 (m, 2H), 3.04-2.92 (m, 6H), 2.86 (s, 3H), 2.82 (s, 3H), 1.93 (s, 9H).<br>LC-MS: m/z: (M + H)+ = 551.30. | I-72 |
| 158 | 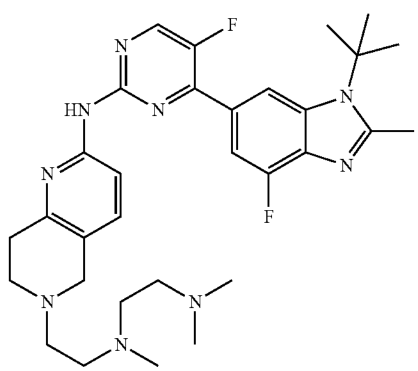 [SMILES: Cc1nc2c(F)cc(-c3nc(Nc4ccc5c(n4)CCN(CCN(C)CCN(C)C)C5)ncc3F)cc2n1C(C)(C)C] | Pale yellow solid.<br>$^1$H NMR (400 MHz, CDCl$_3$) δ 8.41 (d, J = 3.8 Hz, 1H), 8.39 (d, J = 1.2 Hz, 1H), 8.20 (d, J = 8.4 Hz, 1H), 8.09 (s, 1H), 7.73 (d, J = 11.4 Hz, 1H), 7.35 (d, J = 8.5 Hz, 1H), 3.66 (s, 2H), 2.95 (t, J = 6.0 Hz, 2H), 2.89 (d, J = 5.6 Hz, 2H), 2.86 (s, 3H), 2.77-2.67 (m, 6H), 2.67-2.61 (m, 2H), 2.40 (s, 6H), 2.36 (s, 3H), 1.90 (s, 9H).<br>LC-MS m/z: (M + H)+ = 578.40. | I-153 |
| 159 | 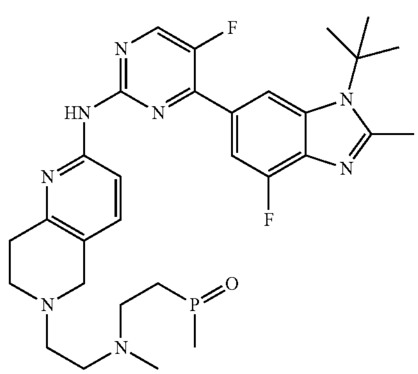 | Pale yellow solid.<br>LC-MS m/z: (M + H)+ = 611.2. | I-3 |

TABLE 1-continued

List of embodiments

| Embodiment | Structure | Analytic data | Method |
|---|---|---|---|
| 160 | 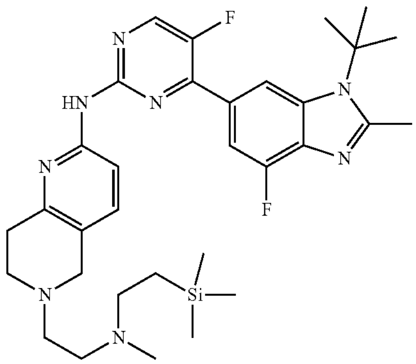 [SMILES: Cc1nc2c(F)cc(-c3nc(Nc4ccc5c(n4)CCN(CCN(C)CC[Si](C)(C)C)C5)ncc3F)cc2n1C(C)(C)C] | Pale yellow solid.<br>$^1$H NMR (400 MHz, CD$_3$OD) δ 8.51 (d, J = 4.0 Hz, 1H), 8.48 (d, J = 1.0 Hz, 1H), 8.43 (s, 1H), 8.16 (d, J = 8.5 Hz, 1H), 7.73 (d, J = 11.7 Hz, 1H), 7.47 (d, J = 8.6 Hz, 1H), 3.74 (s, 2H), 3.39 (t, J = 5.6 Hz, 2H), 3.31-3.23 (m, 2H), 2.96 (m, 6H), 2.91 (s, 3H), 2.88 (s, 3H), 1.95 (s, 9H), 1.10-1.02 (m, 2H), 0.11 (s, 9H).<br>LC-MS m/z: (M + H)$^+$ = 607.3. | I-72 |
| 161 | 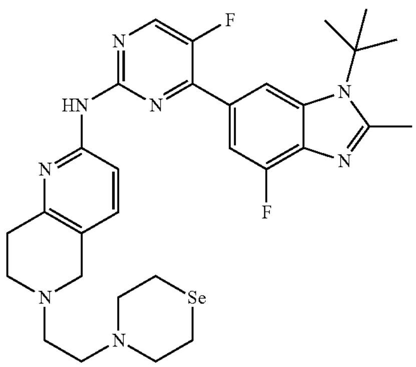 [SMILES: Cc1nc2c(F)cc(-c3nc(Nc4ccc5c(n4)CCN(CCN4CC[Se]CC4)C5)ncc3F)cc2n1C(C)(C)C] | Pale yellow solid.<br>LC-MS m/z: (M + H)$^+$ = 627.2. | I-52 |
| 162 | 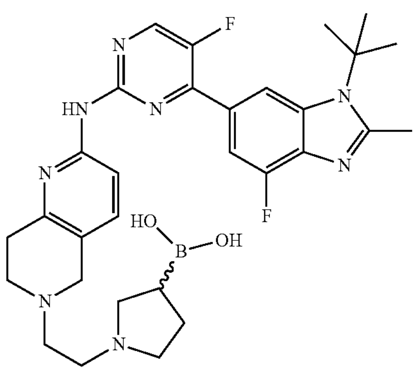 [SMILES: Cc1nc2c(F)cc(-c3nc(Nc4ccc5c(n4)CCN(CCN4CCC(B(O)O)C4)C5)ncc3F)cc2n1C(C)(C)C] | Pale yellow solid.<br>LC-MS m/z: (M + H)$^+$ = 591.3. | I-52 |
| 163 | 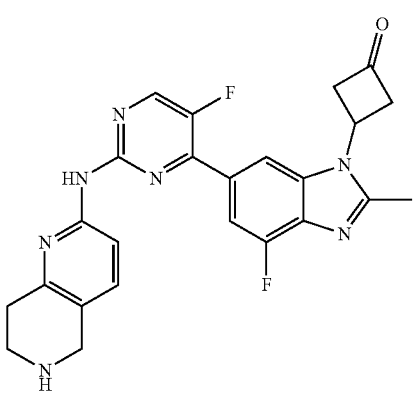 [SMILES: Cc1nc2c(F)cc(-c3nc(Nc4ccc5c(n4)CCNC5)ncc3F)cc2n1C1CC(=O)C1] | Pale yellow solid.<br>LC-MS m/z: (M + H)$^+$ = 462.3. | Preparation embodiment 4 |

TABLE 1-continued

List of embodiments

| Embodiment | Structure | Analytic data | Method |
|---|---|---|---|
| 164 | 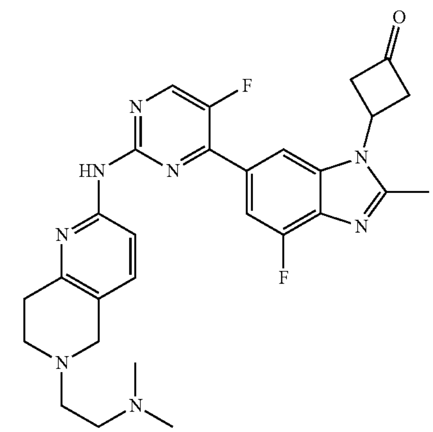 [SMILES: Cc1nc2c(F)cc(-c3nc(Nc4ccc5c(n4)CCN(CCN(C)C)C5)ncc3F)cc2n1C1CC(=O)C1] | Pale yellow solid.<br>LC-MS m/z: $(M + H)^+$ = 533.3. | I-52 |
| 165 | 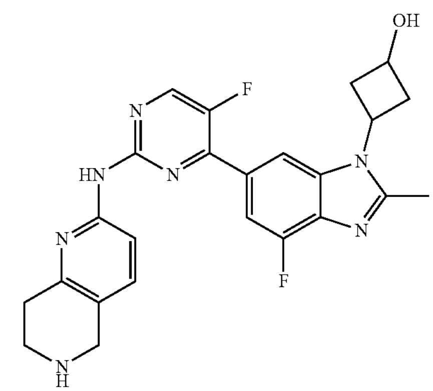 [SMILES: Cc1nc2c(F)cc(-c3nc(Nc4ccc5c(n4)CCNC5)ncc3F)cc2n1C1CC(O)C1] | Pale yellow solid.<br>LC-MS m/z: $(M + H)^+$ = 464.2. | Preparation embodiment 4 |
| 166 | 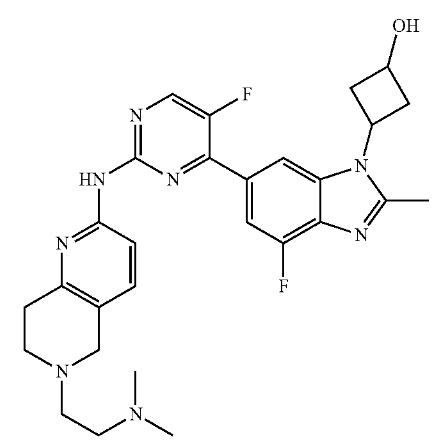 [SMILES: Cc1nc2c(F)cc(-c3nc(Nc4ccc5c(n4)CCN(CCN(C)C)C5)ncc3F)cc2n1C1CC(O)C1] | Pale yellow solid.<br>LC-MS m/z: $(M + H)^+$ = 535.2. | I-52 |

TABLE 1-continued

List of embodiments

| Embodiment | Structure | Analytic data | Method |
|---|---|---|---|
| 167 | 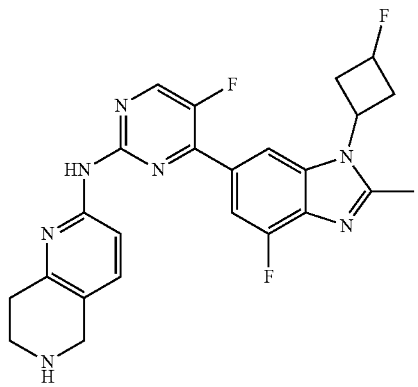 [SMILES: Cc1nc2c(F)cc(-c3nc(Nc4ccc5c(n4)CCNC5)ncc3F)cc2n1C1CC(F)C1] | Pale yellow solid.<br>LC-MS m/z: (M + H)⁺ = 466.2. | Preparation embodiment 4 |
| 168 | 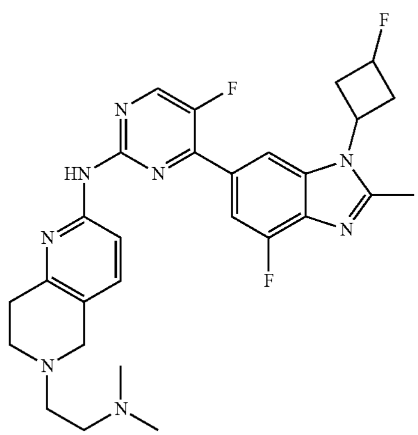 [SMILES: Cc1nc2c(F)cc(-c3nc(Nc4ccc5c(n4)CCN(CCN(C)C)C5)ncc3F)cc2n1C1CC(F)C1] | Pale yellow solid.<br>LC-MS m/z: (M + H)⁺ = 537.2. | I-52 |
| 169 | 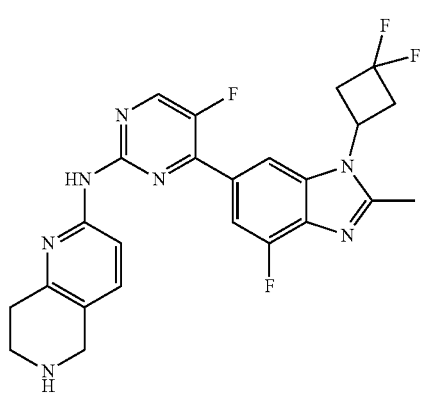 [SMILES: Cc1nc2c(F)cc(-c3nc(Nc4ccc5c(n4)CCNC5)ncc3F)cc2n1C1CC(F)(F)C1] | Pale yellow solid.<br>LC-MS m/z: (M + H)⁺ = 484.2. | Preparation embodiment 4 |

TABLE 1-continued

List of embodiments

| Embodiment | Structure | Analytic data | Method |
|---|---|---|---|
| 170 | 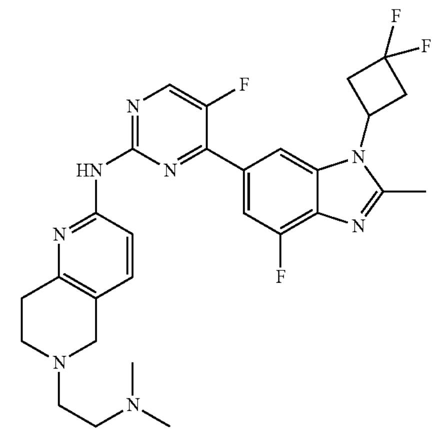 [SMILES: Cc1nc2c(F)cc(-c3nc(Nc4ccc5c(n4)CCN(CCN(C)C)C5)ncc3F)cc2n1C1CC(F)(F)C1] | Pale yellow solid.<br>LC-MS m/z: (M + H)$^+$ = 555.2. | I-52 |
| 171 | 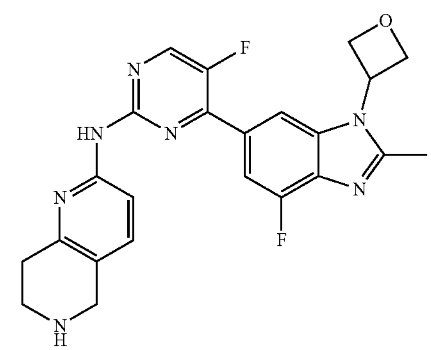 [SMILES: Cc1nc2c(F)cc(-c3nc(Nc4ccc5c(n4)CCNC5)ncc3F)cc2n1C1COC1] | Pale yellow solid.<br>LC-MS m/z: (M + H)$^+$ = 450.2. | Preparation embodiment 4 |
| 172 | 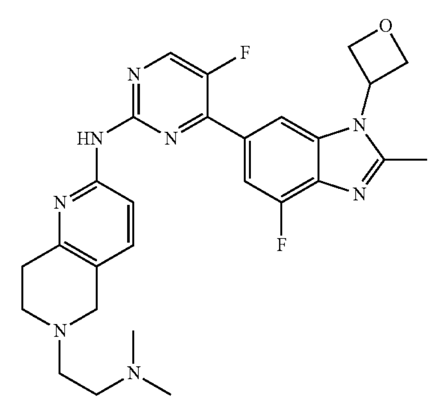 [SMILES: Cc1nc2c(F)cc(-c3nc(Nc4ccc5c(n4)CCN(CCN(C)C)C5)ncc3F)cc2n1C1COC1] | Pale yellow solid.<br>LC-MS m/z: (M + H)$^+$ = 521.2. | I-52 |

TABLE 1-continued

List of embodiments

| Embodiment | Structure | Analytic data | Method |
|---|---|---|---|
| 173 | 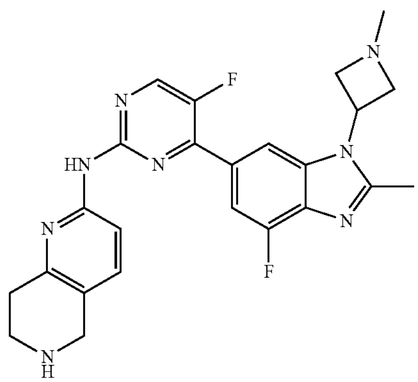 [SMILES: Cc1nc2c(F)cc(-c3nc(Nc4ccc5c(n4)CCNC5)ncc3F)cc2n1C1CN(C)C1] | Pale yellow solid.<br>LC-MS m/z: (M + H)$^+$ = 463.2. | Preparation embodiment 4 |
| 174 | 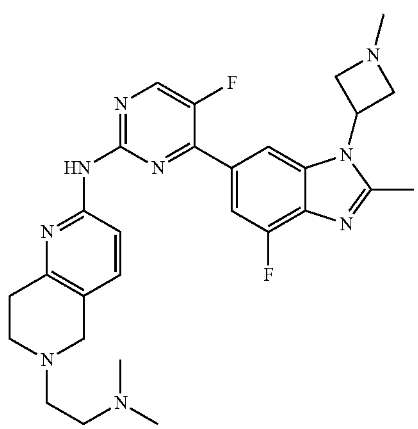 [SMILES: Cc1nc2c(F)cc(-c3nc(Nc4ccc5c(n4)CCN(CCN(C)C)C5)ncc3F)cc2n1C1CN(C)C1] | Pale yellow solid.<br>LC-MS m/z: (M + H)$^+$ = 534.2. | I-52 |
| 175 | 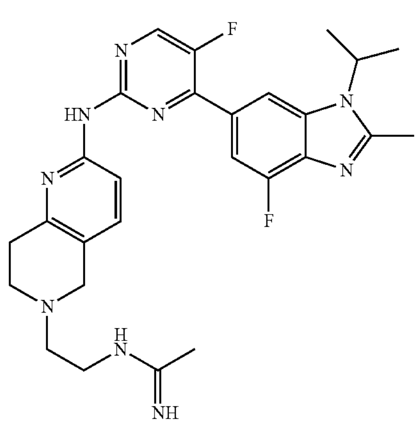 [SMILES: CC(=N)NCCN1CCc2nc(Nc3ncc(F)c(-c4cc(F)c5nc(C)n(C(C)C)c5c4)n3)ccc2C1] | Yellow solid.<br>$^1$H NMR (400 MHz, CD$_3$OD) δ 8.51 (d, J = 3.9 Hz, 1H), 8.31 (d, J = 1.3 Hz, 1H), 8.16 (d, J = 8.5 Hz, 1H), 7.74 (d, J = 12.0 Hz, 1H), 7.46 (d, J = 8.6 Hz, 1H), 4.94-4.87 (m, 1H), 3.66 (s, 2H), 3.44 (t, J = 6.7 Hz, 2H), 2.93 (d, J = 4.9 Hz, 2H), 2.90 (d, J = 5.0 Hz, 2H), 2.70 (d, J = 6.6 Hz, 2H), 2.68 (s, 3H), 1.95 (s, 3H), 1.72 (s, 3H), 1.70 (s, 3H).<br>LC-MS m/z: (M + H)$^+$ = 520.3. | I-3 |

TABLE 1-continued
List of embodiments
| Embodiment | Structure | Analytic data | Method |
|---|---|---|---|
| 176 | 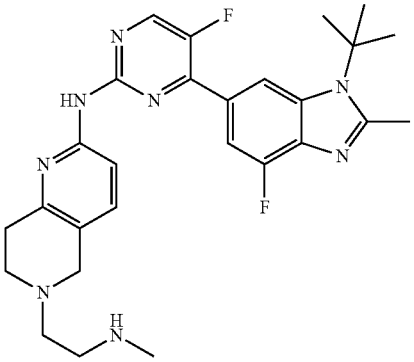 [SMILES: CNCCN1CCc2nc(Nc3ncc(F)c(-c4cc(F)c5nc(C)n(C(C)(C)C)c5c4)n3)ccc2C1] | Pale yellow solid.<br>$^1$H NMR (400 MHz, CD$_3$OD) δ 8.47 (d, J = 4.2 Hz, 1H), 8.36 (s, 1H), 8.01 (d, J = 8.4 Hz, 1H), 7.52 (d, J = 11.5 Hz, 1H), 7.29-7.21 (m, 1H), 3.52 (s, 2H), 2.80 (d, J = 12.8 Hz, 9H), 2.66 (d, J = 6.6 Hz, 2H), 2.44 (s, 3H), 1.87 (s, 9H).<br>LC-MS m/z: (M + H)$^+$ = 507.3. | I-77 |
| 177 | 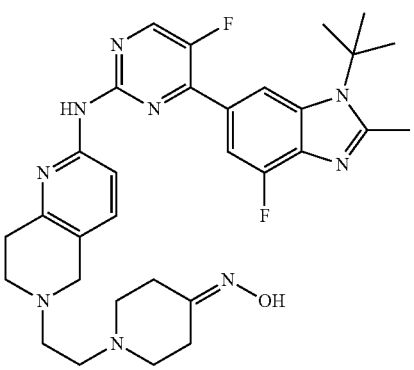 [SMILES: Cc1nc2c(F)cc(-c3nc(Nc4ccc5c(n4)CCN(CCN4CCC(=NO)CC4)C5)ncc3F)cc2n1C(C)(C)C] | Pale yellow solid.<br>LC-MS m/z: (M + H)$^+$ = 590.3. | I-95 |
| 178 | 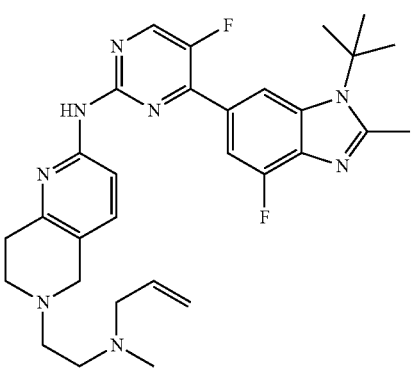 [SMILES: C=CCN(C)CCN1CCc2nc(Nc3ncc(F)c(-c4cc(F)c5nc(C)n(C(C)(C)C)c5c4)n3)ccc2C1] | Pale yellow solid.<br>LC-MS m/z: (M + H)$^+$ = 547.3. | I-72 |
| 179 | 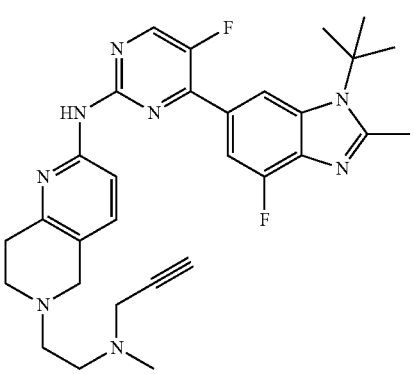 [SMILES: C#CCN(C)CCN1CCc2nc(Nc3ncc(F)c(-c4cc(F)c5nc(C)n(C(C)(C)C)c5c4)n3)ccc2C1] | Pale yellow solid.<br>LC-MS m/z: (M + H)$^+$ = 545.3. | I-72 |

TABLE 1-continued

List of embodiments

| Embodiment | Structure | Analytic data | Method |
|---|---|---|---|
| 180 | 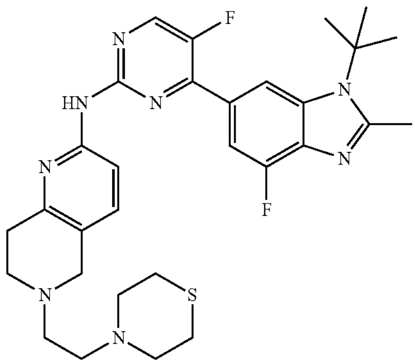 [SMILES: Cc1nc2c(F)cc(-c3nc(Nc4ccc5c(n4)CCN(CCN4CCSCC4)C5)ncc3F)cc2n1C(C)(C)C] | Pale yellow solid.<br>LC-MS m/z: $(M + H)^+ = 579.3$. | I-52 |
| 181 | 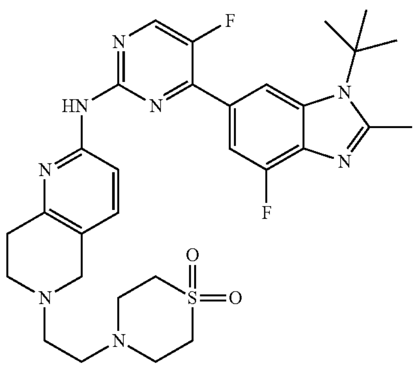 [SMILES: Cc1nc2c(F)cc(-c3nc(Nc4ccc5c(n4)CCN(CCN4CCS(=O)(=O)CC4)C5)ncc3F)cc2n1C(C)(C)C] | Pale yellow solid.<br>LC-MS m/z: $(M + H)^+ = 611.2$. | I-87 |
| 182 | 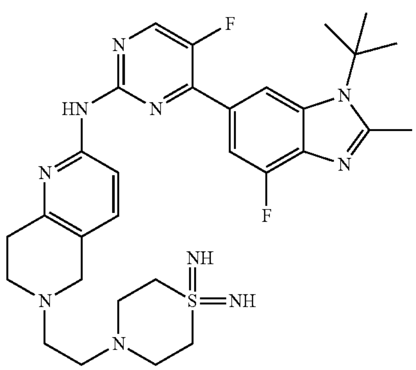 [SMILES: Cc1nc2c(F)cc(-c3nc(Nc4ccc5c(n4)CCN(CCN4CCS(=N)(=N)CC4)C5)ncc3F)cc2n1C(C)(C)C] | Pale yellow solid.<br>LC-MS m/z: $(M + H)^+ = 609.3$. | I-87 |
| 183 | 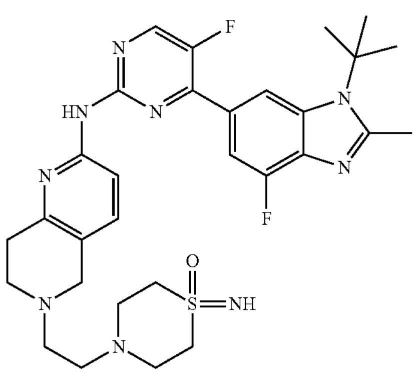 [SMILES: Cc1nc2c(F)cc(-c3nc(Nc4ccc5c(n4)CCN(CCN4CCS(=N)(=O)CC4)C5)ncc3F)cc2n1C(C)(C)C] | Pale yellow solid.<br>LC-MS m/z: $(M + H)^+ = 610.3$. | I-87 |

TABLE 1-continued
List of embodiments
| Embodiment | Structure | Analytic data | Method |
|---|---|---|---|
| 185 | 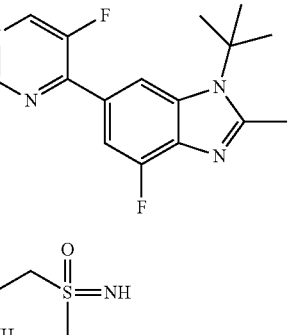 | Pale yellow solid.<br>LC-MS m/z: $(M + H)^+$ = 598.3. | I-87 |
| 186 | 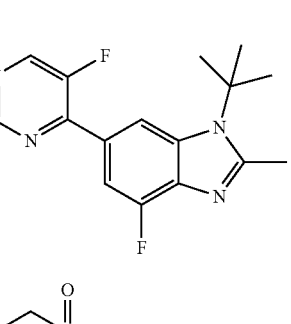 | Pale yellow solid.<br>LC-MS m/z: $(M + H)^+$ = 612.3. | I-87 |
| 188 | 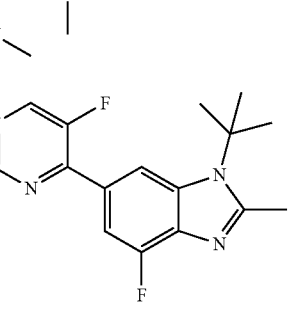 | Pale yellow solid.<br>LC-MS m/z: $(M + H)^+$ = 545.3. | I-52 |
| 189 | 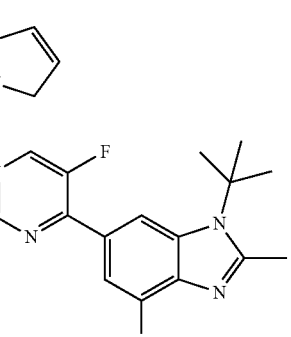 | Pale yellow solid.<br>LC-MS m/z: $(M + H)^+$ = 549.3. | I-52 |

TABLE 1-continued

List of embodiments

| Embodiment | Structure | Analytic data | Method |
|---|---|---|---|
| 190 | 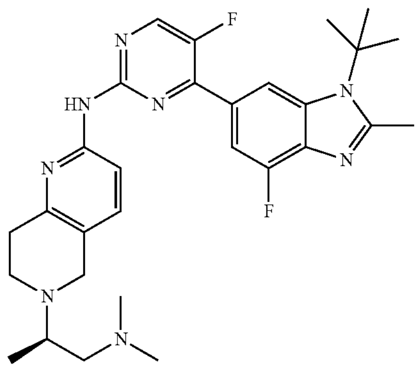 [SMILES: Cc1nc2c(F)cc(-c3nc(Nc4ccc5c(n4)CCN([C@H](C)CN(C)C)C5)ncc3F)cc2n1C(C)(C)C] | Pale yellow solid.<br>LC-MS m/z: (M + H)⁺ = 535.3. | I-52 |
| 191 | 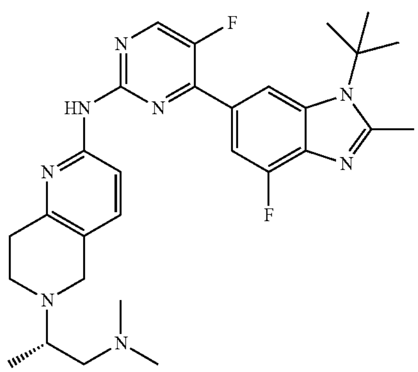 [SMILES: Cc1nc2c(F)cc(-c3nc(Nc4ccc5c(n4)CCN([C@@H](C)CN(C)C)C5)ncc3F)cc2n1C(C)(C)C] | Pale yellow solid.<br>LC-MS m/z: (M + H)⁺ = 535.3. | I-52 |
| 192 | 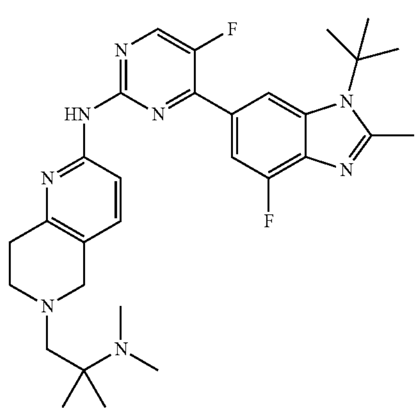 [SMILES: Cc1nc2c(F)cc(-c3nc(Nc4ccc5c(n4)CCN(CC(C)(C)N(C)C)C5)ncc3F)cc2n1C(C)(C)C] | Pale yellow solid.<br>LC-MS m/z: (M + H)⁺ = 549.3. | I-52 |

TABLE 1-continued

List of embodiments

| Embodiment | Structure | Analytic data | Method |
|---|---|---|---|
| 193 | 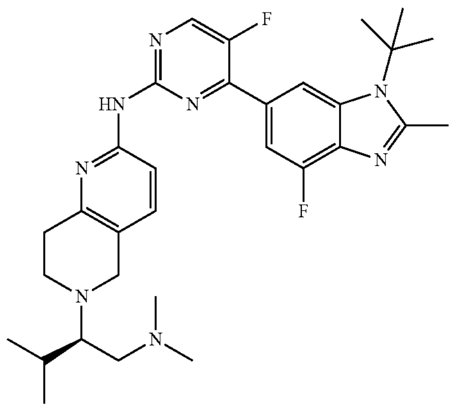 [SMILES: Cc1nc2c(F)cc(-c3nc(Nc4ccc5c(n4)CCN([C@@H](CN(C)C)C(C)C)C5)ncc3F)cc2n1C(C)(C)C] | Pale yellow solid. LC-MS m/z: $(M + H)^+ = 563.3$. | I-52 |
| 194 | 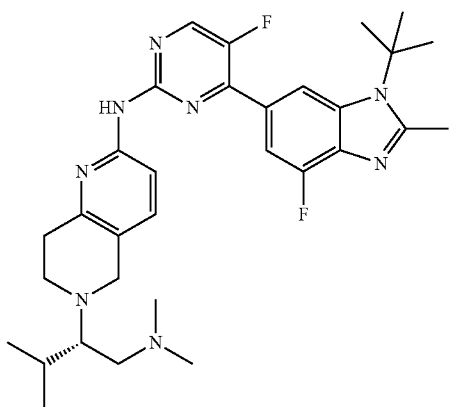 | Pale yellow solid. LC-MS m/z: $(M + H)^+ = 663.3$. | I-52 |
| 195 | 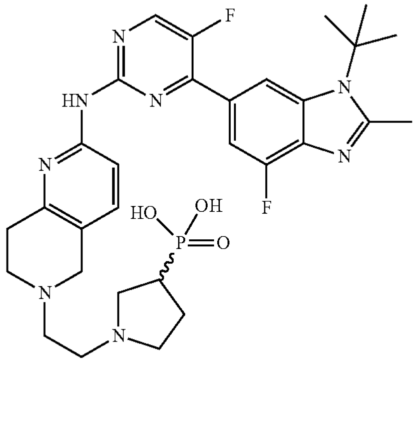 | Pale yellow solid. LC-MS m/z: $(M + H)^+ = 643.3$. | I-3 |

TABLE 1-continued

List of embodiments

| Embodiment | Structure | Analytic data | Method |
|---|---|---|---|
| 196 | 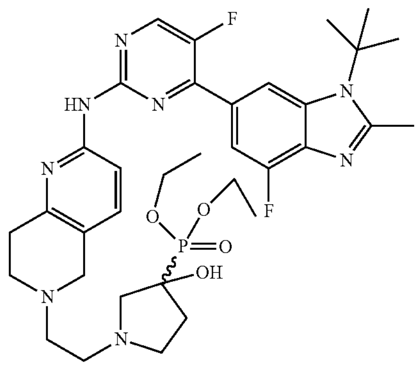 [SMILES: CCOP(=O)(OCC)C1(O)CCN(CCN2CCc3nc(Nc4ncc(F)c(-c5cc(F)c6nc(C)n(C(C)(C)C)c6c5)n4)ccc3C2)C1] | Pale yellow solid.<br>¹H NMR (400 MHz, CDCl₃) δ 8.46 (br.s, 1H), 8.41 (d, J = 3.9 Hz, 1H), 8.35 (d, J = 1.3 Hz, 1H), 8.17 (d, J = 8.4 Hz, 1H), 7.70 (d, J = 11.4 Hz, 1H), 7.29 (d, J = 8.5 Hz, 1H), 4.19 (pd, J = 7.2, 3.4 Hz, 4H), 3.65 (s, 2H), 3.24 (q, J = 7.6 Hz, 1H), 3.17-3.11 (m, 1H), 3.07 (q, J = 7.3 Hz, 1H), 3.01 (dd, J = 11.0, 8.3 Hz, 1H), 2.97-2.86 (m, 6H), 2.84 (s, 3H), 2.79 (t, J = 6.6 Hz, 2H), 2.66 (q, J = 8.2 Hz, 1H), 2.51-2.39 (m, 1H), 2.09-1.99. (m, 1H), 1.88 (s, 9H), 1.32 (t, J = 7.1 Hz, 6H).<br>LC-MS m/z: (M + H)⁺ = 699.35. | I-153 |
| 198 | 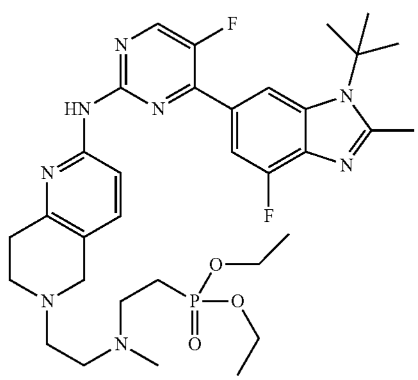 [SMILES: CCOP(=O)(CCN(C)CCN1CCc2nc(Nc3ncc(F)c(-c4cc(F)c5nc(C)n(C(C)(C)C)c5c4)n3)ccc2C1)OCC] | Pale yellow solid.<br>¹H NMR (400 MHz, CD₃OD) δ 8.53 (d, J = 4.3 Hz, 1H), 8.40 (s, 1H), 8.05 (d, J = 8.4 Hz, 1H), 7.55 (d, J = 11.7 Hz, 1H), 7.28 (d, J = 8.5 Hz, 1H), 4.21-4.05 (m, 4H), 3.54 (s, 2H), 2.90 2.73 (m, 9H), 2.66 (s, 4H), 2.33 (s, 3H), 2.13-2.02 (m, 2H), 1.90 (s, 9H), 1.34 (t, J = 7.1 Hz, 6H).<br>LC-MS m/z: (M + H)⁺ = 671.3. | I-72 |
| 199 | 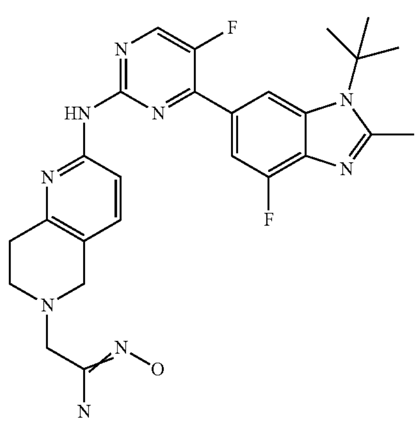 [SMILES: Cc1nc2c(F)cc(-c3nc(Nc4ccc5c(n4)CCN(CC(N)=NO)C5)ncc3F)cc2n1C(C)(C)C] | Pale yellow solid.<br>LC-MS m/z: (M + H)⁺ = 522.3. | I-137 |

TABLE 1-continued

List of embodiments

| Embodiment | Structure | Analytic data | Method |
|---|---|---|---|
| 200 | 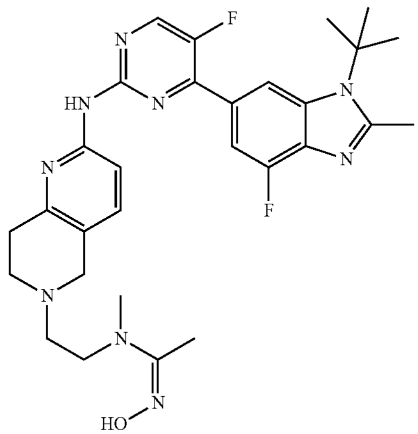 | Pale yellow solid.<br>LC-MS m/z: (M + H)$^+$ = 550.3. | I-137 |
| 202 | 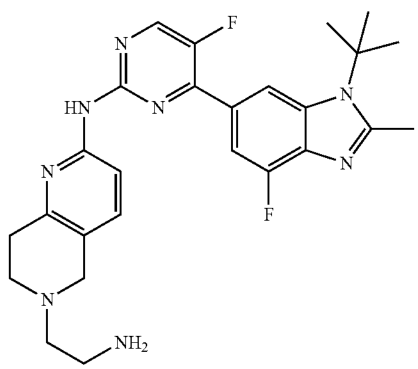 | Pale yellow solid.<br>$^1$H NMR (400 MHz, CD$_3$OD) δ 8.50-8.40 (m, 3H), 8.22 (d, J = 8.3 Hz, 1H), 7.75 (d, J = 11.6 Hz, 1H), 7.45 (d, J = 8.7 Hz, 1H), 3.71 (s, 2H), 3.14 (t, J = 5.6 Hz, 2H), 3.01-2.91 (m, 4H), 2.86 (d, J = 6.7 Hz, 5H), 1.94 (s, 9H).<br>LC-MS m/z: (M + H)$^+$ = 536. | I-71 |
| 203 | 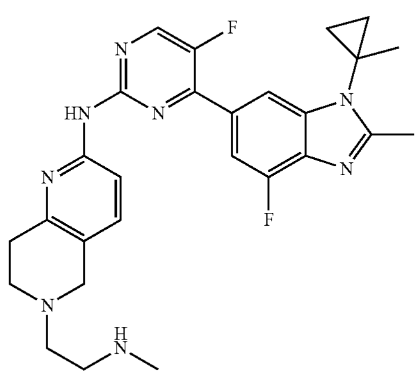 [SMILES: CNCCN1CCc2nc(Nc3ncc(F)c(-c4cc(F)c5nc(C)n(C6(C)CC6)c5c4)n3)ccc2C1] | Pale yellow solid.<br>1H NMR (400 MHz, CD$_3$OD) δ 8.50 (d, J = 4.2 Hz, 1H), 8.13 (s, 1H), 8.01 (d, J = 8.4 Hz, 1H), 7.51 (d, J = 12.0 Hz, 1H), 7.28 (d, J = 8.4 Hz, 1H), 3.54 (s, 2H), 2.81 (dd, J = 16.5, 5.2 Hz, 6H), 2.72-2.64 (m, 5H), 2.45 (s, 3H), 1.57 (s, 3H), 1.25 (t, J = 6.3 Hz, 2H), 1.20 (t, J = 5.6 Hz, 2H).<br>LC-MS m/z: (M + H)$^+$ = 505. | I-71 |
| 206 | 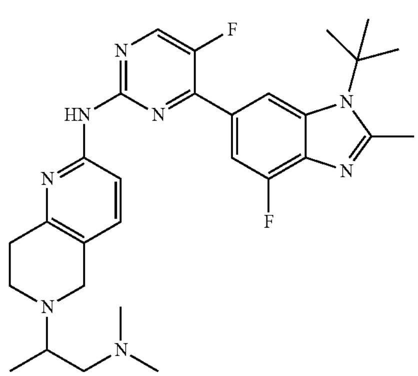 [SMILES: Cc1nc2c(F)cc(-c3nc(Nc4ccc5c(n4)CCN(C(C)CN(C)C)C5)ncc3F)cc2n1C(C)(C)C] | Pale yellow solid.<br>$^1$H NMR (400 MHz, CD$_3$OD) δ 8.43 (d, J = 4.5 Hz, 1H), 8.24 (s, 1H), 7.86 (d, J = 8.3 Hz, 1H), 7.31 (d, J = 11.6 Hz, 1H), 7.04 (d, J = 8.3 Hz, 1H), 3.52-3.34 (m, 3H), 2.79 (s, 3H), 2.74-2.61 (m, 11H), 2.46-2.39 (m, 1H), 1.81 (s, 9H), 1.21 (d, J = 6.5 Hz, 3H).<br>LC-MS m/z: (M + H)$^+$ = 535.40. | I-3 |

TABLE 1-continued

List of embodiments

| Embodiment | Structure | Analytic data | Method |
|---|---|---|---|
| 207 | 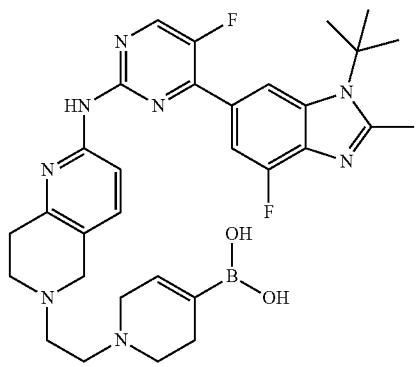 [SMILES: Cc1nc2c(F)cc(-c3nc(Nc4ccc5c(n4)CCN(CCN4CC=C(B(O)O)CC4)C5)ncc3F)cc2n1C(C)(C)C] | 1H-NMR (400 MHz, CD₃OD) δ = 8.53 (d, J = 4.0 Hz, 1H), 8.50 (d, J = 0.8 Hz, 1H), 8.41 (s, 1H), 8.19 (d, J = 8.4 Hz, 1H), 7.77 (d, J = 12.0 Hz, 1H), 7.50 (d, J = 8.4 Hz, 1H), 6.12 1H), 3.83 (s, 2H), 3.78 (s, 2H), 3.40- 3.32 (m, 4H), 3.02-3.00 (m, 6H), 2.89 (s, 3H), 2.47-2.53 (m, 2H), 1.96 (s, 9H).<br>LC-MS: m/z: (M + H)⁺ = 603.4. | I-153 |
| 208 | 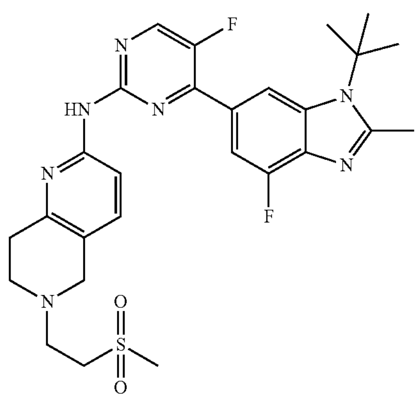 [SMILES: Cc1nc2c(F)cc(-c3nc(Nc4ccc5c(n4)CCN(CCS(C)(=O)=O)C5)ncc3F)cc2n1C(C)(C)C] | Pale yellow solid.<br>1H NMR (400 MHz, DMSO-d6) δ 9.95 (s, 1H), 8.68 (s, 1H), 8.46 (s, 1H), 8.08 (d, J = 8.3 Hz, 1H), 7.69 (d, J = 11.4 Hz, 1H), 7.46 (d, J = 8.0 Hz, 1H), 3.64 (s, 2H), 3.39 (s, 3H), 3.03 (s, 3H), 2.84 (d, J = 6.7 Hz, 8H), 1.88 (s, 9H).<br>LC-MS m/z: (M + H)⁺ = 556.2. | I-3 |
| 209 | 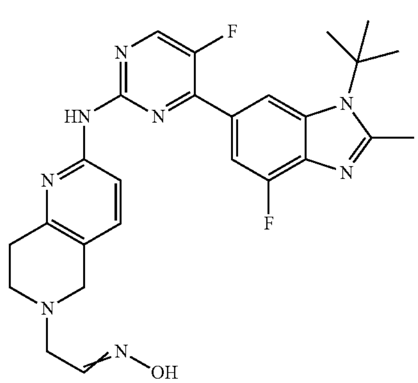 [SMILES: Cc1nc2c(F)cc(-c3nc(Nc4ccc5c(n4)CCN(CC=NO)C5)ncc3F)cc2n1C(C)(C)C] | Pale yellow solid.<br>1H NMR (500 MHz, DMSO-d6) δ 10.80 (s, 1H), 9.98 (d, J = 4.9 Hz, 1H), 8.67 (d, J = 3.8 Hz, 1H), 8.45 (s, 1H), 8.13-7.97 (m, 1H), 7.67 (d, J = 11.6 Hz, 1H), 7.52-7.35 (m, 2H), 3.58 (d, J = 15.6 Hz, 2H), 3.41 (d, J = 4.2 Hz, 1H), 3.24 (d, J = 6.1 Hz, 1H), 2.87-2.77 (m, 7H), 1.86 (s, 9H).<br>LC-MS: 507.2 (M + H)⁺. | I-95 |

TABLE 1-continued

List of embodiments

| Embodiment | Structure | Analytic data | Method |
|---|---|---|---|
| 210 | 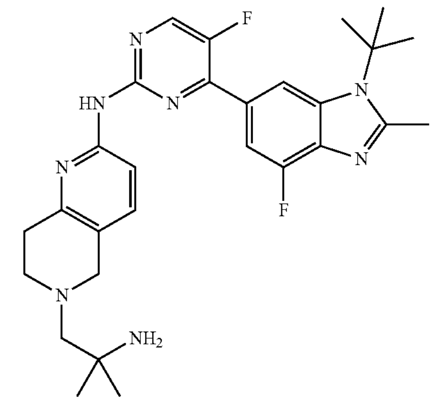 [SMILES: Cc1nc2c(F)cc(-c3nc(Nc4ccc5c(n4)CCN(CC(C)(C)N)C5)ncc3F)cc2n1C(C)(C)C] | Pale yellow solid.<br>LC-MS m/z: (M + H)+ = 521.2. | I-77 |
| 211 | 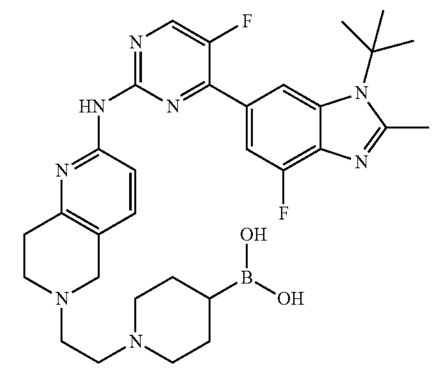 [SMILES: Cc1nc2c(F)cc(-c3nc(Nc4ccc5c(n4)CCN(CCN4CCC(B(O)O)CC4)C5)ncc3F)cc2n1C(C)(C)C] | Pale yellow solid.<br>LC-MS m/z: (M + H)+ 605.2. | I-207 |

Effect Embodiment 1

Test Method:

CDK kinase inhibitory activity assay used LANCE® Ultra technique, test compounds were screened on CDK4/CycD3, CDK6/CycD3 and CDK2/CycA2 kinases at ATP concentration of Km. During the test, the initial concentration of the test compound was 3333 nM, each test compound set 10 serially diluted concentrations, the dilution fold was 3-fold, each concentration set 2 duplicated wells.

CDK4/CycD3, CDK6/CycD3 and CDK2/CycA2 were purchased from Carna Biosciences, Inc.; dimethyl sulfoxide, ATP, DTT solution were purchased from Sigma-Aldrich; EDTA solution was purchased from GIBCO; LANCE® Detection Buffer, 10× and LANCE® Ultra Europium-anti-phospho-eIF4E-binding protein 1 (Thr37/46) and LANCE® Ultra ULight™-eIF4E-bindingprotein 1 (Thr37/46) Peptide were purchased from Perkinelmer.

Test Procedure:

1. Take 10 mM stock solution of the test compound, in 96-well compound plate, DMSO was used to dilute the compound to an initial concentration of 100×, then this concentration was used as the first concentration, 3-fold diluted to make 10 serial concentrations; 1 µL each serial dilution was then added to 19 µL 1× reaction buffer to prepare 5× compound for use; 2 µL 5× compound was transferred from 96-well plate to 384-well plate; compound-free control well was added with 2 µL the following liquid: 1× reaction buffer with the addition of 1 µL DMSO; 2 µL 250 mM EDTA was added to the Min control well.

2. 1× reaction buffer was used to formulate the kinase, substrate and ATP into a 2.5×enzyme/substrate mixture and 2.5×ATP solution respectively. In the experiment, the final concentration of CDK4/CycD3 kinase is 0.76 ng/µL, the final concentration of ATP is 8 µM; the final concentration of CDK6/CycD3 kinase is 0.5 ng/µL, the final concentration of ATP is 50M; the final concentration of CDK2/CycA2 kinase is 0.86 ng/µL, the final concentration of ATP is 1 µM; the final concentration of CDK2/CycE1 kinase is 1.016 ng/µL, the final concentration of ATP is 20M; 2.5×enzyme/substrate mixture was added to a 384-well plate, incubated at room temperature for 5 minutes; then added with 2.5×ATP solution, reacted at room temperature for 30 minutes.

3. LANCE® Detection Buffer was used, 1× to prepare 2×LANCE® Ultra Europium-anti-phospho-eIF4E-binding protein 1 (Thr37/46) for use. After the enzymatic reaction was continued for 30 minutes, 10 mM EDTA was added to 384-well plate and the mixture was reacted at room temperature for 5 minutes. Then LANCE® Ultra Europium-anti-phospho-eIF4E-binding protein 1 (Thr37/46) was added, reacted at room temperature for 1 hour.

4. The 384-well plate was placed in HERAEUS Multifuge X1R centrifuge, centrifuged at 2000 rpm for 2 minutes; data were measured on EnVision™, 337 nM wavelength laser was used as the excitation light, test at RFU665 nM and RFU615 nM, and RFU665 nM/RFU615 nM×10000 was used as the final data for analysis.

5. Graphpad Prism 5.0 was used to perform Log (inhibitor) vs. response-Variable slope (four parameters) curve fitting on the data and the corresponding IC$_{50}$ (half maximal inhibitory concentration) was calculated.

The test result was shown in Table 3.

TABLE 2

Structures of comparative examples A-F and LY2835219 comparative example A

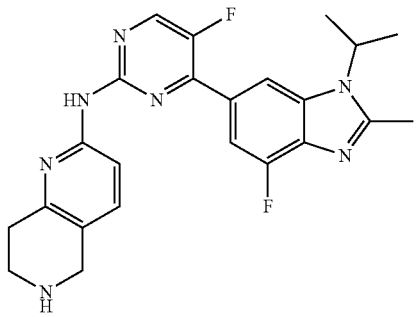 [SMILES: Cc1nc2c(F)cc(-c3nc(Nc4ccc5c(n4)CCNC5)ncc3F)cc2n1C(C)C]

comparative example B

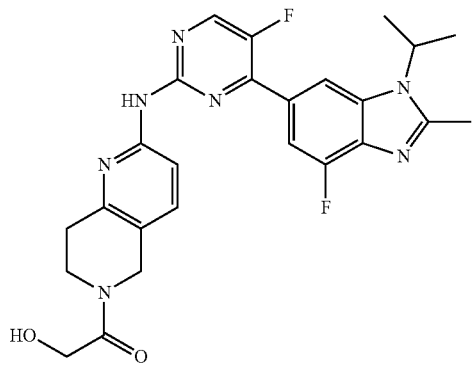 [SMILES: Cc1nc2c(F)cc(-c3nc(Nc4ccc5c(n4)CCN(C(=O)CO)C5)ncc3F)cc2n1C(C)C]

comparative example C

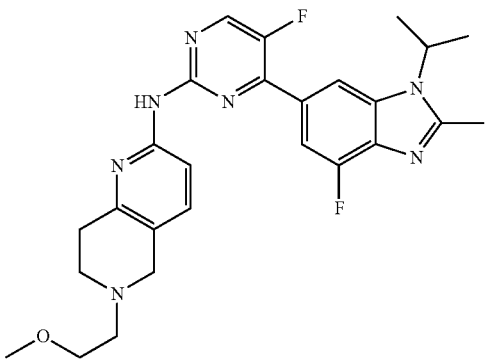

comparative example D

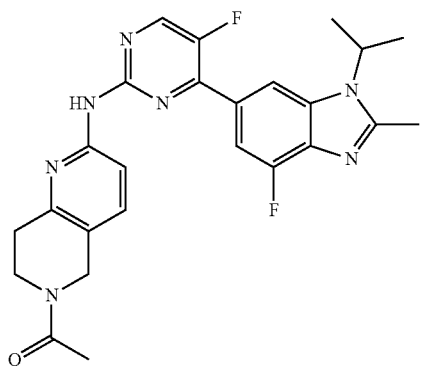 [SMILES: CC(=O)N1CCc2nc(Nc3ncc(F)c(-c4cc(F)c5nc(C)n(C(C)C)c5c4)n3)ccc2C1]

TABLE 2-continued
Structures of comparative examples A-F and LY2835219
comparative example E
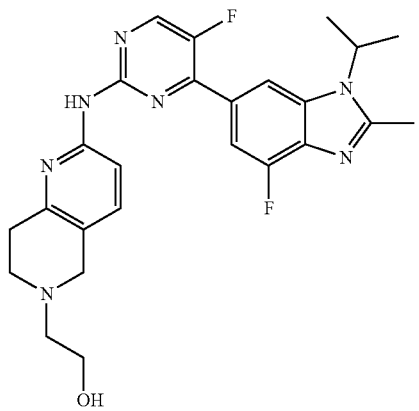 [SMILES: Cc1nc2c(F)cc(-c3nc(Nc4ccc5c(n4)CCN(CCO)C5)ncc3F)cc2n1C(C)C]
comparative example F
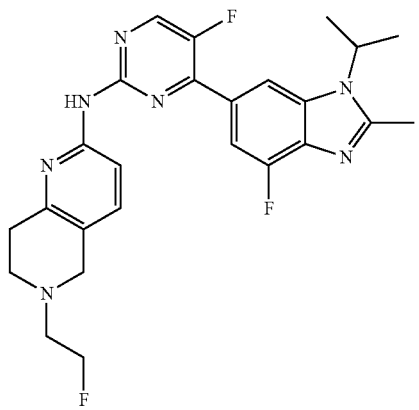 [SMILES: Cc1nc2c(F)cc(-c3nc(Nc4ccc5c(n4)CCN(CCF)C5)ncc3F)cc2n1C(C)C]
LY2835219
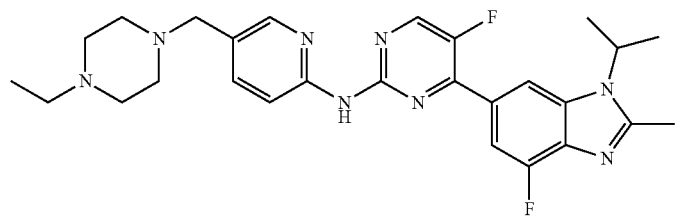 [SMILES: CCN1CCN(Cc2ccc(Nc3ncc(F)c(-c4cc(F)c5nc(C)n(C(C)C)c5c4)n3)nc2)CC1]
TABLE 3
Activity test results on Kinase level
| Compound number | CDK4 IC$_{50}$, nM | CDK6 IC$_{50}$, nM | CDK2 IC$_{50}$, nM |
|---|---|---|---|
| LY2835219 | 2.51 | 11.7 | 52.2 |
| I-3 | 2.08 | 10.4 | 35.0 |
| I-4 | 1.72 | 3.49 | 29.6 |
| I-5 | 1.64 | 4.14 | 33.7 |
| I-6 | 1.72 | 7.57 | 28.7 |
| I-8 | 2.05 | 7.07 | 15.5 |
| I-9 | 1.74 | 7.09 | 13.4 |
| I-10 | 2.21 | 7.81 | 10.4 |
| I-12 | 3.55 | 14.2 | 60.4 |
| I-13 | 42.3 | 327 | 558 |
| I-14 | 14 | 140 | 1090 |
| I-15 | 20.1 | 113 | 306 |
| I-17 | 2.54 | 4.88 | 37.2 |
| I-19 | 2.34 | 12.4 | 38.2 |
| I-20 | 4.49 | 22.3 | 7.34 |
| I-21 | 4.84 | 25.0 | 128 |
| I-22 | 3.49 | 10.6 | 193 |
| I-23 | 2.88 | 4.17 | 14.8 |
| I-24 | 3.90 | 6.44 | 31.1 |
| I-25 | 3.08 | 5.78 | 57.9 |
| I-26 | 2.23 | 8.12 | 37.2 |
| I-27 | 5.23 | 14.1 | 151 |
| I-28 | 4.11 | 18.9 | 143 |
| I-29 | 1.81 | 4.98 | 304 |
| I-30 | 2.23 | 3.38 | 154 |
| I-31 | 2.35 | 4.84 | 20.4 |
| I-32 | 3.54 | 13.2 | 146 |
| I-33 | 1.65 | 6.23 | 65.5 |
| I-34 | 2.07 | 2.56 | 89.7 |
| I-35 | 1.97 | 4.53 | 87.6 |
| I-36 | 2.75 | 7.41 | 281 |
| I-37 | 4.68 | 16.1 | 413 |
| I-38 | 2.34 | 4.37 | 32.3 |
| I-39 | 2.18 | 7.43 | 72.1 |

TABLE 3-continued

Activity test results on Kinase level

| Compound number | CDK4 IC$_{50}$, nM | CDK6 IC$_{50}$, nM | CDK2 IC$_{50}$, nM |
|---|---|---|---|
| I-40 | 2.53 | 3.59 | 40.6 |
| I-41 | 74.9 | 272 | >3330 |
| I-42 | 7.05 | 13.4 | 84.3 |
| I-43 | 2.94 | 3.57 | 122 |
| I-44 | 3.21 | 2.82 | 54.1 |
| I-45 | 7.14 | 22.7 | 710 |
| I-46 | 2.52 | 3.42 | 346 |
| I-47 | 2.36 | 4.16 | 559 |
| I-48 | 1.65 | 4.88 | 91.0 |
| I-49 | 3.36 | 5.17 | 28.2 |
| I-50 | 2.71 | 3.94 | 334 |
| I-51 | 1.83 | 2.88 | 129 |
| I-52 | 3.88 | 3.81 | 700 |
| I-53 | 1.70 | 5.46 | 314 |
| I-54 | 4.27 | 7.50 | 294 |
| I-55 | 2.47 | 3.56 | 58.9 |
| I-57 | 3.55 | 6.14 | 109 |
| I-58 | 3.20 | 6.14 | 93.7 |
| I-59 | 3.14 | 4.78 | 93.4 |
| I-60 | 1.47 | 3.47 | 79.4 |
| I-61 | 1.12 | 2.55 | 364 |
| I-62 | 1.44 | 4.51 | 28.3 |
| I-63 | 1.12 | 2.0 | 47.7 |
| I-64 | 3.26 | 8.47 | >1020 |
| I-65 | 1.35 | 3.75 | >3470 |
| I-66 | 1.06 | 6.36 | 661 |
| I-67 | 1.53 | 6.24 | 212 |
| I-68 | 1.09 | 2.97 | 18.5 |
| I-69 | 1.13 | 1.57 | 54.9 |
| I-70 | 1.68 | 5.51 | 1490 |
| I-71 | 1.34 | 3.47 | 167 |
| I-72 | 1.12 | 2.58 | 110 |
| I-73 | 3.14 | 6.91 | 371 |
| I-74 | 2.08 | 3.15 | 317 |
| I-75 | 3.37 | 5.16 | 74.9 |
| I-76 | 2.45 | 4.58 | 33.9 |
| I-77 | 2.07 | 3.15 | 249 |
| I-78 | 4.41 | 5.60 | 567 |
| I-79 | 1.92 | 2.69 | 35.5 |
| I-80 | 2.22 | 3.67 | 647 |
| I-81 | 1.68 | 3.34 | 207 |
| I-82 | 0.86 | 3.16 | 16.5 |
| I-83 | 1.08 | 1.55 | 17.4 |
| I-84 | 1.54 | 3.21 | 15.0 |
| I-85 | 0.94 | 2.54 | 135 |
| I-86 | 0.96 | 1.49 | 16.3 |
| I-87 | 0.92 | 2.21 | 10.3 |
| I-88 | 0.91 | 1.41 | 16.3 |
| I-89 | 3.74 | 17.9 | 62.4 |
| I-90 | 1.16 | 1.56 | 28.5 |
| I-91 | 0.99 | 1.70 | 16.3 |
| I-92 | 0.99 | 1.39 | 14.3 |
| I-93 | 0.96 | 1.33 | 16.3 |
| I-94 | 1.16 | 1.37 | 10.3 |
| I-95 | 1.18 | 2.02 | 6.02 |
| I-97 | 1.73 | 2.11 | 15.0 |
| I-98 | 1.04 | 5.01 | 670 |
| I-101 | 1.79 | 2.90 | 14.5 |
| I-102 | 1.02 | 2.41 | 19.2 |
| I-103 | 1.02 | 0.97 | 23.8 |
| I-104 | 4.21 | 9.25 | 31.1 |
| I-106 | 1.33 | 2.67 | 83.3 |
| I-107 | 1.56 | 4.59 | 135 |
| I-108 | 1.61 | 2.23 | 116 |
| I-109 | 1.59 | 3.86 | 30.7 |
| I-110 | 2.00 | 5.89 | 14.5 |
| I-111 | 1.09 | 2.98 | 11.2 |
| I-112 | 1.37 | 1.70 | 44.9 |
| I-114 | 1.74 | 1.77 | 23.6 |
| I-126 | 2.21 | 6.26 | 232 |
| I-127 | 1.65 | 4.88 | 444 |
| I-129 | 0.70 | 1.13 | 62.4 |
| I-130 | 1.02 | 1.48 | 14.3 |
| I-131 | 0.91 | 1.41 | 28.5 |
| I-132 | 0.99 | 0.77 | 19.4 |
| I-133 | 1.52 | 1.82 | 78.2 |
| I-134 | 1.35 | 1.59 | 25.1 |
| I-135 | 17.7 | 111 | 147 |
| I-136 | 14.1 | 84.2 | 486 |
| I-137 | 1.55 | 4.78 | 8.43 |
| I-138 | 4.26 | 33.0 | >3330 |
| I-139 | 8.12 | 29.3 | 126 |
| I-140 | 2.35 | 5.67 | 358 |
| I-142 | 1.96 | 3.25 | 301 |
| I-153 | 2.26 | 1.87 | 42.8 |
| I-154 | 1.9 | 1.97 | 39.6 |
| I-155 | 1.45 | 2.08 | 67.0 |
| I-157 | 2.06 | 2.03 | 48.4 |
| I-158 | 1.27 | 1.60 | 73.1 |
| I-160 | 3.77 | 2.46 | 34.6 |
| I-175 | 1.86 | 3.86 | 21.0 |
| I-176 | 1.49 | 1.51 | 6.68 |
| I-192 | 1.54 | 1.53 | 29.0 |
| I-196 | 3.06 | 2.99 | 60.2 |
| I-197 | 15.9 | 12.9 | 27.6 |
| I-198 | 1.91 | 2.03 | 59.3 |
| I-199 | 1.53 | 2.31 | 27.0 |
| I-200 | 2.15 | 5.89 | 40.2 |
| I-202 | 1.14 | 1.11 | 20.8 |
| I-203 | 1.51 | 1.28 | 20.0 |
| I-204 | 12.1 | 25.7 | 1250 |
| I-205 | 4.83 | 14.7 | 117 |
| I-206 | 1.56 | 1.76 | 50.3 |
| I-207 | 2.27 | 1.73 | 32.0 |
| I-208 | 1.39 | 2.58 | 13.1 |
| I-209 | 1.48 | 2.39 | 14.0 |
| I-210 | 2.11 | 1.80 | 18.0 |
| I-211 | 1.45 | 1.36 | 18.5 |
| comparative example A | 3.80 | 13.2 | 17.0 |
| comparative example B | 2.93 | 7.58 | 13.5 |
| comparative example C | 2.37 | 7.26 | 21.5 |
| comparative example D | 2.06 | 7.22 | 31.9 |
| comparative example E | 2.06 | 9.17 | 19.9 |
| comparative example F | 1.72 | 2.67 | 22.5 |

Effect Embodiment 2

MCF-7, T-47D, ZR-75-1, COLO 205 and A549 cell proliferation inhibition assays were performed using the CellTiter-Glo® Luminescent Cell Viability Assay method. Experiments were performed on human breast cancer MCF-7, T-47D and ZR-75-1 cell, human colon cancer COLO 205 cell, and human non-small cell carcinoma A549 cell, used CellTiter method to determine the inhibition effect of the compound on proliferation of five cell lines. During the test, the initial concentration of the test compound was 10 μM, all test compounds set 10 serially diluted concentrations, the dilution-fold was 3-fold, each concentration set 2 duplicated wells.

Mcf-7 cell, purchased from ATCC, article No. HTB-22;
T-47D, purchased from ATCC, article No. HTB-133;
ZR-75-1, purchased from Shanghai Cell Bank, article No. TCHu126;
COLO 205 human colon cancer cell, purchased from Cell Bank of Type Culture Collection of the Chinese Academy of Sciences/Cell BankShanghai Institutes for Biological Sciences, Chinese Academy of Sciences, catalogue No. TCHu102;

A549 human non-small cell cancer cell, purchased from ATCC, catalogue No. CCL-185™;

CellTiter-Glo® luminescent cell viability assay kit, purchased from Promega, Catalog No. G7573;

RPMI-1640, purchased from Life technologies, article No. A1049101;

F-12K Nutrient Mixture, purchased from Life technologies, article No. 21127-002;

FBS, purchased from Life technologies, article No. 10099-141;

Antibiotic, purchased from Life technologies, article No. 10378-016;

PBS, purchased from Life technologies, article No. 10010-023;

Dimethyl sulfoxide, purchased from Sigma-Aldrich, article No. D8418;

384-well cell culture plate, purchased from Corning, article No. 3570.

Test Procedure:

1. Normally cultured human breast cancer cells, normally cultured 12th generation COLO 205 human colon cancer cells, and normally cultured 7th generation A549 cells were plated in 384-well plate at a certain cell density; MCF-7 and T-47D cells were plated at a density of 500 cells/well, ZR-75-1, COLO 205 cells and A549 cells were plated at a density of 250 cells/well, the cell culture plate was placed at 37° C. in 5% $CO_2$ condition for 24 hours.

2. One day after human breast cancer cells were plated, one plate was used to measure the background Celltiter value which was recorded as Control Dl. Dosing on the remaining plates to set cell control group. The initial concentration of the test compound was 10M, followed by 10 serial dilutions, the dilution-fold was 3-fold, each concentration set 2 duplicated well.

2'. After COLO 205 cells and A549 cells were plated for 24 hours, the configured concentration gradient of drug was added to the corresponding cell wells, respectively. The control group Conctrol was a drug-free, medium solution containing 0.2% DMSO. The untreated cell well was used to measure the background value which was recorded as Blank. The cell culture plate was placed at 37° C., COLO 205 cells were cultured in 5% $CO_2$ condition for 6 days, A549 cells were cultured in 5% $CO_2$ condition for 4 days.

3. Human breast cancer cells: After 6 days treatment of the test compound, 50 μL CellTiter detection solution was added to each well, the mixture was shaken for 2 min, mixed thoroughly, centrifuged, left to stand for 10 min, the fluorescent signal was recorded. The drug group was recorded as Drug D7. The control group was recorded as Control D7.

3'. COLO 205 cells and A549 cells: the microplate was taken out from incubator and equilibrated at room temperature for 30 minutes. 50 μL CellTiter-Glo® Luminescent Cell Viability Assay which had been equilibrated at room temperature was added to each well, the mixture was shaken at 700 rpm at room temperature for 2 minutes, the microplate was placed in HERAEUS Multifuge X1R centrifuge at 2000 rpm for 1 minute; equilibrated at room temperature for 10 minutes, the fluorescence signal value was measured on EnVision™.

4. Graphpad Prism 5.0 was used to perform Log (inhibitor) vs. response-Variable slope (four parameters) curve fitting on the data and the corresponding $IC_{50}$ (half maximal inhibitory concentration) was calculated.

The test results were shown in Table 4, wherein the structures of comparative examples A-F refer to those recited in effect embodiment 1.

TABLE 4

Activity results at Cell level

| Compound number | MCF-7 $IC_{50}$, nM | T-47D $IC_{50}$, nM | ZR-75-1 $IC_{50}$, nM | COLO 205 $IC_{50}$, nM | A549 $IC_{50}$, nM |
|---|---|---|---|---|---|
| LY2835219 | 116. | 38.4 | 108 | 411 | 436 |
| I-3 | 82.1 | 79.3 | 110 | 213 | |
| I-4 | 185 | 267 | 85.2 | 103 | |
| I-5 | 69.4 | 9.02 | 78.4 | 121 | |
| I-6 | 119 | 322 | 253 | | |
| I-8 | 154 | 110 | 63.2 | 267 | |
| I-9 | 241 | 418 | 176 | | |
| I-10 | 895 | 8680 | 838 | | |
| I-12 | 138 | 141 | 1390 | | |
| I-13 | 3520 | 2880 | 4940 | | |
| I-14 | 1590 | 1370 | 2230 | | |
| I-15 | >33300 | >33300 | 4760 | | |
| I-17 | 176 | 330 | 314 | | |
| I-19 | 533 | 198 | 426 | | |
| I-20 | 2090 | 985 | 3390 | | |
| I-21 | 684 | 809 | 335 | | |
| I-22 | 245 | 116 | 324 | | |
| I-23 | 108 | 20.7 | 187 | 120 | |
| I-24 | 93.5 | 464 | 235 | | |
| I-25 | 96.3 | 39.4 | 139 | 235 | |
| I-26 | 145 | 637 | 301 | | |
| I-27 | 275 | 122 | 1260 | | |
| I-28 | 525 | 212 | 381 | | |
| I-29 | 28.0 | 16.9 | 50.0 | 352 | |
| I-30 | 188 | 229 | 1010 | | |
| I-31 | 218 | 660 | 369 | | |
| I-32 | 457 | 4930 | 605 | | |
| I-33 | 648 | 1320 | 269 | | |
| I-34 | 116 | 131 | 141 | | |
| I-35 | 92.3 | 66.0 | 73.9 | 1150 | |
| I-36 | 140 | 32.9 | 72.5 | 542 | |
| I-37 | 666 | 243 | 409 | 1150 | |
| I-38 | 94.1 | 137 | 219 | 161 | |
| I-39 | 2490 | 137 | 146 | 816 | |
| I-40 | 1090 | 484 | 369 | 303 | |
| I-41 | 1320 | 1430 | 1500 | 786 | |
| I-42 | 1050 | 1200 | 354 | 575 | |
| I-43 | 1590 | 26.1 | 60.5 | 598 | |
| I-44 | 771 | 410 | 126 | 367 | |
| I-45 | 2810 | 283 | 352 | 1340 | |
| I-46 | 15.8 | 47.0 | 160 | 522 | |
| I-47 | 35.0 | 58.8 | 62.1 | 637 | |
| I-48 | 27.9 | 32.5 | 119 | 1210 | |
| I-49 | 1590 | 396 | 220 | 195 | |
| I-50 | 88.0 | 34.6 | 68.8 | 614 | |
| I-51 | 314 | 42.0 | 83.4 | 461 | |
| I-52 | 23.3 | 19.8 | 25.5 | 563 | 49.3 |
| I-53 | 73.2 | 23.4 | 57.0 | 468 | 317 |
| I-54 | 94.1 | 30.3 | 56.2 | 573 | |
| I-55 | 377 | 16.4 | 82.5 | 360 | |
| I-57 | 214 | 1120 | 210 | 478 | |
| I-58 | 431 | 56.0 | 88.9 | 485 | |
| I-59 | 62.3 | 44.0 | 35.8 | 533 | |
| I-60 | 36.2 | 24.3 | 61.4 | 521 | |
| I-61 | 41.5 | 13.1 | 68.6 | 361 | |
| I-62 | 22.6 | 21.9 | 49.9 | 194 | |
| I-63 | 7.03 | 8.62 | 21.5 | 94.5 | 75.3 |
| I-64 | 443 | 72.7 | 244 | 3600 | |
| I-65 | 139 | 33.0 | 109 | 72.9 | |
| I-66 | 165 | 48.1 | 142 | 1340 | |
| I-67 | 182 | 43.8 | 74.3 | 607 | 465 |
| I-68 | 73.8 | 131 | 75.3 | 96.1 | |
| I-69 | 18.7 | 5.05 | 14.1 | 56.0 | 58.7 |
| I-70 | 102 | 56.7 | 139 | 1420 | 125 |
| I-71 | 609 | 2000 | 692 | 871 | |
| I-72 | 247 | 797 | 130 | 219 | |
| I-73 | 344 | 21.3 | 184 | 1270 | |
| I-74 | 21.0 | 8.05 | 36.1 | 302 | 44.1 |
| I-75 | 308 | 64.6 | 272 | 463 | |
| I-76 | 461 | 197 | 232 | 375 | |
| I-77 | 163 | 26.9 | 61.4 | 541 | |
| I-78 | 136 | 87.9 | 164 | 803 | |
| I-79 | 39.4 | 14.8 | 53.6 | 202 | |

TABLE 4-continued

Activity results at Cell level

| Compound number | MCF-7 IC$_{50}$, nM | T-47D IC$_{50}$, nM | ZR-75-1 IC$_{50}$, nM | COLO 205 IC$_{50}$, nM | A549 IC$_{50}$, nM |
|---|---|---|---|---|---|
| I-80 | 32.7 | 42.0 | 69.6 | 431 | 30.8 |
| I-81 | 145 | 29.9 | 60.0 | 449 | |
| I-82 | 27.4 | 130 | 65.7 | 150 | |
| I-83 | 12.6 | 8.26 | 13.6 | 68.0 | 179 |
| I-84 | 22.2 | 73.9 | 52.0 | 93.2 | |
| I-85 | 69.1 | 16.3 | 174 | 250 | 69.0 |
| I-86 | 19.9 | 7.81 | 29.3 | 84.0 | 93.1 |
| I-87 | 98.4 | 189 | 97.0 | 130 | 72.6 |
| I-88 | 21.0 | 6.29 | 16.8 | 70.8 | 93.3 |
| I-89 | 522 | 738 | 492 | 770 | 573 |
| I-90 | 27.9 | 8.99 | 14.5 | 105 | 140 |
| I-91 | 1940 | 336 | 1300 | 3530 | 3130 |
| I-92 | 115 | 18.5 | 80.0 | 78.3 | 69.9 |
| I-93 | 44.6 | 14.0 | 141 | 189 | 441 |
| I-94 | 48.9 | 25.1 | 114 | 335 | 376 |
| I-95 | 56.4 | 179 | 85.7 | 114 | 226 |
| I-97 | 1380 | 375 | 1610 | 2690 | 6830 |
| I-98 | 49.3 | 47.7 | 191 | 578 | 612 |
| I-101 | 31.0 | 61.9 | 50.7 | 89.8 | 54.4 |
| I-102 | 54.0 | 62.8 | 141 | 1130 | 1510 |
| I-103 | 6.99 | 5.21 | 16.3 | 50.4 | 139 |
| I-104 | 71.6 | 237 | 162 | 199 | 148 |
| I-106 | 23.4 | 34.7 | 123 | 170 | 337 |
| I-107 | 551 | 29.0 | 110 | 387 | 934 |
| I-108 | 239 | 118 | 674 | 1730 | 2190 |
| I-109 | 28.1 | 94.3 | 76.7 | 157 | 74.7 |
| I-110 | 152 | 344 | 353 | 350 | 451 |
| I-111 | 19.4 | 77.9 | 46.4 | 89.4 | 70.0 |
| I-112 | 21.1 | 4.69 | 15.0 | 44.2 | 195 |
| I-114 | 7.73 | 3.24 | 9.65 | 40.7 | 259 |
| I-126 | 21.2 | 26.2 | 61.8 | 284 | 68.5 |
| I-127 | 27.9 | 32.5 | 118 | 1210 | |
| I-129 | 33.1 | 9.18 | 133 | 299 | 353 |
| I-130 | 47.14 | 9.04 | 45.10 | 572.50 | 454 |
| I-131 | 44.5 | 30.5 | 77.2 | 762 | 1360 |
| I-132 | 39.6 | 405 | 731 | >10000 | >10000 |
| I-133 | 882 | 810 | 1360 | 6210 | 2690 |
| I-134 | 86.2 | 750 | 479 | 189 | 352 |
| I-135 | 963 | 1680 | 1260 | 1310 | 1290 |
| I-136 | 1080 | 1670 | 1420 | 1870 | 1550 |
| I-137 | 185.90 | 140.40 | 268.40 | 386.20 | 482 |
| I-138 | 224 | 188 | 608 | 2290 | 3570 |
| I-139 | 756 | 808 | 452 | 929 | 1180 |
| I-140 | 23.2 | 15.2 | 80.5 | 384 | 2900 |
| I-142 | 224 | 15.0 | 57.9 | 265 | 816 |
| I-153 | 14.8 | 333.6 | 41.5 | 80.6 | 169 |
| I-154 | 72.9 | 9.89 | 31.3 | 68.3 | |
| I-155 | 157 | 106 | 40.2 | | 425 |
| I-157 | 296 | 7.20 | 19.4 | 42.2 | 113 |
| I-158 | 76.0 | 45.0 | 82.5 | | 546 |
| I-160 | 118 | 70.5 | 438 | 240 | 424 |
| I-175 | 612 | 74.4 | 261 | 117 | 305 |
| I-176 | 238 | 5.91 | 40.4 | 11.4 | 37.2 |
| I-187 | 454 | 340 | 574 | 660 | 1100 |
| I-192 | 17.4 | 10.6 | 17.7 | | |
| I-196 | 51.7 | 1500 | 149 | 425 | |
| I-197 | 957 | 1240 | >10000 | 7620 | >10000 |
| I-198 | 95.6 | 26.6 | 114 | 96.0 | 213 |
| I-199 | 135 | 169 | 92.0 | | |
| I-200 | 399 | 76.6 | 132 | 125 | 422 |
| I-202 | 158 | 36.0 | 122 | 59.4 | 52.0 |
| I-203 | 29.8 | 4.25 | 14.9 | 26.1 | 205 |
| I-204 | 568 | 555 | 1930 | 5830 | >10000 |
| I-205 | 150 | 140 | 452 | | 1060 |
| I-206 | 20.5 | 17.8 | 35.2 | | |
| I-207 | 67.2 | 484 | 74.8 | | |
| I-208 | 66.8 | 182 | 56.0 | | |
| I-209 | 86.2 | 127 | 76.5 | | |
| I-210 | 54.6 | 28.2 | 72.8 | | |
| I-211 | 88.7 | 229 | 56.1 | | |
| comparative example A | 79.1 | 129 | 108 | 114 | |
| comparative example B | 134 | 229 | 309 | 114 | |
| comparative example C | 148 | 119 | 75.1 | 371 | |
| comparative example D | 152 | 406 | 367 | | |
| comparative example E | 176 | 134 | 59.3 | 132 | |
| comparative example F | 291 | 740 | 178 | | |

Effect Embodiment 3

In vitro proliferation inhibition experiments of U87, MGU251, K562, THP1, HepG2, SK-HEP-1, SNU-5, N87, H1975, H1993, CFPAC1, PANC-1, LNCap, and PC-3 cell lines was used CellTiter-Glo® luminescent cell viability assay method. Experiments were performed on U87, MGU251, K562, THP1, HepG2, SK-HEP-1, SNU-5, N87, H1975, H1993, CFPAC1, PANC-1, LNCap and PC-3 cells, CellTiter method was used to determine the inhibition effect of the compound on proliferation. During the test, the initial concentration of the test compound was 10M, each test compound set 10 serially diluted concentrations, the dilution-fold was 3-fold, each concentration set 2 duplicated wells.

U87MG human brain astrocytoma cell line, purchased from ATCC, article No. HTB-14

K-562 cell, purchased from Cell Bank of Type Culture Collection of the Chinese Academy of Sciences, article No. TCHu191;

PANC-1 cell, purchased from Cell Bank of Type Culture Collection of the Chinese Academy of Sciences, article No. TCHu98;

THP1 cell, purchased from ATCC, article No. TIB-202;

HepG2 human hepatoma cell line, purchased from ATCC, article No. HB-8065;

SK-HEP-1 cell, purchased from Cell Bank of Type Culture Collection of the Chinese Academy of Sciences, article No. TCHu109;

SNU-5 cell, purchased from ATCC, article No. CRL-5973;

N87 cell, purchased from ATCC, article No. CRL-5822;

H1975 non-small cell lung cancer cell, purchased from ATCC, article No. CRL-5908;

H1993 cell, purchased from ATCC, article No. CRL-5909;

CFPAC1 cell, purchased from ATCC, article No. CRL-1918;

MGU251 cell, purchased from Cell Bank of Type Culture Collection of the Chinese Academy of Sciences, article No. TCHu58;

LNCap cell, purchased from ATCC, article No. CRL-1740;

PC-3 cell, purchased from ATCC, article No. TCHu158;

RPMI-1640 medium, purchased from Life technologies, article No. A1049101;

IMDM medium, purchased from Life technologies, article No. 12440;

DMEM medium, purchased from Life technologies, article No. 11995;

MEM medium, purchased from Life technologies, article No. 51200;

FBS, purchased from Life technologies, article No. 10099;

Antibiotic, purchased from Life technologies, article No. 10378;

PBS, purchased from Life technologies, article No. 10010;

β-mercaptoethanol, purchased from Life technologies, article No. 1150809;

F-12K, purchased from Life technologies, article No. 21127022;

HepG2, purchased from ATCC, article No. HB-8065; U87MG, purchased from ATCC, article No. HTB-14; PC-3, purchased from Cell Bank, Shanghai, article No. TCHu158; CellTiter-Glo® luminescent cell viability assay kit, purchased from Promega, Catalog No. G7573; 384-well cell culture plate, purchased from Corning, article No. 3570; 96-well compound plate, purchased from Nunc, article No. 267245.

Test Procedure:

1. U87MG (DMED medium, 11th generation, 12th generation and 13th generation), MGU251 (4th generation), K562 (10th generation, cell plate density 125 cells/well), THP1 (6th generation, 8th generation and 10th generation), HepG2 (DMED medium, 7th generation, 10th generation and 13th generation), SK-HEP-1 (7th generation), SNU-5 (5th generation), N87 (1640 medium, Assay1: 11th generation, Assay2: 12th generation, Assay3: 13th generation), H1975 (RPMI medium, 6th generation, 9th generation, 11th generation), H1993 (8th generation), CFPAC1 (IMDM medium, Assay1: 9th generation, Assay2: 10th generation, Assay3: 12th generation), PANC-1 (5th generation), LNCap (7th generation, 10th generation and 12th generation, cell plate density 625 cells/well), PC-3 (8th generation), plated in 384-well plate at a cell density of 250 cells/well.

2. One day after plated, one plate was used to measure the background Celltiter value which was recorded as Control D1. Dosing on the remaining plates to set cell control group. The initial concentration of the test compound was 10M, followed by 10 serial dilutions, the dilution-fold was 3-fold, each concentration set 2 duplicated well.

3. After certain days (U87MG cell for 4 days, MGU251 cell for 6 days, K562 cell for 4 days, THP1 cell for 4 days, HepG2 cell for 4 days, SK-HEP-1 cell for 4 days, SNU-5 cell for 6 days, N87 cell for 4 days, H1975 cell for 4 days, H1993 cell for 6 days, CFPAC1 cell for 4 days, PANC-1 cell for 4 days, LNCap cell for 6 days, PC-3 cell for 6 days) of treatment of the test compound, 50 μL CellTiter detection solution was added to each well, the mixture was shaken for 2 min, mixed thoroughly, centrifuged, left to stand for 10 min, detected and recorded the fluorescent signal. The drug group was recorded as Drug D7. The control group was recorded as Control D7.

4. Graphpad Prism 5.0 was used to perform Log (inhibitor) vs. response-Variable slope (four parameters) curve fitting on the data and the corresponding $IC_{50}$ (half maximal inhibitory concentration) was calculated.

The test results were shown in Table 5 and Table 6.

TABLE 5

Activity data of I-52 on different tumor cells

| Cell line | LY283521 ($IC_{50}$, nM) | | | I-52 ($IC_{50}$, nM) | | |
|---|---|---|---|---|---|---|
| | Assay 1 | Assay 2 | Assay 3 | Assay 1 | Assay 2 | Assay 3 |
| HepG2 | 246 | 204 | 198 | 35.5 | 22.6 | 21.8 |
| U87MG | 711 | 792 | 614 | 37.9 | 35.5 | 22.2 |
| LNCap | 73.2 | 81.0 | 97.8 | 35.6 | 67.0 | 37.5 |
| PC-3 | 5850 | 11800 | >10000 | 4190 | 8760 | 37500 |
| THP1 | 251 | 123 | 187 | 36.8 | 34.1 | 36.6 |

TABLE 6

Activity data of I-63 on different tumor cells

| Cell line | LY283521 ($IC_{50}$, nM) | | | I-63 ($IC_{50}$, nM) | | |
|---|---|---|---|---|---|---|
| | Assay 1 | Assay 2 | Assay 3 | Assay 1 | Assay 2 | Assay 3 |
| U87 | 711 | 792 | 614 | 198 | 154 | 267 |
| MGU251 | 232 | 403 | 246 | 111 | 181 | 114 |
| K562 | 974 | 1110 | 1190 | 211 | 334 | 352 |
| THP1 | 251 | 123 | 187 | 61.5 | 40.9 | 44.8 |
| HepG2 | 246 | 204 | 198 | 33.3 | 24.7 | 21.8 |
| SK-HEP-1 | 430 | 401 | 402 | 147 | 108 | 153 |
| SNU-5 | 422 | 460 | 685 | 226 | 206 | 340 |
| N87 | 573 | 592 | 391 | 392 | 530 | 346 |
| H1975 | 603 | 1040 | 677 | 346 | 367 | 268 |
| H1993 | 1120 | 1240 | 1100 | 1000 | 619 | 663 |
| CFPAC1 | 508 | 378 | 228 | 2670 | 178 | 272 |
| PANC-1 | 664 | 658 | 782 | 288 | 373 | 297 |
| LNCap | 73.2 | 80.9 | 97.8 | 16.1 | 31.7 | 20.1 |
| PC-3 | 5850 | 11800 | 8310 | 541 | 535 | 1480 |

Effect Embodiment 4 (In Vivo Pharmacodynamics of the Compounds on Human Breast Cancer MCF-7 Cell in BALB/c Nude Mice Subcutaneous Xenograft Model)

Experimental Objective:

Evaluate in vivo pharmacodynamics of the test compounds on human breast cancer MCF-7 cell in BALB/c nude mice subcutaneous xenograft model.

Experimental Design:

64 of BALB/c nude mice, 6-8 weeks old, weight 18-22 g, female, provided by Shanghai Sippr-bk Laboratory Animal Ltd., according to Table 7.

TABLE 7

In vivo pharmacodynamics of experimental animals grouping and dosage regimen

| Group | $N^1$ | compound | Dose | Dosing volume | Administration route | Dosing frequency |
|---|---|---|---|---|---|---|
| 1 | 8 | menstruum | — | 10 mL/kg | PO | QD × 19 days |
| 2 | 8 | Test compound I-52 | 25 mg/kg | 10 mL/kg | PO | QD × 19 days |
| 3 | 8 | Test compound I-52 | 50 mg/kg | 10 mL/kg | PO | QD × 19 days |

TABLE 7-continued

In vivo pharmacodynamics of experimental animals grouping and dosage regimen

| Group | N[1] | compound | Dose | Dosing volume | Administration route | Dosing frequency |
|---|---|---|---|---|---|---|
| 4 | 8 | Test compound I-52 | 100 mg/kg | 10 mL/kg | PO | QD × 19 days |
| 5 | 8 | Test compound I-63 | 10 mg/kg | 10 mL/kg | PO | QD × 19 days |
| 6 | 8 | Test compound I-63 | 25 mg/kg | 10 mL/kg | PO | QD × 19 days |
| 7 | 8 | Test compound I-63 | 50 mg/kg | 10 mL/kg | PO | QD × 19 days |
| 8 | 8 | Test compound LY2835219 | 50 mg/kg | 10 mL/kg | PO | QD × 19 days |

Note:
N[1]: the number of mice per group

Dosing volume: 10 μL/g based on the weight of mice. If the weight loss exceeded 15%, the dosage regimen should be adjusted accordingly.

Experiment Route

1. Cell culture: human breast cancer cell line MCF-7 was cultured in a monolayer in vitro, the culture condition was in accordance with the supplier's technical specification or the references. Passage cells were treated with trypsin-EDTA for conventional digestion twice a week. When the cell saturation was 80%-90% and the quantity reached the requirements, cells were collected, counted, and inoculated.

2. Estrogen tablet inoculation and urination: 2 days before cell inoculation, the (3-estradiol sustained-release tablet was inoculated into the left back of each mice. One week after inoculation, the animal urinated 3 times per week, the animal urinated daily if necessary.

3. Tumor cell inoculation: 0.2 mL 10×10$^6$ MCF-7 cells was subcutaneously inoculated into the right back of each nude mice (PBS:Matrigel=1:1). When the average tumor volume reached 195 mm$^3$, the compound was administered according to the dosage regimen (see Table 7).

4. Preparation of the test sample, see Table 8.

TABLE 8

Preparation method of the test compounds

| Compound | Preparation method | Concentration | Storage condition |
|---|---|---|---|
| vehicle | 1, liquid A: Taking 16.6 m/L phosphoric acid, adding water to 1000 mL, shaking; 2, liquid B: Taking 7.163 g disodium phosphate, adding water to 100 mL and making it dissolved; 3, mixing 145 mL the liquid A and 55 mL liquid B, shaking; adding 350 mL pure water, mixing, shaking, determining pH with pH meter to give the phosphate buffer (20 mM, pH 2.0); 4, weighing 5 g hydroxyethyl cellulose, taking 500 mL phosphate buffer (20 mM, pH 2.0), mixing under magnetic stirring, storing at 4° C. in dark ready for use. | 1% | 4° C., in dark |
| I-52 | Weighing 18 mg compound I-52, being added to 7.2 mL 1% HEC in phosphate buffer, mixing until homogeneous | 2.5 mg/mL | 4° C., in dark |
| I-52 | Weighing 36 mg compound I-52, being added into 7.2 mL 1% HEC in phosphate buffer, mixing until homogeneous | 5 mg/mL | 4° C., in dark |
| I-52 | Weighing 72 mg compound I-52, being added into 7.2 mL 1% HEC in phosphate buffer, mixing until homogeneous | 10 mg/mL | 4° C., in dark |
| I-63 | Weighing 7.2 mg compound I-52, being added into 7.2 mL 1% HEC in phosphate buffer, mixing until homogeneous | 1 mg/mL | 4° C., in dark |
| I-63 | Weighing 18 mg compound I-52, being added into 7.2 mL 1% HEC in phosphate buffer, mixing until homogeneous | 2.5 mg/mL | 4° C., in dark |
| I-63 | Weighing 36 mg compound I-52, being added into 7.2 mL 1% HEC in phosphate buffer, mixing until homogeneous | 5 mg/mL | 4° C., in dark |
| LY2835219 | Weighing 36 mg compound LY2835219, being added into 7.2 mL 1% HEC in phosphate buffer, mixing until homogeneous | 5 mg/mL | 4° C., in dark |

Note:
It is necessary to gently homogeneously mix the drug before the drug was administered to the animal.

5, Tumor measurement and experimental indicator: The experimental indicator was to examine whether the tumor growth was inhibit, delayed or cured. Tumor diameter was measured twice a week with a vernier caliper. The formula for calculating the tumor volume was $V=0.5a \times b^2$, a and b denoted the long diameter and short diameter of the tumor respectively. The antitumor activity of the compounds was evaluated by TGI (%) or relative tumor proliferation rate T/C (%). TGI (%) reflected the tumor growth inhibition rate. Calculation for TGI (%): TGI (%)=[(1−(mean tumor volume at the end of dosing of a treatment group—mean tumor volume at the beginning of dosing of the treatment group))/ (mean tumor volume at the end of treatment of the solvent control group-mean tumor volume at the beginning of treatment of the solvent control group)]×100%. Relative tumor proliferation rate T/C (%): the calculation formula was as follows: T/C %=$T_{RTV}/C_{RTV}$×100% ($T_{RTV}$: RTV of treatment group; $C_{RTV}$: RTV of solvent control group). The relative tumor volume (RTV) was calculated based on the result of tumor measurement, the calculation formula was RTV=$V_t/V_0$, wherein $V_0$ was the mean tumor volume measured at the beginning (do) of dosing, and $V_t$ was the mean tumor volume measured at a certain time, $T_{RTV}$ and $C_{RTV}$ took at the same day. At the end of the experiment, the tumor weight was measured and the tumor weight inhibition rate IR (%) was calculated: the calculation formula was IR (%)=(1−Tw/Vw)×100, Tw: mean tumor weight of the treatment group, Vw: mean tumor weight of the solvent control group.

6. Data summary and statistical analysis: The treatment group showed the best treatment effect on the 19th day after dosing at the end of the experiment. Therefore, based on the data, statistical analysis was performed to evaluate the differences between groups. T-test was used for the comparison between two groups, and one-way ANOVA was used for comparison among three groups or multiple groups. If the variance was not homogeneous, the Games-Howell method was used for test. If variance was homogeneous, the Dunnet (2-sided) method was used for analysis. All data analysis were performed with SPSS 19.0. p<0.05 was considered statistically significant.

Experimental Results

1, Comparison between two groups of the treatment group relative to the control group, see Table 9.

TABLE 9 pharmacodynamics of the compound of the inhibition on MCF-8 xenograft tumorgrowth

| Group | Day 6 | | | Day 13 | | | Day 19 | | |
|---|---|---|---|---|---|---|---|---|---|
| | T/C[a] (%) | TGI[a] (%) | T-test p[b] | T/C (%) | TGI (%) | T-test p | T/C (%) | TGI (%) | T-test p |
| Vehicle | — | — | — | — | — | — | — | — | — |
| LY2835219 50 mg/kg | 68.96 | 111.13 | 0.044 | 46.02 | 94.99 | 0.023 | 36.58 | 82.66 | 0.032 |
| I-52 25 mg/kg | 69.27 | 110.04 | 0.047 | 38.21 | 108.73 | 0.013 | 33.66 | 86.41 | 0.028 |
| I-52 50 mg/kg | 66.78 | 118.92 | 0.040 | 35.49 | 113.46 | 0.011 | 23.09 | 100.18 | 0.016 |
| I-52 100 mg/kg | 63.65 | 130.17 | 0.028 | 29.9 | 123.36 | 0.007 | 19.44 | 104.95 | 0.013 |
| I-63 10 mg/kg | 66.45 | 120.15 | 0.036 | 45.53 | 95.84 | 0.022 | 39.49 | 78.82 | 0.038 |
| I-63 25 mg/kg | 68.73 | 111.98 | 0.047 | 31.43 | 120.67 | 0.008 | 19.49 | 104.88 | 0.014 |
| I-63 50 mg/kg | 34.11 | 235.8 | 0.001 | 14.48 | 150.43 | 0.003 | 9.82 | 117.45 | 0.009 |

Note:
[a]tumor growth inhibition was calculated by T/C and TGI (TGI(%) = [1 − ($T_{6/13/19} - T_0$)/($V_{6/13/19} - V_0$)] × 100);
[b]p-value compared the treatment group with the vehicle group using T-test according to tumor volume.

Each treatment group exhibited inhibitory activity on tumor growth at the 6th day, 13th day and 19th day after dosing compared to the control group. At 19th day after dosing, the mean tumor volume of tumor-bearing mice in the solvent control group reached 840 mm$^3$, compared to that, the effect of the test compounds I-52, I-63 and LY2835219 at different doses was statistically significant. The tumor growth inhibition rate (TGI) of compound I-52 at 25, 50 and 100 mg/kg reached 86.41%, 100.18%, and 104.95%, respectively; the tumor weight inhibition rate (IR) was 72.92%, 81.93%, and 86.35%, respectively; The tumor growth inhibition rate (TGI) of compound I-63 at 10, 25 and 50 and mg/kg reached 78.82%, 104.88%, and 117.45%, respectively; the tumor weight inhibition rate (IR) was 60.42%, 83.38%, and 92.26%, respectively; the tumor growth inhibition rate (TGI) of LY2835219 at 50 mg/kg reached 82.66%, the tumor weight inhibition rate (IR) was 56.18%. The T-test indicated that there was a statistically significant difference with between the treatment group and the vehicle group (p<0.05).

2, Comparison between compound I-52 and compound I-63 at 50 mg/kg, see Table 10.

TABLE 10

Comparison of antitumor activity at 50 mg/kg on MCF-7 xenograft tumor model(based on the tumor volume on the 19th day after dosing)

| Group | Tumor volumn (mm³)$^a$ (19th day) | T/C$^b$ (%) | TGI$^b$ (%) | Pvalue | p value |
|---|---|---|---|---|---|
| LY2835219 50 mg/kg | 306 ± 30 | 36.58 | 82.66 | 0.008$^d$ | — |
| I-52 50 mg/kg | 193 ± 26 | 23.09 | 100.18 | — | 0.008$^e$ |
| I-63 50 mg/kg | 82 ± 7 | 9.82 | 117.45 | 0.015$^d$ | 0.000$^e$ |

Note:
$^a$mean value ± SEM;
$^b$tumor growth inhibition was calculated by T/C and TGI (TGI(%) = [1 − (T$_{19}$ − T$_0$)/V$_{19}$ − V$_0$)] × 100);
c. p-value was calculated based on tumor volume;
$^d$compared to I-52, 50 mg/kggroup;
$^e$compared to LY2835219, 50 mg/kggroup.

The one-way ANOVA or T-test analysis of the two compounds at 50 mg/kg indicated that there was a significant difference in the inhibitory effect of the three compounds at the same dose on this model (p<0.05) (Table 10)

3, Dose-effect analysis of compound I-52 and I-63, see Table 11

TABLE 11

Comparison of anti-tumor activity of compound I-52 and I-63 at different dose on MCF-7 xenograft tumor model (based on the tumor volume on the 19th day after dosing)

| Group | Tumor volumn (mm³)$^a$ (19th day) | T/C$^b$ (%) | TGI$^b$ (%) | P value | P value |
|---|---|---|---|---|---|
| I-52 25 mg/kg | 283 ± 23 | 33.66 | 86.41 | — | 0.004$^e$ |
| I-52 50 mg/kg | 193 ± 26 | 23.09 | 100.18 | 0.031$^d$ | 0.570$^e$ |
| I-52 100 mg/kg | 163 ± 22 | 19.44 | 104.95 | 0.004$^d$ | — |
| I-63 10 mg/kg | 332 ± 32 | 39.49 | 78.82 | — | 0.000$^g$ |
| I-63 25 mg/kg | 164 ± 16 | 19.49 | 104.88 | 0.002$^f$ | 0.003$^g$ |
| I-63 50 mg/kg | 82 ± 7 | 9.82 | 117.45 | 0.000$^f$ | — |

Note:
$^a$mean value ± SEM;
$^b$tumor growth inhibition was calculated by T/C and TGI (TGI(%) = [1 − (T$_{19}$ − T$_0$)/(V$_{19}$ − V$_0$)] × 100);
c. p-value was calculated based on tumor volume;
$^d$compared to I-52, 25 mg/kg group;
$^e$compared to I-52, 100 mg/kg group;
$^f$compared to I-63, 10 mg/kg group;
$^g$compared to I-63, 50 mg/kg group;

When one-way ANOVA analysis was performed on the three dose groups of compound I-52 respectively, the result indicated that at different doses, there was a significant difference in the anti-tumor activity between the low dose group of compound I-52 and the middle, high dose group of compound I-52 (p<0.05), but there was no significant difference between the medium dose group and the high dose group (Table 10).

When one-way ANOVA analysis was performed on the three dose groups of compound I-63 respectively, the result indicated that at different doses, there was a significant difference in the anti-tumor activity of compound I-63 (Table 11).

Effect Embodiment 5

Test Method:
CDK kinase inhibitory activity assay used LANCE® Ultra technique, test compounds were screened on CDK1/CycB, CDK5/p25, CDK7/CycH/MAT1 and CDK9/CycT1 kinases at ATP concentration of Km. During the test, the initial concentration of the test compound was 3333 nM, each test compound set 10 serially diluted concentrations, the dilution-fold was 3-fold, each concentration set 2 duplicated wells.

CDK1/CycB, CDK5/p25 and CDK7/CycH/MAT1 were purchased from Carna Biosciences, Inc.; CDK9/CycT1 was purchased from Lifetech; dimethyl sulfoxide, ATP, DTT solution were purchased from Sigma-Aldrich; EDTA solution was purchased from GIBCO; LANCE® Detection Buffer, 10× and LANCE® Ultra Europium-anti-phospho-eIF4E-binding protein 1 (Thr37/46) and LANCE® Ultra ULight™-eIF4E-bindingprotein 1 (Thr37/46) Peptide were purchased from Perkinelmer.

Test Procedure:
1, Take 10 mM test compound stock solution, in 96-well compound plate, DMSO was used to make compound with an initial concentration of 100×, then this concentration was used as the first concentration, 3-fold diluted to make 10 serial concentrations; 1 µL each serial dilution was then added to 19 µL 1× reaction buffer to prepare 5× compound for use; 2 µL 5× compound was transferred from 96-well plate into 384-well plate; compound-free control well was added 2 µL the following liquid: 19 µL 1× reaction buffer with the addition of 14 L DMSO; 2 µL 250 mM EDTA was added to the Min control well.

2.1× reaction buffer was used to formulate the kinase, substrate, and ATP into a 2.5×enzyme/substrate mixture and 2.5×ATP solution respectively. In the experiment, the final concentration of CDK1/CycB kinase was 3.20 ng/µL, the final concentration of ATP was 12 µM; the final concentration of CDK5/p25 kinase was 0.0334 ng/µL, the final concentration of ATP was 4 µM; the final concentration of CDK7/CycH/MAT1 kinase was 1.93 ng/µL, the final concentration of ATP was 20 µM; the final concentration of CDK9/CycT1 kinase was 0.60 ng/µL, the final concentration of ATP was 12 µM; added 2.5×enzyme/substrate mixture to a 384-well plate, incubated at room temperature for 5 minutes; then added 2.5×ATP solution, reacted at room temperature for 30 minutes.

3, LANCE® Detection Buffer was used, 1× to prepare 2×LANCE® Ultra Europium-anti-phospho-eIF4E-binding protein 1 (Thr37/46) for use. After the enzymatic reaction was continued for 30 minutes, 10 mM EDTA was added to 384-well plate and reacted at room temperature for 5 minutes. Then LANCE® Ultra Europium-anti-phospho-eIF4E-binding protein 1 (Thr37/46) was added, reacted at room temperature for 1 hour.

4,384-well plate was placed in HERAEUS Multifuge X1R centrifuge, centrifuged at 2000 rpm for 2 minutes; data was measured on EnVision™, 337 nM wavelength laser was selected as the excitation light, measured at RFU665 nM and RFU615 nM, and RFU665 nM/RFU615 nM×10000 was used as the final data for analysis.

5, Graphpad Prism 5.0 was used to perform Log (inhibitor) vs. response-Variable slope (four parameters) curve fitting on the data and the corresponding IC$_{50}$ (half maximal inhibitory concentration) was calculated.

The test results were shown in Table 12.

TABLE 12

Activity test result at kinase level

| Compound number | CDK1 IC$_{50}$, nM | CDK5 IC$_{50}$, nM | CDK7 IC$_{50}$, nM | CDK9 IC$_{50}$, nM |
|---|---|---|---|---|
| LY2835219 | 263.2/557.90 | 81.80/51.80 | 667.10/225.90 | 34.55/49.28 |
| I-5 | 97.25 | | 913.41 | 13.04 |
| I-8 | 73.16 | | 393.28 | 11.43 |
| I-9 | 62.25 | | 13156.54 | 7.52 |
| I-22 | 183.44 | | 1044.56 | 36.09 |
| I-23 | 44.80 | | 801.32 | 8.21 |
| I-24 | 61.16 | | 2892.62 | 8.51 |
| I-25 | 86.66 | | 978.09 | 10.54 |
| I-29 | 222.26 | | 573.79 | 48.04 |
| I-38 | 26.21 | | >30000 | 0.92 |
| I-46 | 177.50 | | 1280.02 | 82.04 |
| I-47 | 491.11 | | 563.30 | 104.66 |
| I-50 | 726.02 | | 718.19 | 89.84 |
| I-51 | 119.19 | | 1153.10 | 65.83 |
| I-52 | 368.21 | 91.52 | 223.30 | 332.39 |
| I-54 | 357.21 | | 1817.51 | 80.43 |
| I-59 | 583.83 | | 650.34 | 152.40 |
| I-60 | 306.33 | | 1194.59 | 82.12 |
| I-61 | 347.63 | | 710.25 | 61.45 |
| I-62 | 69.04 | | 2818.63 | 2.44 |
| I-63 | 143.40 | 33.57 | 261.10 | 30.28 |
| I-65 | 360.01 | | 1076.14 | 88.95 |
| I-67 | 232.37 | | 555.53 | 26.64 |
| I-68 | 87.81 | 41.00 | 20.47 | 6.94 |
| I-69 | 138.80 | 11.44 | 129.20 | 16.22 |
| I-70 | 3614.00 | 620.20 | 196.40 | 316.20 |
| I-74 | 911.90 | 36.99 | 104.00 | 211.50 |
| I-79 | 209.00 | 82.39 | 279.80 | 47.45 |
| I-80 | 1096.00 | 91.22 | 146.60 | 223.30 |
| I-82 | 125.5 | 22.56 | 11.40 | 4.97 |
| I-83 | 171.9 | 28.99 | 38.13 | 12.51 |
| I-84 | 107.8 | 42.32 | 16.70 | 6.58 |
| I-86 | 101.9 | 15.35 | 60.97 | 10.68 |
| I-88 | 283.5 | 33.29 | 95.93 | 27.99 |
| I-90 | 218.2 | 40.30 | 36.48 | 22.75 |
| I-92 | 87.39 | 27.99 | 50.13 | 7.47 |
| I-93 | 199.4 | 139.60 | 147.00 | 13.98 |
| I-94 | 264.1 | 67.33 | 66.25 | 13.53 |
| I-98 | 1702.0 | 288.30 | 669.70 | 126.9 |
| I-101 | 78.94 | 3.90 | 56.98 | 6.74 |
| I-109 | 164.7 | 47.24 | 99.42 | 7.03 |
| I-111 | 55.07 | 15.92 | 104.8 | 5.44 |
| I-114 | 161.2 | 14.61 | 195.3 | 15.32 |
| I-126 | 291.56 | | 1181.63 | 47.08 |
| I-127 | 997.52 | | 779.46 | 145.43 |
| I-129 | 132.9 | 55.27 | 53.40 | 10.99 |
| I-130 | 207.9 | 85.75 | 109.10 | 20.79 |
| I-131 | 1054 | 238.60 | 124.10 | 163.70 |
| I-142 | 1233 | 29.33 | 314.7 | 133.1 |
| I-154 | 442.6 | 15.57 | 180.8 | 20.72 |
| I-157 | 273.1 | 21.36 | 214.6 | 23.56 |
| I-176 | 134.6 | 8.37 | 148.7 | 10.54 |
| I-202 | 141.3 | 7.17 | 159.5 | 8.42 |
| I-203 | 546.6 | 28.46 | 250.1 | 42.29 |
| comparative exampleA | 50.78 | | 325.62 | 9.21 |
| comparative exampleB | 41.12 | | 5366.87 | 9.18 |
| comparative exampleC | 131.93 | | 1094.50 | 14.77 |
| comparative exampleE | 83.36 | | 799.36 | 10.80 |

It is to be understood that the foregoing description of the preferred embodiments is intended to be purely illustrative of the principles of the invention, rather than exhaustive thereof, and that changes and variations will be apparent to those skilled in the art, and that the present invention is not intended to be limited other than expressly set forth in the following claims.

What is claimed is:

1. A compound selected from the group consisting of:

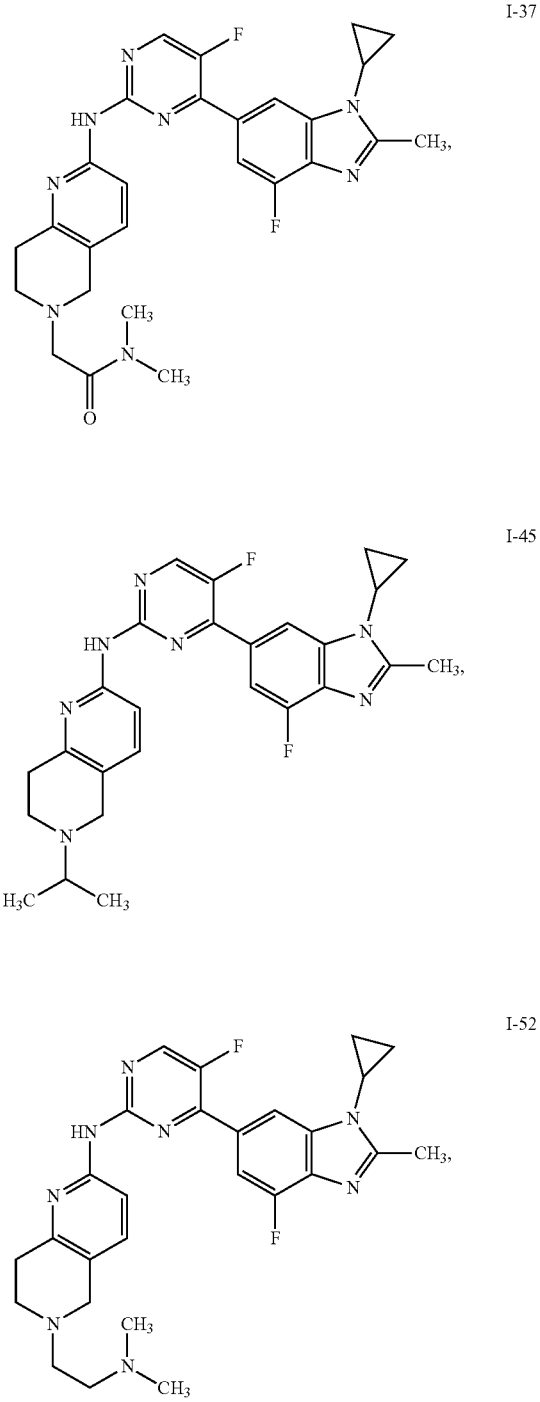

I-70
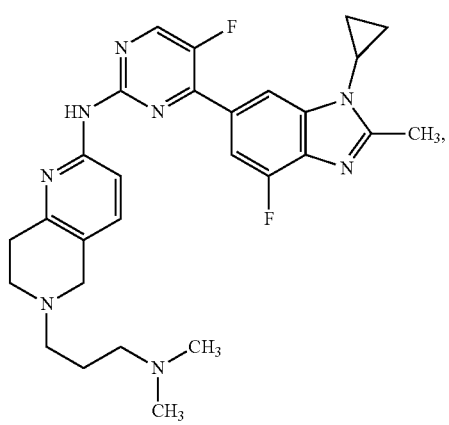
I-73
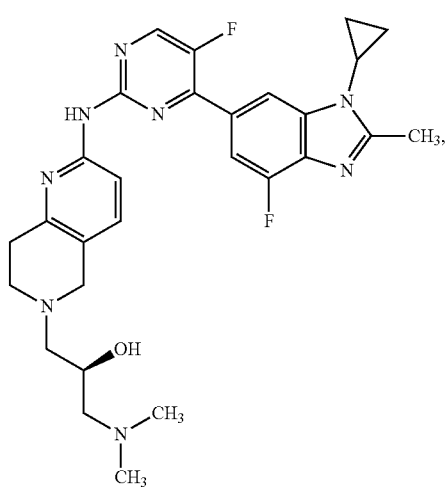
I-74
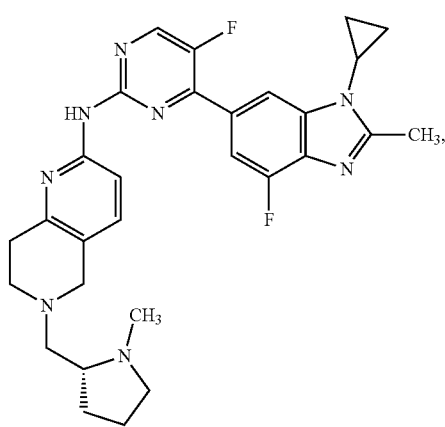
I-77
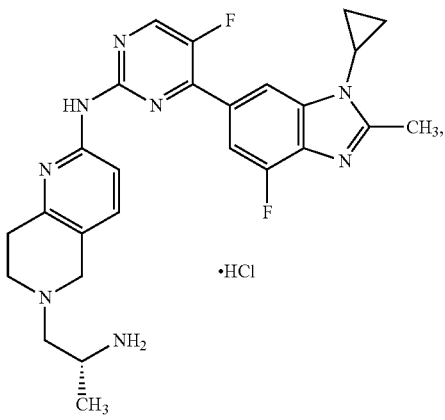
·HCl
I-78
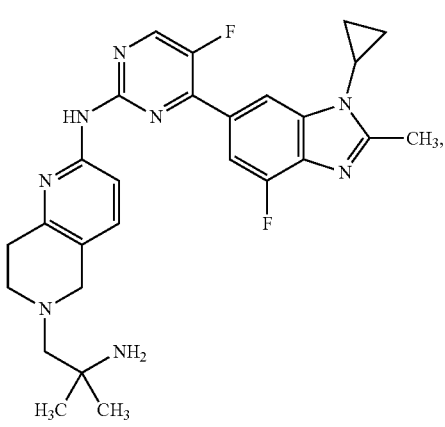
I-80
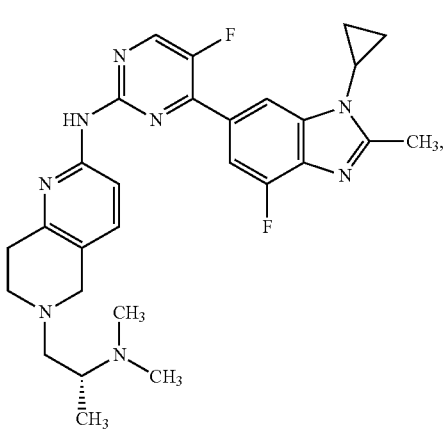

-continued

I-81
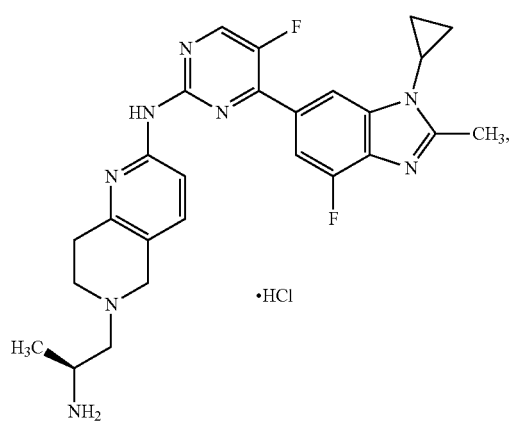
·HCl

I-85
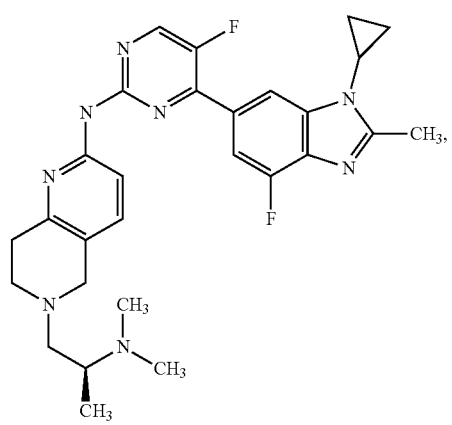

I-88
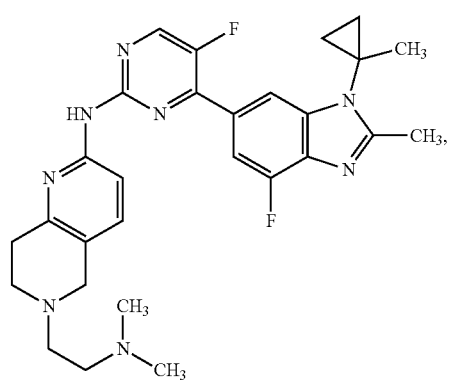

-continued

I-131
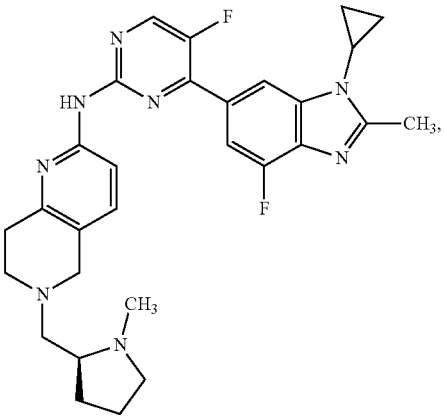

I-142
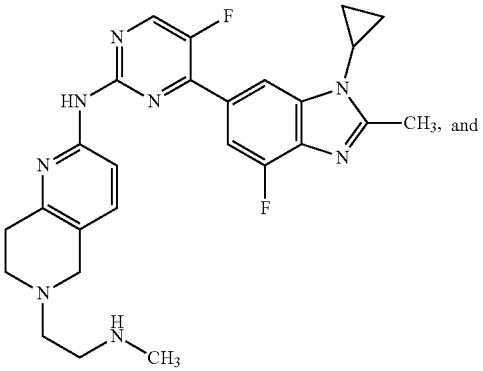

I-203
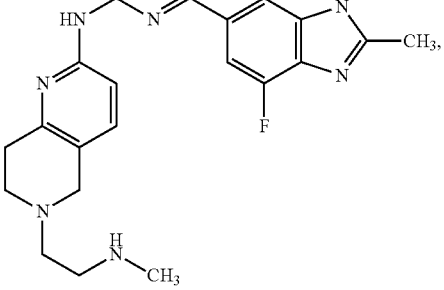

or a pharmaceutically acceptable salt, stereoisomer, or tautomer thereof.

2. A pharmaceutical composition comprising at least one pharmaceutically acceptable excipient and a compound according to claim 1, or a pharmaceutically acceptable salt, stereoisomer, or tautomer thereof.

3. A method for inhibiting cyclin-dependent kinase activity in a subject, comprising administering to the subject in need thereof a therapeutically effective amount of the compound according to claim 1, or a pharmaceutically acceptable salt, stereoisomer, or tautomer thereof.

4. A method for inhibiting tumor cells in a subject, comprising administering to the subject in need thereof a therapeutically effective amount of the compound according to claim 1, or a pharmaceutically acceptable salt, stereoisomer, or tautomer thereof.

* * * * *